United States Patent [19]

Teraji et al.

[11] 4,390,534

[45] * Jun. 28, 1983

[54] CEPHEM AND CEPHAM COMPOUNDS

[75] Inventors: Tsutomu Teraji, Osaka; Kazuo Sakane, Amagasaki; Jiro Goto, Suita, all of Japan

[73] Assignee: Fujisawa Pharmaceutical Co., Ltd., Osaka, Japan

[*] Notice: The portion of the term of this patent subsequent to May 19, 1998, has been disclaimed.

[21] Appl. No.: 255,301

[22] Filed: Apr. 17, 1981

Related U.S. Application Data

[63] Continuation-in-part of Ser. No. 160,904, Jun. 18, 1980, which is a continuation-in-part of Ser. No. 128,260, Mar. 7, 1980, Pat. No. 4,331,665, which is a continuation-in-part of Ser. No. 116,984, Jan. 30, 1980, Pat. No. 4,332,798, which is a continuation-in-part of Ser. No. 108,161, Dec. 28, 1979, abandoned.

[30] Foreign Application Priority Data

Dec. 29, 1978 [GB] United Kingdom ............... 50334/78
Oct. 12, 1979 [GB] United Kingdom ................ 7935538
Oct. 1, 1980 [ZA] South Africa ...................... 80/6068

[51] Int. Cl.$^3$ .................. A61K 31/545; C07D 501/56
[52] U.S. Cl. ...................................... 424/246; 544/22; 544/25; 544/27; 544/28
[58] Field of Search .................. 424/246; 544/25, 22, 544/27, 28

[56] References Cited

U.S. PATENT DOCUMENTS

| | | | |
|---|---|---|---|
| 4,263,291 | 4/1981 | Takaya et al. ..................... | 424/246 |
| 4,268,509 | 5/1981 | Teraji et al. ........................ | 424/246 |
| 4,331,665 | 5/1982 | Teraji et al. ........................ | 544/27 |
| 4,332,798 | 6/1982 | Teraji et al. ........................ | 424/246 |

*Primary Examiner*—Paul M. Coughlan, Jr.
*Attorney, Agent, or Firm*—Oblon, Fisher, Spivak, McClelland & Maier

[57] ABSTRACT

This invention relates to novel 7-thiadiazol-oxyimino-3-cephem and cepham 4-carboxylic acid compounds of high antimicrobial activity.

30 Claims, No Drawings

CEPHEM AND CEPHAM COMPOUNDS

This application is a continuation in part of parent application Ser. No. 160,904, filed June 18, 1980, which in turn is a continuation in part of parent application Ser. No. 128,260, filed Mar. 7, 1980, now U.S. Pat. No. 4,331,665, which in turn is a continuation in part of parent application Ser. No. 116,984, filed Jan. 30, 1980, now U.S. Pat. No. 4,332,798, which in turn is a continuation in part of parent application Ser. No. 108,161, filed Dec. 28, 1979, now abandoned.

This invention relates to new cephem compounds. More particularly, it relates to new 7-substituted-3-cephem and cepham-4-carboxylic acid and pharmaceutically acceptable salt thereof, which have antimicrobial activities, and processes for preparation thereof, to intermediate for preparing the same and processes for preparation thereof, and to pharmaceutical composition comprising the same and methods of using the same prophylactically and therapeutically for treatment of infectious diseases in human being and animals.

Accordingly, the objects of this invention are to provide:

new 7-substituted-3-cephem and cepham-4-carboxylic acid and pharmaceutically acceptable salt thereof, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals; and further intermediate to be used for preparation of pharmaceutically active 7-substituted-3-cephem and cepham-4-carboxylic acid or pharmaceutically acceptable salt thereof and processes for preparation thereof.

The object 7-substituted-3-cephem and cepham-4-carboxylic acid is novel and can be represented by the following general formula (I).

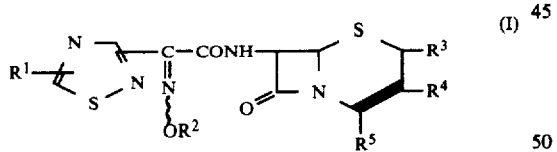

wherein
$R^1$ is amino or a protected amino,
$R^2$ is hydrogen, acyl, aryl which may be substituted with suitable substituent(s), lower alkyl substituted with suitable substituent(s), lower alkenyl, lower alkynyl, cycloalkyl which may be substituted with suitable substituent(s), cyclo(lower)alkenyl, or S or O containing 5-membered heterocyclic group substituted with oxo group(s),
$R^3$ is hydrogen or lower alkyl,
$R^4$ is hydrogen; acyloxy(lower)alkyl; acylthio(lower)alkyl; pyridinium(lower)alkyl which may be substituted with suitable substituent(s); a heterocyclicthio(lower)alkyl which may be substituted with suitable substituent(s); lower alkyl; halogen; hydroxy; or thiazolium(lower)alkyl which may be substituted with suitable substituent(s); and
$R^5$ is carboxy or a protected carboxy,
wherein $R^5$ is $COO^-$ when $R^4$ is pyridinium(lower)alkyl which may be substituted with suitable substituent(s) or thiazolium(lower)alkyl which may be substituted with suitable substituent(s),
and the heavy solid line means single or double bond.

According to the present invention, the object 7-substituted-3-cephem and cepham-4-carboxylic acid (I) can be prepared by the following processes.

Process 1

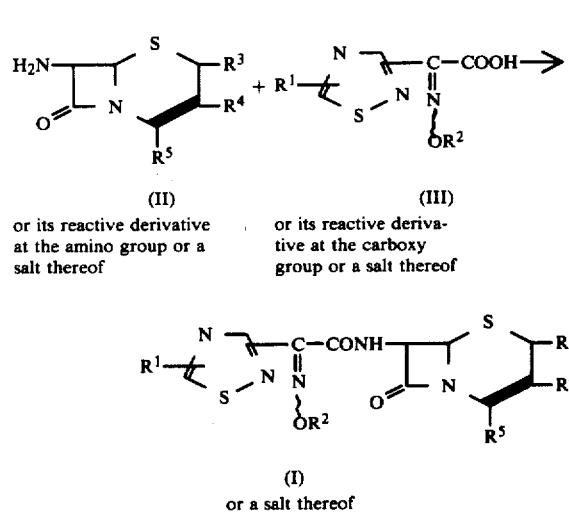

(II)           (III)
or its reactive derivative at the amino group or a salt thereof    or its reactive derivative at the carboxy group or a salt thereof (I)
or a salt thereof Process 2

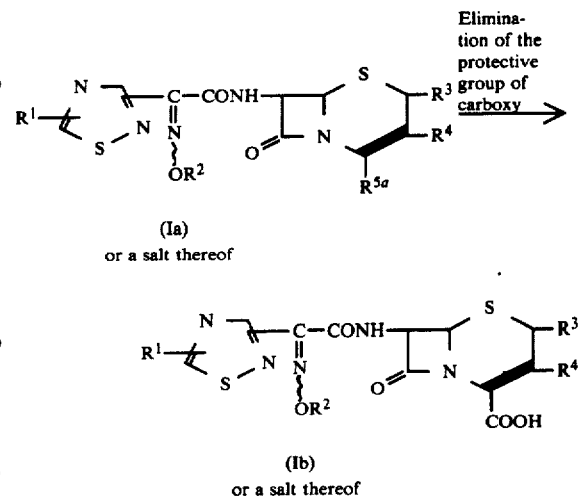

(Ia)
or a salt thereof (Ib)
or a salt thereof

Process 3

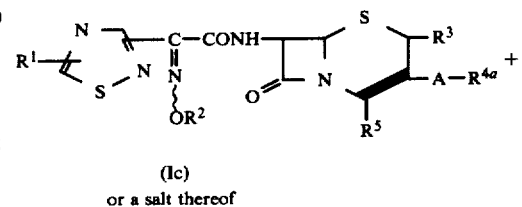

(Ic)
or a salt thereof

3
-continued

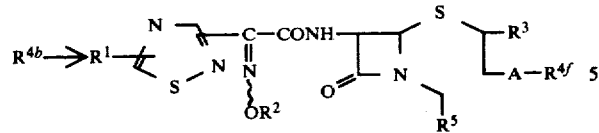

(IV)
or its
reactive
derivative (Id)
or a salt thereof

Process 4

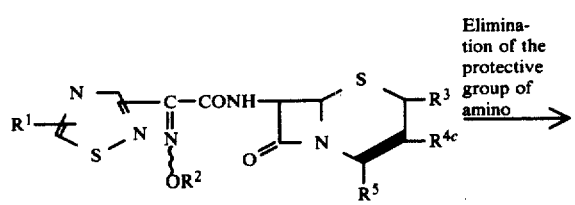

(Ie)
or a salt thereof

Elimination of the protective group of amino →

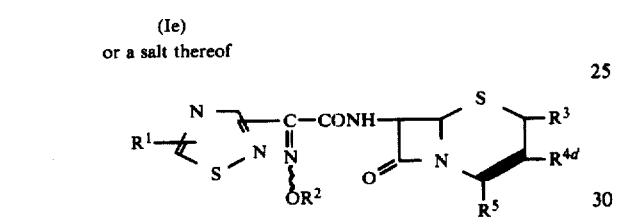

(If)
or a salt thereof

Process 5

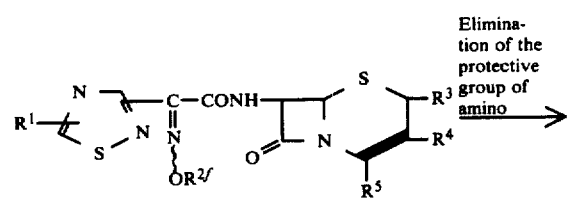

(Ii)
or a salt thereof

Elimination of the protective group of amino →

(Ij)
or a salt thereof

Process 6

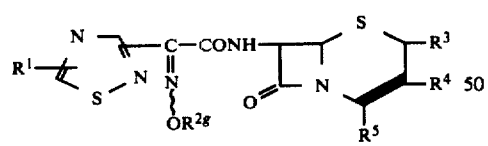

(Ik)
or a salt thereof

Elimination of the protective group of carboxy →

4
-continued

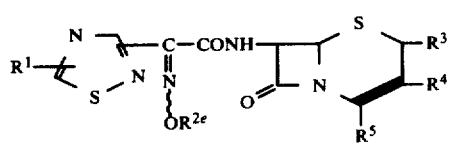

(Il)
or a salt thereof

Process 7

(Im)
or a salt thereof

Esterification →

(In)
or a salt thereof

Process 8

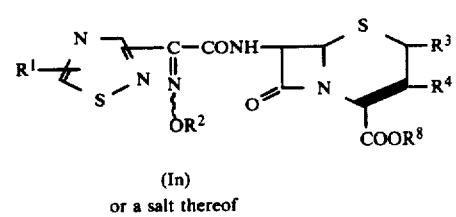

(Ig)
or a salt thereof

Elimination of the protective group of hydroxy →

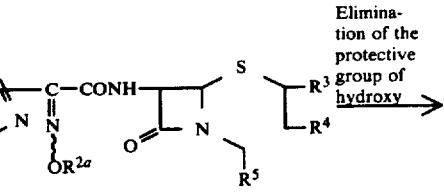

(Ih)
or a salt thereof

Process 9

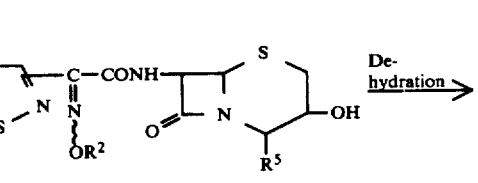

(Io)
or a salt thereof

Dehydration →

-continued

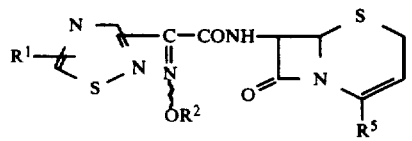

(Ip)

or a salt thereof

Process 10

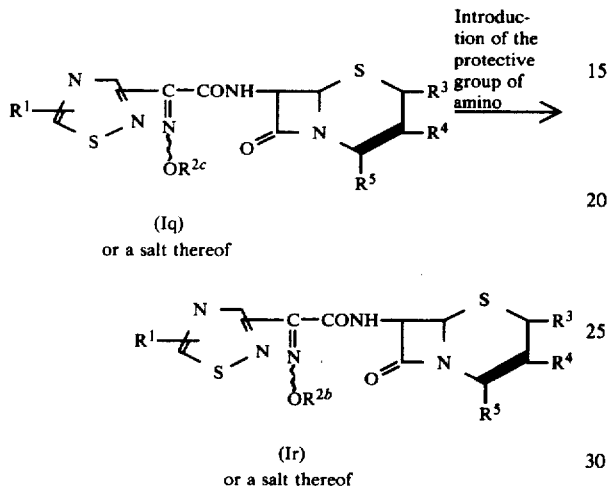

wherein $R^1$, $R^2$, $R^3$, $R^4$ and $R^5$ are each as defined above;

$R^{5a}$ is a protected carboxy;

$R^{4b}$ is pyridine which may be substituted with suitable substituent(s), thiazole which may be substituted with suitable substituent(s) or a group of the formula: $R^{4e}$—SH wherein $R^{4e}$ is acyl or a heterocyclic group which may be substituted with suitable substituent(s);

A is lower alkylene;

$R^{4c}$ is a heterocyclicthio(lower)alkyl substituted with protected amino(lower)alkyl;

$R^{4d}$ is a heterocyclicthio(lower)alkyl substituted with amino(lower)alkyl;

$R^{2a}$ is a protective group of hydroxy;

$R^{4a}$ is a group which can be substituted with a group of the formula: $R^{4f}$ wherein $R^{4f}$ is pyridinium which may be substituted with suitable substituent(s), thiazolium which may be substituted with suitable substituent(s), or a group of the formula: —S—$R^{4e}$ wherein $R^{4e}$ is as defined above;

$R^{4f}$ is as defined above;

$R^{2b}$ is protected amino(lower)alkyl;

$R^{2c}$ is amino(lower)alkyl;

$R^{2d}$ is protected carboxy(lower)alkyl, ar(lower)alkyl substituted with protected carboxy or cycloalkyl substituted with protected carboxy;

$R^{2e}$ is carboxy(lower)alkyl, ar(lower)alkyl substituted with carboxy or cycloalkyl substituted with carboxy;

$R^8$ is an ester moiety of an esterified carboxy represented by a group of the formula: —$COOR^8$, $R^{2f}$ is protected amino(lower)alkyl or ar(lower)alkyl substituted with protected amino(lower)alkyl, and $R^{2g}$ is amino(lower)alkyl or ar(lower)alkyl substituted with amino(lower)alkyl.

Among the starting compounds of the present invention, the compound (III) is novel and can be prepared by the following preparations.

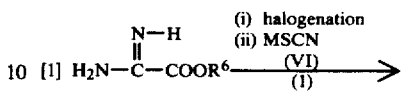

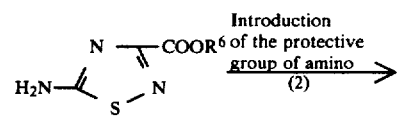

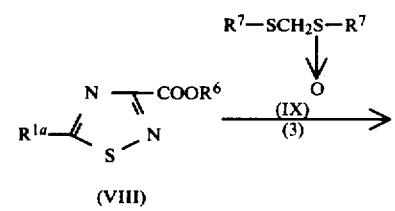

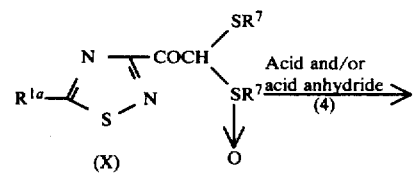

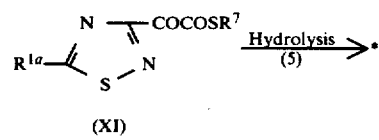

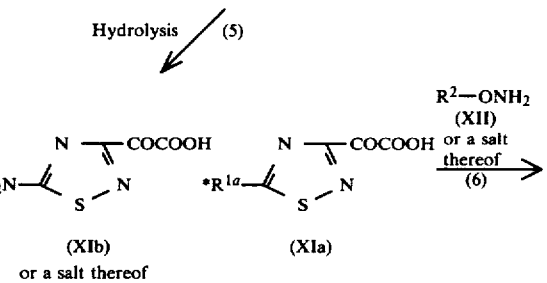

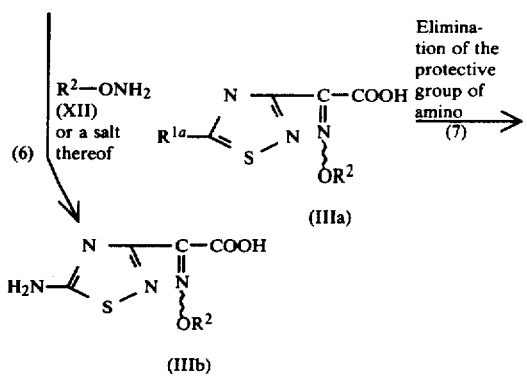

-continued

[2] 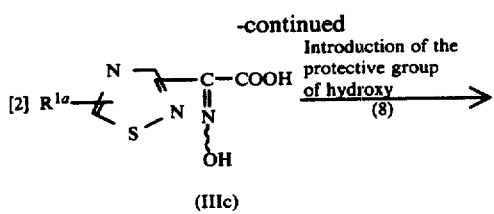 (IIIc) →Introduction of the protective group of hydroxy (8)→

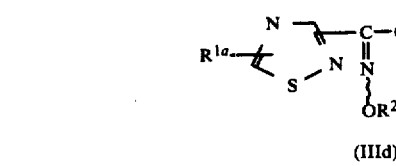 (IIId)

[3] X—R² (XIII) $\xrightarrow{R^9.OH\ (XIV)}_{(9)}$

R⁹.O—R² $\xrightarrow{\text{Elimination of the amino protective group}}_{(10)}$ H₂N—O—R²
(XV) (XVI) or a salt thereof

[4] 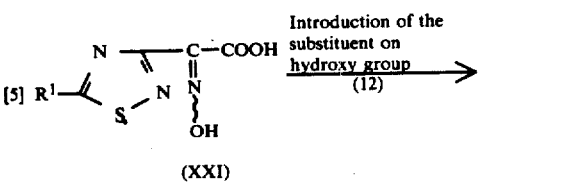 (XIX) →Introduction of the protective group of amino (11)→

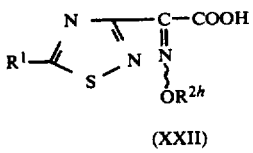 (XX)

[5] 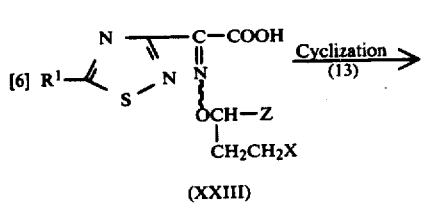 (XXI) →Introduction of the substituent on hydroxy group (12)→

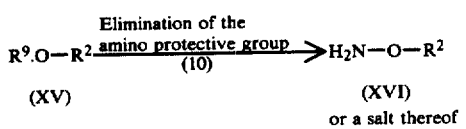 (XXII)

[6] 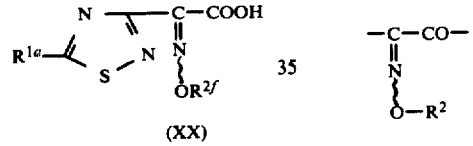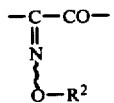 (XXIII) $\xrightarrow{\text{Cyclization}}_{(13)}$

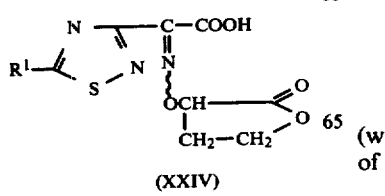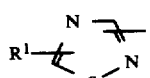 (XXIV)

-continued

[7] R¹⁰—NHCSS—R⁷ $\xrightarrow{\text{HN}_3 \text{ or a salt thereof}}_{(14)}$
(XXV)

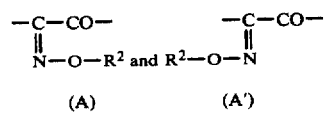

(XXVI)   (XXVII)   (XXVIII)
or a salt thereof   or a salt thereof   or a salt thereof wherein
R², R²ᵃ, R²ᶠ, R²ᵍ and R¹ are each as defined above,
R²ʰ is aryl which may be substituted with suitable substituent(s) or cycloalkyl which may be substituted with suitable substituent(s), Z is carboxy or protected carboxy, R¹⁰ is protected amino(C₃-C₆)alkyl,
R¹¹ is amino(C₃-C₆)alkyl,
R⁶ is a protective group of carboxy,
M is an alkali metal,
X is hydroxy or its reactive derivative,
R⁹ is amino having a protective group,
R¹ᵃ is a protected amino and
R⁷ is lower alkyl.

In the object compound (I) and the starting compound (III), the partial structure represented by the formula:

$$-\underset{\underset{O-R^2}{\overset{\|}{N}}}{C}-CO-$$

is to be understood to include both of the geometrical structures represented by the formulae:

$$-\underset{\underset{O-R^2}{\overset{\|}{N}}}{C}-CO- \quad -\underset{\underset{O-N}{\overset{\|}{R^2}}}{C}-CO-$$

(A)              (A')

In this specification, with regard to all the compounds having the above mentioned partial structure, the compounds having the geometrical structure shown by the formula (A) are referred to as "syn isomer" and the compounds having the alternative one shown by the formula (A') as "anti isomer".

Regarding the object compound of the formula (I) and the starting compound of the formula (III) as mentioned above, it is also to be understood that said object and starting compounds may include tautomeric isomers relating to their thiadiazolyl group. That is, in case that the group represented by the formula:

(wherein R¹ is amino or a protected amino) in formula of said object and starting compounds take the formula:

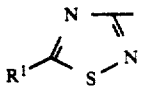
(B)

(wherein R¹ is as defined above), said group of the formula:

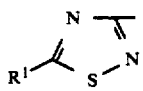

may be also alternatively represented by its tautomeric formula:

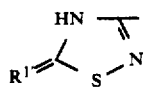
(B')

(wherein R¹' is imino or a protected imino). That is, both of the said group (B) and (B') may be in the state of equilibrium as so-called tautomeric forms which can be represented by the following equilibrium:

(wherein R¹ and R¹' are each as defined above).

In the present specification including claims and examples, the object and starting compounds having said group are represented by using one of the expressions therefor, namely the formula:

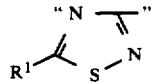
(B)

only for the convenient sake.

Suitable pharmaceutically acceptable salts of the object compound (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc.; an organic salt, for example, an organic amine salt (e.g., trimethylamine salt, triethylamine salt, pyridine salt, procaine salt, picoline salt, dicyclohexylamine salt, N,N'-dibenzylethylene-diamine salt, N-methylglucamine salt, diethanolamine salt, triethanolamine salt, tris(hydroxymethylamino)methane salt, phenylethylbenzylamine salt; dibenzylethylenediamine salt, etc.) etc.: an organic carboxylic or sulfonic acid salt (e.g., formate, acetate, maleate, tartrate, methanesulfonate, benzenesulfonate, toluenesulfonate, etc.); an inorganic acid salt (e.g., hydrochloride, hydrobromide, sulfate, phosphate, etc.); a salt with a basic or acidic amino acid (e.g., arginine, aspartic acid, glutamic acid, lysine, etc.) and the like.

In the above and subsequent descriptions of the present specification, suitable examples and illustration of the various definitions which the present invention intends to include within the scope thereof are explained in detail as follows.

The term "lower" is used to intend a group having 1 to 6 carbon atom(s), unless otherwise provided.

Suitable protected amino may include an acylamino and amino group substituted by a conventional proptective group other than the acyl group, such as ar(lower-)alkyl(e.g., benzyl, trityl, etc.) ar(lower)alkylidene(e.g., benzylidene, etc.), lower alkylidene substituted with lower alkoxycarbonyl or di(lower)alkylamino(e.g., 1-ethoxycarbonyl-2-propylidene, dimethylaminomethylene, etc.) or the like.

Suitable protected imino may include an acylimino and imino group substituted by a conventional protective group other than the acyl group such as aforesaid ar(lower)alkyl or the like.

Suitable acyl and acyl moiety in the terms "acylamino", "acylimino", "acyloxy(lower)alkyl" and "acylthio(lower)alkyl" may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s);

lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 3 to 6 carbon atoms;

lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.); aroyl (e.g., benzoyl, toluoyl, naphthoyl, phthaloyl, indancarbonyl, etc.);

ar(lower)alkanoyl (e.g., phenylacetyl, phenylpropionyl; etc.); cyclo(lower)alkyl(lower)alkanoyl(e.g. cyclohexylacetyl, cyclopentylacetyl, etc.);

ar(lower)alkoxycarbonyl (e.g., benzyloxycarbonyl, phenethyloxycarbonyl, etc.); and the like.

The acyl and acyl moiety as stated above may have 1 to 3 suitable substituent(s) such as halogen (e.g., chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl, etc.), aryl (e.g., phenyl, tolyl, etc.), amino, protected amino, acyl as mentioned above, or the like.

Preferable example of acyl having said substituent(s) may be di(lower)alkylcarbamoyl (e.g., dimethylcarbamoyl, diethylcarbamoyl, dipropylcarbamoyl etc.), phenyl(lower)alkanoyl substituted with amino or lower alkoxycarbonylamino, cyclo(lower)alkyl(lower)alkanoyl substituted with amino, lower alkanoyl(lower)alkanoyl(e.g., acetylacetyl, acetylpropionyl, etc.), etc.

Suitable example of acyl for R² may include halo(-lower)alkanoyl, more preferably dihalo(lower)alkanoyl (e.g., dichloroacetyl, dibromoacetyl, etc.) and the like.

Suitable aryl may include phenyl, tolyl, xylyl, mesityl, cumenyl and the like, and said aryl group may be substituted with 1 to 3 suitable substituent(s) such as halogen(e.g., chlorine, bromine, fluorine or iodine), nitro, lower alkoxy(e.g., methoxy, ethoxy, propoxy, butoxy, pentyloxy, hexyloxy, etc.) preferably one having 1 to 4 carbon atom(s), halo(lower)alkyl (e.g., chloromethyl, dichloromethyl, trichloromethyl, trifluoromethyl, trichloroethyl, etc.) preferably one having 1 to 3 carbon atom(s), protected carboxy as illustrated below, preferably lower alkoxycarbonyl, more preferably one having 2 to 4 carbon atoms, or the like.

Suitable lower alkyl and lower alkyl moiety is the terms "acyloxy(lower)alkyl", "acylthio(lower)alkyl" "pyridinium(lower)alkyl", "protected amino(lower)alkyl", "amino(lower)alkyl", "protected carboxy(lower)alkyl", "carboxy(lower)alkyl", "heterocycliothio(lower)alkyl", "ar(lower)alkyl" and "thiazolium(lower)alkyl" may include straight or branched one having 1 to 6 carbon atom(s), such as methyl, ethyl, propyl, isopropyl, butyl, isobutyl, tert-butyl, pentyl, tert-pentyl, hexyl or the like.

Suitable substituent(s) in the term "lower alkyl substituted with suitable substituent(s)" may include halogen (e.g. chlorine, bromine, fluorine or iodine); cyano; carboxy; protected carboxy as mentioned below; lower alkylthio (e.g., methylthio, ethylthio, propylthio, butylthio, etc.); aryl (e.g., phenyl, tolyl, xylyl, mesityl, cumenyl, etc.); aryloxy (e.g., phenoxy, tolyloxy, mesityloxy, etc.); aforesaid acyl; lower alkoxy(lower)alkoxy (e.g., methoxymethoxy, methoxyethoxy, ethoxyethoxy, propoxyethoxy, butoxyethoxy, pentyloxymethoxy, hexyloxymethoxy, hexyloxyethoxy, etc.); protected amino as mentioned above, preferably acylamino, more preferably lower alkoxycarbonylamino, aryl(lower)alkanoylamino substituted with amino or lower alkoxycarbonylamino, cyclo(lower)alkyl(lower)alkanoylamino substituted with amino; amino; or the like, wherein the afore-said aryl group being the substituent(s) on lower alkyl may be substituted with amino(lower)alkyl (e.g., aminomethyl, aminoethyl, aminopropyl, etc.) or protected amino(lower)alkyl; and suitable number of substituent(s) on lower alkyl group may be 1 to 3.

Suitable protected carboxy may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.), wherein lower alkyl moiety may be preferably one having 1 to 4 carbon atom(s); lower alkenyl ester (e.g., vinyl ester, allyl ester, etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, 1-acetoxypropyl ester, valeryloxymethyl ester, pivaloyloxymethyl ester, hexanoyloxymethyl ester, 1-acetoxyethyl ester, 2-propionyloxyethyl ester, 1-isobutyryloxyethyl ester, etc.); lower alkanesulfonyl(lower)alkyl ester (e.g., mesylmethyl ester, 2-mesylethyl ester etc.);

ar(lower)alkyl ester, for example, phenyl(lower)alkyl ester which may be substituted with one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);

lower alkoxycarbonyloxy(lower)alkyl ester(e.g., methoxycarbonyloxymethyl ester, ethoxycarbonyloxymethyl ester, ethoxycarbonyloxyethyl ester, etc.) which may be substituted with azido;

a heterocyclic ester, preferably benzotetrahydrofuryl ester which may be substituted with oxo group, more preferably phthalidyl ester;

aroyloxy(lower)alkyl ester (e.g., benzoyloxymethyl ester, benzoyloxyethyl ester, toluoyloxyethyl ester, etc.);

aryl ester which may have one or more suitable substituent(s) (e.g., phenyl ester, tolyl ester, tertiary-butylphenyl ester, xylyl ester, mesityl ester, cumenyl ester, etc.), and the like.

Preferable example of protected carboxy may be lower alkoxycarbonyl (e.g., methoxycarbonyl, ethoxycarbonyl, propoxycarbonyl, butoxycarbonyl, t-butoxycarbonyl, t-pentyloxycarbonyl, hexyloxycarbonyl, etc.) having 2 to 7 carbon atoms, preferably one having 2 to 5 carbon atoms, phenyl(lower)alkoxycarbonyl which may be substituted with nitro (e.g., 4-nitrobenzyloxycarbonyl, benzyloxycarbonyl, 4-nitrophenethyloxycarbonyl, etc.), lower alkanoyloxy(lower)alkoxycarbonyl (e.g., acetoxymethoxycarbonyl, pivaloyloxymethoxycarbonyl, hexanoyloxymethoxycarbonyl, 1-acetoxyethoxycarbonyl, 1-acetoxypropoxycarbonyl, 1-isobutyryloxyethoxycarbonyl, etc.) preferably one having 3 to 8 carbon atoms;

lower alkoxycarbonyloxy(lower)alkoxycarbonyl (e.g., ethoxycarbonyloxyethoxycarbonyl, ethoxycarbonyloxypropoxycarbonyl, etc.) which may be substituted with azido, preferably one having 5 to 7 carbon atoms;

phthalidyloxycarbonyl; and aroyloxy(lower)alkoxycarbonyl(e.g., benzoyloxymethoxycarbonyl, benzoyloxyethoxycarbonyl, etc.).

Suitable lower alkenyl may include vinyl, allyl, isopropenyl, 1-propenyl, 2-butenyl, 3-pentenyl and the like, preferably one having 2 to 4 carbon atoms.

Suitable lower alkynyl may include one having 2 to 6 carbon atoms, for example, ethynyl, 2-propynyl, 2-butynyl, 3-pentynyl, 3-hexynyl, or the like, preferably one having 2 to 4 carbon atoms.

Suitable cycloalkyl may include one having 3 to 8 carbon atoms, for example, cyclopropyl, cyclobutyl, cyclopentyl, cyclohexyl, cycloheptyl, or the like, preferably one having 4 to 7 carbon atoms.

Suitable substituent(s) on cycloalkyl can be referred to the ones as exemplified for substituent(s) on lower alkyl, and preferably carboxy or protected carboxy.

Suitable cyclo(lower)alkenyl may include one having 3 to 6 carbon atoms, for example, cyclopentenyl, cyclohexenyl, or the like, preferably one having 5 or 6 carbon atoms.

Suitable S or O containing 5-membered heterocyclic group may include saturated or unsaturated one, for example, dihydrofuryl, tetrahydrofuryl, thiolanyl or the like, which is substituted with 1 or 2 oxo group(s).

Suitable heterocyclic group and heterocyclic moiety in the term "a heterocyclicthio(lower)alkyl" means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3- triazolyl, etc.), tetrazolyl (e.g., 1H-tetrazolyl, 2H-tetrazolyl, etc.), dihydrotriazinyl, etc.;

saturated 3 to 8-membered heteromonocyclic group containing 1 to 4 nitrogen atom(s), for example, pyrrolidinyl, imidazolinyl, piperidino, piperazinyl, etc.;

unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl, dihydrotriazolopyridazinyl, etc.;

unsaturated 3-to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.;

saturated 3 to 8-membered heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, thiazolinyl, thiadiazolyl (e.g., 1,2,4-thiadiazolyl, 1,3,4-thiadiazolyl, 1,2,5-thiadiazolyl, etc.), etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group contaning a sulphur atom, for example, thienyl, etc.;

unsaturated condensed heterocyclic group containing 1 to 2 sulfur atom(s) and 1 to 3 nitrogen atom(s), for example, benzothiazolyl, benzothiadiazolyl, etc. and the like;

wherein said heterocyclic group may be substituted with 1 to 3 suitable substituent(s) such as lower alkyl (e.g., methyl, ethyl, propyl, isopropyl, butyl, isobutyl, pentyl, cyclopentyl, hexyl, cyclohexyl, etc.); lower alkylthio (e.g., methylthio, ethylthio, propylthio, etc.); lower alkenyl (e.g., vinyl, allyl, butenyl, etc.); lower allkenylthio (e.g., vinylthio, allylthio, butenylthio, etc.); hydroxy; aryl (e.g., phenyl, tolyl, etc.); halogen (e.g., chlorine, bromine, iodine or fluorine); amino; di(lower-)alkylamino(lower)alkyl (e.g., dimethylaminomethyl, dimethylaminoethyl, dimethylaminopropyl, diethylaminopropyl, diethylaminobutyl, etc.); carboxy(lower)alkyl (e.g., carboxymethyl, carboxyethyl, carboxypropyl, etc.); esterified carboxy(lower)alkyl wherein the esterified carboxy moiety is exemplified above; amino(lower)alkyl (e.g., aminomethyl, aminoethyl, aminopropyl, 1-aminomethylethyl, aminobutyl, aminohexyl, etc.), protected amino(lower)alkyl wherein the protected amino and lower alkyl moieties are each as exemplified above, preferably lower alkoxycarbonylamino(lower)alkyl (e.g., methoxycarbonylaminomethyl, ethoxycarbonylaminomethyl, t-butoxycarbonylaminomethyl, t-butoxycarbonylaminopropyl, etc.) or lower alkanoylamino(lower)alkyl (e.g., acetylaminomethyl, acetylaminoethyl, acetylaminopropyl, 1-acetylaminomethylethyl, etc.); carboxy; oxo; esterified carboxy as exemplified above, preferably lower alkoxycarbonyl; lower alkoxy(lower)alkyl (e.g., methoxymethyl, methoxyethyl, methoxypropyl, ethoxymethyl, ethoxyethyl, etc.); hydroxy(lower)alkyl(e.g., hydroxymethyl, hydroxyethyl, hydroxypropyl, hydroxybutyl, etc.); lower alkylthio(lower)alkyl (e.g., methylthiomethyl, methylthioethyl, methylthiopropyl, ethylthiomethyl, etc.); sulfo(lower)alkyl (e.g., sulfomethyl, sulfoethyl, sulfopropyl, sulfobutyl, etc.); acyl(lower)alkyl wherein the acyl and lower alkyl moieties are each as exemplified above, preferably lower alkanesulfonyl(lower)alkyl (e.g., mesylmethyl, mesylethyl, ethanesulfonylmethyl, etc.); acylamino(lower)alkyl wherein the acyl and lower alkyl moieties are each as exemplified above, preferably lower alkanesulfonylamino(lower)alkyl (e.g., mesylaminomethyl, mesylaminoethyl, mesylaminopropyl, ethanesulfonylaminomethyl, etc.); carboxy(lower)alkylthio (e.g., carboxymethylthio, carboxyethylthio, etc.); morpholino(lower)alkyl (e.g., morpholinomethyl, morpholinoethyl, morpholinopropyl, etc.); piperidino(lower)alkyl (e.g., piperidinomethyl, piperidinoethyl, piperidinopropyl, etc.); piperazinyl(lower)alkyl which may be substituted with lower alkyl (e.g., 4-methyl-1-piperazinylpropyl, etc.); or the like.

Suitable substituent(s) on pyridinium(lower)alkyl, pyridine and pyridinium may be carbamoyl, lower alkanoyl as stated above, hydroxy(lower)alkyl(e.g., hydroxymethyl, hydroxyethyl, hydroxypropyl, etc.), carboxy(lower)alkyl(e.g., carboxymethyl, carboxyethyl, etc.),. hydroxyiminomethyl, or the like.

Suitable substituent(s) on thiazolium(lower)alkyl, thiazole and thiazolium may include lower alkyl and hydroxy(lower)alkyl.

Suitable halogen can be referred to the ones as exemplified above.

Suitable lower alkylene may include straight or branched bivalent aliphatic hydrocarbon residue having 1 to 6 carbon atom(s), such as methylene, ethylene, methylethylene, propylene, trimethylene, 2-methyltrimethylene or the like, and preferably one having 1 to 4 carbon atom(s), more preferably one having 1 to 2 carbon atom(s) and the most preferably one having 1 carbon atom.

Suitable protected amino(lower)alkyl and amino(lower)alkyl being the substituent of a heterocyclicthio(lower)alkyl for $R^{4c}$ and $R^{4d}$ and protected amino(lower)alkyl and amino(lower)alkyl for $R^{2b}$ and $R^{2c}$ and protected carboxy(lower)alkyl and carboxy(lower)alkyl for $R^{2d}$ and $R^{2e}$ can be referred to the ones as exemplified above.

Suitable protective group of hydroxy may include aforesaid acyl, ar(lower)alkyl, and the like.

Suitable $R^{4a}$ may include aforesaid acyloxy, halogen, azido and the like.

Suitable $R^8$ may be ester moiety as exemplified for protected carboxy.

Suitable protective group of carboxy may be referred to the ones exemplified as aforementioned ester moiety in the esterified carboxy group. Preferable example of protective group of carboxy may be lower alkyl as mentioned above.

Suitable alkali metal may include sodium, potassium, lithium, etc.

Suitable reactive derivative of hydroxy for X may include an acid residue such as aforesaid halogen or the like.

Suitable amino having a protective group for $R^9$ may include phthalimido, succinimido, ethoxycarbonylamino and the like, and preferably phthalimido.

Suitable ar(lower)alkyl may be preferably phenyl(lower)alkyl such as benzyl, phenethyl, or the like.

Suitable $(C_3-C_6)$alkyl in the terms "amino$(C_3-C_6)$alkyl" and "protected amino$(C_3-C_6)$alkyl" may include alkyl having 3 to 6 carbon atoms, for example, propyl, isopropyl, butyl, isobutyl, pentyl, hexyl, or the like.

Suitable protected amino(lower)alkyl and amino(lower)alkyl for $R^{2f}$ and $R^{2g}$ and protected amino moiety in the term "protected amino($C_3$-$C_6$)alkyl" can be referred to the ones as mentioned above.

Preferred embodiments of the object compound (I) are as follows. Preferred embodiment of $R^1$ is amino, acylamino (more preferably lower alkanoylamino) or di(lower)alkylamino(lower)alkylideneamino;

$R^2$ is hydrogen; aryl(more preferably phenyl); lower alkenyl; lower alkynyl; cyano(lower)alkyl; ar(lower)alkyl [more preferably phenyl(lower)alkyl or triphenyl(lower)alkyl]; aryloxy(lower)alkyl [more preferably phenoxy(lower)alkyl]; halo(lower)alkyl [more preferably trihalo(lower)alkyl]; lower alkylthio(lower)alkyl; esterified carboxy(lower)alkyl [more preferably lower alkoxycarbonyl(lower)alkyl]; di(lower)alkylcarbamoyl(lower)alkyl; lower alkoxy(lower)alkoxy(lower)alkyl; lower alkanesulfonyl(lower)alkyl; acylamino(lower)alkyl[more preferably lower alkoxycarbonylamino(lower)alkyl]; amino(lower)alkyl; carboxy(lower)alkyl; cycloalkyl;cyclo(lower)alkenyl; aryl(more preferably phenyl) substituted with halogen, nitro and lower alkoxy, halo(lower)alkyl or lower alkoxycarbonyl; thiolanyl substituted with 2 oxo groups; ar(lower)alkyl substituted with carboxy or lower alkoxycarbonyl; cycloalkyl substituted with carboxy or lower alkoxycarbonyl; ar(lower)alkyl(preferably phenyl(lower)alkyl) substituted with amino(lower)alkyl or lower alkoxycarbonylamino(lower)alkyl; cycloalkyloxycarbonyl(lower)alkyl; ar(lower)alkoxycarbonyl(lower)alkyl;ar(lower)alkanoylamino(lower)alkyl substituted with amino or lower alkoxycarbonylamino; cyclo(lower)alkyl(lower)alkanoylamino(lower)alkyl; tetrahydrofuryl substituted with oxo group;

$R^3$ is hydrogen or lower alkyl;

$R^4$ is hydrogen; acyloxy(lower)alkyl [more preferably lower alkanoyloxy(lower)alkyl or carbamoyloxy(lower)alkyl, most preferably lower alkanoyloxymethyl or carbamoyloxymethyl]; acylthio(lower)alkyl [more preferably lower alkanoylthio(lower)alkyl, most preferably lower alkanoylthiomethyl]; tetrazolylthio(lower)alkyl (more preferably tetrazolylthiomethyl) which may be substituted with lower alkyl,lower alkenyl, lower alkoxy(lower)alkyl, lower alkylthio(lower)alkyl, hydroxy(lower)alkyl, amino(lower)alkyl, lower alkoxycarbonylamino(lower)alkyl, lower alkanoylamino(lower)alkyl, di(lower)alkylamino(lower)alkyl, sulfo(lower)alkyl, carboxy(lower)alkyl, aryl(more preferably phenyl), lower alkoxycarbonyl(lower)alkyl, morpholino(lower)alkyl, piperidino(lower)alkyl or piperazinyl(lower)alkyl substituted with lower alkyl; thiazolium(lower)alkyl substituted with lower alkyl and hydroxy(lower)alkyl; thiadiazolylthio(lower)alkyl (more preferably thiadiazolylthiomethyl) which may be substituted with lower alkyl, lower alkoxy(lower)alkyl, lower alkylthio(lower)alkyl, lower alkenylthio, carboxy, lower alkoxycarbonyl, hydroxy(lower)alkyl, amino(lower)alkyl, lower alkoxycarbonylamino(lower)alkyl, lower alkanesulfonyl(lower)alkyl, lower alkanesulfonylamino(lower)alkyl or carboxy(lower)alkylthio; pyridinium(lower)alkyl which may be substituted with carbamoyl, lower alkanoyl, hydroxy(lower)alkyl, carboxy(lower)alkyl or hydroxyiminomethyl; lower alkyl; halogen; hydroxy; dihydrotriazolopyridazinylthio(lower)alkyl(more preferably dihydrotriazolopyridazinylthiomethyl) substituted with oxo and carboxy(lower)alkyl; dihydrotriazinylthio(lower)alkyl(more preferably dihydrotriazinylthiomethyl) substituted with oxo, hydroxy and lower alkyl; or tetrazolopyridazinylthio(lower)alkyl (more preferably tetrazolopyridazinylthiomethyl); and $R^5$ is carboxy, phenyl(lower)alkoxycarbonyl substituted with nitro, lower alkanoyloxy(lower)alkoxycarbonyl, lower alkoxycarbonyloxy(lower)alkoxycarbonyl which may be substituted with azido, phthalidyloxycarbonyl or aroyl(preferably benzoyl)oxy(lower)alkoxycarbonyl; wherein $R^5$ is $COO^-$ when $R^4$ is pyridinium(lower)alkyl which may be substituted with carbamoyl, lower alkanoyl, hydroxy(lower)alkyl, carboxy(lower)alkyl or hydroxyiminomethyl, or thiazolium(lower)alkyl substituted with lower alkyl and hydroxy(lower)alkyl.

The processes for preparing the object compounds are explained in details in the following.

PROCESS 1

The object compound (I) can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include conventional reactive derivative used in amidation, for example, Schiff's base type imino or its tautomeric enamine type isomer formed by the reaction of the compound (II) with a carbonyl compound; a silyl derivative formed by the reaction of the compound (II) with a silyl compound such as bis (trimethylsilyl)acetamide, trimethylsilylacetamide or the like; a derivative formed by reaction of the compound (II) with phosphorus trichloride or phosgene, and the like.

Suitable salt of the compound (II) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, acetic acid or trichloroacetic acid, etc.) or aromatic carboxylic acid (e.g., benzoic acid, etc.); a symmetrical acid anhydride; an activated amide with imidazole, dimethylpyrazole, triazole or tetrazole; or an activated ester (e.g., cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the compound (III) to be used.

The salts of the compound (III) may be salts with an inorganic base such as an alkali metal salts (e.g., sodium or potassium salt), or an alkaline earth metal salt (e.g., calcium or magnesium salt), a salt with an organic base such as trimethylamine, triethylamine, pyridine, a salt with an acid (e.g., hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

When the compound (III) is used in free acid form of its salt form in the reaction, the reaction is preferably carried out in the presence of a conventional condensing agent such as N,N-dicyclohexylcarbodiimide; N-cyclohexyl-N'-morpholinoethylcarbodiimide; N-cyclohexyl-N'-(4-diethylaminocyclohexyl)carbodiimide; N,N-diethylcarbodiimide; N,N-diisopropylcarbodiimide; N-ethyl-N'-(3-dimethylaminopropyl)carbodiimide; N,N-carbonylbis(2-methylimidazole); pentamethylene-ketene-N-cyclohexylimine; diphenylketene-N-cyclohexylimine; ethoxyacetylene; ethyl polyphosphate; isopropyl polyphosphate; diethyl phosphorochloridite; phosphorus oxychloride; phosphorus trichloride; phosphorus pentachloride; thionyl chloride; oxalyl chloride; triphenylphosphine; N-ethyl-7-hydroxybenzisoxazolium fluoroborate; N-ethyl-5-phenylisoxazolium-3'-sulfonate; 1-(p-chlorobenzenesulfonyloxy)-6-chloro-1H-benzotriazole; so-called Vilsmeier reagent, for example (chloromethylene) dimethylammonium chloride produced by the reaction of dimethylformamide with thionyl chloride or phosgene, a compound produced by the reaction of dimethylformamide with phosphorus oxychloride, etc.; or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorpholine, N,N-di(-lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present invention, a syn-isomer of the object compound (I) can be obtained preferably by conducting the reaction of the compound (II) with a syn-isomer of the starting compound (III).

In the present reaction, amino group for $R^1$ in the compound (III) may be converted into a protected amino group to give the compound (I) wherein $R^1$ is a protected amino, and acyl for $R^2$ may be converted into hydrogen in the course of the reaction according to reaction conditions, and these cases are included within the scope of the present invention.

PROCESS 2

The object compound (Ib) or a salt thereof can be prepared by subjecting the compound (Ia) or a salt thereof to elimination reaction of the protective group of carboxy.

Suitable salt of the compound (Ia) can be referred to the acid addition salt exemplified for the compound (II).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]none-5-ene, 1,4-diazabicyclo[2,2,2]octane, 1,8-diazabicyclo[5,4,0]undecene-7, or the like. Suitable acid may include an organic acid (e.g., formic acid, acetic acid, propionic acid, trifluoroacetic acid, etc.) and an inorganic acid (e.g., hydrochloric acid, hydrobromic acid, sulfuric acid, etc.).

The reaction is usually carried out in a solvent such as water, an alcohol (e.g., methanol, ethanol, etc.), a mixture thereof or any other solvent which does not adversely influence to the reaction. A liquid base or acid can be also used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g., zinc, zinc amalgam, etc.) or a salt of chrome compound (e.g., chromous chloride, chromous acetate, etc.) and an organic or inorganic acid (e.g., acetic acid, propionic acid, hydrochloric acid, etc.); and conventional catalytic reduction in the presence of a conventional metallic catalyst (e.g., palladium-carbon, etc.).

PROCESS 3

The object compound (Id) or a salt thereof can be prepared by reacting the compound (Ic) or a salt thereof with the compound (IV) or its reactive derivative.

Suitable salt of the compound (Ic) can be referred to the ones exemplified for the compound (II).

Suitable reactive derivative of the compound (IV) may include a metal salt such as an alkali metal salt (e.g., sodium salt, potassium salt, etc.) or the like.

The present reaction may be carried out in a solvent such as water, phosphate buffer, acetone, chloroform, nitrobenzene, methylene chloride, ethylene chloride, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (Ic) or the compound (IV) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under slightly heating.

The present invention includes, within its scope, the case that protected carboxy group is converted to free carboxy group during the course of the reaction.

PROCESS 4

The object compound (If) or a salt thereof can be prepared by subjecting the compound (Ie) or a salt thereof to elimination reaction of the protective group of amino.

Suitable salt of the compound (Ie) may include a metal salt, ammonium salt, an organic amine salt and the like as aforementioned.

The present elimination reaction is carried out in accordance with a conventional method such as hydrolysis; reduction; a method by reacting the compound (Ie) wherein the pretective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g., t-pentyloxycarbonyl, t-butoxycarbonyl, etc.), alkanoyl (e.g., formyl, etc.), cycloalkoxycarbonyl, substituted or unsubstituted aralkoxycarbonyl (e.g., benzyloxycarbonyl, substituted benzyloxycarbonyl, etc.), substituted phenylthio, substituted aralkylidene, substituted alkylidene, substituted cycloalkylidene, ar(lower)alkyl (e.g., benzyl, trityl, etc.) or the like.

Suitable acid may include an organic or an inorganic acid, for example, formic acid, trifluoroacetic acid, benzenesulfuric acid, p-toluenesulfonic acid, hydrochloric acid and the like, and preferable acid is, for example, formic-acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include a conventional organic solvent, water or a mixture thereof. When trifluoroacetic acid is used, the elimination reaction may preferably be carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g., dichloroacetyl, trifluoroacetyl, etc.) etc. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1,4-diazabicyclo[2,2,-2]octane, 1,5-diazabicyclo[5,4,0]undecene-5-or the like. The hydrolysis using a base is often carried out in water, a conventional organic solvent or a mixture thereof.

Among the protective group, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g., trichloroethoxycarbonyl etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g., sodium borohydride, etc.) and the like.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present reaction includes, within its scope, the cases that the protected carboxy group for $R^2$ and/or $R^3$ is transformed into the free carboxy group in the course of the elimination reaction as mentioned above or in the post-treatment of the reaction mixture or reaction product.

PROCESS 5

The object compound (Ij) or a salt thereof can be prepared by subjecting the compound (Ii) or a salt thereof to elimination reaction of the protective group of amino.

Suitable salt of the compound (Ii) can be referred to the ones as exemplified for the compound (II).

The present elimination reaction can be carried out according to substantially the same manner as that of Process 4.

The present reaction includes, within its scope, the case that protected amino(lower)alkyl being the substituent on heterocyclicthio(lower)alkyl for $R^4$ is transformed into amino(lower)alkyl.

PROCESS 6

The object compound (II) or a salt thereof can be prepared by subjecting the compound (Ik) or a salt thereof to elimination reaction of the protective group of carboxy.

Suitable salt of the compound (Ik) can be referred to the ones as exemplified for the compound (II).

The present elimination reaction can be carried out according to substantially the same manner as that of

PROCESS 2

The present reaction includes, within its scope, the case that protected amino(lower)alkyl being the substituent on heterocyclicthio(lower)alkyl for $R^4$ is transformed into amino(lower)alkyl.

PROCESS 7

The object compound (In) can be prepared by subjecting the compound (Im) or a salt thereof to esterification.

Suitable salt of the compound (Im) can be referred to the ones as exemplified for the compound (II).

The present reaction may be carried out by reacting the compound (Im) or a salt thereof with esterifying agent.

Suitable esterifying agent may be a compound of the formula:

$$X-R^8 \qquad (XVII)$$

wherein $R^8$ and X are each as defined above.

The present reaction is usually carried out in a solvent such as dimethylformamide, pyridine, hexamethylphosphoric triamide or any other solvent which does not adversely affect the reaction.

In case that the compound (Im) is used in a form of free acid, the reaction is preferably carried out in the presence of a base as mentioned above.

The reaction temperature is not critical and the reaction is preferably carried out under cooling, at ambient temperature or under warming.

PROCESS 8

The object compound (Ih) or a salt thereof can be prepared by subjecting the compound (Ig) or a salt thereof to elimination reaction of the protective group of hydroxy.

Suitable salt of the compound (Ig) can be referred to the ones as exemplified for the compound (II).

The present elimination reaction can be carried out according to substantially the same manner as that of Process 4.

PROCESS 9

The object compound ($I_p$) or a salt thereof can be prepared by subjecting the compound (Io) or a salt thereof to dehydration reaction.

The present invention is preferably carried out by reacting the compound (Ic) or a salt thereof with dehydrating agent.

Suitable dehydrating agent may include an acid such as alkanoic acid which may be substituted with halogen (e.g., pivalic acid, trifluoroacetic acid, etc.), arenesulfonic acid(e.g., toluenesulfonic acid, etc.) or the like; or its halide(e.g., trifluoroacetyl chloride, tosylchloride, pivaloylchloride, phosphorus oxychloride, etc.); or its symmetrical acid anhydride; unsymmetrical mixed acid anhydride; a reactive derivative of diketene or the like; florisil; Girard reagent T; ethyl(carboxysulfamoyl); a ylide compound (e.g. an intramolecular salt of triethylammonium hydroxide, etc.); and the like.

The present reaction may preferably be carried out in the presence of a base.

The preferable base includes an inorganic base such as metal hydroxide (e.g. sodium hydroxide, potassium hydroxide, etc.), metal carbonate (e.g. sodium carbonate, potassium carbonate, magnesium carbonate, etc.), metal bicarbonate (e.g. sodium bicarbonate, potassium bicarbonate, etc.), organic base such as tertiary amine (e.g. trimethyl amine, triethyl amine, pyridine, etc.), alkali metal alkoxide (e.g. sodium methoxide; sodium ethoxide, etc.)

The reaction is usually carried out in a conventional solvent such as an alcohol, tetrahydrofuran, dimethylformamide, chloroform, methylene, chloride or any other solvent which does not adversely influence the reaction, under cooling or at an ambient or somewhat elevated temperature.

PROCESS 10

The object compound (Ir) or a salt thereof can be prepared by subjecting the compound (Iq) or a salt thereof to introduction reaction of the protective group of amino.

Suitable salt of the compound (Iq) can be referred to the ones as exemplified for the compound (II).

The present reaction can be carried out according to substantially the same manner as that of Process 1.

The preparation for preparing the starting compound (III) are explained below in detail.

PREPARATION (1)

The compound (VII) can be prepared by reacting the compound (V) or a salt thereof with halogenating agent and the compound (VI).

Suitable halogenating agent to be used in the present reaction may include bromine, chlorine and the like.

The present reaction is preferably carried out in the presence of a base such as an inorganic base or an organic base, for example, alkali metal carbonate, alkali metal alkoxide, trialkylamine or the like. The present reaction is usually carried out in a solvent such as an alcohol (e.g., methanol, ethanol, etc.) or any other solvent which does not adversely affect the reaction. The reaction temperature is not critical and the reaction is usually carried out under cooling or at ambient temperature. In this reaction, $R^6$ of the compound (V) may be converted into other protective group of carboxy according to reaction conditions and kinds of the protective group and it is included within the scope of the present invention.

PREPARATION (2)

The compound (VIII) can be prepared by subjecting the compound (VII) to introduction reaction of the protective group of amino.

The present process can be carried out in a conventional manner and when the protective group of amino to be introduced into the amino group is acyl, the reaction can be carried out in substantially the same manner as that of Process 1. Accordingly, the detailed explanation therefor is to be referred to said Process 1.

PREPARATION (3)

The compound (X) can be prepared by reacting the compound (VIII) with the compound (IX). This process is usually carried out in the presence of base such as an alkali metal hydride (e.g., sodium hydride, potassium hydride, etc.), an alkaline earth metal hydride (e.g., calcium hydride, etc.) and the like, and usually carried out in a solvent such as dimethylformamide or any other solvent which does not adversely affect the reaction. The reaction temperature is not critical and the reaction is usually carried out under cooling, at ambient temperature or under warming.

PREPARATION (4)

The compound (XI) can be prepared by reacting the compound (X) with an acid and/or acid anhydride such as acetic acid and/or acetic anhydride. The reaction of this process can preferably be carried out in the presence of alkali metal perhaloate (e.g., sodium perchlorate, sodium periodate, potassium perchlorate, etc.), alkaline earth metal perchlorate (e.g., magnesium perchlorate, calcium perchlorate, etc.) and the like, and an acid such as an organic acid (e.g., formic acid, etc.) or an inorganic acid (e.g., hydrochloric acid).

The reaction temperature is not critical and the reaction is usually carried out under warming.

PREPARATIONS (5) AND (7)

The preparation (5) and (7) can be carried out in a conventional manner as shown in Process 2 or 4.

In the preparation (5), according to reaction conditions, there may be obtained the product having $R^{1a}$ (XIa) or the product having amino instead of $R^{1a}$ (XIb) and they are subsequently reacted with the compound (XII) or a salt thereof to give the compound (IIIa) or (IIIb), respectively, as shown in Preparation (6).

PREPARATION (6)

Suitable salt of the compound (XII) is a conventional acid salt such as an inorganic acid salt (e.g., hydrochloride, etc.) and an organic acid salt (e.g., p-toluenesulfonic acid salt, etc.). When salt of said compound (XII) is used in this process, the reaction is usually carried out in the presence of a base such as an alkali metal hydroxide (e.g., sodium hydroxide, potassium hydroxide, etc.). The reaction is usually carried out in a solvent such as water, an alcohol (e.g., methanol, ethanol, etc.) or any other solvent which does not adversely affect the reaction. The reaction temperature is not critical and the reaction is usually carried out at ambient temperature.

PREPARATION (8)

The compound (IIId) can be prepared by subjecting the compound (IIIc) to introduction reaction of the protective group of hydroxy group.

The present process can be carried out in a conventional manner and when the protective group to be introduced into the hydroxy group is acyl, the reaction can be carried out in substantially the same manner as that of Process 1.

In case that the protective group to be introduced is ar(lower)alkyl, the present reaction is carried out by reacting the compound (IIIc) with the compound of the formula:

$$R^{2f}-Y \quad \text{(XVIII)}$$

wherein $R^{2f}$ is ar(lower)alkyl and Y is an acid residue.

Suitable acid residue may include a residue of an acid such as an inorganic acid, for example, hydrohalogenic acid (e.g., hydrochloric acid, hydrobromic acid, etc.), sulfuric acid or the like, or an organic acid, for example, lower alkanesulfonic acid (e.g., methanesulfonic acid, ethanesulfonic acid, etc.), arenesulfonic acid (e.g., benzenesulfonic acid, p-toluenesulfonic acid, etc.) or the like. The present reaction is preferably carried out in the presence of a base as mentioned above and usually carried out in a solvent such as dimethylformamide or the like. The reaction temperature is not critical and the reaction is usually carried out under cooling, at ambient temperature or under warming.

PREPARATION 9

The compound (XV) can be prepared by reacting a compound (XIII) with a compound (XIV).

The reaction is preferably carried out in the presence of a base as exemplified in Process 1 in case that X is an acid residue and in the presence of a condensing agent, for example, one formed by triphenylphosphine and diethyl azoformate in case that X is hydroxy, respectively.

The reaction is usually carried out in a solvent such as acetonitrile, dimethylformamide, tetrahydrofuran or any other solvents which do not adversely influence the reaction. The reaction temperature is not critical and the reaction is usually carried out from cooling to heating around a boiling point of the solvent used.

PREPARATION 10

The compound (XVI) or a salt thereof can be prepared by subjecting a compound (XV) to elimination reaction of the amino protective group.

This elimination reaction of the amino protective group of the compound (XV) can be carried out in a similar manner to that of aforementioned Process 4

Suitable solvents include water, ethanol, chloroform, diethyl ether and the like. The reaction temperature is not critical and the reaction is usually carried out under warming or heating. The present reaction includes, within its scope, the case that protected amino group in $R^2$ is converted into free amino group.

PREPARATION 11

The compound (XX) or a salt thereof can be prepared by subjecting the compound (XIX) or a salt thereof to introduction reaction of the protective group of amino.

The present reaction can be carried out according to substantially the same manner as that of Process 1.

In case that protective group to be introduced is lower alkoxycarbonyl group, this reaction is preferably carried out by reacting the compound (XIX) with a compound of the formula;

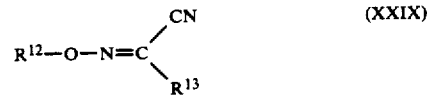
$$\text{(XXIX)}$$

wherein $R^{12}$ is lower alkoxycarbonyl and $R^{13}$ is aryl.

PREPARATION 12

The compound (XXII) or a salt thereof can be prepared by subjecting the compound (XXI) or a salt thereof to introduction reaction of the substituent on hydroxy group.

In case that substituent to be introduced is aryl which may be substituted with suitable substituent(s), the present reaction is conducted by reacting the compound (XXI) or a salt thereof with a compound of the formula:

$$R^{2i}-X^{2\oplus}-R^{2i} Y^{\ominus} \quad \text{(XXX)}$$

wherein $R^{2i}$ is aryl which may be substituted with suitable subsfituent(s), $X^2$ is halogen and Y is an acid residue.

Suitable acid residue may include halogen, toluenesulfonyloxy, residue of sulfuric acid and the like.

The present reaction is usually carried out in a solvent such as alcohol(e.g., methanol, ethanol, etc.), water, mixed solvent thereof, or any other solvent which does not adversely affect the reaction, and preferably carried out in the presence of a base.

The reaction temperature is not critical and the reaction is usually carried out under cooling, at ambient temperature or under warming.

In case that substituent to be introduced is cycloalkyl which may be substituted with suitable substituent(s), the reaction is carried out by reacting the compound (XXI) or a salt thereof with a compound of the formula:

R²ʲ—Y          (XXXI)

wherein R²ʲ is cycloalkyl which may be substituted with suitable substituent(s) and Y is as defined above.

This reaction is carried out according to substantially the same manner as that of Preparation 8.

PREPARATION 13

The compound (XXIV) or a salt thereof can be prepared by subjecting the compound (XXIII) or a salt thereof to cyclization reaction.

The present reaction is usually carried out in a solvent such as alcohol (e.g., methanol, ethanol, etc.) or the like.

This reaction is carried out in the presence of dehydrating agent such as magnesium sulfate, acid anhydride (e.g., acetic anhydride, etc.) or the like.

The reaction temperature is not critical and it is usually carried out under warming or heating or at ambient temperature.

PREPARATION 14

The compound (XXVI) or a salt thereof can be prepared by reacting the compound (XXV) with HN₃ or a salt thereof.

Suitable salt of HN₃ may be alkali metal salt.

The reaction is usually carried out in a solvent such as water, dioxane, mixed solvent thereof or any other one which does not adversely affect the reaction.

The reaction temperature is not critical and the reaction is usually carried out under heating.

PREPARATION 15

The compound (XXVII) or a salt thereof can be prepared by subjecting the compound (XXVI) or a salt thereof to elimination reaction of the protective group of amino.

The present reaction is carried out according to substantially the same manner as that of Process 4.

PREPARATION 16

The compound (XXVIII) or a salt thereof can be prepared by subjecting the compound (XXVII) or a salt thereof to introduction reaction of the protective group of amino.

The present reaction is carried out according to substantially the same manner as that of Preparation 11.

In the aforementioned reactions and/or in the post treatment of the reactions of the present invention, the aforementioned tautomeric isomers may occasionally be transformed into the other tautomeric isomers and such case is also included in the scope of the present invention.

In case that the object compound (I) is obtained in a form of the free acid at 4 position and/or in case that the object compound (I) has free amino group, it may be optionally transformed into its pharmaceutically acceptable salt as aforementioned by a conventional method.

The object compound (I) and pharmaceutically acceptable salt thereof of the present invention are all novel compounds which exhibit high antibacterial activity, inhibiting the growth of a wide variety of pathogenic microorganisms including Gram-positive and Gram-negative bacteria and are useful as antibacterial agents.

Now, in order to show the utility of the object compound (I), with regard to some representative compounds of this invention, the test data on the in vitro anti-bacterial activity are shown in the following.

Test Compounds (1) 7-[2-Cyclopentyloxyimino-2-(5-amino-1,2,4-thiadiazol-3-yl)acetamido]-3-cephem-4-carboxylic acid (syn isomer)

(2) 7-[2-Cyclopentyloxyimino-2-(5-amino-1,2,4-thiadiazol-3-yl)acetamido]-3-(1,3,4-thiadiazol-2-yl)thiomethyl-3-cephem-4-carboxylic acid (syn isomer)

(3) 7-[2-(2-Cyclopenten-1-yl)oxyimino-2-(5-amino-1,2,4-thiadiazol-3-yl)acetamido]-3-cephem-4-carboxylic acid (syn isomer)

(4) 7-[2-(2-Cyclopenten-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer)

(5) 7-[2-(2-Cyclohexen-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer)

(6) 7-[2-(4-Chlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer)

(7) 7-[2-Allyloxyimino-2-(5-amino-1,2,4-thiadiazol-3-yl)acetamido]-3-(1-allyl-1H-tetrazol-5-yl)thiomethyl-3-cephem-4-carboxylic acid (syn isomer)

(8) 7-[2-Carboxymethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer)

(9) 7-[2-(1-Carboxyethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer)

(10) 7-[2-Cyclopentyloxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer)

(11) N-[7-{2-Cyclopentyloxyimino-2-(5-amino-1,2,4-thiadiazol-3-yl)acetamido}-3-cephem-3-ylmethyl]-4'-carbamoylpyridinium-4-carboxylate (syn isomer)

(12) N-[7-{2-Cyclopentyloxyimino-2-(5-amino-1,2,4-thiadiazol-3-yl)acetamido}-3-cephem-3-ylmethyl]-pyridinium-4-carboxylate (syn isomer)

(13) N-[7-{2-(2-Cyclopenten-1-yloxyimino)-2-(5-amino-1,2,4-thiadiazol-3-yl)acetamido}-3-cephem-3-ylmethyl]pyridinium-4-carboxylate (syn isomer)

(14) N-[7-{2-Cyclopentyloxyimino-2-(5-amino-1,2,4-thiadiazol-3-yl)acetamido}-3-cephem-3-ylmethyl]-3'-hydroxymethylpyridinium-4-carboxylate (syn isomer)

(15) N-[7-{2-(2-Cyclopenten-1-yloxyimino)-2-(5-amino-1,2,4-thiadiazol-3-yl)acetamido}-3-cephem-3-ylmethyl]-3'-hydroxymethylpyridinium-4-carboxylate (syn isomer)

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of test compounds, and minimal inhibitory concentration (MIC) was expressed in terms of μg/ml. after incubation at 37° C. for 20 hours.

Test Results

| Test Bacteria | MIC (μg/ml) Test Compound | | | | | | | | | | | | | | |
|---|---|---|---|---|---|---|---|---|---|---|---|---|---|---|---|
| | (1) | (2) | (3) | (4) | (5) | (6) | (7) | (8) | (9) | (10) | (11) | (12) | (13) | (14) | (15) |
| E. coli NIHJ JC - 2 | 0.39 | 0.78 | 0.39 | 0.78 | 3.13 | 3.13 | 0.20 | 0.10 | 0.20 | 0.78 | 1.56 | 0.78 | 1.56 | 0.78 | 0.78 |
| Kl. pneumoniae 12 | 0.78 | 3.13 | 0.78 | 1.56 | 3.13 | 3.13 | 1.56 | 0.10 | 0.20 | 1.56 | 3.13 | 1.56 | 1.56 | 6.25 | 1.56 |
| Pr. vulgaris 2 | 0.39 | 3.13 | 0.39 | 1.56 | 3.13 | 3.13 | 0.78 | 0.10 | 0.20 | 1.56 | 3.13 | 3.13 | 3.13 | 6.25 | 3.13 |
| Ps. aeruginosa NCTC-10490 | 3.13 | 1.56 | 1.56 | 3.13 | 3.13 | 3.13 | 3.13 | 1.56 | 3.13 | 12.5 | 6.25 | 6.25 | 6.25 | 3.13 | 3.13 |

For therapeutic administration, the object compound (I) of the present invention is used in the form of conventional pharmaceutical preparation which contains said compounds, as an active ingredient, in admixture with a pharmaceutically acceptable carriers such as an organic or inorganic solid or liquid excipient which is suitable for oral, parenteral or external administration. The pharmaceutical preparations may be in solid from such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc., an average single dose of about 50 mg., 100 mg., 250 mg, and 500 mg. of the object compound (I) of the present invention has proved to be effective in treating diseases infected by pathogenic bacteria.

In general, daily dose between 5 mg. and about 3,000 mg. or even more may be administered to a patient.

The following Preparations and Examples are given for the purpose of illustrating the present invention:

PREPARATION 1

(1) A mixture of N-hydroxyphthalimide (8.15 g), triethylamine (5.05 g), N,N-dimethylformamide (60 ml) and 1-bromo-2-cyclohexene (8.05 g) was stirred for 3.5 hours at room temperature. The reaction mixture was poured into water (300 ml). The precipitated crystals were collected by filtration, washed successively with water and n-hexane and then dried to give N-(2-cyclohexen-1-yloxy)phthalimide (9.8 g). mp 87° C.

I.R. (Nujol): 1770, 1720, 1610 cm$^{-1}$

N.M.R. (d$_6$-DMSO, δ): 1.50–2.17 (6H, m), 4.60–4.77 (1H, m), 5.73–6.27 (2H, m), 7.90 (4H, s)

(2) A mixture of N-hydroxyphthalimide (52.16 g), bromocycloheptane (62.41 g), dimethylsulfoxide (385 ml) and potassium carbonate (44.16 g) were stirred for 74 hours at 70° C. The reaction mixture was cooled under ice-cooling and added to ice-water (1.5 l). The precipitates were collected by filtration, washed with ice-water (×2) and then dried to give N-(cycloheptyloxy)phthalimide (63 g), mp 110° to 112° C.

N.M.R. (d$_6$-DMSO, δ): 1.57 (8H, m), 1.90 (4H, m), 4.20 (1H, m), 7.93 (4H, s).

(3) A mixture of N-hydroxyphthalimide (58.2 g), 1-chloro-2-cyclopentene (36.9 g), triethylamine (53.9 g) in acetonitrile (370 ml) was treated in similar manners to those of Preparations 1-(1) and 1-(2) to give N-(2-cyclopenten-1-yloxy)phthalimide (56.5 g)

I.R. (Nujol): 1780, 1730, 1610 cm$^{-1}$

N.M.R. (d$_6$-DMSO, δ): 7.92 (4H, s), 6.28 (1H, m), 6.00 (1H, m), 5.42 (1H, m), 2.9–1.98 (4H, m)

PREPARATION 2

A mixture of N-(cycloheptyloxy)phthalimide (2.59 g), hydrazine hydrate (0.45 g) in ethanol (12 ml) was refluxed for 5 minutes.

The reaction mixture was cooled and filtered to give the filtrate containing cycloheptyloxyamine.

PREPARATION 3

(1) A mixture of N-(2-cyclopenten-1-yloxy)phthalimide (22.9 g) and hydrazine hydrate (4.75 g) in ethanol (115 ml) was refluxed for 5 minutes. The reaction mixture was filtered. The filtrate containing (2-cyclopenten-1-yl)oxyamine was added to a solution of sodium 2-(5-formamido-1,2,4-thiadiazol-3-yl)glyoxylate (22.4 g) in water. The mixture was adjusted to pH 2 with 10% hydrochloric acid, stirred for 2 hours and then concentrated. The concentrate was adjusted to pH 1 with 10% hydrochloric acid. The precipitates were collected by filtration and dried to give 2-(2-cyclopenten-1-yl)oxyimino-2-(5-formamido-1,2,4-thiadiazol-3-yl)acetic acid (syn isomer) (20.0 g), mp 150° C. (dec.).

I.R. (Nujol): 3400, 3100, 1720, 1690, 1540 cm$^{-1}$

N.M.R. (d$_6$-DMSO, δ): 1.80–2.50 (4H, m), 5.30–5.50 (1H, m), 5.83–6.30 (2H, m), 8.90 (1H, s)

(2) A mixture of N-(2-cyclohexen-1-yloxy)phthalimide (7.29 g), hydrazine hydrate (1.5 g) in ethanol (40 ml) was refluxed for 5 minutes. The reaction mixture was cooled and filtered to give the filtrate containing (2-cyclohexen-1-yl)oxyamine (filtrate A). On the other hand, a mixture of S-methyl 2-(5-formamido-1,2,4-thiadiazol-3-yl)thioglyoxylate (6.93 g) in 1 N-aqueous solution of sodium hydroxide (90 ml) was stirred for 30 minutes at room temperature. The reaction mixture containing sodium 2-(5-formamido-1,2,4-thiadiazol-3-yl)glyoxylate was adjusted to pH 7 with 10% hydrochloric acid and thereto was added the filtrate A and then the pH was adjusted to 3 with 10% hydrochloric acid. The mixture was stirred for 3 hours at room temperature. The reaction mixture was concentrated and to the concentrate was added ethyl acetate. The mixture was adjusted to pH 1 with 10% hydrochloric acid. The precipitates were collected by filtration to give 2-(2-cyclohexen-1-yl)oxyimino-2-(5-formamido-1,2,4-thiadiazol-3-yl)acetic acid (syn isomer) (2.5 g). On the other hand, the ethyl acetate layer was separated from the filtrate and evaporated. The residue was triturated with diethyl ether to give the same object compound (1.5 g). Total yield: 4.0 g, mp 190° to 192° C. (dec.).

I.R. (Nujol): 3550, 3400, 3200, 2500, 1690, 1590, 1540 cm$^{-1}$

N.M.R. (d$_6$-DMSO, δ): 1.5–2.3 (6H, m), 4.73–5.0 (1H, m), 5.76–6.23 (2H, m), 8.97 (1H, s), 13.60 (1H, broad s)

(3) To a solution of sodium hydroxide (11.2 g) in water (140 ml) was added S-methyl 2-(5-formamido-1,2,4-thiadiazol-3-yl)thioglyoxylate (27 g) at 10° C. and the mixture was stirred for 30 minutes at 20° C. The reaction mixture containing sodium 2-(5-formamido-1,2,4-thiadiazol-3-yl)glyoxylate was cooled, adjusted to pH 7 with 10% hydrochloric acid and thereto was added a solution of cyclopentyloxyamine (15.3 g) in ethanol (150 ml). The mixture was adjusted to pH 3 with 10% hydrochloric acid, and stirred for 1.5 hours. The reaction mixture was adjusted to pH 7 with an aqueous solution of sodium bicarbonate and then evaporated to remove ethanol. The residue was washed with ethyl acetate. To the aqueous layer was added ethyl acetate and the mixture was adjusted to pH 1 with 10% hydrochloric acid. The precipitates were collected by filtration to give 2-cyclopentyloxyimino-2-(5-formamido-1,2,4-thiadiazol-3-yl)acetic acid (syn isomer) (3.99 g). The filtrate was extracted with ethyl acetate and the extract was dried over magnesium sulfate and then concentrated. The precipitates were collected by filtration and washed with diethyl ether to give the same object compound (8.1 g). Total yield: 12.09 g, mp 180° to 185° C. (dec.).

I.R. (Nujol): 3130, 3040, 2680, 2610, 2520, 1720, 1690, 1660, 1600, 1550 cm$^{-1}$ N.M.R. (d$_6$-DMSO, δ): 1.33–2.10 (8H, m), 4.67–5.0 (1H, m), 8.88 (1H, s), 13.50 (1H, s)

(4) The following compound was obtained according to similar manners to those of Preparations 3(1) to 3(3).

2-Cycloheptyloxyimino-2-(5-formamido-1,2,4-thiadiazol-3-yl)acetic acid (syn isomer).

N.M.R. (d$_6$-DMSO, δ): 1.50 (8H, m), 1.80 (4H, m), 4.37 (1H, m), 8.81 (1H, s), 9.88 (1H, s)

PREPARATION 4

A mixture of 2-(2-cyclopenten-1-yl)oxyimino-2-(5-formamido-1,2,4-thiadiazol-3-yl)acetic acid (syn isomer) (20.0 g) and 1 N aqueous solution of sodium hydroxide (200 ml) was stirred for an hour at 50° to 55° C. The reaction mixture was cooled, adjusted to pH 7 with 10% hydrochloric acid and thereto was added ethyl acetate. The mixture was adjusted to pH 1 with 10% hydrochloric acid and extracted with ethyl acetate. The extract was washed with a saturated aqueous solution of sodium chloride, dried over magnesium sulfate and evaporated. The residue was pulverized with diisopropyl ether to give 2-(2-cyclopenten-1-yl)oxyimino-2-(5-amino-1,2,4-thiadiazol-3-yl)acetic acid (syn isomer), mp 150° C. (dec.).

I.R. (Nujol): 3300, 3150, 1710, 1620, 1520 cm$^{-1}$

N.M.R. (d$_6$-DMSO, δ): 1.80–2.50 (4H, m), 5.30–5.50 (1H, m), 5.83–6.30 (2H, m), 8.20 (2H, s)

PREPARATION 5

The following compounds were obtained according to a similar manner to that of Preparation 4.

(1) 2-(2-Cyclohexen-1-yl)oxyimino-2-(5-amino-1,2,4-thiadiazol-3-yl)acetic acid (syn isomer), mp 173° C.

I.R. (Nujol): 3400, 3300, 3200, 1720, 1620, 1600, 1520 cm$^{-1}$

N.M.R. (d$_6$-DMSO, δ): 1.50–2.17 (6H, m), 4.53–4.83 (1H, m), 5.57–6.13 (2H, m), 8.18 (2H, s)

(2) 2-Cyclopentyloxyimino-2-(5-amino-1,2,4-thiadiazol-3-yl)acetic acid (syn isomer), mp 160° to 165° C. (dec.).

I.R. (Nujol): 3470, 3290, 3200, 2400, 1715, 1615, 1600, 1520 cm$^{-1}$

N.M.R. (d$_6$-DMSO, δ): 1.17–2.10 (8H, m), 4.60–4.97 (1H, m), 8.22 (2H, s)

(3) 2-Cycloheptyloxyimino-2-(5-amino-1,2,4-thiadiazol-3-yl)acetic acid (syn isomer), mp 116° to 119° C. (dec.).

I.R. (Nujol): 3250, 3200, 1650, 1600, 1520, 1400, 1260, 1150, 1000, 820, 720 cm$^{-1}$

PREPARATION 6

(1) A solution of 4-(3-aminopropyl)morpholine (122.6 g) in dioxane (520 ml) was added to a solution of 97% sodium hydroxide (35.1 g) in water (420 ml) under 0° C. and thereto was added dropwise carbon disulfide (64.71 g) over a period of 0.5 hour at 0° to 5° C. The mixture was stirred for an hour at the same temperature and thereto was added methyl iodide (120.65 g) over a period of 0.5 hour at 0° to 5° C. The resulting mixture was stirred for 2 hours at the same temperature. The precipitates were collected by filtration, washed with water (×2) and dried to give a pale yellow powder of 4-[3-{N-methylthio(thiocarbonyl)amino}propyl]morpholine (174.55 g).

N.M.R. (d$_6$-DMSO, δ): 1.73 (2H, m), 2.3 (6H, m), 2.48 (3H, s), 3.2–3.9 (6H, m), 9.91 (1H, broad s)

(2) To a solution of 4-[3-{N-methylthio(thiocarbonyl)amino}propyl]morpholine (152 g) in dioxane (430 ml) was added a solution of sodium azide (42.25 g) in water (290 ml). The resulting mixture was refluxed for 2 hours. The reaction mixture was evaporated, adjusted to pH 8 and washed with diethyl ether. The aqueous layer was adjusted to pH 5 and cooled. The precipitates were collected by filtration, washed with ice-water (×2) and then dried to give white crystals of 1-(3-morpholinopropyl)-1H-tetrazole-5-thiol (116 g), mp 210° to 212° C. (dec.).

I.R. (Nujol): 3550, 3500, 2350, 1610, 1410, 1360, 1280, 1190, 1130, 1090, 1050, 990, 880, 825, 785 cm$^{-1}$ N.M.R. (d$_6$-DMSO, δ): 2.14 (2H, m), 2.99 (2H, t, J=7 Hz), 3.09 (4H, m), 3.79 (4H, m), 4.24 (2H, t, J=7 Hz)

PREPARATION 7

(1) The following compound was obtained according to a similar manner to that of Preparation 6(1). 1-[3-{N-Methylthio(thiocarbonyl)amino}propyl]piperidine, white powder, mp 74° to 76° C.

I.R. (Nujol): 3450, 3150, 1670, 1560, 1410, 1340, 1315, 1255, 1030, 1000, 950, 880, 860, 800, 750 cm$^{-1}$ (2) The following compound was obtained according to a similar manner to that of Preparation 6(2). 1-(3-Piperidinopropyl)-1H-tetrazole-5-thiol, mp 142° to 144° C. (dec.).

I.R. (Nujol): 3500, 3350, 2450, 1635, 1360, 1280, 1200, 1185, 1120, 1100, 1085, 1070, 1000, 965, 950, 810 cm$^{-1}$ N.M.R. (d$_6$-DMSO, δ): 1.3–1.9 (6H, m), 2.20 (2H, m), 3.07 (2H, t, J=7 Hz), 3.17 (4H, m), 4.24 (2H, t, J=7 Hz)

PREPARATION 8

(1) To a mixture of tetrabutylammonium bromide (3.22 g) in methylene chloride (300 ml) was added ethyl chloroformate (108.5 g) at −20° C. To the mixture was added a solution of sodium cyanide (49 g) in water (200 ml) over a period of 15 minutes at −10° to −13° C. and the resulting mixture was stirred for a minute at −13° C. The organic layer was separated from the reaction mixture, dried over magnesium sulfate and allowed to warm to room temperature. The methylene chloride layer was separated by decantation and the insoluble material was washed with methylene chloride. The combined methylene chloride layers (370 ml) were distilled at atmospheric pressure to give a solution containing ethyl cyanoformate (335 ml), bp 42° to 117° C.

(2) A solution of hydrogen chloride (32.5 g) in ethanol (34.5 g) was cooled at −10° C. and added to a solution obtained in Preparation 8(1) (335 ml) containing ethyl cyanoformate precooled to −10° C. The resulting solution was stirred for 6 hours at −5° to 5° C., cooled to −10° C. and thereto was added methylene chloride (400 ml). To the mixture were dropwise added a solution of triethylamine (85.8 g) in methylene chloride (80 ml) and water (200 ml) at −5° to 0° C. The methylene chloride layer was separated, washed with water (200 ml×2), dried over magnesium sulfate and evaporated to give the product (112 g) containing 78.8% of ethyl 2-imino-2-ethoxyacetate. This product was purified by distillation (bp 80° to 88° C./40 mmHg) to give pure product.

(3) A mixture of ethyl 2-imino-2-ethoxyacetate (60 g) (purity 78.8%) and ammonium chloride (17.4 g) in methanol (180 ml) was stirred for 3 hours at room temperature and cooled to −15° to −10° C. To the resulting mixture containing 1-methoxycarbonylformamidine hydrochloride were dropwise added bromine (51.2 g) over a period of 10 minutes, triethylamine (71.1 g) over a period of 30 minutes and a solution of potassium thiocyanate (31.0 g) in methanol (150 ml) over a period of 30 minutes. The resulting mixture was stirred at −10° to −5° C. for 15 minutes and at 0° to 5° C. for an additional 1.5 hours. Precipitates were collected by filtration, washed with methanol and thereto was added cold water (200 ml). The mixture was stirred and the precipitates were collected by filtration, washed with cold water and dried to give methyl 5-amino-1,2,4-thiadiazole-3-carboxylate (32.5 g).

(4) To a solution of ethyl cyanoformate (25.0 g) in methylene chloride (55 ml) was added 43.5% ethanolic solution of hydrogen chloride (16.8 g) with stirring at 3° C. The mixture was stirred for 5 hours at 3° to 5° C. and allowed to stand over night at −5° to −3° C. To the resulting mixture were added methylene chloride (120 ml) at below 6° C. and a solution of triethylamine (20.2 g) in methylene chloride (20 ml) over a period of 30 minutes at below 6° C. The mixture was stirred for 40 minutes and thereto was added water (40 ml) at below 6° C. The resulting mixture was stirred for 3 minutes and the methylene chloride layer was separated, dried over magnesium sulfate and then evaporated. After the addition of diisopropyl ether (40 ml) to the residue, insoluble material was separated by filtration and washed with diisopropyl ether (10 ml). The filtrate and washing were combined and then evaporated to give a pale yellow oil of ethyl 2-imino-2-ethoxyacetate (26.2 g). A mixture of the oil (26.2 g) obtained above, ammonium chloride (6.42 g) in methanol (90 ml) was stirred for 2 hours at room temperature and thereto was added diisopropyl ether (450 ml). The mixture was ice-cooled and then stirred for 30 minutes. Precipitates were collected by filtration to give a white powder of 1-methoxycarbonylformamidine hydrochloride (13.8 g), mp 150° to 155° C. (dec.).

I.R. (Nujol): 3350–3050, 1780, 1710, 1695, 1290, 1270, 1070, 980, 800 cm$^{-1}$

N.M.R. (d$_6$-DMSO, δ): 3.97 (3H, s), 9.8 (4H, broad s)

(5) To a solution of 1-methoxycarbonylformamidine hydrochloride (7.6 g) in methanol (55 ml) was dropwise added bromine (8.8 g) over a period of 5 minutes at −5° to 0° C. To the mixture were added triethylamine (11.1 g) over a period of 10 minutes and a solution of potassium thiocyanate (5.3 g) in methanol (30 ml) over a period of 20 minutes at −5° to 0° C. The mixture was stirred for 1.5 hours at 0° to 5° C. Precipitates were collected by filtration, washed with methanol (11 ml), dried and thereto was added water (15.5 ml). The mixture was stirred for 30 minutes and precipitates were collected by filtration, washed with water (5 ml×3) and dried to give a white powder of methyl 5-amino-1,2,4-thiadiazole-3-carboxylate (6.3 g).

(6) A mixture of ethyl 2-imino-2-ethoxyacetate (36.2 g), ammonium bromide (21.2 g) in methanol (180 ml) was stirred for 4 hours at room temperature and thereto was added diisopropyl ether (400 ml) with stirring. The mixture was allowed to stand for 30 minutes. Precipitates were removed by filtration.

To the filtrate was added diisopropyl ether (200 ml) and the mixture was allowed to stand for 10 minutes. Precipitates were collected by filtration to give a white powder of 1-methoxycarbonylformamidine hydrobromide (16.1 g). The filtrate was concentrated to the volume of about 150 ml. To the concentrate was added diisopropyl ether (200 ml) and the mixture was allowed to stand for 30 minutes. Precipitates were collected by filtration to give a white powder of the same (11.6 g). Total yield: 27.7 g.

I.R. (Nujol): 3350–3150, 1780, 1710, 1690, 1290, 1270, 1060, 980, 850, 800, 730 cm$^{-1}$ N.M.R. (d$_6$-DMSO, δ): 3.91 (3H, s), 11.0 (4H, broad s)

(7) A mixture of ethyl 2-imino-2-ethoxyacetate (18.1 g), ammonium chloride (5.8 g) in ethanol (90 ml) was stirred for 6 hours at room temperature. Insoluble materials were separated by filtration and washed with ethanol. The filtrate and washing were combined and evaporated. To the residual oil was added acetone (50 ml). The precipitates were collected by filtration and washed with acetone (10 ml×2) to give a white powder of 1-ethoxycarbonylformamidine hydrochloride (1.2 g). The filtrate and washing were combined and evaporated. The residue was pulverized with acetone (30 ml), collected by filtration, washed successively with acetone, methylene chloride and diisopropyl ether to give a white powder of the same (7.3 g). Total yield: 8.5 g.

I.R. (Nujol): 3400–3100, 1770, 1730–1680, 1650, 1300–1260, 1120, 1010, 860, 760 cm$^{-1}$

PREPARATION 9

Preparation of Methyl 5-amino-1,2,4-thiadiazole-3-carboxylate.

To a solution of 1-ethoxycarbonylformamidine hydrobromide (16.6 g.) in absolute methanol (84 ml) was added a solution of sodium (1.93 g) in absolute methanol (42 ml) at 0° C. To the mixture were added alternately bromine (12.8 g) and a solution of sodium (1.93 g) in absolute methanol (42 ml) at 0° C. and then to the suspension was added potassium thiocyanate (8.1 g) in absolute methanol (100 ml). The reaction mixture was stirred for an hour at 0° C. and for an additional 6 hours at ambient temperature. The mixture was filtered through cellulose powder and the filtrate was evaporated to dryness. The residue was dissolved in a mixture of ethyl acetate and water, and then the ethyl acetate layer was separated and dried over anhydrous magnesium sulfate. The solvent was evaporated and the residue was triturated with diethyl ether to give the title compound (9.0 g), mp. 202° to 205° C.

I.R. (Nujol): 3400, 3250, 3100, 1710, 1610, 1540 cm$^{-1}$
N.M.R. (d$_6$-DMSO): δ: 3.85 (3H, s), 8.25 (2H, s)

PREPARATION 10

Preparation of Methyl 5-formamido-1,2,4-thiadiazole-3-carboxylate.

To a mixture of formic acid (33 g) and acetic anhydride (22 g) was added methyl 5-amino-1,2,4-thiadiazole-3-carboxylate (6.2 g), and then the mixture was stirred for 2 days at ambient temperature. The reaction mixture was concentrated under reduced pressure and the residue was triturated with a mixture of diethyl ether and n-hexane to give the title compound (7.2 g), mp. 210° to 215° C.

I.R. (Nujol): 3100, 1720, 1680 cm$^{-1}$
N.M.R. (d$_6$-DMSO): δ: 3.90 (3H, s), 8.85 (1H, s)

PREPARATION 11

Preparation of 5-Formamido-3-(2-methylthio-2-methylsulfinylacetyl)-1,2,4-thiadiazole.

To a mixture of methyl 5-formamido-1,2,4-thiadiazole-3-carboxylate (9.2 g) and methyl methylthiomethyl sulfoxide (6.1 g) in N,N-dimethylformamide (100 ml) was added 50% sodium hydride (7.1 g) with cooling in an ice-bath. The mixture was stirred for an hour at ambient temperature and for an additional one hour at 40° C. After cooling to ambient temperature, methylene chloride (300 ml) was added to the reaction mixture, and the resulting precipitates were collected by filtration and washed with methylene chloride. The precipitates were added to a stirred mixture of hydrochloric acid (14.7 ml), ice-water (200 ml) and methylene chloride (200 ml). An insoluble material was filtered off and the methylene chloride layer was separated from the filtrate. The solution was dried over anhydrous magnesium sulfate, evaporated and the residue was triturated with diethyl ether to give the title compound (4.5 g), mp. 130° to 132° C.

I.R. (Nujol): 3100, 1680, 1670 cm$^{-1}$
N.M.R. (d$_6$-DMSO)

| δ: | 2.22 | | |
|---|---|---|---|
| | 2.28 | } | (3H, 2s) |
| | 2.68 | } | (2H, 2s) |
| | 2.85 | | |
| | 5.70 | } | (1H, 2s) |
| | 5.80 | | |
| | 8.86 | | (1H, s) |

PREPARATION 12

Preparation of S-methyl(5-formamido-1,2,4-thiadiazol-3-yl)thioglyoxylate.

A mixture of 5-formamido-3-(2-methylthio-2-methylsulfinylacetyl)-1,2,4-thiadiazole (0.85 g) and sodium periodate (0.2 g) in glacial acetic acid (10 ml) was stirred for 45 minutes at 70° C. The reaction mixture was evaporated and the residue was dissolved in a mixture of ethyl acetate and water. The mixture was adjusted to pH 7 with an aqueous solution of sodium bicarbonate and treated with an aqueous solution of sodium thiosulfate. The organic layer was separated, dried over anhydrous magnesium sulfate and evaporated to dryness. The residue was triturated with a mixture of diethyl ether and petroleum ether to give the title compound (280 mg), mp. 186° to 187° C.

I.R. (Nujol): 3100, 1680, 1660 cm$^{-1}$
N.M.R. (d$_6$-DMSO): δ: 2.55 (3H, s), 8.95 (1H, s)

PREPARATION 13

A mixture of 5-formamido-3-(2-methylthio-2-methylsulfinylacetyl)-1,2,4-thiadiazole (10 g) and sodium periodate (2.0 g) in glacial acetic acid (50 ml) was stirred for 50 minutes at 70° C. The solvent was evaporated and the residue was washed with n-hexane. To the residue was added 1 N aqueous solution of sodium hydroxide (160 ml) and the mixture was stirred for an hour at ambient temperature. To the reaction mixture was added O-allylhydroxylamine hydrochloride (4.31 g) and the solution was adjusted to pH 3 to 4 with 10% hydrochloric acid and then stirred for an hour at ambient temperature. After an insoluble material was filtered off, the filtrate was washed with ethyl acetate, adjusted to pH 1 with 10% hydrochloric acid and extracted with ethyl acetate. The extract was dried over magnesium sulfate and evaporated to dryness. The residue was triturated with a mixture of diethyl ether and diisopropyl ether to give 2-allyloxyimino-2-(5-formamido-1,2,4-thiadiazol-3-yl)acetic acid (syn isomer)(5.6 g), mp 169° to 172° C. (dec.).

I.R. (Nujol): 3130, 2500, 1720, 1690, 1590, 1550 cm$^{-1}$
N.M.R. (d$_6$-DMSO): δ: 4.79 (2H, d, J=6 Hz), 5.1–5.6 (2H, m), 5.8–6.4(1H, m), 8.88(1H,s)

PREPARATION 14

The following compounds were obtained according to a similar manner to that of Preparation 13.

(1) 2-Benzyloxyimino-2-(5-formamido-1,2,4-thiadiazol-3-yl)acetic acid (syn isomer), mp. 90° to 95° C. (dec.).

I.R. (Nujol): 1720, 1680, 1590, 1550, 1530 cm$^{-1}$
N.M.R. (d$_6$-DMSO): δ: 5.28 (2H, s), 7.37 (5H, s), 8.83 (1H, s)

(2) 2-(2-Propynyloxyimino)-2-(5-formamido-1,2,4-thiadiazol-3-yl)acetic acid (syn isomer), mp. 150° to 155° C. (dec.).

I.R. (Nujol): 3570, 3360, 3260, 3120, 1720, 1670, 1550, 1530 cm$^{-1}$
N.M.R. (d$_6$-DMSO): δ: 3.55 (1H, t, J=2 Hz), 4.88 (2H, d, J=2 Hz), 8.85 (1H, s)

(3) 2-(2-Phenoxyethoxyimino)-2-(5-formamido-1,2,4-thiadiazol-3-yl)acetic acid (syn isomer), mp. 147° to 150° C. (dec.).

I.R. (Nujol): 3200, 1740, 1720, 1640, 1590, 1530 cm$^{-1}$
N.M.R. (d$_6$-DMSO): δ: 4.0–4.7 (4H, m), 6.7–7.5 (5H, m), 8.83 (1H, s)

(4) 2-Hydroxyimino-2-(5-formamido-1,2,4-thiadiazol-3-yl)acetic acid (syn isomer), mp. 240° to 241° C. (dec.).

I.R. (Nujol): 3550, 3460, 1665, 1635, 1560 cm$^{-1}$

PREPARATION 15

A solution of S-methyl (5-formamido-1,2,4-thiadiazol-3-yl)thioglyoxylate (6.64 g) in 1 N aqueous solution of sodium hydroxide (80 ml) was adjusted to pH 8.5 with 10% hydrochloric acid and stirred for 30 minutes at ambient temperature. On the other hand, a mixture of N-(2,2,2-trifluoroethoxy)phthalimide (8.78 g) and hydrazine hydrate (1.7 g) in ethanol (40 ml) was refluxed for 5 minutes and then cooled in an ice bath. A resulting precipitates were filtered off and washed with ethanol. The filtrate and the washings were combined and the combined solution containing O-(2,2,2-trifluoroethyl)hydroxylamine was added to the above aqueous solution. The mixture was adjusted to pH 3 to 4 with 10% hydrochloric acid and stirred for 1.5 hours at ambient temperature. The solution was neutralized with an aqueous solution of sodium bicarbonate, concentrated to half volume in vacuo and washed with ethyl acetate. The aqueous solution was acidified with 10% hydrochloric acid and extracted with ethyl acetate. The extract was dried over magnesium sulfate, evaporated to dryness and the residue was triturated with diisopropyl ether to give 2-(2,2,2-trifluoroethoxyimino)-2-(5-formamido-1,2,4-thiadiazol-3-yl)acetic acid (syn isomer)(2.46 g), mp. 180° to 185° C. (dec.).

N.M.R. (d$_6$-DMSO): δ: 4.80 and 5.07 (2H, ABq, J=9 Hz), 8.85 (1H, s)

PREPARATION 16

The following compounds were obtained according to a similar manner to that of Preparation 15.

(1) 2-Methylthiomethoxyimino-2-(5-formamido-1,2,4-thiadiazol-3-yl)acetic acid (syn isomer), mp. 146° to 148° C. (dec.).

I.R. (Nujol): 3300, 2600, 2550, 1730, 1705, 1680, 1600, 1530 cm$^{-1}$

N.M.R. (d$_6$-DMSO): δ: 2.23 (3H, s), 5.40 (2H, s), 8.87 (1H, s)

(2) 2-(2-Methylthioethoxyimino)-2-(5-formamido-1,2,4-thiadiazol-3-yl)acetic acid (syn isomer).

I.R. (Nujol): 3230, 1720, 1690, 1590, 1520 cm$^{-1}$

N.M.R. (d$_6$-DMSO): δ: 2.17 (3H, s), 2.82 (2H, t, J=7 Hz), 4.42 (2H, t, J=7 Hz), 8.87 (1H, s)

(3) 2-Phenoxyimino-2-(5-formamido-1,2,4-thiadiazol-3-yl)acetic acid (syn isomer), mp. 145° to 147° C. (dec.).

I.R. (Nujol): 3130, 1720, 1690, 1585, 1550 cm$^{-1}$

N.M.R. (d$_6$-DMSO): δ: 7.0–7.6 (5H, m), 8.88 (1H, s)

(4) 2-[2-(2-Hexyloxyethoxy)ethoxyimino]-2-(5-formamido-1,2,4-thiadiazol-3-yl)acetic acid (syn isomer).

I.R. (CHCl$_3$): 3420, 3180, 1740, 1700, 1600, 1530, 1460 cm$^{-1}$

N.M.R. (d$_6$-DMSO): δ: 0.87 (3H, t, J=5 Hz), 0.87–1.73 (8H, m), 3.20–3.90 (8H, m), 4.23–4.53 (2H, m), 8.84 (1H, s), 13.55 (1H, broad s)

(5) 2-Trityloxyimino-2-(5-formamido-1,2,4-thiadiazol-3-yl)acetic acid (anti isomer), mp. 188° to 190° C. (dec.).

I.R. (Nujol): 3150, 1620, 1600, 1540 cm$^{-1}$

N.M.R. (d$_6$-DMSO): δ: 7.00 (15H, s), 8.92 (1H, s)

PREPARATION 17

A mixture of S-methyl(5-formamido-1,2,4-thiadiazol-3-yl)thioglyoxylate (6 g) and an aqueous solution (50 ml) of sodium hydroxide (4.2 g) was stirred for an hour at 50° to 55° C. The mixture was cooled to ambient temperature and adjusted to pH 7 with 10% hydrochloric acid. On the other hand, a mixture of N-(ethoxycarbonylmethoxy)phthalimide (12.9 g) and hydrazine hydrate (2.08 g) in ethanol (60 ml) was refluxed for 5 minutes and cooled in an ice bath. A resulting precipitate was filtered off and washed with ethanol. The filtrate and the washings were combined and the combined solution containing O-(ethoxycarbonylmethyl)-hydroxylamine was added to the above aqueous solution. The mixture was adjusted to pH 3 to 4 with 10% hydrochloric acid and stirred for 1.5 hours at ambient temperature. The solution was neutralized with an aqueous solution of sodium bicarbonate, concentrated to half volume in vacuo and washed with ethyl acetate. The aqueous solution was acidified with 10% hydrochloric acid and extracted with ethyl acetate. The extract was dried over magnesium sulfate, evaporated to dryness and the residue was triturated with diisopropyl ether to give 2-ethoxycarbonylmethoxyimino-2-(5-amino-1,2,4-thiadiazol-3-yl)acetic acid (syn isomer) (1.8 g), mp. 135° to 140° C. (dec.).

I.R. (Nujol): 3500,3330,3210,2670,2550,1740,1610,1540 cm$^{-1}$

N.M.R. (d$_6$-DMSO): δ: 1.24 (3H,t, J=7 Hz), 4.14 (2H,q, J=7 Hz), 4.80 (2H, s), 8.15 (2H, broad s)

PREPARATION 18

The following compounds were obtained according to a similar manner to that of Preparation 17.

(1) 2-Cyanomethoxyimino-2-(5-amino-1,2,4-thiadiazol-3-yl)acetic acid (syn isomer), mp. 130° to 135° C. (dec.).

I.R. (Nujol): 3350,3150,1730,1630, 1540 cm$^{-1}$

N.M.R. (d$_6$-DMSO): δ: 5.17 (2H, s), 8.28 (2H, broad s)

(2) 2-(1-Ethoxycarbonyl-1-methylethoxyimino)-2-(5-amino-1,2,4-thiadiazol-3-yl)acetic acid (syn isomer), mp. 165° to 168° C. (dec.).

I.R. (Nujol): 3450,3350,3240,1750,1730,1630,1530 cm$^{-1}$

N.M.R. (d$_6$-DMSO): δ: 1.18 (3H,t,J=7 Hz), 1.50 (6H,s), 4.15 (2H, q, J=7 Hz), 8.23 (2H, broad s)

(3) 2-(N,N-Diethylcarbamoylmethoxyimino)-2-(5-amino-1, 2,4-thiadiazol-3-yl)acetic acid (syn isomer), mp. 150° to 155° C. (dec.).

I.R. (Nujol): 3400,3150,1745,1635,1610,1595,1535 cm$^{-1}$

N.M.R. (d$_6$-DMSO): δ: 1.03 (3H,t,J=7 Hz), 1.10 (3H, t, J=7 Hz), 3.28 (4H, q, J=7 Hz), 4.90 (2H,s), 8.23 (2H, broad s)

(4) 2-Mesylmethoxyimino-2-(5-amino-1,2,4-thiadiazol-3-yl)acetic acid (syn isomer).

I.R. (Nujol): 3450, 3400, 3270, 2600, 2460, 1735, 1640, 1620, 1530 cm$^{-1}$

N.M.R. (d$_6$-DMSO): δ: 3.00(3H, s), 5.38 (2H,s), 8.22 (2H, broad s)

PREPARATION 19

The following compounds were obtained according to a similar manner to that of Preparation 4.

(1) 2-Allyloxyimino-2-(5-amino-1,2,4-thiadiazol-3-yl)acetic acid (syn isomer), mp. 93° to 95° C. (dec.).

I.R. (Nujol): 3430, 3100, 1710, 1615,1525 cm$^{-1}$

N.M.R. (d$_6$-DMSO): δ: 4.72 (2H, d, J=6 Hz), 5.1–5.5 (2H, m), 5.7–6.3 (1H, m), 8.17 (1H, broad s)

(2) 2-Benzyloxyimino-2-(5-amino-1,2,4-thiadiazol-3-yl)acetic acid (syn isomer), mp. 158° to 160° C. (dec.).

I.R. (Nujol): 3430, 3380, 3260, 1730, 1640, 1610, 1535 cm$^{-1}$

N.M.R. (d$_6$-DMSO): δ: 5.22 (2H, s), 7.33 (5H, s), 8.17 (2H, broad s)

(3) 2-(2-Propynyloxyimino)-2-(5-amino-1,2,4-thiadiazol-3-yl)acetic acid (syn isomer), mp. 155° to 157° C. (dec.).

I.R. (Nujol): 3500, 3310, 3160, 2600, 2480, 1745, 1610, 1535 cm$^{-1}$

N.M.R. (d$_6$-DMSO): δ: 3.53 (1H, t, J=2 Hz), 4.87 (2H, d, J=2 Hz), 8.23 (2H, broad s)

(4) 2-(2-Phenoxyethoxyimino)-2-(5-amino-1,2,4-thiadiazol-3-yl)acetic acid (syn isomer), mp. 150° to 153° C. (dec.).

I.R. (Nujol): 3470, 3300, 3150, 2550, 1750, 1620, 1600, 1540, 1500 cm$^{-1}$

N.M.R. (d$_6$-DMSO): δ: 4.0–4.7 (4H, m), 6.7–7.5 (5H, m), 8.20 (2H, broad s)

(5) 2-(2,2,2-Trifluoroethoxyimino)-2-(5-amino-1,2,4-thiadiazol-3-yl)acetic acid (syn isomer), mp. 140° to 143° C. (dec.).

I.R. (Nujol): 3450, 3350, 3260, 1745, 1670, 1645, 1615, 1515 cm$^{-1}$

N.M.R. (d$_6$-DMSO): δ: 4.72 and 4.95 (2H, ABq, J=9 Hz), 8.25 (2H, broad s)

(6) 2-Methylthiomethoxyimino-2-(5-amino-1,2,4-thiadiazol-3-yl)acetic acid (syn isomer), mp. 140° to 143° C. (dec.).

I.R. (Nujol): 3500, 3300, 3150, 2670, 2580, 1740, 1615, 1605, 1530 cm$^{-1}$

N.M.R. (d$_6$-DMSO): δ: 2.22 (3H, s), 5.33 (2H, s), 8.20 (2H, broad s)

(7) 2-(2-Methylthioethoxyimino)-2-(5-amino-1,2,4-thiadiazol-3-yl)acetic acid (syn isomer), mp. 140° to 143° C. (dec.).

I.R. (Nujol): 3430, 3340, 3230, 2650, 2450, 1720, 1610, 1520 cm$^{-1}$

N.M.R. (d$_6$-DMSO): δ: 2.08 (3H, s), 2.72 (2H, t, J=7 Hz), 4.28 (2H, t, J=7 Hz), 8.17 (2H, broad s)

(8) 2-Phenoxyimino-2-(5-amino-1,2,4-thiadiazol-3-yl)acetic acid (syn isomer), mp. 145° to 147° C. (dec.).

I.R. (Nujol): 3350, 3170, 2500, 1730, 1710, 1645, 1630, 1595, 1535 cm$^{-1}$

N.M.R. (d$_6$-DMSO): δ: 7.0–7.5 (5H, m), 8.30 (2H, broad s)

(9) 2-[2-(2-Hexyloxyethoxy)ethoxyimino]-2-(5-amino-1,2,4-thiadiazol-3-yl)acetic acid (syn isomer).

I.R. (CHCl$_3$): 3350, 3230, 2600, 2500, 1730, 1620, 1520, 1460 cm$^{-1}$

N.M.R. (d$_6$-DMSO): δ: 0.87 (3H, t, J=5 Hz), 0.87–1.73 (8H, m), 3.20–3.90 (8H, m), 4.13–4.47 (2H, m), 8.17 (2H, broad s)

(10) 2-Trityloxyimino-2-(5-amino-1,2,4-thiadiazol-3-yl)acetic acid (syn isomer), mp. 173° to 174° C. (dec.).

I.R. (Nujol): 3450, 1735, 1620, 1540 cm$^{-1}$

N.M.R. (d$_6$-DMSO): δ: 7.35 (15H, s), 8.22 (2H, s)

(11) 2-Trityloxyimino-2-(5-amino-1,2,4-thiadiazol-3-yl)acetic acid (anti isomer), mp. 170° to 171° C.

I.R. (Nujol): 3300, 3150, 1680, 1635, 1520 cm$^{-1}$

N.M.R. (d$_6$-DMSO): δ: 7.33 (15H, s), 8.13 (2H, s)

PREPARATION 20

A mixture of 2-hydroxyimino-2-(5-formamido-1,2,4-thiadiazol-3-yl)acetic acid (syn isomer) (3.3 g) and dichloroacetyl chloride (9.0 g) in methylene chloride (50 ml) was stirred for 6.5 hours at ambient temperature. A resulting precipitates were filtered and dissolved in ethyl acetate. After removing of an insoluble substance by filtration, the filtrate was evaporated to dryness. The residue was triturated with diisopropyl ether to give 2-dichloroacetoxyimino-2-(5-formamido-1,2,4-thiadiazol-3-yl)acetic acid (syn isomer) (2.3 g) mp. 123° C.

I.R. (Nujol): 3150, 1790, 1690, 1550 cm$^{-1}$

PREPARATION 21

To a mixture of 2-hydroxyimino-2-(5-formamido-1,2,4-thiadiazol-3-yl)acetic acid (syn isomer) (9.5 g) and dimethylformamide (80 ml) was added with stirring at ambient temperature trityl chloride (22.8 g), and triethylamine (4.1 g) was gradually added thereto after 3 minutes stirring. The resulting mixture was stirred for 10 minutes and ethyl acetate (250 ml) was added thereto. The mixture was washed three times with water and with a saturated aqueous solution of sodium chloride, dried over magnesium sulfate and concentrated. To the residue were added an aqueous solution of sodium bicarbonate (50 ml) and diisopropyl ether (100 ml). Precipitates were collected by filtration and the aqueous layer in the filtrate was separated. The collected precipitates were suspended in the separated aqueous layer and ethyl acetate was added thereto. The mixture was adjusted to pH 2 with 10% hydrochloric acid and extracted with ethyl acetate. The extract was dried over magnesium sulfate and concentrated in vacuo. The residue was washed with hexane to give 2-trityloxyimino-2-(5-formamido-1,2,4-thiadiazol-3-yl)acetic acid (syn isomer) (17.1 g), mp. 175° to 176° C. (dec.).

I.R. (Nujol): 3180, 3070, 1700, 1600, 1540 cm$^{-1}$

N.M.R. (d$_6$-DMSO): δ: 7.35 (15H, s), 8.83 (1H, s), 13.52 (1H, broad s)

PREPARATION 22

(1) A solution of N-(3-aminopropyl)acetamide (146 g) in dioxane (710 ml) was added to a solution of 97% sodium hydroxide (52 g) in water (620 ml) and then carbon disulfide (96 g) was added dropwise thereto over 35 minutes at −1° to 3° C. The mixture was stirred for 1 hour at 0° to 2° C. To the mixture containing sodium N-(3-acetamidopropyl)dithiocarbamate was added dropwise methyl iodide (179 g) over 35 minutes at 0° to 5° C. and then the resulting mixture was stirred for 3 hours at the same temperature. Dioxane was distilled off in vacuo from the reaction mixture and the residue was extracted with ethyl acetate (300 ml, 200 ml×4). The extracts were dried over magnesium sulfate and concentrated in vacuo to give oil of methyl N-(3-acetamidopropyl)dithiocarbamate (193.18 g).

(2) A mixture of a solution of methyl N-(3-acetamidopropyl)dithiocarbamate (193 g) in dioxane (610 ml) and a solution of sodium azide (79.42 g) in water (500 ml) was refluxed under stirring for 4 hours. Dioxane was distilled off and the remaining aqueous layer was washed with diethyl ether (150 ml×2), adjusted to pH 1 with 17.5% hydrochloric acid, and cooled in an ice bath. Precipitates were collected by filtration and washed with ice-water to give white powder of 1-(3-acetamidopropyl)-1H-tetrazol-5-thiol (91.75 g), mp. 152° to 154° C.

N.M.R. (d$_6$-DMSO): δ: 1.87 (3H, s), 1.97 (2H, m), 3.17 (2H, m), 4.28 (2H, t, J=7 Hz), 7.9 (1H, broad s), 15.0 (1H, broad s)

(3) A mixture of 1-(3-acetamidopropyl)-1H-tetrazole-5-thiol (85 g) and 6 N hydrochloric acid (1 l) was refluxed for 75 minutes under stirring. The reaction mixture was concentrated in vacuo and precipitates were collected by filtration and washed with hexane and diethyl ether to give 1-(3-aminopropyl)-1H-tetrazole-5-thiol hydrochloride (67.15 g).

N.M.R. (D$_2$O): δ: 2.45 (2H, m), 3.23 (2H, t, J=7 Hz), 4.50 (2H, t, J=7 Hz)

(4) A solution of 2-t-butoxycarbonyloxyimino-2-phenylacetonitrile (12.3 g) in dioxane (30 ml) was added under ice-cooling to a stirred solution of 1-(3-aminopropyl)-1H-tetrazole-5-thiol hydrochloride (9.78 g) and triethylamine (11.1 g) in a mixture of dioxane (25 ml) and water (25 ml), and then the resulting mixture was stirred for 1.75 hours at ambient temperature. Dioxane was distilled off and to the residue were added diethyl ether and a small amount of water. After shaking, the aqueous layer was separated and the organic layer was extracted twice with 10% potassium carbonate. The extracts combined with the separated aqueous layer were washed three times with diethyl ether, adjusted to pH 1 with hydrochloric acid and extracted with diethyl ether. The extract was washed with water, dried and evaporated in vacuo. The residual oil (10.92 g) was pulverized with diisopropyl ether to give 1-[3-(N-t-butoxycarbonylamino)propyl]-1H-tetrazole-5-thiol (9.6 g), mp. 75° to 77° C.

I.R. (Nujol): 3380, 3260, 1650, 1530, 1170, 1050 cm$^{-1}$

N.M.R. (CDCl$_3$): δ: 1.50 (9H, s), 2.14 (2H, m), 3.25 (2H, m), 4.39 (2H, t, J=7 Hz), 4.9–6.7 (1H, broad)

EXAMPLE 1

To a cold solution of phosphorus pentachloride (450 mg) in methylene chloride (10 ml) was added 2-(4-chlorophenoxyimino)-2-(5-amino-1,2,4-thiadiazol-3-yl)acetic acid (syn isomer) (650 mg) at −15° C. and the mixture was stirred for 30 minutes at the same temperature. On the other hand, a mixture of 7-amino-3-(1,3,4-thiadiazol-2-yl)thiomethyl-3-cephem-4-carboxylic acid (785 mg) and trimethylsilylacetamide (2.1 g) in methylene chloride (10 ml) was warmed to make a clear solution and then cooled to −20° C. The solution was added to the above activated mixture at −20° C. and the mixture was stirred for 40 minutes at −15° C. The reaction mixture was poured into cold aqueous solution of sodium bicarbonate (20 ml) and stirred at ambient temperature for 30 minutes. Methylene chloride was distilled off and ethyl acetate was added to the residual aqueous solution. The mixture was adjusted to pH 3 or 4 with 10% hydrochloric acid and extracted with ethyl acetate. The extract was dried over magnesium sulfate, treated with an activated charcoal and evaporated to dryness. The residue was triturated with diethyl ether and reprecipitated from a mixed solvent of acetone and diethyl ether. Precipitates were dissolved in an aqueous solution of sodium bicarbonate and the solution was adjusted to pH 1 or 2 with 10% hydrochloric acid to give precipitates. The precipitates were collected by filtration and washed with water to give 7-[2-(4-chlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer) (0.35 g), mp 150° to 155° C. (dec.).

I.R. (Nujol): 3300, 3200, 1770, 1670, 1620, 1520 cm$^{-1}$

N.M.R. (d$_6$-DMSO, δ): 3.67 (2H, broad s), 4.27 and 4.50 (2H, ABq, J=14 Hz), 5.17 (1H, d, J=4 Hz), 5.80 (1H, dd, J=4 and 8 Hz), 7.00–7.50 (4H, m), 8.22 (2H, s), 9.50 (1H, s), 9.80 (1H, d, J=8 Hz).

EXAMPLE 2

To a cold solution of phosphorus pentachloride (1.04 g) in methylene chloride (25 ml) was added 2-(4-fluorophenoxyimino)-2-(5-amino-1,2,4-thiadiazol-3-yl)acetic acid (syn isomer) (1.4 g) at −15° C. and the mixture was stirred for 30 minutes at the same temperature. On the other hand, a mixture of 7-amino-3-(1,3,4-thiadiazol-2-yl)thiomethyl-3-cephem-4-carboxylic acid (1.65 g) and trimethylsilylacetamide (5 g) in methylene chloride (25 ml) was warmed to make a clear solution and then cooled to −15° C. The solution was added to the above activated mixture and the mixture was stirred for 1 hour at 0° to 5° C. The reaction mixture was concentrated and to the residue were added ethyl acetate and water. After filtering off an insoluble material, the ethyl acetate layer was poured into an aqueous solution of sodium bicarbonate. The aqueous layer was separated out, adjusted to pH 4 with 10% hydrochloric acid after addition of ethyl acetate and extracted with ethyl acetate. The extract was dried over magnesium sulfate and evaporated to a volume of about 10 ml. Precipitates were collected by filtration, washed with ethyl acetate and diethyl ether and dried to give 7-[2-(4-fluorophenoxyimino)-2-(5-amino-1,2,4-thiadiazol-3-yl)-acetamido]-3-(1,3,4-thiadiazol-2-yl)thiomethyl-3-cephem-4-carboxylic acid (syn isomer) (1.2 g), mp 140° to 145° C. (dec.).

I.R. (Nujol): 3300, 3200, 1770, 1680, 1620, 1520 cm$^{-1}$

N.M.R. (d$_6$-DMSO, δ): 3.57 and 3.80 (2H, ABq, J=18 Hz), 4.27 and 4.57 (2H, ABq, J=13 Hz), 5.20 (1H, d, J=4 Hz), 5.87 (1H, dd, J=4 and 8 Hz), 7.17–7.3 (4H, m), 8.20 (2H, s), 9.50 (1H, s), 9.83 (1H, d, J=8 Hz)

EXAMPLE 3

To a cold solution of phosphorus pentachloride (2.08 g) in methylene chloride (50 ml) was added at −15° C. 2-phenoxyimino-2-(5-amino-1,2,4-thiadiazol-3-yl)acetic acid (syn isomer) (2.64 g) and the mixture was stirred for 30 minutes at the same temperature. On the other hand, a mixture of 4-nitrobenzyl 7-amino-3-cephem-4-carboxylate (3.35 g) and trimethylsilylacetamide (10 g) in methylene chloride (50 ml) was warmed to make a clear solution and then cooled to −15° C. The solution was added to the above activated mixture and the mixture was stirred for 0.5 hour at 0° to 5° C. The reaction mixture was poured into cold aqueous solution (100 ml) of sodium bicarbonate (5.9 g). The methylene chloride layer was dried over magnesium sulfate and evaporated to dryness. The residue was pulverized with diethyl ether. The resulting powder was collected by filtration and dried to give 4-nitrobenzyl 7-[2-phenoxyimino-2-(5-amino-1,2,4-thiadiazol-3-yl)acetamido]-3-cephem-4-carboxylate (syn isomer) (5.1 g), mp 140° to 145° C. (dec.).

I.R. (Nujol): 3300, 1775, 1720, 1680, 1625, 1600, 1590, 1520 cm$^{-1}$

N.M.R. (d$_6$-DMSO, δ): 3.60 (2H, broad s), 5.23 (1H, d, J=4 Hz), 5.42 (2H, s), 6.00 (1H, dd, J=4 and 8 Hz), 6.67 (1H, t, J=4 Hz), 7.0–7.50 (5H, m), 7.73 (2H, d, J=8 Hz), 8.27 (2H, d, J=8 Hz), 8.30 (2H, s), 9.97 (1H, d, J=8 Hz)

EXAMPLE 4

The following compounds were obtained according to similar manners to those of Examples 1 to 3, 5 and 7 to 12.

(1) 7-[2-Phenoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 175° to 180° C. (dec.).

I.R. (Nujol): 3400, 3200, 1770, 1700, 1660, 1620, 1580, 1510 cm$^{-1}$

N.M.R. (d$_6$-DMSO, δ): 3.70 (2H, broad s), 4.23 and 4.50 (2H, ABq, J=14 Hz), 5.17 (1H, d, J=4 Hz), 5.30 (2H, s), 5.89 (1H, dd, J=4 and 8 Hz), 7.0–7.5 (5H, m), 8.22 (1H, s), 9.83 (1H, d, J=8 Hz)

(2) 7-[2-Phenoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 145° to 150° C. (dec.)

I.R. (Nujol): 3450, 3350, 3180, 1780, 1710, 1680, 1610, 1590, 1510 cm$^{-1}$

N.M.R. (d$_6$-DMSO, δ): 3.70 (2H, broad s), 4.28 and 4.45 (2H, ABq, J=13 Hz), 4.83-5.10 (2H, m), 5.18 (1H, d, J=4 Hz), 5.20-5.43 (2H, m), 5.93 (1H, dd, J=4 and 8 Hz), 5.67-6.30 (1H, m), 7.0-7.57 (5H, m), 8.30 (2H, s), 9.92 (1H, d, J=8 Hz)

(3) 7-[2-Phenoxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 155° to 158° C. (dec.)

I.R. (Nujol): 3400, 3300, 3200, 1770, 1720, 1680, 1620, 1590, 1520 cm$^{-1}$

N.M.R. (d$_6$-DMSO, δ): 3.77 (2H, broad s), 3.95 (3H, s), 4.33 (2H, broad s), 5.27 (1H, d, J=4 Hz), 5.93 (1H, dd, J=4 and 8 Hz), 7.0-7.67 (5H, m), 8.37 (2H, s), 10.0 (1H, d, J=8 Hz)

(4) 7-[2-Phenoxyimino-2-(5-amino-1,2,4-thiadiazol-3-yl)acetamido]cephalosporanic acid (syn isomer), mp 150° to 155° C. (dec.)

I.R. (Nujol): 3450, 3350, 3180, 1775, 1710, 1680, 1610, 1580, 1515 cm$^{-1}$

N.M.R. (d$_6$-DMSO, δ): 2.03 (3H, s), 3.62 (2H, broad s), 4.77 and 5.03 (2H, ABq, J=14 Hz), 5.28 (1H, d, J=4 Hz), 5.97 (1H, dd, J=4 and 8 Hz), 7.0-7.67 (5H, m), 8.37 (2H, s), 9.97 (1H, d, J=8 Hz)

(5) 7-[2-(2-Methoxy-5-nitrophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 160° to 169° C. (dec.)

I.R. (Nujol): 3380, 3220, 3100, 1780, 1690, 1620, 1600, 1520, 1340, 1280, 1085, 1065, 820, 750 cm$^{-1}$ N.M.R. (d$_6$-DMSO, δ): 3.71 (2H, m), 3.98 (3H, s), 4.25 and 4.66 (2H, ABq, J=14 Hz), 5.23 (1H, d, J=5 Hz), 5.94 (1H, dd, J=5 and 9 Hz), 7.33 (1H, d, J=8 Hz), 8.10 (1H, d, J=8 Hz), 8.19 (1H, s), 8.34 (2H, broad s), 9.58 (1H, s), 9.87 (1H, d, J=9 Hz)

(6) 7-[2-(4-Fluorophenoxyimino)-2-(5-amino-1,2,4-thiadiazol-3-yl)acetamido]-3-(tetrazol[1,5-b]pyridazin-6-yl)thiomethyl-3-cephem-4-carboxylic acid (syn isomer), mp 125° to 130° C. (dec.).

I.R. (Nujol): 3300, 3190, 1770, 1670, 1615, 1520, 1495 cm$^{-1}$

N.M.R. (d$_6$-DMSO, δ): 3.80 (2H, broad s), 4.30 and 4.65 (2H, ABq, J=13 Hz), 5.27 (1H, d, J=5 Hz), 5.95 (1H, dd, J=5 and 8 Hz), 7.25 (2H, s), 7.35 (2H, s), 7.80 (1H, d, J=10 Hz), 8.37 (2H, broad s), 8.62 (1H, d, J=10 Hz), 9.92 (1H, d, J=8 Hz)

(7) 4-Nitrobenzyl 7-[2-(4-fluorophenoxyimino)-2-(5-amino-1,2,4-thiadiazol-3-yl)acetamido]-3-cephem-4-carboxylate (syn isomer), mp 135° to 140° C. (dec.).

I.R. (Nujol): 3300, 3200, 1770, 1720, 1680, 1625, 1605, 1500, 1495 cm$^{-1}$

N.M.R. (d$_6$-DMSO, δ): 3.45-3.75 (2H, m), 5.15 (1H, d, J=5 Hz), 5.35 (2H, s), 5.92 (1H, dd, J=5 and 8 Hz), 6.58 (1H, t, J=4 Hz), 7.08 (2H, s), 7.18 (2H, s), 7.60 (2H, d, J=8 Hz), 8.13 (2H, d, J=8 Hz), 8.17 (2H, broad s), 9.75 (1H, d, J=8 Hz)

(8) 7-[2-(4-Chlorophenoxyimino)-2-(5-amino-1,2,4-thiadiazol-3-yl)acetamido]-3-(5-hydroxymethyl-1,3,4-thiadiazol-2-yl)thiomethyl-3-cephem-4-carboxylic acid (syn isomer), mp 135° to 140° C. (dec.).

I.R. (Nujol): 3450, 3280, 3180, 1760, 1720, 1660, 1620, 1580, 1520, 1480 cm$^{-1}$ N.M.R. (d$_6$-DMSO, δ): 3.72 (2H, broad s), 4.27 and 4.55 (2H, ABq, J=13 Hz), 4.80 (2Hz, s), 5.22 (1H, d, J=5 Hz), 5.88 (1H, dd, J=5 and 8 Hz), 7.25 (2H, d, J=9 Hz), 7.42 (2H, d, J=9 Hz), 8.23 (2H, broad s), 9.85 (1H, d, J=8 Hz)

(9) 7-[2-(4-Chlorophenoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 135° to 140° C. (dec.).

I.R. (Nujol): 3400, 3250, 3170, 1765, 1700, 1680, 1650, 1615, 1580, 1510, 1480 cm$^{-1}$ N.M.R. (d$_6$-DMSO, δ): 3.70 (2H, broad s), 4.27 and 4.48 (2H, ABq, J=13 Hz), 5.22 (1H, d, J=5 Hz), 5.30 (2H, s), 5.93 (1H, dd, J=5 and 8 Hz), 7.35 (2H, d, J=9 Hz), 7.48 (2H, d, J=9 Hz), 8.37 (2H, broad s), 9.97 (1H, d, J=8 Hz)

(10) 7-[2-(4-Chlorophenoxyimino)-2-(5-amino-1,2,4-thiadiazol-3-yl)acetamido]-2-methyl-3-cephem-4-carboxylic acid (syn isomer), mp 150° to 155° C. (dec.).

I.R. (Nujol): 3400, 3270, 3180, 1770, 1620, 1580, 1520, 1480 cm<$^1$

N.M.R. (d$_6$-DMSO, δ): 1.45 (3H, d, J=7 Hz), 3.60-4.10 (1H, m), 5.20 (1H, d, J=5 Hz), 5.80 (1H, dd, J=5 and 8 Hz), 6.62 (1H, d, J=6 Hz), 7.35 (2H, d, J=9 Hz), 7.48 (2H, d, J=9 Hz), 8.03-8.73 (2H, m), 9.97 (1H, d, J=8 Hz)

(11) 4-Nitrobenzyl 7-[2-(4-Chlorophenoxyimino)-2-(5-amino-1,2,4-thiadiazol-3-yl)acetamido]-3-cephem-4-carboxylate (syn isomer), mp 155° to 160° C. (dec.).

I.R. (Nujol): 3300, 3180, 1770, 1720, 1680, 1625, 1600, 1580, 1520, 1480 cm$^{-1}$ N.M.R. (d$_6$-DMSO, δ): 3.62 (2H, broad s), 5.18 (1H, d, J=5 Hz), 5.38 (2H, s), 5.95 (1H, dd, J=5 and 8 Hz), 6.63 (1H, t, J=4 Hz), 7.25 (2H, d, J=9 Hz), 7.38 (2H, d, J=9 Hz), 7.65 (2H, d, J=8 Hz), 8.20 (2H, d, J=8 Hz), 8.23 (2H, broad s), 9.85 (1H, d, J=8 Hz)

(12) 7-[2-(4-Chlorophenoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 120° to 125° C. (dec.).

I.R. (Nujol): 3400, 3300, 3180, 1765, 1670, 1615, 1580, 1520, 1480 cm$^{-1}$

N.M.R. (d$_6$-DMSO, δ): 3.50-3.93 (4H, m), 4.12-4.48 (4H, m), 5.18 (1H, d, J=5 Hz), 5.88 (1H, dd, J=5 and 8 Hz), 7.28 (2H, d, J=9 Hz), 7.45 (2H, d, J=9 Hz), 8.30 (2H, broad s), 9.94 (1H, d, J=8 Hz)

(13) 7-[2-(3,4-Dichlorophenoxyimino)-2-(5-amino-1,2,4-thiadiazol-3-yl)acetamido]cephalosporanic acid (syn isomer), decomposed by 200° C.

I.R. (Nujol): 3600, 3400, 1770, 1720, 1680, 1530, 1250, 1120, 970 cm$^{-1}$

N.M.R. (d$_6$-DMSO, δ): 2.03 (3H, s), 3.60 (2H, m), 4.65 and 5.05 (2H, ABq, J=15 Hz), 5.27 (1H, d, J=5 Hz), 5.97 (1H, dd, J=5 and 8 Hz), 7.13-7.77 (3H, m), 8.35 (2H, m), 9.90 (1H, d, J=8 Hz)

(14) 7-[2-(3,4-Dichlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), decomposed by 160° C.

I.R. (Nujol): 3300, 3200, 1770, 1680, 1620, 1520, 1250, 1205, 1060 cm$^{-1}$

N.M.R. (d$_6$-DMSO, δ): 3.77 (2H, m), 4.28 and 4.68 (2H, ABq, J=14 Hz), 5.37 (1H, d, J=5 Hz), 5.97 (1H, dd, J=5 and 8 Hz), 7.16-7.80 (3H, m), 8.36 (2H, s), 9.60 (1H, s), 9.93 (1H, d, J=8 Hz)

(15) 4-Nitrobenzyl 7-[2-(3-trifluoromethylphenoxyimino)-2-(5-amino-1,2,4-thiadiazol-3-yl)acetamido]-3-cephem-4-carboxylate (syn isomer), mp 136° to 140° C. (dec.).

I.R. (Nujol): 3370, 3200, 1780, 1730, 1690, 1680, 1630, 1610, 1520, 1450, 1325, 1280, 1160, 1125, 975, 850, 740 cm$^{-1}$ N.M.R. (d$_6$-DMSO, δ): 3.7 (2H, m), 5.22 (1H, d, J=5 Hz), 5.37 (2H, s), 5.99 (1H, dd, J=5 and 8 Hz), 6.63 (1H, m), 7.50 (4H, broad s), 7.66 (2H, d, J=9 Hz), 8.20 (2H, d, J=9 Hz), 9.89 (1H, d, J=8 Hz)

(16) 7-[2-(3-Trifluoromethylphenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), decomposed by 164° C.

I.R. (Nujol): 3300, 3180, 1765, 1670, 1610, 1520, 1320, 1165, 1120, 1060, 930, 790, 700 cm$^{-1}$ N.M.R. (d$_6$-DMSO, δ): 3.73 (2H, m), 4.23 and 5.63 (2H, ABq, J=14 Hz), 5.27 (1H, d, J=5 Hz), 5.93 (1H, dd, J=5 and 8 Hz), 7.55 (4H, broad s), 8.34 (2H, broad s), 9.60 (1H, s), 9.99 (1H, d, J=8 Hz)

(17) 7-[2-(3-Ethoxycarbonylphenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), decomposed by 162° C.

I.R. (Nujol): 3350-3150, 1770, 1720-1660, 1620, 1520, 1290, 1270, 1100, 1060, 900, 760 cm$^{-1}$ N.M.R. (d$_6$-DMSO, δ): 1.32 (3H, t, J=7 Hz), 3.71 (2H, m), 4.25 and 4.60 (2H, ABq, J=14 Hz), 4.32 (2H, q, J=7 Hz), 5.23 (1H, d, J=5 Hz), 5.73 (1H, dd, J=5 and 8 Hz), 7.40-7.95 (4H, m), 8.67 (2H, broad s), 9.59 (1H, s), 9.98 (1H, d, J=8 Hz)

(18) 7-[2-(4-Fluorophenoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 145° to 150° C. (dec.).

I.R. (Nujol): 3300, 3200, 1770, 1670, 1610, 1520 cm$^{-1}$

N.M.R. (d$_6$-DMSO, δ): 3.50-3.83 (4H, m), 4.0-4.53 (4H, m), 5.13 (1H, d, J=4 Hz), 5.83 (1H, dd, J=4 and 8 Hz), 7.12 (2H, s), 7.23 (2H, s), 8.18 (2H, s), 9.77 (1H, d, J=8 Hz)

(19) 7-[2-(4-Fluorophenoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 150° to 155° C. (dec.).

I.R. (Nujol): 3300, 3200, 1770, 1720, 1670, 1620, 1520, 1500 cm$^{-1}$

N.M.R. (d$_6$-DMSO, δ): 3.57 (2H, broad s), 4.27 and 4.53 (2H, ABq, J=14 Hz), 5.23 (1H, d, J=8 Hz), 5.37 (2H, s), 5.93 (1H, dd, J=4 and 8 Hz), 7.25 (2H, s), 7.37 (2H, s), 8.32 (2H, s), 9.92 (1H, d, J=8 Hz)

(20) 7-[2-(4-Fluorophenoxyimino)-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp 165° to 170° C. (dec.).

I.R. (Nujol): 3300, 3200, 1770, 1710, 1620, 1540, 1520, 1500 cm$^{-1}$

N.M.R. (d$_6$-DMSO, δ): 3.67 and 3.90 (2H, ABq, J=18 Hz), 4.13 and 4.37 (2H, ABq, J=13 Hz), 4.73 (2H, s), 5.23 (1H, d, J=4 Hz), 5.90 (1H, dd, J=4 and 8 Hz), 7.08 (1H, d, J=10 Hz), 7.17 (2H, s), 7.28 (2H, s), 7.72 (1H, d, J=10 Hz), 8.23 (2H, s), 9.83 (1H, d, J=8 Hz)

(21) 7-[2-(4-Fluorophenoxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 140° to 145° C. (dec.).

I.R. (Nujol): 3300, 3200, 1770, 1700, 1620, 1520, 1500 cm$^{-1}$

N.M.R. (d$_6$-DMSO, δ): 2.90 (2H, t, J=6 Hz), 3.70 (2H, broad s), 4.40 (2H, t, J=6 Hz), 4.27 and 4.47 (2H, ABq, J=13 Hz), 5.17 (1H, d, J=4 Hz), 5.87 (1H, dd, J=4 and 8 Hz), 7.15 (2H, s), 7.25 (2H, s), 8.22 (2H, s), 9.83 (1H, d, J=8 Hz)

(22) 7-[2-(4-Fluorophenoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 145° to 150° C. (dec.).

I.R. (Nujol): 3450, 3350, 3150, 1780, 1705, 1670, 1610, 1510 cm$^{-1}$

N.M.R. (d$_6$-DMSO, δ): 3.66 and 3.84 (2H, ABq, J=18 Hz), 4.30 and 4.50 (2H, ABq, J=14 Hz), 5.00 (2H, d, J=5 Hz), 5.24 (1H, d, J=4 Hz), 5.20-5.40 (2H, m), 5.96 (1H, dd, J=4 and 8 Hz), 5.80-6.20 (1H, m), 7.28 (2H, s), 7.34 (2H, s), 8.32 (2H, s), 9.96 (1H, d, J=8 Hz)

(23) 7-[2-(4-Fluorophenoxyimino)-2-(5-amino-1,2,4-thiadiazol-3-yl)acetamido]cephalosporanic acid (syn isomer), mp 156° to 161° C. (dec.).

I.R. (Nujol): 3450, 3300, 3200, 1770, 1730, 1680, 1610, 1510, 1500 cm$^{-1}$

N.M.R. (d$_6$-DMSO, δ): 2.04 (3H, s), 3.52 and 3.68 (2H, ABq, J=18 Hz), 4.74 and 5.02 (2H, ABq, J=14 Hz), 5.26 (1H, d, J=4 Hz), 5.94 (1H, dd, J=4 and 8 Hz), 7.26 (2H, s), 7.34 (2H, s), 8.30 (2H, s), 9.94 (1H, d, J=8 Hz)

(24) 7-[2-Phenoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 175° to 180° C. (dec.).

I.R. (Nujol): 3300, 3200, 1775, 1680, 1615, 1585, 1520 cm$^{-1}$

(25) 7-[2-Phenoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 150° to 155° C. (dec.).

I.R. (Nujol): 3300, 3200, 1770, 1680, 1620, 1590, 1520 cm$^{-1}$

(26) 7-[2-(3-Trifluoromethylphenoxyimino)-2-(5-amino-1,2,4-thiadiazol-3-yl)acetamido]-3-cephem-4-carboxylic acid (syn isomer), which is decomposed by 193° C.

I.R. (Nujol): 3450, 3320, 3200, 1770, 1710, 1665, 1630, 1560, 1515, 1325, 1170, 1110, 940 cm$^{-1}$

(27) 7-[2-Phenoxyimino-2-(5-amino-1,2,4-thiadiazol-3-yl)acetamido]-3-cephem-4-carboxylic acid (syn isomer), mp 168° to 170° C. (dec.).

I.R. (Nujol): 3400, 3200, 1780, 1660, 1620, 1600, 1590, 1540 cm$^{-1}$

(28) 7-[2-(4-chlorophenoxyimino)-2-(5-amino-1,2,4-thiadiazol-3-yl)acetamido]-3-cephem-4-carboxylic acid (syn isomer), mp 145° to 150° C. (dec.).

I.R. (Nujol): 3400, 3260, 3180, 1775, 1675, 1625, 1600, 1520, 1480 cm$^{-1}$

(29) 7-[2-(4-Fluorophenoxyimino)-2-(5-amino-1,2,4-thiadiazol-3-yl)acetamido]-3-cephem-4-carboxylic acid (syn isomer), mp 130° to 135° C. (dec.).

I.R. (Nujol): 3400, 3270, 3180, 1765, 1675, 1605, 1500 cm$^{-1}$

(30) 7-[2-Phenoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 180° to 185° C. (dec.).

I.R. (Nujol): 3300, 3250, 1760, 1670, 1620, 1590, 1520 cm$^{-1}$

EXAMPLE 5

To a cold solution of phosphorus pentachloride (2.08 g) in methylene chloride (45 ml) was added 2-(t-butoxycarbonylmethoxyimino)-2-(5-amino-1,2,4-thiadiazol-3-yl)acetic acid (syn isomer) (2.51 g) at −17° C. and the mixture was stirred for 50 minutes at the same temperature. On the other hand, a mixture of 7-amino-3-(tetrazolo[1,5-b]pyridazin-6-yl)thiomethyl-3-cephem-4-carboxylic acid (3.34 g) and trimethylsilylacetamide (12 g) in methylene chloride (45 ml) was warmed to make a clear solution and then cooled to −20° C. The solution was added to the above activated mixture and the mixture was stirred for 1 hour at −10° to −15° C. The reaction mixture was evaporated and to the residue were added ethyl acetate and an aqueous solution of sodium bicarbonate. The aqueous layer was separated out, adjusted to pH 3 to 4 with 10% hydrochloric acid and extracted with ethyl acetate. The extract was dried over magnesium sulfate and evaporated under reduced pressure. The residue was triturated with diethyl ether to give 7-[2-(t-butoxycarbonylmethoxyimino)-2-(5-amino-1,2,4-thiadiazol-3-yl)acetamido]-3-(tetrazolo[1,5-b]pyridazin-6-yl)thiomethyl-3-cephem-4-carboxylic acid (syn isomer) (2.4 g), mp 125° to 130° C. (dec.).

I.R. (Nujol): 3400, 3300, 3180, 1770, 1720, 1680, 1620, 1525 cm$^{-1}$

N.M.R. (d$_6$-DMSO, δ): 1.47 (9H, s), 3.73 (2H, broad s), 4.28 and 4.60 (2H, ABq, J=13 Hz), 4.65 (2H, s), 5.18 (1H, d, J=5 Hz), 5.87 (1H, dd, J=5 and 8 Hz), 7.78 (1H, d, J=10 Hz), 8.17 (2H, broad s), 8.62 (1H, d, J=10 Hz), 9.55 (1H, d, J=8 Hz)

EXAMPLE 6

The following compounds were obtained according to similar manners to those of Examples 1 to 3, 5 and 7 to 12.

(1) 7-[2-{3-(N-t-Butoxycarbonylamino)propoxyimino}-2-(5-amino-1,2,4-thiadiazol-3-yl)acetamido]-3-methyl-3-cephem-4-carboxylic acid (syn isomer), mp 114° to 119° C. (dec.).

N.M.R. (d$_6$-DMSO, δ): 1.40 (9H, s), 1.74 (3H, s), 1.80 (2H, m), 3.00 (4H, m), 4.14 (2H, m), 5.10 (1H, d, J=5 Hz), 5.72 (1H, dd, J=5 and 8 Hz), 6.70 (1H, broad s), 8.10 (2H, broad s), 9.44 (1H, d, J=8 Hz)

(2) 4-Nitrobenzyl 7-[2-{3-(N-t-butoxycarbonylamino)propoxyimino}-2-(5-amino-1,2,4-thiadiazol-3-yl)acetamido]-3-chloro-3-cephem-4-carboxylate (syn isomer), mp 91° to 100° C. (dec.).

N.M.R. (d$_6$-DMSO+D$_2$O, δ): 1.38 (9H, s), 1.80 (2H, m), 3.06 (2H, m), 3.7–4.3 (4H, m), 5.33 (1H, d, J=5 Hz), 5.49 (2H, s), 5.95 (1H, d, J=5 Hz), 7.74 (2H, d, J=9 Hz), 8.92 (2H, d, J=9 Hz)

(3) 7-[2-{3-(N-t-Butoxycarbonylamino)propoxyimino}-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 107° to 112° C. (dec.).

N.M.R. (d$_6$-DMSO+D$_2$O, δ): 1.32 (9H, s), 1.34 (9H, s), 1.80 (2H, m), 3.10 (2H, m), 3.30 (2H, m), 3.70 (2H, m), 4.0–4.5 (6H, m), 5.13 (1H, d, J=5 Hz), 5.83 (1H, d, J=5 Hz).

(4) 4-Nitrobenzyl 7-[2-allyloxyimino-2-(5-amino-1,2,4-thiadiazol-3-yl)acetamido]-3-cephem-4-carboxylate (syn isomer), mp 125° to 130° C. (dec.).

I.R. (Nujol): 3300, 1770, 1720, 1680, 1630, 1610, 1520 cm$^{-1}$

N.M.R. (d$_6$-DMSO, δ): 3.60 (2H, broad s), 4.57–4.83 (2H, m), 5.17 (1H, d, J=4 Hz), 5.0–5.35 (2H, m), 5.40 (2H, s), 5.93 (1H, dd, J=4 and 8 Hz), 5.87–6.17 (1H, m), 6.63 (1H, t, J=3 Hz), 7.70 (2H, d, J=9 Hz), 8.10 (2H, s), 8.23 (2H, d, J=9 Hz), 9.57 (1H, d, J=8 Hz)

(5) 7-[2-(2,2,2-Trifluoroethoxyimino)-2-(5-amino-1,2,4-thiadiazol-3-yl)acetamido]cephalosporanic acid (syn isomer), mp 185° to 195° C. (dec.).

I.R. (Nujol): 3470, 3330, 3210, 3060, 1770, 1735, 1700, 1670, 1620, 1555, 1520 cm$^{-1}$ N.M.R. (d$_6$-DMSO, δ): 2.00 (3H, s), 3.53 (2H, broad s), 4.65 and 4.87 (2H, ABq, J=9 Hz), 4.70 and 4.93 (2H, ABq, J=13 Hz), 5.12 (1H, d, J=5 Hz), 5.78 (1H, dd, J=5 and 8 Hz), 8.12 (2H, broad s), 9.62 (1H, d, J=8 Hz)

(6) 7-[2-(2,2,2-Trifluoroethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 125° to 130° C. (dec.).

I.R. (Nujol): 3300, 3200, 1770, 1680, 1620, 1520 cm$^{-1}$

N.M.R. (d$_6$-DMSO, δ): 3.68 (2H, broad s), 4.30 and 4.40 (2H, ABq, J=13 Hz), 4.68 and 4.92 (2H, ABq, J=9 Hz), 4.87–5.10 (2H, m), 5.15 (1H, d, J=5 Hz), 5.17–5.47 (2H, m), 5.83 (1H, dd, J=5 and 8 Hz), 5.67–6.27 (1H, m), 8.25 (2H, broad s), 9.77 (1H, d, J=8 Hz)

(7) 7-[2-(2,2,2-Trifluoroethoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 145° to 150° C. (dec.).

I.R. (Nujol): 3300, 3200, 1770, 1680, 1620, 1525 cm$^{-1}$

N.M.R. (d$_6$-DMSO, δ): 3.70 (2H, broad s), 3.95 (3H, s), 4.32 (2H, broad s), 4.68 and 4.92 (2H, ABq, J=9 Hz), 5.15 (1H, d, J=5 Hz), 5.85 (1H, dd, J=5 and 8 Hz), 8.25 (2H, broad s), 9.75 (1H, d, J=8 Hz)

(8) 7-[2-{2-(N-t-Butoxycarbonylamino)ethoxyimino}-2-(5-amino-1,2,4-thiadiazol-3-yl)acetamido]-2-methyl-3-cephem-4-carboxylic acid (syn isomer), mp 215° to 220° C. (dec.).

I.R. (Nujol): 3230, 3150, 1775, 1680, 1620, 1525 cm$^{-1}$

N.M.R. (d$_6$-DMSO+D$_2$O, δ): 1.37 (9H, s), 1.43 (3H, d, J=7 Hz), 3.0–3.5 (2H, m), 4.0–4.4 (2H, m), 5.10 (1H, d, J=4.5 Hz), 5.8–6.1 (1H, m), 6.53 (1H, d, J=6.9 Hz)

(9) 7-[2-{2-(N-t-Butoxycarbonylamino)ethoxyimino}-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 181° to 186° C. (dec.).

I.R. (Nujol): 3320,1780, 1680, 1620, 1520, 1165 cm$^{-1}$

N.M.R. (d$_6$-DMSO+D$_2$O, δ): 1.32 (18H, s), 3.07–3.52 (4H, m), 3.7 (2H, broad s), 4.0–4.5 (6H, m), 5.15 (1H, d, J=4.5 Hz), 5.85 (1H, d, J=4.5 Hz), 8.23 (2H, broad s)

(10) 7-[2-Trityloxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 147° to 161° C. (dec.).

I.R. (Nujol): 3420, 1780, 1680, 1615, 1525 cm$^{-1}$

N.M.R. (d$_6$-DMSO+D$_2$O, δ): 2.72 (3H, s), 3.73 (2H, broad s), 4.30 and 4.67 (2H, ABq, J=14 Hz), 5.35 (1H, d, J=5.0 Hz), 6.15 (1H, d, J=5.0 Hz), 7.50 (15H, s)

(11) 7-[2-{2-(N-t-Butoxycarbonylamino)ethoxyimino}-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 105° C. (dec.).

I.R. (Nujol): 3305, 3160, 1770,1670, 1520, 1245 cm$^{-1}$

N.M.R. (d$_6$-DMSO+D$_2$O, δ): 1.37 (9H, s), 3.0–3.5 (2H, m), 3.72 (2H, broad s), 3.9–4.3 (2H, m), 4.1–4.6 (2H, m), 5.13 (1H, d, J=4.5 Hz), 5.33 (2H, s), 5.7–6.0 (1H, m)

(12) 7-[2-(t-Butoxycarbonylmethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 145° C. (dec.).

I.R. (Nujol): 3300, 3175, 1770, 1720, 1680, 1620, 1520 cm$^{-1}$

N.M.R. (d$_6$-DMSO, δ): 1.50 (9H, s), 3.73 (2H, broad s), 4.33 and 4.58 (2H, ABq, J=13 Hz), 4.65 (2H, s), 5.17

(1H, d, J=4 Hz), 5.85 (1H, dd, J=4 and 8 Hz), 8.18 (2H, s), 9.50 (1H, d, J=8 Hz), 9.53 (1H, s)

(13) 7-[2-(t-Butoxycarbonylmethoxyimino)-2-(5-amino-1,2,4-thiadiazol-3-yl)acetamido]cephalosporanic acid (syn isomer), mp 125° to 130° C. (dec.).

I.R. (Nujol): 3300, 3200, 1770, 1720, 1680, 1620, 1520 cm$^{-1}$

N.M.R. (d$_6$-DMSO, δ): 1.50 (9H, s), 2.10 (3H, s), 3.62 (2H, broad s), 4.68 (2H, s), 4.77 and 5.03 (2H, ABq, J=13 Hz), 5.20 (1H, d, J=4 Hz), 5.88 (1H, dd, J=4 and 8 Hz), 8.18 (2H, s), 9.55 (1H, d, J=8 Hz)

(14) 7-[2-(t-Butoxycarbonylmethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 130° to 135° C. (dec.).

I.R. (Nujol): 3400, 3280, 3180, 1770, 1720, 1680, 1620, 1520 cm$^{-1}$

N.M.R. (d$_6$-DMSO, δ): 1.42 (9H, s), 3.67 (2H, broad s), 4.27 and 4.43 (2H, ABq, J=13 Hz, )4.62 (2H, s), 4.87–5.07 (2H, m), 5.10 (1H, d, J=5 Hz), 5.13–5.43 (2H, m), 5.82 (1H, dd, J=5 and 8 Hz), 5.60–6.20 (1H, m), 8.10 (2H, broad s), 9.47 (1H, d, J=8 Hz)

(15) 7-[2-(t-Butoxycarbonylmethoxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 110° to 115° C. (dec.).

I.R. (Nujol): 3300, 3200, 1775, 1680, 1620, 1520 cm$^{-1}$

N.M.R. (d$_6$-DMSO, δ): 1.32 (9H, s), 1.42 (9H, s), 3.33 (2H, broad s), 3.53–3.80 (2H, m), 4.13–4.47 (4H, m), 4.58 (2H, s), 5.08 (1H, d, J=5 Hz), 5.78 (1H, dd, J=5 and 8 Hz), 8.07 (2H, broad s), 9.45 (1H, d, J=8 Hz)

(16) 7-[2-(t-Butoxycarbonylmethoxyimino)-2-(5-amino-1,2,4-thiadiazol-3-yl)acetamido]-3-(1-phenyl-1H-tetrazol-5-yl)thiomethyl-3-cephem-4-carboxylic acid (syn isomer), mp 135° to 140° C. (dec.).

I.R. (Nujol): 3400, 3300, 3200, 1775, 1720, 1685, 1620, 1525, 1500 cm$^{-1}$

N.M.R. (d$_6$-DMSO, δ): 1.43 (9H, s), 3.70 (2H, broad s), 4.32 and 4.57 (2H, ABq, J=13 Hz), 4.65 (2H, s), 5.12 (1H, d, J=5 Hz), 5.85 (1H, dd, J=5 and 8 Hz), 7.67 (5H, s), 8.17 (2H, broad s), 9.50 (1H, d, J=8 Hz)

(17) 7-[2-{3-(N-t-Butoxycarbonylamino)propoxyimino}-2-(5-amino-1,2,4-thiadiazol-3-yl)acetamido]-2-methyl-3-cephem-4-carboxylic acid (syn isomer), mp 133° to 146° C. (dec.).

I.R. (Nujol): 3280, 3170, 1775, 1685, 1670, 1625, 1520 cm$^{-1}$

N.M.R. (d$_6$-DMSO+D$_2$O, δ): 1.40 (9H, s), 1.46 (3H, d, J=7 Hz), 1.56–2.06 (2H, m), 3.03 (2H, t, J=7 Hz), 3.1–4.1 (1H, m), 4.23 (2H, t, J=7 Hz), 5.13 (1H, d, J=5 Hz), 5.97 (1H, d, J=5 Hz), 6.65 (1H, d, J=6.5 Hz)

(18) 7-[2-Allyloxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 150° to 155° C. (dec.).

I.R. (Nujol): 3300, 3200, 1775, 1670, 1620, 1520 cm$^{-1}$

(19) 7-[2-Allyloxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 180° to 185° C. (dec.).

I.R. (Nujol): 3300, 3200, 1770, 1670, 1620, 1525 cm$^{-1}$

(20) 7-[2-(2,2,2-Trifluoroethoxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), powder.

(21) 7-[2-(2,2,2-Trifluoroethoxyimino)-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp 150° to 155° C. (dec.).

I.R. (Nujol): 3300, 3180, 1760, 1670, 1610, 1520 cm$^{-1}$

(22) 7-[2-(2,2,2-Trifluoroethoxyimino)-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 165° to 170° C. (dec.).

I.R. (Nujol): 3420, 3300, 3190, 1770, 1705, 1670, 1620, 1525 cm$^{-1}$

(23) 7-[2-{3-(N-t-Butoxycarbonylamino)propoxyimino}-2-(5-amino-1,2,4-thiadiazol-3-yl)acetamido]-3-chloro-3-cephem-4-carboxylic acid (syn isomer), mp 111° to 115° C. (dec.).

I.R. (Nujol): 3300–3100, 1780, 1690–1660, 1520, 1270 cm$^{-1}$

(24) 7-[2-Allyloxyimino-2-(5-amino-1,2,4-thiadiazol-3-yl)acetamido]-3-cephem-4-carboxylic acid (syn isomer), mp 160° to 165° C. (dec.).

(25) 7-[2-(3-Aminopropoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 184° to 196° C. (dec.).

I.R. (Nujol): 3400–3100, 1760, 1660, 1610, 1520, 1170, 1060, 1010 cm$^{-1}$

(26) 7-[2-(2-Aminoethoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 190° to 198° C. (dec.).

I.R. (Nujol): 3250, 3160, 1760, 1650, 1615, 1522, 1020 cm$^{-1}$

(27) 7-[2-Carboxymethoxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 170° to 175° C. (dec.).

I.R. (Nujol): 3250, 3150, 1770, 1710, 1680, 1610, 1520 cm$^{-1}$

(28) 7-[2-Carboxymethoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 145° to 150° C. (dec.).

I.R. (Nujol): 3400, 3300, 3200, 1765, 1720, 1680, 1620, 1520 cm$^{-1}$

(29) 7-[2-Carboxymethoxyimino-2-(5-amino-1,2,4-thiadiazol-3-yl)acetamido]cephalosporanic acid (syn isomer), mp 160° to 165° C. (dec.).

I.R. (Nujol): 3300, 3200, 1770, 1720, 1680, 1520 cm$^{-1}$

(30) 7-[2-(2-Aminoethoxyimino)-2-(5-amino-1,2,4-thiadiazol-3-yl)acetamido]-2-methyl-3-cephem-4-carboxylic acid (syn isomer), mp 190° to 195° C. (dec.).

I.R. (Nujol): 3300, 3150, 1760, 1660, 1575, 1520, 1400 cm$^{-1}$

(31) 7-[2-(3-Aminopropoxyimino)-2-(5-amino-1,2,4-thiadiazol-3-yl)acetamido]-2-methyl-3-cephem-4-carboxylic acid (syn isomer), mp 182° to 187° C. (dec.).

I.R. (Nujol): 3260, 3150, 1758, 1660, 1616, 1575, 1520, 1400 cm$^{-1}$

(32) 7-[2-Carboxymethoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3180, 1765, 1720, 1680, 1615, 1520 cm$^{-1}$

(33) 7-[2-(3-Aminopropoxyimino)-2-(5-amino-1,2,4-thiadiazol-3-yl)acetamido]-3-methyl-3-cephem-4-carboxylic acid (syn isomer), mp 175° to 195° C. (dec.).

I.R. (Nujol): 3300–3100, 1770–1740, 1660, 1620, 1570, 1520, 1280, 1170, 1060, 1020 cm$^{-1}$

(34) 7-[2-(3-Aminopropoxyimino)-2-(5-amino-1,2,4-thiadiazol-3-yl)acetamido]-3-chloro-3-cephem-4-carboxylic acid (syn isomer), mp 190° to 205° C. (dec.).

I.R. (Nujol): 3400-3150, 1760, 1660, 1630-1590, 1520, 1340, 1170, 1030 cm$^{-1}$

(35) 7-[2-(2-Aminoethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 182° to 187° C. (dec.).

I.R. (Nujol): 3350, 3150, 1760, 1660, 1625, 1565, 1520 cm$^{-1}$

(36) 7-[2-Carboxymethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 185° to 190° C. (dec.).

I.R. (Nujol): 3250, 1755, 1660, 1590, 1520 cm$^{-1}$

(37) 7-[2-(2,2,2-Trifluoroethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 185° to 190° C. (dec.).

I.R. (Nujol): 3300, 3170, 1760, 1670, 1615, 1500 cm$^{-1}$

(38) 7-[2-Carboxymethoxyimino-2-(5-amino-1,2,4-thiadiazol-3-yl)acetamido]-3-(1-phenyl-1H-tetrazol-5-yl)thiomethyl-3-cephem-4-carboxylic acid (syn isomer), mp 155° to 160° C. (dec.).

I.R. (Nujol): 3400, 3300, 3180, 1765, 1720, 1680, 1615, 1520, 1495 cm$^{-1}$

(39) 7-[2-Hydroxyimino-2-(5-amino-1,2,4-thiadiazol-3-yl)acetamido]-3-(5-methyl-1,3,4-thiadiazol-2-yl)-thiomethyl-3-cephem-4-carboxylic acid (syn isomer), mp 153° to 162° C. (dec.).

I.R. (Nujol): 3260, 3160, 1763, 1665, 1608, 1520 cm$^{-1}$

(40) Pivaloyloxymethyl 7-[2-hydroxyimino-2-(5-amino-1,2,4-thiadiazol-3-yl)acetamido]-3-(5-methyl-1,3,4-thiadiazol-2-yl)thiomethyl-3-cephem-4-carboxylate (sym isomer), mp 132° to 135° C. (dec.).

I.R. (Nujol): 3270, 3160, 1775, 1745, 1675, 1610, 1520, 1115 cm$^{-1}$

EXAMPLE 7

To a cold solution of phosphorus pentachloride (2.5 g) in methylene chloride (60 ml) was added 2-(2-cyclopenten-1-yl)oxyimino-2-(5-amino-1,2,4-thiadiazol-3-yl)acetic acid (syn isomer) (2.54 g) at −15° C. and the mixture was stirred for 45 minutes at the same temperature. On the other hand, a mixture of 7-amino-3-(1,3,4-thiadiazol-2-yl)thiomethyl-3-cephem-4-carboxylic acid (4.0 g) and trimethylsilylacetamide (12 g) in methylene chloride (60 ml) was warmed to make a clear solution and then cooled to −15° C. The solution was added to the above activated mixture and the mixture was stirred for 0.5 at 0° to −5° C. The reaction mixture was poured into cold aqueous solution (150 ml) of sodium bicarbonate (7.1 g) and stirred at ambient temperature for 15 minutes. The aqueous layer was separated out and added to ethyl acetate. The mixture was adjusted to pH 3 with 10% hydrochloric acid and then filtered. The ethyl acetate layer was separated from the filtrate, washed with a saturated aqueous solution of sodium chloride, dried over magnesium sulfate and evaporated to dryness. The residue was triturated with diethyl ether and precipitates were collected by filtration and then dried to give a crude product (1.8 g). This product was dissolved in an aqueous solution of sodium bicarbonate and the solution was adjusted to pH 3 with 10% hydrochloric acid. Precipitates were collected by filtration, washed with water and then dried to give 7-[2-(2-cyclopenten-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer) (1.4 g), mp 155° to 160° C.

I.R. (Nujol): 3300, 3200, 1770, 1670, 1620, 1520 cm$^{-1}$

N.M.R. (d$_6$-DMSO, δ): 2.0-2.50 (4H, m), 3.70 (2H, broad s), 4.30 and 4.57 (2H, ABq, J=13 Hz), 5.13 (1H, d, J=4 Hz), 5.27-5.43 (1H, m), 5.80 (1H, dd, J=4 and 8 Hz), 5.83-6.20 (2H, m), 8.08 (2H, s), 9.45 (1H, d, J=8 Hz), 9.50 (1H, s).

EXAMPLE 8

To a cold solution of phosphorus pentachloride (2.5 g) in methylene chloride (60 ml) was added 2-(2-cyclopenten-1-yl)oxyimino-2-(5-amino-1,2,4-thiadiazol-3-yl)acetic acid (syn isomer) (2.54 g) at −15° C. and the mixture was stirred for 30 minutes at the same temperature. On the other hand, a mixture of 7-amino-3-cephem-4-carboxylic acid (2.2 g) and trimethylsilylacetamide (11 g) in methylene chloride (60 ml) was warmed to make a clear solution and then cooled to −15° C. To the solution was added the above activated mixture and the mixture was stirred for 20 minutes at −5° C. The reaction mixture was poured into cold aqueous solution (150 ml) of sodium bicarbonate (7 g) and stirred at ambient temperature for an hour. The aqueous layer was separated out and added to ethyl acetate. The mixture was adjusted to pH 3 with 10% hydrochloric acid and extracted with ethyl acetate. The extract was washed with a saturated aqueous solution of sodium chloride, dried over magnesium sulfate and evaporated to dryness. Precipitated crystals were collected by filtration, washed successively with ethyl acetate and diethyl ether to give a crude product (1.5 g). This product was dissolved in an aqueous solution of sodium bicarbonate and the pH was adjusted to 2 with dil. hydrochloric acid. Precipitates were collected by filtration, washed with water and then dried. The obtained product (1.2 g) was dissolved in aqueous acetone, treated with activated charcoal and then evaporated. The precipitates were collected by filtration, washed with water and dried to give 7-[2-(2-cyclopenten-1-yl)oxyimino-2-(5-amino-1,2,4-thiadiazol-3-yl)acetamido]-3-cephem-4-carboxylic acid (syn isomer) (0.93 g). mp 180° to 185° C. (dec.).

I.R. (Nujol): 3500, 3430, 3300, 3200, 1770, 1690, 1660, 1640, 1620, 1580, 1510 cm$^{-1}$ N.M.R. (d$_6$-DMSO, δ): 1.87-2.50 (4H, m), 3.60 (2H, broad s), 5.07 (1H, d, J=8 Hz), 5.27-5.50 (1H, m), 5.80 (1H, dd, J=4 and 8 Hz), 5.87-6.23 (2H, m), 6.47 (1H, broad s), 8.10 (2H, s), 9.47 (1H, d, J=8 Hz)

EXAMPLE 9

To a cold solution of phosphorus pentachloride (1.25 g) in methylene chloride (30 ml) was added 2-(2-cyclohexen-1-yl)oxyimino-2-(5-amino-1,2,4-thiadiazol-3-yl)acetic acid (syn isomer) (1.34 g) at −15° C. and the mixture was stirred for 30 minutes at the same temperature. On the other hand, a mixture of 7-amino-3-(1,3,4-thiadiazol-2-yl)thiomethyl-3-cephem-4-carboxylic acid (1.98 g) and trimethylsilylacetamide (6 g) in methylene chloride (30 ml) was warmed to make a clear solution and then cooled to −15° C. The solution was added to the above activated mixture and the mixture was stirred for 0.5 hour at 0° to 5° C. The reaction mixture was poured into cold aqueous solution (100 ml) of sodium bicarbonate (4.03 g) and stirred at ambient temperature for 30 minutes. The aqueous layer was separated, added to ethyl acetate, adjusted to pH 4 with 10% hydrochloric acid and extracted with ethyl acetate. The extract was dried over magnesium sulfate and evaporated to dryness. The residue was triturated with diethyl ether, collected by filtration and dried to give a crude product (400 mg). This product was dissolved in an aqueous solution of sodium bicarbonate and the pH was adjusted to 2 with hydrochloric acid. Precipitates were collected by filtration, washed with water and then dried to give 7-[2-(2-cyclohexen-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer) (250 mg). mp 150° to 155° C. (dec.).

I.R. (Nujol): 3300, 3180, 1770, 1660, 1620, 1520 cm$^{-1}$

N.M.R. (d$_6$-DMSO, δ): 1.50–2.17 (6H, m), 3.70 (2H, broad s), 4.33 and 4.58 (2H, ABq, J=14 Hz), 4.67–4.83 (1H, m), 5.17 (1H, d, J=4 Hz), 5.83 (1H, dd, J=4 and 8 Hz), 5.60–6.12 (2H, m), 8.15 (2H, s) 9.53 (1H, d, J=8 Hz), 9.93 (1H, s)

EXAMPLE 10

To a cold solution of phosphorus pentachloride (1.50 g) in methylene chloride (30 ml) was added 2-(2-cyclohexen-1-yl)oxyimino-2-(5-amino-1,2,4-thiadiazol-3-yl)acetic acid (syn isomer) (1.61 g) at −15° C. The mixture was stirred for 30 minutes at −13° to −10° C. and evaporated and then to the residue was added tetrahydrofuran (20 ml). On the other hand, a mixture of 7-amino-3-(tetrazolo]1,5-b]pyridazin-6-yl)thiomethyl-3-cephem-4-carboxylic acid (2.86 g), sodium bicarbonate (2.52 g), water (80 ml) and acetone (45 ml) was cooled to 5° to 10° C. To the solution was added the above activated mixture. The mixture was stirred for 20 minutes at 5° to 10° C., allowed to warm to room temperature and then evaporated. To the residue was added ethyl acetate and the mixture was adjusted to pH 2 with 10% hydrochloric acid and then extracted with ethyl acetate. The extract was treated with activated charcoal (0.5 g), dried over magnesium sulfate and then evaporated. The residue was triturated with diethyl ether, collected by filtration to give a crude product (2.37 g). This product was dissolved in an aqueous solution of sodium bicarbonate and the pH was adjusted to 2 with hydrochloric acid. Precipitates were collected by filtration to give 7-[2-(2-cyclohexen-1-yl)oxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer) (2.28 g), mp 170° to 175° C. (dec.).

I.R. (Nujol): 3400, 3300, 3180, 1670, 1620, 1520 cm$^{-1}$

N.M.R. (d$_6$-DMSO, δ): 1.40–2.20 (6H, m), 3.73 (2H, broad s), 4.27 and 4.65 (2H, ABq, J=13 Hz), 4.65–4.88 (1H, m), 5.18 (1H, d, J=5 Hz), 5.80 (1H, dd, J=5 and 8 Hz), 5.78–6.02 (2H, m), 7.80 (1H, d, J=10 Hz), 8.17 (2H, broad s), 8.60 (1H, d, J=10 Hz), 9.55 (1H, d, J=8 Hz)

EXAMPLE 11

To a cold solution of phosphorus pentachloride (1.5 g) in methylene chloride (30 ml) was added 2-cyclopentyloxyimino-2-(5-amino-1,2,4-thiadiazol-3-yl)acetic acid (syn isomer) (1.37 g) at −15° C. and the mixture was stirred for 30 minutes at −13° to −10° C. On the other hand, a mixture of 7-amino-3-(1,3,4-thiadiazol-2-yl)thiomethyl-3-cephem-4-carboxylic acid (2.18 g) and trimethylsilylacetamide (6 g) in methylene chloride (30 ml) was warmed to make a clear solution and then cooled to −20° C. The solution was added to the above activated mixture and the mixture was stirred for 0.5 hour at −10° C. The reaction mixture was poured into a cold saturated aqueous solution (60 ml) of sodium bicarbonate and stirred at ambient temperature for 30 minutes. The aqueous layer was separated out, added to ethyl acetate, adjusted to pH 2 to 3 with 10% hydrochloric acid and extracted with ethyl acetate. The extract was dried over magnesium sulfate and evaporated to dryness. The residue was washed with diethyl ether to give a crude product (2.62 g). This product was dissolved in an aqueous solution of sodium bicarbonate and the pH was adjusted to 2 with hydrochloric acid. Precipitates were collected by filtration to give 7-[2-cyclopentyloxyimino-2-(5-amino-1,2,4-thiadiazol-3-yl)acetamido]-3-(1,3,4-thiadiazol-2-yl)thiomethyl-3-cephem-4-carboxylic acid (syn isomer) (2.22 g). mp 140° to 145° C. (dec.).

I.R. (Nujol): 3400, 3300, 3200, 1770, 1670, 1620, 1525 cm$^{-1}$

N.M.R. (d$_6$-DMSO, δ): 1.33–2.10 (8H, m), 3.72 (2H, broad s), 4.33 and 4.58 (2H, ABq, J=13 Hz), 4.60–4.90 (1H, m), 5.17 (1H, d, J=5 Hz), 5.82 (1H, dd, J=5 and 8 Hz), 8.15 (2H, s), 9.52 (1H, d, J=8 Hz), 9.58 (1H, s).

EXAMPLE 12

To a cold solution of phosphorus pentachloride (1.25 g) in methylene chloride (25 ml) was added 2-cyclopentyloxyimino-2-(5-amino-1,2,4-thiadiazol-3-yl)acetic acid (syn isomer) (1.28 g) at −15° C. and the mixture was stirred for 30 minutes at −13° to −10° C. On the other hand, a mixture of 7-amino-3-cephem-4-carboxylic acid (1.1 g), and trimethylsilylacetamide (5.5 g) in methylene chloride (25 ml) was warmed to make a clear solution and then cooled to −15° C. The solution was added to the above activated mixture and the mixture was stirred for 0.5 hour at −10° C. The reaction mixture was poured into a saturated aqueous solution (55 ml) of sodium bicarbonate and stirred at ambient temperature for 30 minutes and then evaporated to remove methylene chloride. The residue was washed with ethyl acetate and to the aqueous layer was added ethyl acetate. The mixture was adjusted to pH 3 with 10% hydrochloric acid and extracted with ethyl acetate. The extract was dried over magnesium sulfate, treated with activated charcoal (1.0 g) and then evaporated. The residue was washed with diethyl ether to give a crude product (1.03 g). This product was dissolved in an aqueous solution of sodium bicarbonate and the solution was adjusted to pH 3 with 10% hydrochloric acid. Precipitates were collected by filtration to give 7-[2-cyclopentyloxyimino-2-(5-amino-1,2,4-thiadiazol-3-yl)acetamido]-3-cephem-4-carboxylic acid (syn isomer) (860 mg). mp 170° to 175° C.

I.R. (Nujol): 3520, 3420, 3320, 3220, 3160, 1770, 1685, 1655, 1635, 1625, 1570, 1505 cm$^{-1}$ N.M.R. (d$_6$-DMSO, δ): 1.33–2.07 (8H, m), 3.43–3.77 (2H, m), 4.60–4.93 (1H, m), 5.15 (1H, d, J=5 Hz), 5.90 (1H, dd, J=5 and 8 Hz), 6.43–6.67 (1H, m), 8.23 (2H, broad s), 9.63 (1H, d, J=8 Hz)

EXAMPLE 13

The following compounds were obtained according to similar manners to those of Examples 1 to 3, 5 and 7 to 12.

(1) 7-[2-(2-Cyclopenten-1-yl)oxyimino-2-(5-amino-1,2,4-thiadiazol-3-yl)acetamido]cephalosporanic acid (syn isomer). mp 154° to 159° C. (dec.).

I.R. (Nujol) 3300, 1770, 1720, 1670, 1620, 1520 cm$^{-1}$

N.M.R. (d$_6$-DMSO, δ): 2.0 (3H, s), 2.0–2.40 (4H, m), 3.52 (2H, broad s), 4.70 and 4.97 (2H, ABq, J=14 Hz), 5.12 (1H, d, J=4 Hz), 5.27–5.40 (1H, m), 5.82 (1H, dd, J=4 and 8 Hz), 5.83–6.17 (2H, m), 8.13 (2H, s), 9.50 (1H, d, J=8 Hz)

(2) 7-[2-(2-Cyclopenten-1-yl)oxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 155° to 160° C. (dec.).

I.R. (Nujol): 3300, 1770, 1670, 1620, 1520 cm$^{-1}$

N.M.R. (d$_6$-DMSO, δ): 1.90–2.30 (4H, m), 3.62 (2H, broad s), 3.88 (3H, s), 4.25 (2H, broad s), 5.07 (1H, d, J=4 Hz), 5.20–5.40 (1H, m), 5.80 (1H, dd, J=4 and 8 Hz), 5.83–6.17 (2H, m), 8.08 (2H, s), 9.47 (1H, d, J=8 Hz)

(3) 7-[2-(2-Cyclopenten-1-yl)oxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer). mp 155° to 160° C. (dec.).

I.R. (Nujol): 3300, 3200, 1770, 1720. 1670, 1620, 1520 cm$^{-1}$

N.M.R. (d$_6$-DMSO, δ): 1.83–2.50 (4H, m), 3.67 (2H, broad s), 4.27 and 4.48 (2H, ABq, J=14 Hz), 5.17 (1H, d, J=4 Hz), 5.30 (2H, s), 5.27–5.50 (1H, m), 5.82 (2H, dd, J=4 and 8 Hz), 5.83–6.20 (2H, m), 8.17 (2H, s), 9.50 (1H, d, J=8 Hz)

(4) 7-[2-(2-Cyclopenten-1-yl)oxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer). mp 150° to 155° C. (dec.).

I.R. (Nujol): 3300, 3200, 1770, 1720, 1670, 1620, 1520 cm$^{-1}$

N.M.R. (d$_6$-DMSO, δ): 1.90–2.50 (4H, m), 2.97 (2H, t, J=6 Hz), 3.73 (2H, broad s), 4.30 and 4.50 (2H, ABq, J=14 Hz), 4.52 (2H, t, J=6 Hz), 5.20 (1H, d, J=4 Hz), 5.30–5.57 (1H, m), 5.90 (1H, dd, J=4 and 8 Hz), 5.93–6.33 (2H, m), 8.33 (2H, s), 9.77 (1H, d, J=8 Hz)

(5) 7-[2-(2-Cyclopenten-1-yl)oxyimino-2-(5-amino-1,2,4-thiadiazol-3-yl)acetamido]-3-(1-allyl-1H-tetrazol-5-yl)thiomethyl-3-cephem-4-carboxylic acid (syn isomer). mp 160° to 165° C. (dec.).

I.R. (Nujol): 3300, 1770, 1670, 1620, 1520 cm$^{-1}$

N.M.R. (d$_6$-DMSO, δ): 1.93–2.33 (4H, m), 3.60 (2H, broad s), 4.22 and 4.37 (2H, ABq, J=13 Hz), 4.83–5.0 (2H, m), 5.0–5.40 (4H, m), 5.60–6.17 (4H, m), 8.07 (2H, s), 9.47 (1H, d, J=8 Hz)

(6) 7-[2-(2-Cyclopenten-1-yl)oxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer). mp 170° to 175° C. (dec.).

I.R. (Nujol): 3400, 3300, 3190, 1770, 1670, 1615, 1620 cm$^{-1}$

N.M.R. (d$_6$-DMSO, δ): 1.90–2.43 (4H, m), 3.68 (2H, broad s), 4.22 and 4.58 (2H, ABq, J=13 Hz), 5.10 (1H, d, J=5 Hz), 5.20–5.47 (1H, m), 5.78 (1H, dd, J=5 and 8 Hz), 5.80–6.20 (2H, m), 7.75 (1H, d, J=10 Hz), 8.13 (2H, broad s), 8.55 (1H, d, J=10 Hz), 9.52 (1H, d, J=8 Hz)

(7) 7-[2-(2-Cyclopenten-1-yl)oxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer). mp 95° to 100° C. (dec.).

I.R. (Nujol): 3300, 3190, 1770, 1680, 1620, 1520 cm$^{-1}$

N.M.R. (d$_6$-DMSO, δ): 1.40 (9H, s), 2.07–2.50 (4H, m), 3.30–3.57 (2H, m), 3.67–3.87 (2H, m), 4.27–4.57 (4H, m), 5.17 (1H, d, J=5 Hz), 5.23–5.57 (1H, m), 5.70–6.30 (3H, m), 8.17 (2H, broad s), 9.53 (1H, d, J=8 Hz)

(8) 7-[2-(2-Cyclohexen-1-yl)oxyimino-2-(5-amino-1,2,4-thiadiazol-3-yl)acetamido]-3-cephem-4-carboxylic acid (syn isomer). mp 175° to 180° C. (dec.).

I.R. (Nujol): 3300, 3200, 1770, 1670, 1630, 1520 cm$^{-1}$

N.M.R. (d$_6$-DMSO, δ): 1.50–2.13 (6H, m), 3.63 (2H, broad s), 4.60–4.83 (1H, m), 5.12 (1H, d, J=4 Hz), 5.77–6.0 (3H, m), 6.50 (1H, t, J=3Hz), 8.15 (2H, s), 9.55 (1H, d, J=8 Hz)

(9) 7-[2-(2-Cyclohexen-1-yl)oxyimino-2-(5-amino-1,2,4-thiadiazol-3-yl)acetamido]cephalosporanic acid (syn isomer). mp 160° to 165° C. (dec.).

I.R. (Nujol): 3300, 3200, 1775, 1720, 1670, 1620, 1520 cm$^{-1}$

N.M.R. (d$_6$-DMSO, δ): 1.50–2.10 (6H, m), 2.07 (3H, s), 3.60 (2H, broad s), 4.67–4.83 (1H, m), 4.77 and 5.03 (2H, ABq, J=14 Hz), 5.17 (1H, d, J=4 Hz), 5.77–6.10 (3H, m), 8.17 (2H, s), 9.60 (1H, d, J=8 Hz)

(10) 7-[2-(2-Cyclohexen-1-yl)oxyimino-2-(5-amino-1,2,4-thiadiazol-3-yl)acetamido]3-(1-methyl-1H-tetrazol-5-yl)thiomethyl-3-cephem-4-carboxylic acid (syn isomer). mp 170° to 173° C. (dec.).

I.R. (Nujol): 3350, 3250, 1780, 1680, 1620, 1520 cm$^{-1}$

N.M.R. (d$_6$-DMSO, δ): 1.50–2.17 (6H, m), 3.16 (2H, broad s), 3.93 (3H, s), 4.30 (2H, broad s), 4.55–4.80 (1H, m), 5.10 (1H, d, J=4 Hz), 5.80 (1H, dd, J=4 and 8 Hz), 5.80–5.93 (2H, m), 8.08 (2H, s), 9.50 (1H, d, J=8 Hz)

(11) 7-[2-(2-Cyclohexen-1-yl)oxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer). mp 170° to 175° C. (dec.).

I.R. (Nujol): 3300, 3200, 1770, 1720, 1650, 1620, 1520 cm$^{-1}$

N.M.R. (d$_6$-DMSO, δ): 1.50–2.27 (6H, m), 3.75 (2H, broad s), 4.30 and 4.55 (2H, ABq, J=14 Hz), 4.67–4.83 (1H, m), 5.17 (1H, d, J=4 Hz), 5.37 (2H, s), 6.17–5.77 (3H, m), 8.18 (2H, s), 9.57 (1H, d, J=8 Hz)

(12) 7-[2-(2-Cyclohexen-1-yl)oxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer). mp 165° to 170° C.

I.R. (Nujol): 3300, 3200, 1770, 1720, 1670, 1620, 1520 cm$^{-1}$

N.M.R. (d$_6$-DMSO, δ): 1.50–2.17 (6H, m), 3.77 (2H, broad s), 4.37 and 4.50 (2H, ABq, J=14 Hz), 4.53 (2H, t, J=6 Hz), 4.67–4.93 (1H, m), 5.23 (1H, d, J=4 Hz), 5.93 (1H, dd, J=4 and 8 Hz), 5.97–6.17 (2H, m), 8.70 (2H, s), 9.80 (1H, d, J=8 Hz)

(13) 7-[2-(2-Cyclohexen-1-yl)oxyimino-2-(5-amino-1,2,4-thiadiazol-3-yl)acetamido]-3-(1-allyl-1H-tetrazol-5-yl)thiomethyl-3-cephem-4-carboxylic acid (syn isomer). mp 160° to 165° C. (dec.).

I.R. (Nujol): 3300, 3200, 1780, 1680, 1620, 1520 cm$^{-1}$

N.M.R. (d$_6$-DMSO, δ): 1.50–2.16 (6H, m), 3.66 (2H, broad s), 4.25 and 4.43 (2H, ABq, J=14 Hz), 4.55–4.80 (1H, m), 4.93–5.0 (2H, m), 5.10 (1H, d, J=4 Hz), 5.20–5.37 (2H, m), 5.67–6.20 (4H, m), 8.08 (2H, s), 9.50 (1H, d, J=8 Hz)

(14) 7-[2-(2-Cyclohexen-1-yl)oxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer). mp 100° to 105° C. (dec.).

I.R. (Nujol): 3300, 3170, 1770, 1670, 1620, 1520 cm$^{-1}$

N.M.R. (d$_6$-DMSO, δ): 1.37 (9H, s), 1.50–2.20 (8H, m), 2.92 (2H, t, J=6 Hz), 3.68 (2H, broad s), 4.07–4.47 (4H, m), 4.53–4.83 (1H, m), 5.10 (1H, d, J=5 Hz), 5.80 (1H, dd, J=5 and 8 Hz), 5.70–5.93 (2H, m), 8.10 (2H, broad s), 9.47 (1H, d, J=8 Hz)

(15) 7-[2-Cyclopentyloxyimino-2-(5-amino-1,2,4-thiadiazol-3-yl)acetamido]cephalosporanic acid (syn isomer). mp 140° to 145° C. (dec.).

I.R. (Nujol): 3480, 3370, 3250, 1785, 1730, 1680, 1630, 1530 cm$^{-1}$

N.M.R. (d$_6$-DMSO, δ): 1.33–2.17 (8H, m), 2.03 (3H, s), 3.57 (2H, broad s), 4.60–4.90 (1H, m), 4.73 and 4.97 (2H, ABq, J=13 Hz), 5.15 (1H, d, J=5 Hz), 5.80 (1H, dd, J=5 and 8 Hz), 8.10 (2H, broad s), 9.47 (1H, d, J=8 Hz)

(16) 7-[2-Cyclopentyloxyimino-2-(5-amino-1,2,4-thiadiazol-3-yl)acetamido]-3-(1-methyl-1H-tetrazol-5- yl)thiomethyl-3-cephem-4-carboxylic acid (syn isomer). mp 145° to 150° C. (dec.).

I.R. (Nujol): 3400, 3290, 3180, 1770, 1670, 1620, 1520 cm$^{-1}$

N.M.R. (d$_6$-DMSO, δ): 1.33–2.07 (8H, m), 3.70 (2H, broad s), 3.93 (3H, s), 4.32 (2H, broad s), 4.10–4.90 (1H, m), 5.12 (1H, d, J=5 Hz), 5.78 (1H, dd, J=5 and 8 Hz), 8.10 (2H, broad s), 9.47 (1H, d, J=8 Hz)

(17) 7-[2-Cyclopentyloxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer). mp 155°–160° C. (dec.).

I.R. (Nujol): 3400, 3290, 3180, 1765, 1720, 1670, 1620, 1520 cm$^{-1}$

N.M.R. (d$_6$-DMSO, δ): 1.27–2.07 (8H, m), 3.70 (2H, broad s), 4.28 and 4.53 (2H, ABq, J=13 Hz), 4.70–4.93 (1H, m), 5.17 (1H, d, J=5 Hz), 5.33 (2H, s), 5.85 (1H, dd, J=5 and 8 Hz), 8.23 (2H, broad s), 9.60 (1H, d, J=8 Hz)

(18) 7-[2-Cyclopentyloxyimino-2-(5-amino-1,2,4-thiadiazol-3-yl)acetamido]-3-(1-allyl-1H-tetrazol-5-yl)thiomethyl-3-cephem-4-carboxylic acid (syn isomer). mp 135° to 140° C. (dec.).

I.R. (Nujol): 3400, 3300, 3190, 1770, 1670, 1620, 1520 cm$^{-1}$

N.M.R. (d$_6$-DMSO, δ): 1.30–2.10 (8H, m), 3.73 (2H, broad s), 4.32 and 4.50 (2H, ABq, J=13 Hz), 4.60–4.90 (1H, m), 4.83–5.17 (2H, m), 5.17 (1H, d, J=5 Hz), 5.17–5.50 (2H, m), 5.87 (1H, dd, J=5 and 8 Hz), 5.67–6.33 (1H, m), 8.20 (2H, broad s), 9.60 (1H, d, J=8 Hz)

(19) 7[2-Cyclopentyloxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer). mp 160° to 165° C. (dec.).

I.R. (Nujol): 3570, 3440, 3320, 3180, 1775, 1710, 1660, 1620, 1580, 1540, 1520 cm$^{-1}$ N.M.R. (d$_6$-DMSO, δ): 1.40–2.03 (8H, m), 3.78 (2H, broad s), 4.27 and 4.65 (2H, ABq, J=13 Hz), 4.67–4.93 (1H, m), 5.20 (1H, d, J=5 Hz), 5.87 (1H, dd, J=5 and 8 Hz), 7.78 (1H, d, J=10 Hz), 8.15 (2H, broad s), 8.58 (1H, d, J=10 Hz), 9.53 (1H, d, J=8 Hz)

(20) 7-[2-Cyclopentyloxyimino-2-(5-amino-1,2,4-thiadiazol-3-yl)acetamido]-3-[1-(2-methoxycarbonylethyl)-1H-tetrazol-5-yl]thiomethyl-3-cephem-4-carboxylic acid (syn isomer). mp 125° to 130° C. (dec.).

I.R. (Nujol): 3480, 3370, 3250, 1780, 1740, 1685, 1625, 1530 cm$^{-1}$

N.M.R. (d$_6$-DMSO, δ): 1.30–2.07 (8H, m), 2.80–3.20 (2H, m), 3.58 (3H, s), 3.67 (2H, broad s), 4.20–4.70 (4H, m), 4.60–4.90 (1H, m), 5.12 (1H, d, J=5 Hz), 5.78 (1H, dd, J=5 and 8 Hz), 8.07 (2H, broad s), 9.43 (1H, d, J=8 Hz)

(21) 7-[2-Cyclopentyloxyimino-2-(5-amino-1,2,4-thiadiazol-3-yl)acetamido]-3-(4-methyl-5-oxo-6-hydroxy-4,5-dihydro-1,2,4-triazin-3-yl)thiomethyl-3-cephem-4-carboxylic acid (syn isomer). pale yellow powder. mp 195° to 199° C. (dec.).

I.R. (Nujol): 3300, 3200, 1770, 1710–1670, 1590, 1520, 1240, 1170, 1090, 1000, 720 cm$^{-1}$

(22) 7-[2-Cycloheptyloxyimino-2-(5-amino-1,2,4-thiadiazol-3-yl)acetamido]-3-(1,3,4-thiadiazol-2-yl)thiomethyl-3-cephem-4-carboxylic acid (syn isomer). white powder. mp 150° to 154° C. (dec.).

I.R. (Nujol): 3300, 3200, 1770, 1670, 1620, 1520, 1400, 1240, 1160, 1060, 1000 cm$^{-1}$ N.M.R. (d$_6$-DMSO, δ): 1.50 (8H, m), 1.82 (4H, m), 3.54 and 3.76 (2H, ABq, J=20 Hz), 4.32 (1H, m), 4.24 and 4.60 (2H, ABq, J=14 Hz), 5.10 (1H, d, J=5 Hz), 5.74 (1H, dd, J=5 and 8 Hz), 8.02 (2H, m), 9.48 (1H, s), 9.38 (1H, d, J=8 Hz)

(23) 7-[2-Cycloheptyloxyimino-2-(5-amino-1,2,4-thiadiazol-3-yl)acetamido]-3-cephem-4-carboxylic acid (syn isomer). white powder. mp 170° to 175° C. (dec.).

I.R. (Nujol): 3400, 3300, 3200, 1770, 1670, 1620, 1520, 1280, 1240, 1160, 1000, 980, 730 cm$^{-1}$ N.M.R. (d$_6$-DMSO, δ): 1.50 (8H, m), 1.85 (4H, m), 3.60 (2H, m), 4.0–4.50 (1H, m), 5.13 (1H, d, J=5 Hz), 5.87 (1H, dd, J=5 and 8 Hz), 6.50 (1H, m), 8.13 (2H, m), 9.37 (1H, d, J=8 Hz)

(24) N-[7-{2-Cyclopentyloxyimino-2-(5-amino-1,2,4-thiadiazol-3-yl)acetamido}-3-cephem-3-ylmethyl]-4'-carbamoylpyridinium-4-carboxylate (syn isomer). mp 230° to 235° C. (dec.).

I.R. (Nujol): 3300, 3200, 1770, 1680, 1610, 1560, 1520, 1510 cm$^{-1}$

(25) 7-[2-Cyclopentyloxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer). pale brown powder.

I.R. (Nujol): 3300, 1770, 1670, 1520, 1240, 1160, 1000 cm$^{-1}$

(26) 7-[2-Cyclopentyloxyimino-2-(5-amino-1,2,4-thiadiazol-3-yl)acetamido]-3-(1,2,4-thiadiazol-5-yl)thiomethyl-3-cephem-4-carboxylic acid (syn isomer). mp 175° to 178° C. (dec.).

I.R. (Nujol): 3300, 3200, 1775, 1680, 1620, 1525 cm$^{-1}$

(27) 7-[2-Cyclopentyloxyimino-2-(5-amino-1,2,4-thiadiazol-3-yl)acetamido]-3-[1-(3-morpholinopropyl)-1H-tetrazol-5-yl]thiomethyl-3-cephem-4-carboxylic acid (syn isomer). mp 183° to 188° C. (dec.).

I.R. (Nujol): 3300, 3150, 1770, 1670, 1610, 1530 cm$^{-1}$

(28) 7-[2-(2-Cyclopenten-1-yl)oxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 175° to 180° C. (dec.).

I.R. (Nujol): 3400, 3300, 3170, 1760, 1665, 1610, 1520 cm$^{-1}$

(29) 7-[2-Cyclopentyloxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer). white powder. mp 195° to 199° C. (dec.).

I.R. (Nujol): 3300, 3150, 1760, 1660, 1620, 1520, 1280, 1180, 1000 cm$^{-1}$

(30) 7-[2-(2-Cyclohexen-1-yl)oxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer). mp 185° to 190° C. (dec.).

I.R. (Nujol): 3280, 3150, 1760, 1665, 1620, 1520 cm$^{-1}$

(31) 7-[2-Cyclopentyloxyimino-2-(5-amino-1,2,4-thiadiazol-3-yl)acetamido]-3-[1-(3-piperidinopropyl)-1H-tetrazol-5-yl]thiomethyl-3-cephem-4-carboxylic acid (syn isomer). mp 230° C. (dec.).

I.R. (Nujol): 3300, 3200, 1770, 1670, 1600, 1520 cm$^{-1}$

EXAMPLE 14

A mixture of 7-[2-phenoxyimino-2-(5-amino-1,2,4-thiadiazol-3-yl)acetamido]cephalosporanic acid (syn isomer) (3.5 g), tetrazolo[1,5-b]pyridazine-6-thiol (1.35 g) and sodium bicarbonate (1.1 g) in pH 6.8 phosphate buffer solution (130 ml) was stirred for 2 hours at 70° C. The reaction mixture was cooled in an ice bath, mixed with ethyl acetate and adjusted to pH 3 with 10% hydrochloric acid. An insoluble material was filtered off and the filtrate was extracted with ethyl acetate. The extract was dried over magnesium sulfate and evaporated to dryness. The residue was triturated with diethyl ether to give 7-[2-phenoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer) (0.7 g), mp 175° to 180° C. (dec.).

I.R. (Nujol): 3300, 3200, 1775, 1680, 1615, 1585, 1520 cm$^{-1}$

N.M.R. (d$_6$-DMSO, δ): 3.77 (2H, broad s), 4.23 and 4.63 (2H, ABq, J=13 Hz), 5.23 (1H, d, J=4 Hz), 5.93 (1H, dd, J=4 and 8 Hz), 7.00–7.50 (5H, m), 7.77 (1H, d, J=10 Hz), 8.30 (2H, s), 8.60 (1H, d, J=10 Hz), 9.85 (1H, d, J=8 Hz)

EXAMPLE 15

A mixture of 7-[2-phenoxyimino-2-(5-amino-1,2,4-thiadiazol-3-yl)acetamido]cephalosporanic acid (syn isomer) (4.0 g), 1-[2-(N-t-butoxycarbonylamino)ethyl]-1H-tetrazole-5-thiol (2.45 g) and sodium bicarbonate (1.3 g) in pH 6.8 phosphate buffer solution (150 ml) was stirred for 1.5 hours at 70° C. The reaction mixture was cooled in an ice bath, mixed with ethyl acetate and adjusted to pH 3 with 10% hydrochloric acid. An insoluble material was filtered off and the filtrate was extracted with ethyl acetate. The extract was dried over magnesium sulfate and evaporated to dryness. The residue was triturated with diethyl ether to give 7-[2-phenoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer) (1.4 g), mp 150° to 155° C. (dec.).

I.R. (Nujol): 3300, 3200, 1770, 1680, 1620, 1590, 1520 cm$^{-1}$

N.M.R. (d$_6$-DMSO, δ): 1.27 (9H, s), 3.3–3.5 (2H, m), 3.70 (2H, broad s), 4.3–4.6 (4H, m), 5.18 (1H, d, J=4 Hz), 5.90 (1H, dd, J=4 and 8 Hz), 7.0–7.5 (5H, m), 8.28 (2H, s), 9.88 (1H, d, J=8 Hz)

EXAMPLE 16

A mixture of 7-[2-allyloxyimino-2-(5-amino-1,2,4-thiadiazol-3-yl)acetamido]cephalosporanic acid (syn isomer) (3.3 g), 1-allyl-1H-tetrazole-5-thiol (1.4 g) and sodium bicarbonate (1.3 g) in pH 6.8 phosphate buffer solution (210 ml) was stirred 2 hours at 70° C. The reaction mixture was cooled in an ice bath, mixed with ethyl acetate and adjusted to pH 2 with 10% hydrochloric acid. An insoluble material was filtered off and the filtrate was extracted with ethyl acetate. The extract was dried over magnesium sulfate and evaporated to dryness. The residue was triturated with diethyl ether to give 7-[2-allyloxyimino-2-(5-amino-1,2,4-thiadiazol-3-yl)acetamido]-3-(1-allyl-1H-tetrazol-5-yl)thiomethyl-3-cephem-4-carboxylic acid (syn isomer) (2.1 g), mp 150° to 155° C. (dec.).

I.R. (Nujol): 3300, 3200, 1775, 1670, 1620, 1520 cm$^{-1}$

N.M.R. (d$_6$-DMSO, δ): 3.68 (2H, broad s), 4.28 and 4.45 (2H, ABq, J=13 Hz), 4.60–4.83 (2H, m), 4.93–5.07 (2H, m), 5.12 (1H, d, J=4 Hz), 5.17–5.57 (4H, m), 5.83 (1H, dd, J=4 and 8 Hz), 5.77–6.37 (2H, m), 8.22 (2H, s), 9.67 (1H, d, J=8 Hz)

EXAMPLE 17

A mixture of 7-[2-cyclopentyloxyimino-2-(5-amino-1,2,4-thiadiazol-3-yl)acetamido]cephalosporanic acid (syn isomer) (5.1 g), sodium bicarbonate (840 mg), water (50 ml), potassium thiocyanate (24.3 g) and isonicotinamide (1.83 g) was stirred for 22 hours at 50° to 55° C. The reaction mixture was cooled and added to ethyl acetate. The mixture was adjusted to pH 2 with 10% hydrochloric acid and filtered. The aqueous layer was separated from the filtrate, washed with ethyl acetate and evaporated. The residue was subjected to column chromatography (non-ionic adsorption resin, Diaion HP20 prepared by Mitsubishi Chemical Industries) and the column was washed with water (0.7 l) and then eluted with 30% aqueous methanol (0.7 l). The eluates containing the object compound were collected, washed with ethyl acetate and then evaporated. The residue was lyophilized to give N-[7-{2-cyclopentyloxyimino-2-(5-amino-1,2,4-thiadiazol-3-yl)acetamido}-3-cephem-3-ylmethyl]-4'-carbamoylpyridinium-4-carboxylate (syn isomer) (1.0 g), mp 230° to 235° C. (dec.).

I.R. (Nujol): 3300, 3200, 1770, 1680, 1610, 1560, 1520, 1510 cm$^{-1}$

N.M.R. (d$_6$-DMSO, δ): 1.30–1.95 (8H, m), 3.15 and 3.50 (2H, ABq, J=18 Hz), 5.60–5.75 (1H, m), 5.06 (1H, d, J=4 Hz), 5.30 and 5.65 (2H, ABq, J=14 Hz), 5.70 (1H, dd, J=4 and 8 Hz), 8.12 (2H, s), 8.45 (2H, d, J=6 Hz), 9.42 (2H, d, J=6 Hz), 9.50 (1H, d, J=8 Hz)

EXAMPLE 18

The following compounds were obtained according to similar manners to those of Examples 14 to 17.

(1) 7-[2-Allyloxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 180° to 185° C. (dec.).

I.R. (Nujol): 3300, 3200, 1770, 1670, 1620, 1525 cm$^{-1}$

N.M.R. (d$_6$-DMSO, δ): 3.73 (2H, broad s), 4.27 and 4.63 (2H, ABq, J=14 Hz), 4.60–4.83 (2H, m), 5.18 (1H, d, J=4 Hz), 5.23–5.53 (2H, m), 5.83 (1H, dd, J=4 and 8 Hz), 5.87–6.33 (1H, m), 7.82 (1H, d, J=10 Hz), 8.20 (2H, s), 8.68 (1H, d, J=10 Hz), 9.68 (1H, d, J=8 Hz)

(2) 7-[2-(2,2,2-Trifluoroethoxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), powder.

(3) 7-[2-(2,2,2-Trifluoroethoxyimino)-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp 150° to 155° C. (dec.).

I.R. (Nujol): 3300, 3180, 1760, 1670, 1610, 1520 cm$^{-1}$

N.M.R. (d$_6$-DMSO, δ): 3.60 (2H, broad s), 4.05 and 4.28 (2H, ABq, J=13 Hz), 4.57 (2H, s), 4.73 and 4.95 (2H, ABq, J=9 Hz), 5.07 (1H, d, J=5 Hz), 5.73 (1H, dd, J=5 and 8 Hz), 8.17 (2H, broad s), 9.63 (1H, d, J=8 Hz)

(4) 7-[2-(2,2,2-Trifluoroethoxyimino)-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 165° to 170° C. (dec.).

I.R. (Nujol): 3420, 3300, 3190, 1770, 1705, 1670, 1620, 1525 cm$^{-1}$

N.M.R. (d$_6$-DMSO, δ): 3.60 and 3.80 (2H, ABq, J=18 Hz), 4.23 and 4.58 (2H, ABq, J=13 Hz), 4.67 and 4.87 (2H, ABq, J=9 Hz), 5.13 (1H, d, J=5 Hz), 5.82 (1H, dd, J=5 and 8 Hz), 7.72 (1H, d, J=10 Hz), 8.17 (2H, broad s), 8.55 (1H, d, J=10 Hz), 9.68 (1H, d, J=8 Hz)

(5) 7-[2-Cyclopentyloxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), pale brown powder.

I.R. (Nujol): 3300, 1770, 1670, 1520, 1240, 1160, 1000 cm$^{-1}$

N.M.R. (d$_6$-DMSO, δ): 1.33 (9H, s), 1.40–2.07 (10H, m), 2.95 (2H, m), 3.63 (2H, m), 4.0–4.43 (4H, m), 4.70

(1H, m), 5.07 (1H, d, J=5 Hz), 5.73 (1H, dd, J=5 and 8 Hz), 6.80 (1H, m), 8.07 (2H, m), 9.89 (1H, d, J=8 Hz)

(6) 7-[2-Cyclopentyloxyimino-2-(5-amino-1,2,4-thiadiazol-3-yl)acetamido]-3-(1,2,4-thiadiazol-5-yl)thiomethyl-3-cephem-4-carboxylic acid (syn isomer), mp 175° to 178° C. (dec.).

I.R. (Nujol): 3300, 3200, 1775, 1680, 1620, 1525 cm$^{-1}$

N.M.R. (d$_6$-DMSO, δ): 1.50–2.00 (8H, m), 3.67 (2H, broad s), 4.34 and 4.60 (2H, ABq, J=14 Hz), 4.67–4.83 (1H, m), 5.17 (1H, d, J=4 Hz), 5.82 (1H, dd, J=4 and 8 Hz), 8.12 (2H, s), 8.73 (1H, s), 9.50 (1H, d, J=8 Hz)

(7) 7-[2-Cyclopentyloxyimino-2-(5-amino-1,2,4-thiadiazol-3-yl)acetamido]-3-[1-(3-morpholinopropyl)-1H-tetrazol-5-yl]thiomethyl-3-cephem-4-carboxylic acid (syn isomer), mp 183° to 188° C. (dec.).

I.R. (Nujol): 3300, 3150, 1770, 1670, 1610, 1530 cm$^{-1}$

N.M.R. (d$_6$-DMSO, δ): 1.50–1.90 (8H, m), 2.00–2.27 (2H, m), 2.50–2.83 (6H, m), 3.50–3.83 (6H, m), 4.23–4.53 (4H, m), 4.70–4.86 (1H, m), 5.13 (1H, d, J=4 Hz), 5.80 (1H, dd, J=4 and 8 Hz), 8.13 (2H, s), 9.50 (1H, d, J=8 Hz)

(8) 7-[2-(2-Cyclopenten-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer) (1.4 g), mp 155° to 160° C.

I.R. (Nujol): 3300, 3200, 1770, 1670, 1620 1520 cm$^{-1}$ (9) 7-[2-(2-Cyclopenten-1-yl)oxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 155° to 160° C. (dec.).

I.R. (Nujol): 3300, 1770, 1670, 1620, 1520 cm$^{-1}$

(10) 7-[2-(2-Cyclopenten-1-yl)oxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 155° to 160° C. (dec.).

I.R. (Nujol): 3300, 3200, 1770, 1720, 1670, 1620, 1520 cm$^{-1}$

(11) 7-[2-(2-Cyclopenten-1-yl)oxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 150° to 155° C. (dec.).

I.R. (Nujol): 3300, 3200, 1770, 1720, 1670, 1620, 1520 cm$^{-1}$

(12) 7-[2-(2-Cyclopenten-1-yl)oxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 160° to 165° C. (dec.).

I.R. (Nujol): 3300, 1770, 1670, 1620, 1520 cm$^{-1}$

(13) 7-[2-(2-Cyclopenten-1-yl)oxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3190, 1770, 1670, 1615, 1520 cm$^{-1}$

(14) 7-[2-(2-Cyclopenten-1-yl)oxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 95° to 100° C. (dec.).

I.R. (Nujol): 3300, 3190, 1770, 1680, 1620, 1520 cm$^{-1}$

(15) 7-[2-(2-Cyclopenten-1-yl)oxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 175° to 180° C.

I.R. (Nujol): 3400, 3300, 3170, 1760, 1665, 1610, 1520 cm$^{-1}$

(16) 7-[2-(2-Cyclohexen-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

I.R. (Nujol): 3300, 3180, 1770, 1660, 1620, 1520 cm$^{-1}$

(17) 7-[2-(2-Cyclohexen-1-yl)oxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3180, 1670, 1620, 1520 cm$^{-1}$

(18) 7-[2-(2-Cyclohexen-1-yl)oxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 170° to 173° C. (dec.).

I.R. (Nujol): 3350, 3250, 1780, 1680, 1620, 1520 cm$^{-1}$

(19) 7-[2-(2-Cyclohexen-1-yl)oxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 170° to 175° C. (dec.).

I.R. (Nujol): 3300, 3200, 1770, 1720, 1650, 1620, 1520 cm$^{-1}$

(20) 7-[2-(2-Cyclohexen-1-yl)oxyimino-2-(5-amino-1,2,4-thiadiazol-3-yl)acetamido]-3-{1-(2-carboxyethyl)-1H-tetrazol-5-yl}thiomethyl-3-cephem-4-carboxylic acid (syn isomer), mp 165° to 170° C.

I.R. (Nujol): 3300, 3200, 1770, 1720, 1670, 1620, 1520 cm$^{-1}$

(21) 7-[2-(2-Cyclohexen-1-yl)oxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 160° to 165° C. (dec.).

I.R. (Nujol): 3300, 3200, 1780, 1680, 1620, 1520 cm$^{-1}$

(22) 7-[2-(2-Cyclohexen-1-yl)oxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 100° to 105° C. (dec.).

I.R. (Nujol): 3300, 3170, 1770, 1670, 1620, 1520 cm$^{-1}$

(23) 7-[2-(2-Cyclohexen-1-yl)oxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 185° to 190° C. (dec.).

I.R. (Nujol): 3280, 3150, 1760, 1665, 1620, 1520 cm$^{-1}$

(24) 7-[2-Cyclopentyloxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 145° C. (dec.).

I.R. (Nujol): 3400, 3300, 3200, 1770, 1670, 1620, 1525 cm$^{-1}$

(25) 7-[2-Cyclopentyloxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 145° to 150° C. (dec.).

I.R. (Nujol): 3400, 3290, 3180, 1770, 1670, 1620, 1520 cm$^{-1}$

(26) 7-[2-Cyclopentyloxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 155° to 160° C. (dec.).

I.R. (Nujol): 3400, 3290, 3180, 1765, 1720, 1670, 1620, 1520 cm$^{-1}$

(27) 7-[2-Cyclopentyloxyimino-2-(5-amino-1,2,4-thiadiazol-3-yl)acetamido]-3-(1-allyl-1H-tetrazol-5-yl)thiomethyl-3-cephem-4-carboxylic acid (syn isomer); mp 135° to 140° C. (dec.).

I.R. (Nujol): 3400, 3300, 3190, 1770, 1670, 1620, 1520 cm$^{-1}$

(28) 7-[2-Cyclopentyloxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 160° to 165° C. (dec.).

I.R. (Nujol): 3570, 3440, 3320, 3180, 1775, 1710, 1660, 1620, 1580, 1540, 1520 cm$^{-1}$

(29) 7-[2-Cyclopentyloxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), white powder, mp 195° to 199° C. (dec.).

I.R. (Nujol): 3300, 3150, 1760, 1660, 1620, 1520, 1280, 1180, 1000 cm$^{-1}$

(30) 7-[2-Cyclopentyloxyimino-2-(5-amino-1,2,4-thiadiazol-3-yl)acetamido]-3-[1-(2-methoxycarbonylethyl)-1H-tetrazol-5-yl]thiomethyl-3-cephem-4-carboxylic acid (syn isomer), mp 125° to 130° C. (dec.).

I.R. (Nujol): 3480, 3370, 3250, 1780, 1740, 1685, 1625, 1530 cm$^{-1}$ (3 7-[2-Cyclopentyloxyimino-2-(5-amino-1,2,4-thiadiazol-3-yl)acetamido]-3-(4-methyl-5-oxo-6-hydroxy-4,5-dihydro-1,2,4-triazin-3-yl)thiomethyl-3-cephem-4-carboxylic acid (syn isomer), yellow powder, mp 195° to 199° C. (dec.).

I.R. (Nujol): 3300, 3200, 1770, 1710–1670, 1590, 1520, 1240, 1170, 1090, 1000, 720 cm$^{-1}$ N.M.R. (d$_6$-DMSO, δ): 1.3–2.1 (8H, m), 3.32 (3H, s), 3.66 (2H, m), 4.11 (2H, m), 4.76 (1H, m), 5.16 (1H, d, J=5 Hz), 5.83 (1H, dd, J=5 and 8 Hz), 8.13 (2H, broad s), 9.50 (1H, d, J=8 Hz), 12.50 (1H, broad s)

(32) 7-[2-Cycloheptyloxyimino-2-(5-amino-1,2,4-thiadiazol-3-yl)acetamido]-3-(1,3,4-thiadiazol-2-yl)thiomethyl-3-cephem-4-carboxylic acid (syn isomer), white powder, mp 150° to 154° C. (dec.).

I.R. (Nujol): 3300, 3200, 1770, 1670, 1620, 1520, 1400, 1240, 1160, 1060, 1000 cm$^{-1}$

(33) 7-[2-Cyclopentyloxyimino-2-(5-amino-1,2,4-thiadiazol-3-yl)acetamido]-3-[1-(3-piperidinopropyl)-1H-tetrazol-5-yl]thiomethyl-3-cephem-4-carboxylic acid (syn isomer), mp 230° C. (dec.).

I.R. (Nujol): 3300, 3200, 1770, 1670, 1600, 1520 cm$^{-1}$

N.M.R. (d$_6$-DMSO, δ): 1.3–2.0 (6H, m), 2.10–2.3 (2H, m), 2.73–3.10 (6H, m), 3.57 (2H, broad s), 4.10–4.50 (4H, m), 4.60–4.80 (1H, m), 5.00 (1H, d, J=4 Hz), 5.67 (1H, dd, J=4 and 8 Hz), 9.06 (2H, s), 9.37 (1H, d, J=8 Hz)

EXAMPLE 19

A solution of 4-nitrobenzyl 7-[2-(3-trifluoromethylphenoxyimino)-2-(5-amino-1,2,4-thiadiazol-3-yl)acetamido]-3-cephem-4-carboxylate (syn isomer) (4.4 g) in a mixture of tetrahydrofuran (80 ml), water (50 ml) and acetic acid (4.4 ml) was hydrogenated over 10% palladium-charcoal (2.2 g) at atmospheric pressure at room temperature for 3 hours. The catalyst was filtered and washed with tetrahydrofuran. The filtrate and washing were combined and then evaporated. To the residue were added ethyl acetate and an aqueous solution of sodium bicarbonate so that the pH was adjusted to 8. The aqueous layer was separated, adjusted to pH 1 to 2, and extracted with ethyl acetate. The extract was washed successively with water and an aqueous solution of sodium chloride, treated with activated charcoal, dried over magnesium sulfate and then evaporated. The residue was washed with diethyl ether to give a yellow powder (1.0 g). Water (10 ml) was added to this crude product and the mixture was stirred for 30 minutes. The precipitates were collected by filtration, washed with water and dried under reduced pressure to give a yellow powder of 7-[2-(3-trifluoromethylphenoxyimino)-2-(5-amino-1,2,4-thiadiazol-3-yl)acetamido]-3-cephem-4-carboxylic acid (syn isomer) (1.0 g), decomposed by 193° C.

I.R. (Nujol): 3450, 3320, 3200, 1770, 1710, 1665, 1630, 1560, 1515, 1325, 1170, 1110, 940 cm$^{-1}$ N.M.R. (d$_6$-DMSO, δ): 3.63 (2H, m), 5.21 (1H, d, J=5 Hz), 5.94 (1H, dd, J=5 and 8 Hz), 6.48 (1H, m), 7.53 (4H, broad s), 8.27 (2H, broad s), 9.87 (1H, d, J=8 Hz)

EXAMPLE 20

A solution of 4-nitrobenzyl 7-[2-phenoxyimino-2-(5-amino-1,2,4-thiadiazol-3-yl)acetamido]-3-cephem-4-carboxylate (syn isomer)(4.5 g) in a mixture of tetrahydrofuran (45 ml) and water (20 ml) was hydrogenated over 10% palladium-charcoal (2.5 g) for 3 hours at atmospheric pressure at room temperature. The catalyst was filtered and the filtrate was evaporated. To the residue was added ethyl acetate and the mixture was adjusted to pH 8 with an aqueous solution of sodium bicarbonate. The aqueous layer was separated and thereto was added ethyl acetate, and then the pH was adjusted to 3 with hydrochloric acid. The resulting mixture was extracted with ethyl acetate and the extract was washed with water, dried over magnesium sulfate and then evaporated to give 7-[2-phenoxyimino-2-(5-amino-1,2,4-thiadiazol-3-yl)-acetamido]-3-cephem-4-carboxylic acid (syn isomer) (1.4 g), mp 168° to 170° C. (dec.).

I.R. (Nujol): 3400, 3200, 1780, 1660, 1620, 1600, 1590, 1540 cm$^{-1}$

N.M.R. (DMSO-d$_6$, δ): 3.58 (2H, broad s), 5.15 (1H, d, J=4 Hz), 5.90 (1H, dd, J=4 and 8 Hz), 6.47 (1H, t, J=3 Hz), 6.97–7.60 (5H, m), 8.27 (2H, s), 9.92 (1H, d, J=8 Hz)

EXAMPLE 21

The following compounds were obtained according to similar manners to those of Examples 19 and 20.

(1) 7-[2-{3-(N-t-Butoxycarbonylamino)propoxyimino}-2-(5-amino-1,2,4-thiadiazol-3-yl)acetamido]-3-chloro-3-cephem-4-carboxylic acid (syn isomer).

I.R. (Nujol): 3300–3100, 1780, 1690–1660, 1520, 1270 cm$^{-1}$ (2) 7-[2-(4-Chlorophenoxyimino)-2-(5-amino-1,2,4-thiadiazol-3-yl)acetamido]-3-cephem-4-carboxylic acid (syn isomer), mp 145° to 150° C. (dec.).

I.R. (Nujol): 3400, 3260, 3180, 1775, 1675, 1625, 1600, 1520, 1480 cm$^{-1}$

N.M.R. (d$_6$-DMSO, δ): 3.63 (2H, broad s), 5.20 (1H, d, J=5 Hz), 5.93 (1H, dd, J=5 and 8 Hz), 6.52 (1H, t, J=4 Hz), 7.33 (2H, d, J=9 Hz), 7.47 (2H, d, J=9 Hz), 8.32 (2H, broad s), 9.90 (1H, d, J=8 Hz)

(3) 7-[2-(4-Fluorophenoxyimino)-2-(5-amino-1,2,4-thiadiazol-3-yl)acetamido]-3-cephem-4-carboxylic acid (syn isomer), mp 130° to 135° C. (dec.).

I.R. (Nujol): 3400, 3270, 3180, 1765, 1675, 1605, 1500 cm$^{-1}$

N.M.R. (d$_6$-DMSO, δ): 3.63 (2H, broad s), 5.22 (1H, d, J=5 Hz), 5.97 (1H, dd, J=5 and 8 Hz), 6.53 (1H, t, J=4 Hz), 7.25 (2H, s), 7.37 (2H, s), 8.30 (2H, broad s), 9.90 (1H, d, J=8 Hz)

(4) 7-[2-Allyloxyimino-2-(5-amino-1,2,4-thiadiazol-3-yl)acetamido]-3-cephem-4-carboxylic acid (syn isomer), mp 160° to 165° C. (dec.).

N.M.R. (d$_6$-DMSO, δ): 3.53 (2H, d, J=4 Hz), 4.60–4.77 (2H, m), 5.07 (1H, d, J=4 Hz), 5.0–5.50 (2H, m), 5.83 (1H, dd, J=4 and 8 Hz), 5.70–6.23 (1H, m), 6.45 (1H, t, J=4 Hz), 8.13 (2H, s), 9.57 (1H, d, J=8 Hz)

(5) 7-[2-(2-Cyclopenten-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 155° to 160° C.

I.R. (Nujol): 3300, 3200, 1770, 1670, 1620, 1520 cm$^{-1}$ (6) 7-[2-(2-Cyclopenten-1-yl)oxyimino-2-(5-amino-1,2,4-thiadiazol-3-yl)acetamido]-3-cephem-4-carboxylic acid (syn isomer), mp 180° to 185° C. (dec.).

I.R. (Nujol): 3500, 3430, 3300, 3200, 1770, 1690, 1660, 1640, 1620, 1580, 1510 cm$^{-1}$ (7) 7-[2-(2-Cyclopenten-1-yl)oxyimino-2-(5-amino-1,2,4-thiadiazol-3-yl)acetamido]cephalosporanic acid (syn isomer), mp 154° to 159° C. (dec.).

I.R. (Nujol): 3300, 1770, 1720, 1670, 1620, 1520 cm$^{-1}$ (8) 7-[2-(2-Cyclopenten-1-yl)oxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 155° to 160° C. (dec.).

I.R. (Nujol): 3300, 1770, 1670, 1620, 1520 cm$^{-1}$ (9) 7-[2-(2-Cyclopenten-1-yl)oxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 155° to 160° C. (dec.).

I.R. (Nujol): 3300, 3200, 1770, 1720, 1670, 1620, 1520 cm$^{-1}$

(10) 7-[2-(2-Cyclopenten-1-yl)oxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 150° to 155° C. (dec.).

I.R. (Nujol): 3300, 3200, 1770, 1720, 1670, 1620, 1520 cm$^{-1}$

(11) 7-[2-(2-Cyclopenten-1-yl)oxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 160° to 165° C. (dec.).

I.R. (Nujol): 3300, 1770, 1670, 1620, 1520 cm$^{-1}$

(12) 7-[2-(2-Cyclopenten-1-yl)oxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3190, 1770, 1670, 1615, 1520 cm$^{-1}$

(13) 7-[2-(2-Cyclopenten-1-yl)oxyimino-2-(5-amino-1,2,4-thiadiazol-3-yl)acetamido]-3-[1-{2-(N-t-butoxycarbonylamino)ethyl}-1H-tetrazol-5-yl]-thiomethyl-3-cephem-4-carboxylic acid (syn isomer), mp 95° to 100° C. (dec.).

I.R. (Nujol): 3300, 3190, 1770, 1680, 1620, 1520 cm$^{-1}$

(14) 7-[2-(2-Cyclopenten-1-yl)oxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 175° to 180° C. (dec.).

I.R. (Nujol): 3400, 3300, 3170, 1760, 1665, 1610, 1520 cm$^{-1}$

(15) 7-[2-(2-Cyclohexen-1-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

I.R. (Nujol): 3300, 3180, 1770, 1660, 1620, 1520 cm$^{-1}$

(16) 7-[2-(2-Cyclohexen-1-yl)oxyimino-2-(5-amino-1,2,4-thiadiazol-3-yl)acetamido]-3-cephem-4-carboxylic acid (syn isomer), mp 175° to 180° C. (dec.).

I.R. (Nujol): 3300, 3200, 1770, 1670, 1630, 1520 cm$^{-1}$

(17) 7-[2-(2-Cyclohexen-1-yl)oxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3180, 1670, 1620, 1520 cm$^{-1}$

(18) 7-[2-(2-Cyclohexen-1-yl)oxyimino-2-(5-amino-1,2,4-thiadiazol-3-yl)acetamido]cephalosporanic acid (syn isomer), mp 160° to 165° C. (dec.).

I.R. (Nujol): 3300, 3200, 1775, 1720, 1670, 1620, 1520 cm$^{-1}$

(19) 7-[2-(2-Cyclohexen-1-yl)oxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 170° to 173° C. (dec.).

I.R. (Nujol): 3350, 3250, 1780, 1680, 1620, 1520 cm$^{-1}$

(20) 7-[2-(2-Cyclohexen-1-yl)oxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 170° to 175° C. (dec.).

I.R. (Nujol): 3300, 3200, 1770, 1720, 1650, 1620, 1520 cm$^{-1}$

(21) 7-[2-(2-Cyclohexen-1-yl)oxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 165° to 170° C.

I.R. (Nujol): 3300, 3200, 1770, 1720, 1670, 1620, 1520 cm$^{-1}$

(22) 7-[2-(2-Cyclohexen-1-yl)oxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 160° to 165° C. (dec.).

I.R. (Nujol): 3300, 3200, 1780, 1680, 1620, 1520 cm$^{-1}$

(23) 7-[2-(2-Cyclohexen-1-yl)oxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 100° to 105° C. (dec.).

I.R. (Nujol): 3300, 3170, 1770, 1670, 1620, 1520 cm$^{-1}$

(24) 7-[2-(2-Cyclohexen-1-yl)oxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 185° to 190° C. (dec.).

I.R. (Nujol): 3280, 3150, 1760, 1665, 1620, 1520 cm$^{-1}$

(25) 7-[2-Cyclopentyloxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 145° C. (dec.).

I.R. (Nujol): 3400, 3300, 3200, 1770, 1670, 1620, 1525 cm$^{-1}$

(26) 7-[2-Cyclopentyloxyimino-2-(5-amino-1,2,4-thiadiazol-3-yl)acetamido]-3-cephem-4-carboxylic acid (syn isomer), mp 170° to 175° C.

I.R. (Nujol): 3520, 3420, 3320, 3220, 3160, 1770, 1685, 1655, 1635, 1625, 1570, 1505 cm$^{-1}$

(27) 7-[2-Cyclopentyloxyimino-2-(5-amino-1,2,4-thiadiazol-3-yl)acetamido]cephalosporanic acid (syn isomer), mp 140° to 145° C. (dec.).

I.R. (Nujol): 3480, 3370, 3250, 1785, 1730, 1680, 1630, 1530 cm$^{-1}$

(28) 7-[2-Cyclopentyloxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 145° to 150° C. (dec.).

I.R. (Nujol): 3400, 3290, 3180, 1770, 1670, 1620, 1520 cm$^{-1}$

(29) 7-[2-Cyclopentyloxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 155° to 160° C. (dec.).

I.R. (Nujol): 3400, 3290, 3180, 1765, 1720, 1670, 1620, 1520 cm$^{-1}$

(30) 7-[2-Cyclopentyloxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 135° to 140° C. (dec.).

I.R. (Nujol): 3400, 3300, 3190, 1770, 1670, 1620, 1520 cm$^{-1}$

(31) 7-[2-Cyclopentyloxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 160° to 165° C. (dec.).

I.R. (Nujol): 3570, 3440, 3320, 3180, 1775, 1710, 1660, 1620, 1580, 1540, 1520 cm$^{-1}$

(32) 7-[2-Cyclopentyloxyimino-2-(5-amino-1,2,4-thiadiazol-3-yl)acetamido]-3-[1-{3-(N-t-butoxycarbonylamino)propyl}-1H-tetrazol-5-yl]thiomethyl-3- cephem-4-carboxylic acid (syn isomer), pale brown powder.

I.R. (Nujol): 3300, 1770, 1670, 1520, 1240, 1160, 1000 cm$^{-1}$

(33) 7-[2-Cyclopentyloxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), white powder, mp 195° to 199° C. (dec.).

I.R. (Nujol): 3300, 3150, 1760, 1660, 1620, 1520, 1280, 1180, 1000 cm$^{-1}$

(34) 7-[2-Cyclopentyloxyimino-2-(5-amino-1,2,4-thiadiazol-3-yl)acetamido]-3-[1-(2-methoxycarbonylethyl)-1H-tetrazol-5-yl]thiomethyl-3-cephem-4-carboxylic acid (syn isomer), mp 125° to 130° C. (dec.).

I.R. (Nujol): 3480, 3370, 3250, 1780, 1740, 1685, 1625, 1530 cm$^{-1}$

(35) 7-[2-Cyclopentyloxyimino-2-(5-amino-1,2,4-thiadiazol-3-yl)acetamido]-3-(4-methyl-5-oxo-6-hydroxy-4,5-dihydro-1,2,4-triazin-3-yl)thiomethyl-3-cephem-4-carboxylic acid (syn isomer), yellow powder, mp 195° to 199° C. (dec.).

I.R. (Nujol): 3300, 3200, 1770, 1710–1670, 1590, 1520, 1240, 1170, 1090, 1000, 720 cm$^{-1}$

(36) N-[7-{2-Cyclopentyloxyimino-2-(5-amino-1,2,4-thiadiazol-3-yl)acetamido}-3-cephem-3-ylmethyl]-4'-carbamoylpyridinium-4-carboxylate (syn isomer), mp 230° to 235° C. (dec.).

I.R. (Nujol): 3300, 3200, 1770, 1680, 1610, 1560, 1520, 1510 cm$^{-1}$

(37) 7-[2-Cyclopentyloxyimino-2-(5-amino-1,2,4-thiadiazol-3-yl)acetamido]-3-(1,2,4-thiadiazol-5-yl)thiomethyl-3-cephem-4-carboxylic acid (syn isomer), mp 175° to 178° C. (dec.).

I.R. (Nujol): 3300, 3200, 1775, 1680, 1620, 1525 cm$^{-1}$

(38) 7-[2-Cyclopentyloxyimino-2-(5-amino-1,2,4-thiadiazol-3-yl)acetamido]-3-[1-(3-morpholinopropyl)-1H-tetrazol-5-yl]thiomethyl-3-cephem-4-carboxylic acid (syn isomer), mp 183° to 188° C. (dec.).

I.R. (Nujol): 3300, 3150, 1770, 1670, 1610, 1530 cm$^{-1}$

(39) 7-[2-Cycloheptyloxyimino-2-(5-amino-1,2,4-thiadiazol-3-yl)acetamido]-3-(1,3,4-thiadiazol-2-yl)thiomethyl-3-cephem-4-carboxylic acid (syn isomer), white powder, mp 150° to 154° C. (dec.).

I.R. (Nujol): 3300, 3200, 1770, 1670, 1620, 1520, 1400, 1240, 1160, 1060, 1000 cm$^{-1}$

(40) 7-[2-Cycloheptyloxyimino-2-(5-amino-1,2,4-thiadiazol-3-yl)acetamido]-3-cephem-4-carboxylic acid (syn isomer), white powder, mp 170° to 175° C. (dec.).

I.R. (Nujol): 3400, 3300, 3200, 1770, 1670, 1620, 1520, 1280, 1240, 1160, 1000, 980, 730 cm$^{-1}$

(41) 7-[2-Cyclopentyloxyimino-2-(5-amino-1,2,4-thiadiazol-3-yl)acetamido]-3-[1-(3-piperidinopropyl)-1H-tetrazol-5-yl]thiomethyl-3-cephem-4-carboxylic acid (syn isomer), mp 230° C. (dec.).

I.R. Nujol: 3300, 3200, 1770, 1670, 1600, 1520 cm$^{-1}$

EXAMPLE 22

A solution of 7-[2-phenoxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer) (1.4 g) in formic acid (14 ml) was stirred at ambient temperature for 3 hours and evaporated to dryness. The residue was dissolved in a mixture of ethyl acetate and an aqueous solution of sodium bicarbonate and adjusted to pH 2 with 10% hydrochloric acid. The aqueous layer was separated out, washed with ethyl acetate and concentrated to remove ethyl acetate. The aqueous solution was subjected to column chromatography on Diaion HP-20 resin (Trademark: prepared by Mitsubishi Chemical Industries Ltd.). After the column was washed with water, elution was carried out with 50% aqueous methanol. The eluent was evaporated to remove methanol under reduced pressure and the resultant aqueous solution was lyophilized to give 7-[2-phenoxyimino-2-(5-amino-1,2,4-thiadiazol-3-yl)-acetamido]-3-[1-(2-aminoethyl)-1H-tetrazol-5-yl]-thiomethyl-3-cephem-4-carboxylic acid (syn isomer) (0.3 g), mp 180° to 185° C. (dec.).

I.R. (Nujol): 3300, 3250, 1760, 1670, 1620, 1590, 1520 cm$^{-1}$

N.M.R. (d$_6$-DMSO, δ): 3.40 (2H, broad s), 3.60 (2H, broad s), 4.23 (2H, broad s), 4.60 (2H, broad s), 5.13 (1H, d, J=4 Hz), 5.83 (1H, dd, J=4 and 8 Hz), 7.0–7.5 (5H, m), 8.33 (2H, s), 9.90 (1H, d, J=8 Hz)

EXAMPLE 23

A solution of 7-[2-{3-(N-t-butoxycarbonylamino)propoxyimino}-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer)(4.0 g) informic acid (40 ml) was stirred for 2.5 hours at ambient temperature. The reaction mixture was evaporated and dried under reduced pressure to give oil. To the oil were added water (40 ml) and 1 N hydrochloric acid (5 ml) to give clear solution. The solution was subjected to column chromatography on Diaion HP-20 resin (Trademark: prepared by Mitsubishi Chemical Industries Ltd.) and eluted successively with water and 5% aqueous methanol to give 7-[2-(3-aminopropoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer) (0.95 g), mp 184° to 196° C. (dec.).

I.R. (Nujol): 3400–3100, 1760, 1660, 1610, 1520, 1170, 1060, 1010 cm$^{-1}$

N.M.R. (d$_6$-DMSO+D$_2$O, δ): 1.9 (2H, m), 2.8 (2H, m), 3.3 (2H, m), 3.5 (2H, m), 4.1 (4H, m), 4.5 (2H, m), 4.90 (1H, d, J=5 Hz), 5.56 (1H, d, J=5 Hz)

EXAMPLE 24

A solution of 7-[2-{2-(N-t-butoxycarbonylamino)ethoxyimino}-2-(5-amino-1,2,4-thiadiazol-3-yl)acetamido]-3-(1-carboxymethyl-1H-tetrazol-5-yl)thiomethyl-3-cephem-4-carboxylic acid (syn isomer) (1.9 g) in formic acid (28 ml) was stirred for 2 hours at ambient temperature. The reaction mixture was post-treated in a conventional manner to give 7-[2-(2-aminoethoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer) (0.55 g), mp 190° to 198° C. (dec.).

I.R. (Nujol): 3250, 3160, 1760, 1650, 1615, 1522, 1020 cm$^{-1}$

N.M.R. (DCl, δ): 3.11 (2H, broad s), 3.28–3.65 (2H, m), 4.35 (2H, broad s), 4.48–4.78 (2H, m), 5.25 (1H, d, J=4.5 Hz), 5.42 (2H, s), 5.88 (1H, d, J=4.5 Hz)

EXAMPLE 25

A mixture of 7-[2-(2-cyclopenten-1-yl)oxyimino-2-(5-amino-1,2,4-thiadiazol-3-yl)acetamido]-3-[1-{2-(N-t-butoxycarbonylaminoethyl}-1H-tetrazol-5-yl]thiomethyl-3-cephem-4-carboxylic acid (syn isomer) (3.5 g) and formic acid (35 ml) was stirred for 2 hours at room temperature. The reaction mixture was evaporated and the residue was washed successively with diethyl ether and acetone. The washed residue (2.65 g) was added to an aqueous solution of sodium bicarbonate (60 ml.). The mixture was stirred and then filtered to separate insoluble materials. To the filtrate was added ethyl acetate and the mixture was adjusted to pH 3 with 3% hydrochloric acid and then the aqueous layer was separated. On the other hand, to the filtered materials obtained above were added water and ethyl acetate. The mixture was adjusted to pH 3 with 10% hydrochloric acid and then the aqueous layer was separated. The separated aqueous layers were combined, adjusted to pH 2 with 10% hydrochloric acid, washed with ethyl acetate and evaporated to remove ethyl acetate. The residue was subjected to column chromatography (non ionic adsorption resin, Diaion HP-20 prepared by Mitsubishi Chemical Industries), eluting with water, 30% methanol, 50% methanol and 100% methanol. The fractions containing the object compound were collected, evaporated and then lyophilized to give 7-[2-(2-cyclopenten-1-yl)oxyimino-2-(5-amino-1,2,4-thiadiazol-3-yl)acetamido]-3-[1-(2-aminoethyl)-1H-tetrazol-5-yl)thiomethyl-3-cephem-4-carboxylic acid (syn isomer) (580 mg), mp 175° to 180° C. (dec.).

I.R. (Nujol): 3400, 3300, 3170, 1760, 1665, 1610, 1520 cm$^{-1}$

N.M.R. (d$_6$-DMSO, δ): 1.87–2.52 (4H, m), 3.27–3.73 (4H, m), 4.13–4.37 (2H, m), 4.57–4.80 (2H, m), 5.03 (1H, d, J=5 Hz), 5.27–5.53 (1H, m), 5.70 (1H, d, J=5 Hz), 5.85–6.27 (2H, m)

EXAMPLE 26

The following compounds were obtained according to similar manners to those of Examples 22 to 25.

(1) 7-[2-(2-Aminoethoxyimino)-2-(5-amino-1,2,4-thiadiazol-3-yl)acetamido]-2-methyl-3-cephem-4-carboxylic acid (syn isomer), mp 190° to 195° C. (dec.).

I.R. (Nujol): 3300, 3150, 1760, 1660, 1575, 1520, 1400 cm$^{-1}$

N.M.R. (D$_2$O+DCl, δ): 1.55 (3H, d, J=7 Hz), 3.5 (2H, t, J=4.6 Hz), 3.7–4.2 (1H, m), 4.67 (2H, t, J=4.6 Hz), 5.27 (1H, d, J=4.5 Hz), 6.03 (1H, d, J=4.5 Hz), 6.90 (1H, d, J=6 Hz)

(2) 7-[2-(3-Aminopropoxyimino)-2-(5-amino-1,2,4-thiadiazol-3-yl)acetamido]-2-methyl-3-cephem-4-carboxylic acid (syn isomer), mp 182° to 187° C. (dec.).

I.R. (Nujol): 3260, 3150, 1758, 1660, 1616, 1575, 1520, 1400 cm$^{-1}$

N.M.R. (DCl+D$_2$O, δ): 1.55 (3H, d, J=6.5 Hz), 1.93–2.50 (2H, m), 3.25 (2H, t, J=7 Hz), 3.70–4.15 (1H, m), 4.5 (2H, t, J=6 Hz), 5.23 (1H, d, J=4.5 Hz), 6.05 (1H, d, J=4.5 Hz), 6.88 (1H, d, J=6 Hz)

(3) 7-[2-(3-Aminopropoxyimino)-2-(5-amino-1,2,4-thiadiazol-3-yl)acetamido]-3-methyl-3-cephem-4-carboxylic acid (syn isomer), mp 175° to 195° C. (dec.).

I.R. (Nujol): 3300–3100, 1770–1740, 1660, 1620, 1570, 1520, 1280, 1170, 1060, 1020 cm$^{-1}$ N.M.R. (d$_6$-DMSO+D$_2$O, δ): 1.87 (3H, s), 1.9 (2H, m), 2.9 (2H, m), 3.2 (2H, m), 4.2 (2H, m), 4.93 (1H, d, J=5 Hz), 5.60 (1H, d, J=5 Hz)

(4) 7-[2-(3-Aminopropoxyimino)-2-(5-amino-1,2,4-thiadiazol-3-yl)acetamido]-3-chloro-3-cephem-4-carboxylic acid (syn isomer), mp 190° to 205° C. (dec.).

I.R. (Nujol): 3400–3150, 1760, 1660, 1630–1590, 1520, 1340, 1170, 1030 cm$^{-1}$ N.M.R. (d$_6$-DMSO, δ): 2.00 (2H, m), 2.90 (2H, m), 3.33 and 3.83 (2H, ABq, J=16 Hz), 4.20 (2H, m), 5.09 (1H, d, J=5 Hz), 5.60 (1H, m), 8.15 (2H, m), 9.50 (1H, m)

(5) 7-[2-(2-Aminoethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 182° to 187° C. (dec.).

I.R. (Nujol): 3350, 3150, 1760, 1660, 1625, 1565, 1520 cm$^{-1}$

N.M.R. (d$_6$-DMSO, δ): 3.2–3.9 (6H, m), 4.05,4.32 (2H, ABq, J=14 Hz), 4.4–5.0 (4H, m), 5.22 (1H, d, J=4.5 Hz)

(6) 7-[2-(2,2,2-Trifluoroethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 185° to 190° C. (dec.).

I.R. (Nujol): 3300, 3170, 1760, 1670, 1615 1500 cm$^{-1}$

N.M.R. (d$_6$-DMSO, δ): 3.17–3.83 (4H, m), 4.28 (2H, broad s), 4.47–4.93 (4H, m), 5.10 (1H, d, J=5 Hz), 5.73 (1H, dd, J=5 and 8 Hz), 8.20 (2H, broad s), 9.65 (1H, d, J=8 Hz)

(7) 7-[2-Cyclopentyloxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), white powder, mp 195° to 199° C. (dec.).

I.R. (Nujol): 3300, 3150, 1760, 1660, 1620, 1520, 1280, 1180, 1000 cm$^{-1}$

N.M.R. (d$_6$-DMSO, δ): 1.70 (8H, m), 2.20 (2H, m), 2.87 (2H, m), 3.57 (2H, m), 4.03–4.60 (4H, m), 4.70 (1H, m), 5.00 (1H, d, J=5 Hz), 5.63 (1H, dd, J=5 and 8 Hz), 8.10 (2H, m), 9.40 (1H, d, J=8 Hz)

(8) 7-[2-(2-Cyclohexen-1-yl)oxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 185° to 190° C. (dec.).

I.R. (Nujol): 3280, 3150, 1760, 1665, 1620, 1520 cm$^{-1}$

N.M.R. (d$_6$-DMSO, δ): 1.47–2.30 (8H, m), 2.73–3.13 (2H, m), 3.63 (2H, broad s), 4.17–4.60 (4H, m), 4.60–4.90 (1H, m), 5.03 (1H, d, J=5 Hz), 5.73 (1H, dd, J=5 and 8 Hz), 5.75–5.99 (2H, m), 8.13 (2H, broad s), 9.43 (1H, d, J=8 Hz)

EXAMPLE 27

A mixture of 7-[2-t-butoxycarbonylmethoxyimino-2-(5-amino-1,2,4-thiadiazol-3-yl)acetamido]-3-(1,3,4-thiadiazol-2-yl)thiomethyl-3-cephem-4-carboxylic acid (syn isomer) (1.6 g.), trifluoroacetic acid (10 ml) and anisole (2 ml) was stirred for 30 minutes at ambient temperature. The reaction mixture was evaporated and the residue was pulverized with diethyl ether, collected by filtration and then dried. The obtained product (1.6 g) was dissolved in an aqueous solution of sodium bicarbonate, washed with ethyl acetate and then added to ethyl acetate. The mixture was adjusted to pH 2 with 1 N hydrochloric acid and extracted with ethyl acetate. The extract was washed with a saturated aqueous solution of sodium chloride, dried over magnesium sulfate and then evaporated. The residue was pulverized with diethyl ether, collected by filtration and dried to give 7-[2-carboxymethoxyimino-2-(5-amino-1,2,4-thiadiazol-3-yl)acetamido]-3-(1,3,4-thiadiazol-2-yl)thiomethyl-3-cephem-4-carboxylic acid (syn isomer) (0.52 g), mp 170° to 175° C. (dec.).

I.R. (Nujol): 3250, 3150, 1770, 1710, 1680, 1610, 1520 cm$^{-1}$

N.M.R. (d$_6$-DMSO, δ): 3.67 (2H, broad s), 4.55 (2H, ABq, J=13 Hz), 4.63 (2H, s), 5.12 (1H, d, J=4 Hz), 5.80 (1H, dd, J=4 and 8 Hz), 8.15 (2H, s), 9.55 (1H, d, J=8 Hz), 9.58 (1H, s).

EXAMPLE 28

The following compounds were obtained according to a similar manner to that of Example 27.

(1) 7-[2-Carboxymethoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 145° to 150° C. (dec.).

I.R. (Nujol): 3400, 3300, 3200, 1765, 1720, 1680, 1620, 1520 cm$^{-1}$

N.M.R. (d$_6$-DMSO, δ): 3.70 (2H, broad s), 4.30 and 4.47 (2H, ABq, J = 13 Hz), 4.68 (2H, s), 4.83–5.15 (2H, m), 5.15 (1H, d, J = 5 Hz), 5.17–5.50 (2H, m), 5.85 (1H, dd, J = 5 and 8 Hz), 5.60–6.20 (1H, m), 8.13 (2H, broad s), 9.53 (1H, d, J = 8 Hz)

(2) 7-[2-Carboxymethoxyimino-2-(5-amino-1,2,4-thiadiazol-3-yl)acetamido]cephalosporanic acid (syn isomer), mp 160° to 165° C. (dec.).

I.R. (Nujol): 3300, 3200, 1770, 1720, 1680, 1520 cm$^{-1}$

N.M.R. (d$_6$-DMSO, δ): 2.10 (3H, s), 3.60 (2H, broad s), 4.70 (2H, s), 4.77 and 5.03 (2H, ABq, J = 14 Hz), 5.20 (1H, d, J = 4 Hz), 5.88 (1H, dd, J = 4 and 8 Hz), 8.18 (2H, s), 9.57 (1H, d, J = 8 Hz)

(3) 7-[2-Carboxymethoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3180, 1765, 1720, 1680, 1615, 1520 cm$^{-1}$

N.M.R. (d$_6$-DMSO, δ): 3.75 (2H, broad s), 4.28 and 4.60 (2H, ABq, J = 13 Hz), 4.67 (2H, s), 5.17 (1H, d, J = 5 Hz), 5.87 (1H, dd, J = 5 and 8 Hz), 7.77 (1H, d, J = 10 Hz), 8.17 (2H, broad s), 8.60 (1H, d, J = 10 Hz), 9.57 (1H, d, J = 8 Hz)

(4) 7-[2-Carboxymethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 185° to 190° C. (dec.).

I.R. (Nujol): 3250, 1755, 1660, 1590, 1520 cm$^{-1}$

N.M.R. (d$_6$-DMSO, δ): 3.23–3.67 (4H, m), 4.07 and 4.35 (2H, ABq, J = 13 Hz), 4.23–4.80 (4H, m), 5.03 (1H, d, J = 5 Hz), 5.70 (1H, dd, J = 5 and 8 Hz), 8.15 (2H, broad s), 11.03 (1H, d, J = 8 Hz)

(5) 7-[2-Carboxymethoxyimino-2-(5-amino-1,2,4-thiadiazol-3-yl)acetamido]-3-(1-phenyl-1H-tetrazol-5-yl)thiomethyl-3-cephem-4-carboxylic acid (syn isomer), mp 155° to 160° C. (dec.).

I.R. (Nujol): 3400, 3300, 3180, 1765, 1720, 1680, 1615, 1520, 1495 cm$^{-1}$

N.M.R. (d$_6$-DMSO, δ): 3.65 (2H, broad s), 4.28 and 4.52 (2H, ABq, J = 13 Hz), 4.63 (2H, s), 5.07 (1H, d, J = 5 Hz), 5.80 (1H, dd, J = 5 and 8 Hz), 7.63 (5H, s), 8.10 (2H, broad s), 9.47 (1H, d, J = 8 Hz)

EXAMPLE 29

A mixture of 7-[2-trityloxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer) (4.5 g), conc.hydrochloric acid (4.5 ml) and methanol (45 ml) was stirred for 7 hours at ambient temperature. Methanol was distilled off from the reaction mixture and the residue was adjusted to pH 5 by adding ethyl acetate and an aqueous solution of sodium bicarbonate. To the separated aqueous layer was added ethyl acetate and the mixture was adjusted to pH 2 with 10% hydrochloric acid. The separated ethyl acetate layer was dried over magnesium sulfate and evaporated in vacuo to a volume of 10 ml. Precipitates were collected by filtration, washed with ethyl acetate and diethyl ether and dried to give 7-[2-hydroxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer) (1.4 g), mp 153° to 162° C. (dec.).

I.R. (Nujol): 3260, 3160, 1763, 1665, 1608, 1520 cm$^{-1}$

N.M.R. (d$_6$-DMSO, δ): 2.67 (3H, s), 3.67 (2H, broad s), 4.23 and 4.53 (2H, ABq, J = 13 Hz), 5.12 (1H, d, J = 4.5 Hz), 5.82 (1H, dd, J = 4.5 and 8.5 Hz), 7.98 (2H, broad s), 9.37 (1H, d, J = 8.5 Hz)

EXAMPLE 30

A solution of 7-[2-hydroxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer) (257.3 mg) and sodium bicarbonate (42 mg) in water (10 ml) was lyophilized. The obtained product was dissolved in N,N-dimethylformamide (5 ml) and to the solution was added a solution of iodomethyl pivalate (142.5 mg) in N,N-dimethylformamide (1 ml) with stirring and the stirring was continued for 20 minutes. The reaction mixture was washed with water (×3), dried over magnesium sulfate and evaporated. The residue was pulverized with diethyl ether to give pivaloyloxymethyl 7-[2-hydroxyimino-2-(5-amino-1,2,4-thiadiazol-3-yl)acetamido]-3-(5-methyl-1,3,4-thiadiazol-2-yl)thiomethyl-3-cephem-4-carboxylate (syn isomer) (240 mg), mp 132° to 135° C. (dec.).

I.R. (Nujol): 3270, 3160, 1775, 1745, 1675, 1610, 1520, 1115 cm$^{-1}$

N.M.R. (d$_6$-DMSO, δ): 1.09 (9H, s), 2.70 (3H, s), 3.66 and 3.82 (2H, ABq, J = 15 Hz), 4.18 and 4.58 (2H, ABq, J = 14 Hz), 5.20 (1H, d, J = 4.5 Hz), 5.80–6.2 (3H, m), 8.04 (2H, broad s), 9.47 (1H, d, J = 7.5 Hz)

EXAMPLE 31

The following compounds were obtained according to a similar manner to that of Example 30.

(1) 4-Nitrobenzyl 7-[2-(4-chlorophenoxyimino)-2-(5-amino-1,2,4-thiadiazol-3-yl)acetamido]-3-cephem-4-carboxylate (syn isomer), mp 155° to 160° C. (dec.).

I.R. (Nujol): 3300, 3180, 1770, 1720, 1680, 1625, 1600, 1580, 1520, 1480 cm$^{-1}$ (2) 4-Nitrobenzyl 7-[2-phenoxyimino-2-(5-amino-1,2,4-thiadiazol-3-yl)acetamido]-3-cephem-4-carboxylate (syn isomer), mp 140° to 145° C. (dec.).

I.R. (Nujol): 3300, 1775, 1720, 1680, 1625, 1600, 1590, 1520 cm$^{-1}$ (3) 4-Nitrobenzyl 7-[2-(3-trifluoromethylphenoxyimino)-2-(5-amino-1,2,4-thiadiazol-3-yl)acetamido]-3-cephem-4-carboxylate (syn isomer), mp 136° to 140° C. (dec.).

I.R. (Nujol): 3370, 3200, 1780, 1730, 1690, 1680, 1630, 1610, 1520, 1450, 1325, 1280, 1160, 1125, 975, 850, 740 cm$^{-1}$ (4) 4-Nitrobenzyl 7-[2-(4-fluorophenoxyimino)-2-(5-amino-1,2,4-thiadiazol-3-yl)acetamido]-3-cephem-4-carboxylate (syn isomer), mp 135° to 140° C. (dec.).

I.R. (Nujol): 3300, 3200, 1770, 1720, 1680, 1625, 1605, 1500, 1495 cm$^{-1}$ (5) 4-Nitrobenzyl 7-[2-{3-(N-t-butoxycarbonylamino)propoxyimino}-2-(5-amino-1,2,4-thiadiazol-3-yl)-acetamido]-3-chloro-3-cephem-4-carboxylate (syn isomer), mp 91° to 100° C. (dec.).

N.M.R. (d$_6$-DMSO+D$_2$O, δ): 1.38 (9H, s), 1.80 (2H,m), 3.06 (2H, m), 3.7–4.3 (4H, m), 5.33 (1H, d, J = 5 Hz), 5.49 (2H, s), 5.95 (1H, d, J = 5 Hz), 7.74 (2H, d, J = 9 Hz), 8.92 (2H, d, J = 9 Hz)

(6) 4-Nitrobenzyl 7-[2-allyloxyimino-2-(5-amino-1,2,4-thiadiazol-3-yl)acetamido]-3-cephem-4-carboxylate (syn isomer), mp 125° to 130° C. (dec.).

I.R. (Nujol): 3300, 1770, 1720, 1680, 1630, 1610, 1520 cm$^{-1}$

EXAMPLE 32

A mixture of 2-allyloxyimino-2-(5-amino-1,2,4-thiadiazol-3-yl)acetic acid (syn isomer) (1.37 g) and phosphorus oxychloride (3.67 g) in methylane chloride (30 ml) was stirred for 2 hours at ambient temperature and then cooled to $-12°$ to $-15°$ C. To the cold mixture was added dimethylformamide (2.4 ml) and the mixture was stirred for 45 minutes at $-8°$ to $-10°$ C. On the other hand, a mixture of 7-amino-3-(1,3,4-thiadiazol-2-yl)thiomethyl-3-cephem-4-carboxylic acid (2.9 g) and trimethylsilylacetamide (8 g) in methylene chloride (40 ml) was warmed to make a solution. The solution was cooled to $-25°$ C. and added to the above activated mixture. The reaction mixture was stirred for 30 minutes at $-8°$ to $-10°$ C. and poured into a cold aqueous solution of sodium bicarbonate. The mixture was stirred for 30 minutes at ambient temperature and the aqueous layer was separated out. The aqueous solution was adjusted to pH 1 with 10% hydrochloric acid and extracted with ethyl acetate. The extract was dried over magnesium sulfate and evaporated to dryness. The residue was triturated with diethyl ether to give a crude 7-[2-allyloxyimino-2-(5-amino-1,2,4-thiadiazol-3-yl)acetamido]-3-(1,3,4-thiadiazol-2-yl)thiomethyl-3-cephem-4-carboxylic acid (syn isomer) (2.1 g). The crude product was dissolved in an aqueous solution of sodium bicarbonate and reprecipitated with an addition of 10% hydrochloric acid to give pure object compound (1.15 g). mp 138° to 140° C. (dec.)

I.R. (Nujol): 3350, 3230, 1780, 1680, 1620, 1530 cm$^{-1}$

N.M.R. (d$_6$-DMSO, δ): 3.63 (2H, broad s), 4.27 and 4.52 (2H, ABq, J=14 Hz), 4.5–4.8 (2H, m), 5.10 (1H, d, J=5 Hz), 5.0–5.5 (2H, m), 5.78 (1H, dd, J=5 and 9 Hz), 5.7–6.3 (1H, m), 8.09 (2H, broad s), 9.48 (1H, s), 9.53 (1H, d, J=9 Hz)

EXAMPLE 33

A mixture of 2-(2,2,2-trifluoroethoxyimino)-2-(5-amino-1,2,4-thiadiazol-3-yl)acetic acid (syn isomer) (1.62 g) and phosphorus oxychloride (3.67 g) in methylene chloride (30 ml) was stirred for 1.5 hours at ambient temperature and then cooled to $-12°$ to $-15°$ C. To the cold mixture was added dimethylformamide (2.4 ml) and the mixture was stirred for 45 minutes at $-8°$ to $-10°$ C. On the other hand, a mixture of 7-amino-3-(1,3,4-thiadiazol-2-yl)thiomethyl-3-cephem-4-carboxylic acid (2.9 g) and trimethylsilylacetamide (8 g) in methylene chloride (40 ml) was warmed to make a solution. The solution was cooled to $-25°$ C. and added to the above activated mixture. The reaction mixture was stirred for 30 minutes at $-10°$ C. and poured into a cold aqueous solution of sodium bicarbonate. The mixture was stirred for 30 minutes at ambient temperature and the aqueous layer was separated out. The aqueous solution was adjusted to pH 2 with 10% hydrochloric acid and extracted with ethyl acetate. The extract was dried over magnesium sulfate and evaporated to dryness. The residue was triturated with diethyl ether to give a crude 7-[2-(2,2,2-trifluoroethoxyimino)-2-(5-amino-1,2,4-thiadiazol-3-yl)acetamido]-3-(1,3,4-thiadiazol-2-yl)thiomethyl-3-cephem-4-carboxylic acid (syn isomer) (2.45 g). The crude product was dissolved in an aqueous solution of sodium bicarbonate and reprecipitated with an addition of 10% hydrochloric acid to give pure object compound (1.42 g). mp 153° to 158° C. (dec.).

I.R. (Nujol): 3350, 3250, 1780, 1680, 1625 cm$^{-1}$

N.M.R. (d$_6$-DMSO, δ): 3.70 (2H, broad s), 4.33 and 4.58 (2H, ABq, J=13 Hz), 4.70 and 4.92 (2H, ABq, J=9 Hz), 5.17 (1H, d, J=5 Hz), 5.82 (1H, dd, J=5 and 8 Hz), 8.18 (2H, broad s), 9.55 (1H, s), 9.70 (1H, d, J=8 Hz)

EXAMPLE 34

A mixture of dimethylformamide (6 ml) and phosphorus oxychloride (918 mg) was stirred for 30 minutes at ambient temperature. Methylene chloride (6 ml) was added thereto and then 2-dichloroacetoxyimino-2-(5-formamido-1,2,4-thiadiazol-3-yl)acetic acid (syn isomer) (1.6 g) was added thereto at $-20°$ to $-25°$ C. The mixture was stirred for 30 minutes at $-10°$ to $-15°$ C. To the resulting mixture was added at $-10°$ to $-15°$ C. a solution of 7-amino-3-(1,3,4-thiadiazol-2-yl)thiomethyl-3-cephem-4-carboxylic acid (2.0 g) and trimethylsilylacetamide (6 g) in methylene chloride (30 ml), and the mixture was stirred for 30 minutes at $-5°$ to $-15°$ C. Methylene chloride was evaporated from the reaction mixture and to the residue were added ice-water and ethyl acetate. The resulting mixture containing 7-[2-dichloroacetoxyimino-2-(5-formamido-1,2,4-thiadiazol-3-yl)acetamido]-3-(1,3,4-thiadiazol-2-yl)thiomethyl-3-cephem-4-carboxylic acid (syn isomer) was adjusted to pH 5 with an aqueous solution of sodium bicarbonate. An aqueous layer was separated and ethyl acetate was added thereto. The mixture was adjusted to pH 2 with 10% hydrochloric acid and an insoluble substance was filtered off. The filtrate was extracted three times with ethyl acetate. The extracts were dried over magnesium sulfate and evaporated. The residue was triturated with diethyl ether and precipitates were collected by filtration and washed with diethyl ether to give 7-[2-hydroxyimino-2-(5-formamido-1,2,4-thiadiazol-3-yl)acetamido]-3-(1,3,4-thiadiazol-2-yl)thiomethyl-3-cephem-4-carboxylic acid (syn isomer) (0.9 g). mp 155° to 160° C. (dec.)

I.R. (Nujol): 3200, 1780, 1680, 1620 cm$^{-1}$ N.M.R. (d$_6$-DMSO, δ): 3.67 (2H, broad s), 4.27 and 4.73 (2H, ABq, J=13 Hz), 5.13 (1H, d, J=4 Hz), 5.83 (1H, dd, J=4 and 8 Hz), 8.80 (1H, s), 9.50 (1H, d, J=8 Hz), 9.53 (1H, s), 12.22 (1H, s)

EXAMPLE 35

The following compounds were obtained according to similar manners to those of Examples 32 to 34.

(1) 7-[2-(2-Propynyloxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 140° to 145° C. (dec.)

I.R. (Nujol): 3330, 3250, 1780, 1680, 1620, 1530 cm$^{-1}$

N.M.R. (d$_6$-DMSO, δ): 3.47 (1H, t, J=2 Hz), 3.67 (2H, broad s), 4.28 and 4.53 (2H, ABq, J=13 Hz), 4.77 (2H, d, J=2 Hz), 5.12 (1H, d, J=5 Hz), 5.78 (1H, dd, J=5 and 8 Hz), 8.13 (2H, broad s), 9.55 (1H, s), 9.67 (1H, d, J=8 Hz)

(2) 7-[2-Benzyloxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 135° C. (dec.)

I.R. (Nujol): 3360, 3250, 1780, 1680, 1625, 1530 cm$^{-1}$

N.M.R. (d$_6$-DMSO, δ): 3.63 (2H, broad s), 4.35 and 4.58 (2H, ABq, J=13 Hz), 5.13 (1H, d, J=5 Hz), 5.23 (2H, s), 5.80 (1H, dd, J=5 and 8 Hz), 7.38 (5H, s), 8.13 (2H, broad s), 9.57 (1H, s) 9.63 (1H, d, J=8 Hz)

(3) 7-[2-(2-Phenoxyethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 163° to 167° C. (dec.).

I.R. (Nujol): 3350, 3250, 1780, 1680, 1630, 1600, 1530, 1500 cm$^{-1}$

N.M.R. (d$_6$-DMSO, δ): 3.30 and 3.60 (2H, ABq, J=18 Hz), 4.0–4.70 (6H, m), 5.10 (1H, d, J=4 Hz), 5.93 (1H, dd, J=4 and 8 Hz), 6.7–7.5 (5H, m), 8.13 (2H, s), 9.50 (1H, s), 9.57 (1H, d, J=8 Hz)

(4) 7-[2-Methylthiomethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 168° to 170° C. (dec.)

I.R. (Nujol): 3350, 3250, 1780, 1680, 1620, 1530 cm$^{-1}$

N.M.R. (d$_6$-DMSO, δ): 2.17 (3H, s), 3.65 (2H, broad s), 4.30 and 4.57 (2H, ABq, J=14 Hz), 5.12 (1H, d, J=4 Hz), 5.20 (2H, s), 5.80 (1H, dd, J=4 and 8 Hz), 8.17 (2H, s), 9.53 (1H, s), 9.62 (1H, d, J=8 Hz)

(5) 7-[2-(2-Methylthioethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 125° to 130° C. (dec.)

I.R. (Nujol): 3350, 3250, 1780, 1680, 1625, 1530 cm$^{-1}$

N.M.R. (d$_6$-DMSO, δ): 2.08 (3H, s), 2.72 (2H, t, J=7 Hz), 3.68 (2H, broad s), 4.28 (2H, t, J=7 Hz), 4.30 and 4.55 (2H, ABq, J=13 Hz), 5.13 (1H, d, J=5 Hz), 5.82 (1H, dd, J=5 and 8 Hz), 8.15 (2H, broad s), 9.52 (1H, d, J=8 Hz), 9.53 (1H, s)

(6) 7-[2-Phenoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 145° to 150° C. (dec.)

I.R. (Nujol): 3350, 3230, 1780, 1680, 1620, 1590, 1530 cm$^{-1}$

N.M.R. (d$_6$-DMSO, δ): 3.70 (2H, broad s), 4.30 and 4.60 (2H, ABq, J=14 Hz), 5.23 (1H, d, J=5 Hz), 5.92 (1H, dd, J=5 and 8 Hz), 7.0–7.6 (5H, m), 8.30 (2H, broad s), 9.52 (1H, s), 9.83 (1H, d, J=8 Hz)

(7) 7-[2-Cyanomethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 105° to 110° C. (dec.)

I.R. (Nujol): 3350, 3250, 1780, 1680, 1620, 1530 cm$^{-1}$

N.M.R. (d$_6$-DMSO, δ): 3.6 and 3.76 (2H, ABq, J=18 Hz), 4.3 and 4.56 (2H, ABq, J=13 Hz), 5.12 (2H, s), 5.14 (1H, d, J=5 Hz), 5.80 (1H, dd, J=5 and 8 Hz), 8.20 (2H, broad s), 9.52 (1H, s), 9.78 (1H, d, J=8 Hz)

(8) 7-[2-(N,N-Diethylcarbamoyl)methoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 175° to 180° C. (dec.)

I.R. (Nujol): 3480, 3310, 3200, 1775, 1740, 1680, 1630, 1610, 1515 cm$^{-1}$

N.M.R. (d$_6$-DMSO, δ): 1.00 (3H, t, J=7 Hz), 1.08 (3H, t, J=7 Hz), 3.27 (4H, q, J=7 Hz), 3.62 and 3.72 (2H, ABq, J=18 Hz), 4.53 and 4.55 (2H, ABq, J=14 Hz), 4.88 (2H, s), 5.15 (1H, d, J=5 Hz), 5.83 (1H, dd, J=5 and 9 Hz), 8.13 (2H, broad s), 9.55 (1H, s), 9.62 (1H, d, J=9 Hz)

(9) 7-[2-(1-Ethoxycarbonyl-1-methylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 135° C. (dec.)

I.R. (Nujol): 3360, 3240, 1780, 1730, 1690, 1630, 1530 cm$^{-1}$

N.M.R. (d$_6$-DMSO, δ): 1.18 (3H, t, J=7 Hz), 1.50 (6H, s), 3.72 (2H, broad s), 4.13 (2H, q, J=7 Hz), 4.33 and 4.58 (2H, ABq, J=13 Hz), 5.18 (1H, d, J=5 Hz), 5.85 (1H, dd, J=5 and 8 Hz), 8.18 (2H, broad s), 9.48 (1H, d, J=8 Hz), 9.57 (1H, s)

(10) 7-[2-Ethoxycarbonylmethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 120° to 125° C. (dec.)

I.R. (Nujol): 3370, 3250, 1780, 1690, 1625, 1530 cm$^{-1}$

N.M.R. (d$_6$-DMSO, δ): 1.23 (3H, t, J=7 Hz), 3.72 (2H, broad s), 4.20 (2H, q, J=7 Hz), 4.35 and 4.58 (2H, ABq, J=13 Hz), 4.78 (2H, s), 5.17 (1H, d, J=5 Hz), 5.83 (1H, dd, J=5 and 8 Hz), 8.20 (2H, broad s), 9.58 (1H, d, J=8 Hz), 9.60 (1H, s)

(11) 7-[2-Hydroxyimino-2-(5-formamido-1,2,4-thiadiazol-3-yl)acetamido]-3-(1,3,4-thiadiazol-2-yl)thiomethyl-3-cephem-4-carboxylic acid (syn isomer). mp 155° to 160° C. (dec.)

I.R. (Nujol): 3200, 1780, 1680, 1620 cm$^{-1}$

(12) 7-[2-{2-(2-Hexyloxyethoxy)ethoxyimino}2-(5-amino-1,2,4-thiadiazol-3-yl)acetamido]-3-(1,3,4-thiadiazol-2-yl)thiomethyl-3-cephem-4-carboxylic acid (syn isomer). mp 100° to 105° C. (dec.)

I.R. (Nujol): 3340, 3210, 1785, 1685, 1620, 1525 cm$^{-1}$

N.M.R. (d$_6$-DMSO, δ): 0.87 (3H, t, J=5 Hz), 0.87–1.73 (8H, m), 3.10–3.93 (10H, m), 4.10–4.47 (2H, m), 4.30 and 4.58 (2H, ABq, J=13 Hz), 5.17 (1H, d, J=5 Hz), 5.83 (1H, dd, J=5 and 8 Hz), 8.12 (2H, broad s), 9.55 (1H, d, J=8 Hz), 9.57 (1H, s)

(13) 7-[2-Mesylmethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 164° to 167° C. (dec.)

I.R. (Nujol): 3360, 3230, 1780, 1690, 1620, 1530 cm$^{-1}$

N.M.R. (d$_6$-DMSO, δ): 3.02 (3H, s), 3.72 (2H, broad s), 4.33 and 4.57 (2H, ABq, J=13 Hz), 5.15 (1H, d, J=5 Hz), 5.30 (2H, s), 5.83 (1H, dd, J=5 and 8 Hz), 8.20 (2H, broad s), 9.55 (1H, s), 9.78 (1H, d, J=8 Hz)

(14) 7-[2-Trityloxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 163° to 167° C. (dec.)

I.R. (Nujol): 3480, 3350, 3250, 1785, 1690, 1620, 1530 cm$^{-1}$

N.M.R. (d$_6$-DMSO, δ): 3.64 and 3.72 (2H, ABq, J=18 Hz), 3.90 (3H, s), 4.24 and 4.38 (2H, ABq, J=14 Hz), 5.18 (1H, d, J=4 Hz), 5.98 (1H, dd, J=4 and 8 Hz), 7.30 (15H, s), 8.08 (2H, s), 9.84 (1H, d, J=8 Hz)

(15) 7-[2-Trityloxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 175° to 178° C. (dec.)

I.R. (Nujol): 3450, 3350, 3200, 1790, 1690, 1620, 1530 cm$^{-1}$

N.M.R. (d$_6$-DMSO, δ): 3.73 (2H, broad s), 4.33 and 4.63 (2H, ABq, J=13 Hz), 5.10 (1H, d, J=4 Hz), 6.03 (1H, dd, J=4 and 8 Hz), 7.37 (15H, s), 8.13 (2H, s), 9.60 (1H, s), 9.87 (1H, d, J=8 Hz)

(16) 7-[2-Allyloxyimino-2-(5-amino-1,2,4-thiadiazol-3-yl)acetamido]cephalosporanic acid (syn isomer). mp 131° to 133° C. (dec.)

I.R. (Nujol): 3350, 3240, 1780, 1730, 1680, 1530, 1240 cm$^{-1}$

N.M.R. (d$_6$-DMSO, δ): 2.07 (3H, s), 3.57 (2H, broad s), 4.5–5.1 (2H, m), 4.7 (2H, broad s), 5.1–5.6 (2H, m), 5.15 (1H, d, J=4 Hz), 5.6–6.4 (1H, m), 5.84 (1H, dd, J=4.5 and 9 Hz), 8.13 (2H, broad s), 9.67 (1H, d, J=9 Hz)

(17) 7-[2-Allyloxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 154° to 156° C. (dec.)

I.R. (Nujol): 3380, 3245, 1780, 1680, 1625, 1527 cm$^{-1}$

N.M.R. (d₆-DMSO, δ): 3.53 and 3.77 (2H, ABq, J=14 Hz), 3.90 (3H, s), 4.27 (2H, broad s), 4.5–4.8 (2H, m), 5.0–5.6 (2H, m), 5.15 (1H, d, J=4.5 Hz), 5.6–6.3 (1H, m), 5.85 (1H, dd, J=4.5 and 9 Hz), 7.23 (2H, broad s), 9.77 (1H, d, J=9 Hz)

(18) 7-[2-Trityloxyimino-2-(5-amino-1,2,4-thiadiazol-3-yl)acetamido]-3-(1,3,4-thiadiazol-2-yl)thiomethyl-3-cephem-4-carboxylic acid (anti isomer). mp 165° to 170° C. (dec.)

I.R. (Nujol): 3350, 3200, 1785, 1690, 1620, 1515 cm⁻¹

N.M.R. (d₆-DMSO, δ): 3.70 (2H, broad s), 4.33 and 4.60 (2H, ABq, J=13 Hz), 5.10 (1H, d, J=4 Hz), 5.73 (1H, dd, J=4 and 8 Hz), 7.33 (15H, s), 8.17 (1H, d, J=8 Hz), 8.23 (2H, s), 9.60 (1H, s)

(19) 7-[2-Allyloxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 161° to 164° C. (dec.)

I.R. (Nujol): 3350, 3220, 1770, 1670, 1620, 1525 cm⁻¹

(20) 7-[2-Allyloxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer). powder.

(21) 7-[2-Allyloxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 165° to 169° C. (dec.)

I.R. (Nujol): 3350, 3200, 1768, 1670, 1610, 1522 cm⁻¹

(22) 7-[2-Hydroxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 165° to 170° C. (dec.)

I.R. (Nujol): 3350, 3250, 1780, 1680, 1620, 1530 cm⁻¹

(23) 7-[2-Hydroxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 170° to 175° C. (dec.)

I.R. (Nujol): 3480, 3350, 1770, 1690, 1620, 1530 cm⁻¹

(24) 7-[2-Hydroxyimino-2-(5-amino-1,2,4-thiadiazol-3-yl)acetamido]-3-(1,3,4-thiadiazol-2-yl)thiomethyl-3-cephem-4-carboxylic acid (anti isomer). mp 155° to 160° C. (dec.)

I.R. (Nujol): 3350, 3250, 1780, 1680, 1620, 1520 cm⁻¹

EXAMPLE 36

The following compounds were obtained according to similar manners to those of Examples 14 to 17.

(1) 7-[2-Hydroxyimino-2-(5-formamido-1,2,4-thiadiazol-3-yl)acetamido]-3-(1,3,4-thiadiazol-2-yl)thiomethyl-3-cephem-4-carboxylic acid (syn isomer). mp 155° to 160° C. (dec.)

I.R. (Nujol): 3200,1780,1680,1620 cm⁻¹

(2) 7-[2-Allyloxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 138° to 140° C. (dec.)

I.R. (Nujol): 3350,3230,1780,1680,1620,1530 cm⁻¹

(3) 7-[2-(2,2,2-Trifluoroethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 153° to 158° C.

I.R. (Nujol): 3350, 3250,1780,1680,1625 cm⁻¹

(4) 7-[2-(2-Propynyloxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 140° to 145° C. (dec.)

I.R. (Nujol): 3330, 3250, 1780, 1680, 1620, 1530 cm⁻¹

(5) 7-[2-Benzyloxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 135° C. (dec.)

I.R. (Nujol): 3360, 3250, 1780, 1680, 1625, 1530 cm⁻¹

(6) 7-[2-(2-Phenoxyethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 163° to 167° C. (dec.)

I.R. (Nujol): 3350, 3250, 1780, 1680, 1630, 1600, 1530, 1500 cm⁻¹

(7) 7-[2-Methylthiomethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 168° to 170° C. (dec.)

I.R. (Nujol): 3350, 3250, 1780, 1680, 1620, 1530 cm⁻¹

(8) 7-[2-(2-Methylthioethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 125° to 130° C. (dec.)

I.R. (Nujol): 3350, 3250, 1780, 1680, 1625, 1530 cm⁻¹

(9) 7-[2-Phenoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 145° to 150° C. (dec.)

I.R. (Nujol): 3350, 3230, 1780, 1680, 1620, 1590, 1530 cm⁻¹

(10) 7-[2-Cyanomethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 105° to 110° C. (dec.)

I.R. (Nujol): 3350, 3250, 1780, 1680, 1620, 1530 cm⁻¹

(11) 7-[2-(N,N-Diethylcarbamoyl)methoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 175° to 180° C. (dec.)

I.R. (Nujol): 3480, 3310, 3200, 1775, 1740, 1680, 1630, 1610, 1515 cm⁻¹

(12) 7-[2-(1-Ethoxycarbonyl-1-methylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer). mp 130° to 135° C. (dec.)

I.R. (Nujol): 3360, 3240, 1780, 1730, 1690, 1630, 1530 cm⁻¹

(13) 7-[2-Ethoxycarbonylmethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 120° to 125° C. (dec.)

I.R. (Nujol): 3370, 3250, 1780, 1690, 1625, 1530 cm⁻¹

(14) 7-[2-{2-(2-Hexyloxyethoxy)ethoxyimino}-2-(5-amino-1,2,4-thiadiazol-3-yl)acetamido]-3-(1,3,4-thiadiazol-2-yl)thiomethyl-3-cephem-4-carboxylic acid (syn isomer). mp 100° to 105° C. (dec.)

I.R. (Nujol): 3340, 3210, 1785, 1685, 1620, 1525 cm⁻¹

(15) 7-[2-Mesylmethoxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 164° to 167° C. (dec.)

I.R. (Nujol): 3360, 3230, 1780, 1690, 1620, 1530 cm⁻¹

(16) 7-[2-trityloxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 163° to 167° C. (dec.)

I.R. (Nujol): 3480, 3350, 3250, 1785, 1690, 1620, 1530 cm⁻¹

(17) 7-[2-Trityloxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 175° to 178° C. (dec.)

I.R. (Nujol): 3450, 3350, 3200, 1790, 1690, 1620, 1530 cm⁻¹

(18) 7-[2-Allyloxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 154° to 156° C. (dec.)

I.R. (Nujol): 3380, 3245, 1780, 1680, 1625, 1527 cm$^{-1}$

(19) 7-[2-Trityloxyimino-2-(5-amino-1,2,4-thiadiazol-3-yl)acetamido]-3-(1,3,4-thiadiazol-2-yl)thiomethyl-3-cephem-4-carboxylic acid (anti isomer). mp 165° to 170° C. (dec.)

I.R. (Nujol): 3350, 3200, 1785, 1690, 1620, 1515 cm$^{-1}$

(20) 7-[2-Allyloxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 161° to 164° C. (dec.)

I.R. (Nujol): 3350, 3220, 1770, 1670, 1620, 1525 cm$^{-1}$

N.M.R. (d$_6$-DMSO+D$_2$O, δ): 3.6 (2H, broad s), 4.35 and 4.58 (2H, ABq, J=15 Hz), 4.2–4.8 (4H, m), 5.0–5.5 (2H, m), 5.05 (1H, d, J=5 Hz), 5.75 (1H, d, J=5 Hz), 5.7–6.4 (1H, m)

(21) 7-[2-Allyloxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer). powder.

(22) 7-[2-Allyloxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 165° to 169° C. (dec.)

I.R. (Nujol): 3350,3200,1768,1670,1610,1522 cm$^{-1}$

(23) 7-[2-Hydroxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 165° to 170° C. (dec.)

I.R. (Nujol): 3350,3250,1780,1680,1620,1530 cm$^{-1}$

(24) 7-[2-Hydroxyimino-2-(5-amino-1,2,4-thiadiazol-3-yl)acetamido]-3-(1,3,4-thiadiazol-2-yl)thiomethyl-3-cephem-4-carboxylic acid (syn isomer). mp 170° C. to 175° C. (dec.)

I.R. (Nujol): 3480,3350,1770,1690,1620,1530 cm$^{-1}$

(25) 7-[2-Hydroxyimino-2-(5-amino-1,2,4-thiadiazol-3-yl)acetamido]-3-(1,3,4-thiadiazol-2-yl)thiomethyl-3-cephem-4-carboxylic acid (anti isomer). mp 155° to 160° C. (dec.)

I.R. (Nujol): 3350,3250,1780,1680,1620,1520 cm$^{-1}$

EXAMPLE 37

The following compounds were obtained according to similar manners to those of Examples 22 to 25.

(1) 7-[2-Allyloxyimino-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer). mp 161° to 164° C. (dec.)

I.R. (Nujol): 3350, 3220, 1770, 1670, 1620, 1525 cm$^{-1}$ (2) 7-[2-Allyloxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer). mp 165° to 169° C. (dec.)

I.R. (Nujol): 3350, 3200, 1768, 1670, 1610, 1522 cm$^{-1}$

N.M.R. (d$_6$-DMSO+D$_2$O, δ): 3.41 (2H, broad s), 3.60 (2H, broad s), 4.3–5.0 (4H, m), 5.05 (1H, d, J=4.5 Hz), 5.73 (1H, d, J=4.5 Hz), 4.9–5.6 (2H, m), 5.7–6.4 (1H, m)

EXAMPLE 38

A mixture of 7-[2-trityloxyimino-2-(5-amino-1,2,4-thiadiazol-3-yl)acetamido]-3-(1,3,4-thiadiazol-2-yl)thiomethyl-3-cephem-4-carboxylic acid (syn isomer) (0.95 g), conc.hydrochloric acid (0.6 ml) and methanol (10 ml) was stirred for 7 hours at ambient temperature. Methanol was distilled off from the reaction mixture and the residue was adjusted to pH 5 by adding ethyl acetate and an aqueous solution of sodium bicarbonate. To the separated aqueous layer was added ethyl acetate and the mixture was adjusted to pH 2 with 10% hydrochloric acid. The separated ethyl acetate layer was dried over magnesium sulfate and evaporated in vacuo to a volume of 10 ml. Precipitates were collected by filtration, washed with ethyl acetate and diethyl ether and dried to give 7-[2-hydroxyimino-2-(5-amino-1,2,4-thiadiazol-3-yl)acetamido]-3-(1,3,4-thiadiazol-2-yl)thiomethyl-3-cephem-4-carboxylic acid (syn isomer) (0.3 g). mp 170° to 175° C. (dec.)

I.R. (Nujol): 3480, 3350, 1770, 1690, 1620, 1530 cm$^{-1}$

N.M.R. (d$_6$-DMSO, δ): 3.61 and 3.73 (2H, ABq, J=18 Hz), 4.30 and 4.57 (2H, ABq, J=13 Hz), 5.13 (1H, d, J=4 Hz), 5.83 (1H, dd, J=4 and 8 Hz), 8.03 (2H, s), 9.40 (1H, d, J=8 Hz), 9.57 (1H, s), 11.93 (1H, s)

EXAMPLE 39

The following compounds were obtained according to a similar manner to that of Example 38.

(1) 7-[2-Hydroxyimino-2-(5-amino-1,2,4-thiadiazol-3-yl)acetamido]-3-(1-methyl-1H-tetrazol-5-yl)thiomethyl-3-cephem-4-carboxylic acid (syn isomer). mp 165° to 170° C. (dec.)

I.R. (Nujol): 3350, 3250, 1780, 1680, 1620, 1530 cm$^{-1}$

N.M.R. (d$_6$-DMSO, δ): 3.70 (2H, broad s), 3.97 (3H, s), 4.33 (2H, broad s), 5.13 (1H, d, J=4 Hz), 5.83 (1H, dd, J=4 and 8 Hz), 8.03 (2H, s), 9.43 (1H, d, J=8 Hz), 11.93 (1H, s)

(2) 7-[2-Hydroxyimino-2-(5-amino-1,2,4-thiadiazol-3-yl)acetamido]-3-(1,3,4-thiadiazol-2-yl)thiomethyl-3-cephem-4-carboxylic acid (anti isomer). mp 155° to 160° C. (dec.)

I.R. (Nujol): 3350, 3250, 1780, 1680, 1620, 1520 cm$^{-1}$

N.M.R. (d$_6$-DMSO, δ): 3.70 (2H, broad s), 4.35 and 4.53 (2H, ABq, J=13 Hz), 5.13 (1H, d, J=4 Hz), 5.73 (1H, dd, J=4 and 8 Hz), 8.03 (2H, s), 8.92 (1H, d, J=8 Hz), 9.53 (1H, s)

EXAMPLE 40

A mixture of phosphorus pentachloride (1.89 g) and methylene chloride (20 ml) was stirred for 15 minutes at ambient temperature. 2-(1-t-Butoxycarbonylethoxyimino)-2-(5-amino-1,2,4-thiadiazol-3-yl)acetic acid (syn isomer) (2.2 g) was added thereto at −15° C. and the mixture was stirred for 30 minutes at −10° to −15° C. A solution of 7-amino-3-cephem-4-carboxylic acid (1.4 g) and trimethylsilylacetamide (8.4 g) in methylene chloride (20 ml) was added thereto at −20° C. and the mixture was stirred for 30 minutes at −10° to −15° C. and for 30 minutes at 0° to 5° C. Methylene chloride was distilled off from the reaction mixture and to the residue were added ethyl acetate and a small amount of water. The resulting solution was poured into an aqueous solution of sodium bicarbonate and the aqueous layer was separated. To the aqueous layer was added ethyl acetate, and the mixture was acidified with 6 N hydrochloric acid and then twice extracted with ethyl acetate. The extract was washed with water, dried over magnesium sulfate, treated with an activated charcoal and concentrated. The residue was triturated with diisopropyl ether and precipitates were collected by filtration to give pale yellow powder of 7-[2-(1-t-butoxycarbonylethoxyimino)-2-(5-amino-1,2,4-thiadiazol-3-yl)acetamido]-3-cephem-4-carboxylic acid (syn isomer) (2.5 g), which is decomposed by 250° C.

IR (Nujol): 3400, 3250, 3150, 1770, 1720, 1680, 1610, 1520, 1290, 1240, 1150, 980, 740 cm$^{-1}$ NMR (DMSO-d$_6$, δ): 1.50 (12H, broad s), 3.63 (2H, m), 4.73 (1H, q, J=7 Hz), 5.17 (1H, d, J=5 Hz), 5.92 (1H, dd, J=5 and 8 Hz), 6.53 (1H, m), 8.17 (2H, m), 9.4 and 9.6 (1H, d, J=8 Hz)

EXAMPLE 41

The following compounds were obtained according to similar manners to those of Examples 1 to 3, 5, 7 to 12, 32 to 34 and 40.

(1) 7-[2-(4-Chlorophenoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 120° to 125° C. (dec.).

IR (Nujol): 3290, 3180, 1770, 1680, 1615, 1580, 1520, 1480 cm$^{-1}$

NMR (DMSO-d$_6$, δ): 3.73 (2H, broad s), 4.40 (2H, broad s), 5.17 (1H, d, J=5 Hz), 4.87–5.20 (2H, m), 5.20–5.60 (2H, m), 5.90 (1H, dd, J=5 and 8 Hz), 5.60–6.30 (1H, m), 7.32 (2H, d, J=9 Hz), 7.48 (2H, d, J=9 Hz), 8.32 (2H, broad s), 9.90 (1H, d, J=8 Hz)

(2) 7-[2-(4-Chlorophenoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 130° to 135° C. (dec.).

IR (Nujol): 3400, 3300, 3280, 1770, 1670, 1615, 1580, 1520, 1480 cm$^{-1}$

NMR (DMSO-d$_6$, δ): 3.72 (2H, broad s), 3.92 (3H, s), 4.32 (2H, broad s), 5.18 (1H, d, J=5 Hz), 5.87 (1H, dd, J=5 and 8 Hz), 7.25 (2H, d, J=9 Hz), 7.42 (2H, d, J=9 Hz), 8.25 (2H, broad s), 9.85 (1H, d, J=8 Hz)

(3) 7-[2-(4-Chlorophenoxyimino)-2-(5-amino-1,2,4-thiadiazol-3-yl)acetamido]cephalosporanic acid (syn isomer), mp 120° to 125° C. (dec.).

IR (Nujol): 3400, 3300, 3190, 1770, 1720, 1650, 1620, 1580, 1520, 1480 cm$^{-1}$ NMR (DMSO-d$_6$, δ): 2.02 (3H, s), 3.58 (2H, broad s), 4.75 and 4.98 (2H, ABq, J=13 Hz), 5.22 (1H, d, J=5 Hz), 5.87 (1H, dd, J=5 and 8 Hz), 7.27 (2H, d, J=9 Hz), 7.42 (2H, d, J=9 Hz), 8.28 (2H, broad s), 9.85 (1H, d, J=8 Hz)

(4) 7-[2-(4-Chlorophenoxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 135° to 140° C. (dec.).

IR (Nujol): 3400, 3270, 3190, 1770, 1680, 1620, 1585, 1520, 1480 cm$^{-1}$

NMR (DMSO-d$_6$, δ): 2.70–3.10 (2H, m), 3.70 (2H, broad s), 4.10–4.60 (4H, m), 5.20 (1H, d, J=5 Hz), 5.87 (1H, dd, J=5 and 8 Hz), 7.28 (2H, d, J=9 Hz), 7.45 (2H, d, J=9 Hz), 8.30 (2H, broad s), 9.85 (1H, d, J=8 Hz)

(5) 7-[2-(4-Chlorophenoxyimino)-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp 140° to 145° C. (dec.).

IR (Nujol): 3400, 3300, 3190, 1765, 1700, 1620, 1580, 1540, 1520, 1480 cm$^{-1}$ NMR (DMSO-d$_6$, δ): 3.80 (2H, broad s), 4.28 (2H, broad s), 4.73 (2H, s), 5.27 (1H, d, J=5 Hz), 5.90 (1H, dd, J=5 and 8 Hz), 7.12 (1H, d, J=10 Hz), 7.32 (2H, d, J=9 Hz), 7.47 (2H, d, J=9 Hz), 7.72 (1H, d, J=10 Hz), 8.30 (2H, broad s), 9.92 (1H, d, J=8 Hz)

(6) 7-[2-(4-Chlorophenoxyimino)-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 140° to 145° C. (dec.).

IR (Nujol): 3350, 3240, 1780, 1685, 1625, 1530, 1490 cm$^{-1}$

NMR (DMSO-d$_6$, δ): 3.70 (2H, broad s), 4.22 and 4.62 (2H, ABq, J=13 Hz), 5.22 (1H, d, J=5 Hz), 5.93 (1H, dd, J=5 and 8 Hz), 7.27 (2H, d, J=9 Hz), 7.42 (2H, d, J=9 Hz), 7.73 (1H, d, J=9 Hz), 8.28 (2H, broad s), 8.59 (1H, d, J=9 Hz), 9.87 (1H, d, J=8 Hz)

(7) 7-[2-(α-t-Butoxycarbonylbenzyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 105° to 110° C. (dec.).

IR (Nujol): 3400, 3300, 3180, 1780, 1720, 1680, 1620, 1520 cm$^{-1}$

NMR (DMSO-d$_6$, δ): 1.40 (9H, s), 3.50–3.83 (2H, m), 4.37 and 4.60 (2H, ABq, J=13 Hz), 5.10 and 5.18 (1H, d, J=5 Hz), 5.63 (1H, s), 5.67–6.0 (1H, m), 7.47 (5H, s), 8.20 (2H, broad s), 9.62 (1/2H, s), 9.64 (1/2H, s), 9.47–9.77 (1H, m)

(8) 7-[2-(α-t-Butoxycarbonylbenzyloxyimino)-2-(5-amino-1,2,4-thiadiazol-3-yl)acetamido]-3-cephem-4-carboxylic acid (syn isomer), mp 90° to 95° C. (dec.).

IR (Nujol): 3400, 3380, 3230, 1780, 1730, 1685, 1635, 1530 cm$^{-1}$

NMR (DMSO-d$_6$, δ): 1.38 (9H, s), 3.60 (2H, broad s), 5.0–5.20 (1H, m), 5.63 (1H, s), 5.72–6.03 (1H, m), 6.37–6.67 (1H, m), 7.47 (5H, s), 8.18 (2H, broad s), 9.43–9.70 (1H, m)

(9) 7-[2-(α-t-Butoxycarbonylbenzyloxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 105° to 110° C. (dec.).

IR (Nujol): 3360, 3220, 1785, 1690, 1625, 1525 cm$^{-1}$

NMR (DMSO-d$_6$, δ): 1.38 (18H, s), 3.17–3.87 (4H, m), 4.17–4.65 (4H, m), 5.0–5.28 (1H, m), 5.12 (1H, s), 5.58–6.0 (1H, m), 7.47 (5H, s), 8.17 (2H, broad s), 9.45–9.75 (1H, m)

(10) 7-[2-(2-Propynyloxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 125° to 130° C. (dec.).

IR (Nujol): 3400, 3260, 3190, 2580, 1765, 1710, 1670, 1620, 1520 cm$^{-1}$

NMR (DMSO-d$_6$, δ): 2.92 (2H, t, J=6 Hz), 3.47 (1H, t, J=2 Hz), 3.67 (2H, broad s), 4.17–4.60 (4H, m), 4.77 (2H, d, J=2 Hz), 5.08 (1H, d, J=5 Hz), 5.77 (1H, dd, J=5 and 8 Hz), 8.08 (2H, broad s), 9.57 (1H, d, J=8 Hz)

(11) 7-[2-(2-Propynyloxyimino)-2-(5-amino-1,2,4-thiadiazol-3-yl)acetamido]cephalosporanic acid (syn isomer).

IR (Nujol): 3400, 3270, 3180, 1770, 1720, 1655, 1520 cm$^{-1}$

NMR (DMSO-d$_6$, δ): 1.98 (3H, s), 2.45 (1H, t, J=2 Hz), 3.48 (2H, broad s), 4.72 (2H, d, J=2 Hz), 4.67 and 4.92 (2H, ABq, J=13 Hz), 5.08 (1H, d, J=5 Hz), 5.77 (1H, dd, J=5 and 8 Hz), 8.07 (2H, broad s), 9.55 (1H, d, J=8 Hz)

(12) 7-[2-t-Butoxycarbonylmethoxyimino-2-(5-amino-1,2,4-thiadiazol-3-yl)acetamido]-3-cephem-4-carboxylic acid (syn isomer), mp 165° to 170° C. (dec.).

IR (Nujol): 3350, 3250, 3180, 1790, 1720, 1660, 1630, 1620, 1520 cm$^{-1}$

NMR (DMSO-d$_6$, δ): 1.40 (9H, s), 3.57 (2H, broad s), 4.60 (2H, s), 5.07 (1H, d, J=4 Hz), 5.83 (1H, dd, J=4 and 8 Hz), 6.47 (1H, broad s), 8.13 (2H, s), 9.50 (1H, d, J=8 Hz)

(13) 7-[2-(Thiolan-1,1-dioxide-3-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 170° to 175° C. (dec.).

IR (Nujol): 3300, 3200, 1770, 1670, 1620, 1520 cm$^{-1}$

NMR (DMSO-d$_6$, δ): 2.30–2.50 (2H, m), 3.0–3.57 (4H, m), 3.70 (2H, broad s), 4.33 and 4.57 (2H, ABq, J=13 Hz), 5.0–5.15 (1H, m), 5.17 (1H, d, J=4 Hz), 5.83 (1H, dd, J=4 and 8 Hz), 8.23 (2H, s), 9.60 (1H, s), 9.67 (1H, d, J=8 Hz)

(14) 7-[2-Allyloxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 140° to 145° C. (dec.).

IR (Nujol): 3300, 3200, 1770, 1720, 1670, 1620, 1520 cm$^{-1}$

NMR (DMSO-d$_6$, δ): 3.63 (2H, broad s), 4.23 and 4.43 (2H, ABq, J=14 Hz), 4.60–4.73 (2H, m), 5.10 (1H, d, J=4 Hz), 5.30 (2H, s), 5.07–5.50 (2H, m), 5.67–6.20 (2H, m), 8.15 (2H, s), 9.63 (1H, d, J=8 Hz)

(15) 7-[2-(2-Propynyloxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 135° to 140° C. (dec.).

IR (Nujol): 3250, 3150, 1770, 1720, 1670, 1620, 1520 cm$^{-1}$

NMR (DMSO-d$_6$, δ): 3.47 (1H, t, J=2 Hz), 3.63 (2H, broad s), 4.22 and 4.43 (2H, ABq, J=14 Hz), 5.07 (1H, d, J=4 Hz), 5.28 (2H, s), 5.80 (1H, dd, J=4 and 8 Hz), 8.15 (2H, s), 9.63 (1H, d, J=8 Hz)

(16) 7-[2-Allyloxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 140° to 145° C. (dec.).

IR (Nujol): 3300, 3200, 1770, 1720, 1670, 1620, 1520 cm$^{-1}$

NMR (DMSO-d$_6$, δ): 2.87 (2H, t, J=6 Hz), 3.63 (2H, broad s), 4.37 (2H, t, J=6 Hz), 4.20 and 4.47 (2H, ABq, J=14 Hz), 4.57–4.67 (2H, m), 5.07 (1H, d, J=4 Hz), 5.10–5.43 (2H, m), 5.67–6.13 (2H, m), 8.10 (2H, s), 9.58 (1H, d, J=8 Hz)

(17) 7-[2-(t-Butoxycarbonylmethoxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 150° to 155° C. (dec.).

IR (Nujol): 3300, 3200, 1770, 1720, 1700, 1620, 1520 cm$^{-1}$

NMR (DMSO-d$_6$, δ): 1.50 (9H, s), 3.00 (2H, t, J=6 Hz), 3.73 (2H, broad s), 4.43 (2H, broad s), 4.50 (2H, t, J=6 Hz), 4.67 (2H, s), 5.17 (1H, d, J=4 Hz), 5.87 (1H, dd, J=4 and 8 Hz), 8.18 (2H, s), 9.53 (1H, d, J=8 Hz)

(18) 7-[2-(t-Butoxycarbonylmethoxyimino)-2-(5-amino-1,2,4-thiadiazol-3-yl)acetamido]-3-[1-{3-(4-methyl-1-piperazinyl)propyl}-1H-tetrazol-5-yl]thiomethyl-3-cephem-4-carboxylic acid (syn isomer), mp 220° to 225° C. (dec.).

IR (Nujol): 3300, 1700, 1680, 1605, 1520 cm$^{-1}$

NMR (DMSO-d$_6$, δ): 1.40 (9H, s), 1.96–2.10 (2H, m), 2.38–2.50 (4H, m), 2.60 (3H, s), 2.95–3.10 (6H, m), 3.52 and 3.65 (2H, ABq, J=16 Hz), 4.20–4.40 (4H, m), 4.60 (2H, s), 5.06 (1H, d, J=4 Hz), 5.70 (1H, dd, J=4 and 8 Hz), 8.12 (2H, s), 9.44 (1H, d, J=8 Hz),

(19) 7-[2-(1-t-Butoxycarbonyl-2-methylpropoxyimino)-2-(5-amino-1,2,4-thiadiazol-3-yl)acetamido]-cephalosporanic acid (syn isomer), mp 130° to 140° C. (dec.).

IR (Nujol): 3400, 3300, 3200, 1780, 1720–1680, 1620, 1520, 1460, 1370, 1230, 1150, 1030, 730 cm$^{-1}$ NMR (DMSO-d$_6$, δ): 1.03 (6H, d, J=7 Hz), 1.43 (9H, s), 2.03 (3H, s), 1.9–2.2 (1H, m), 3.6 (2H, m), 4.26 and 4.34 (1H, d, J=6 Hz), 4.68 and 5.05 (2H, ABq, J=13 Hz), 5.19 (1H, d, J=5 Hz), 5.87 (1H, dd, J=5 and 8 Hz), 8.10 (2H, broad s), 9.48 (1H, d, J=8 Hz)

(20) 7-[2-(1-t-Butoxycarbonylpropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 101° to 105° C. (dec.).

IR (Nujol): 3300, 3150, 1770, 1720, 1620, 1520, 1450, 1370, 1250, 1150, 1010, 900, 840, 720 cm$^{-1}$ NMR (DMSO-d$_6$, δ): 0.93 (3H, t, J=7 Hz), 1.42 (9H, s), 1.8 (2H, m), 3.7 (2H, m), 4.6 (3H, m), 5.18 (1H, d, J=5 Hz), 5.87 (1H, dd, J=5 and 8 Hz), 8.20 (2H, broad s), 9.5 (1H, m), 9.58 (1H, s)

(21) 7-[2-(1-t-Butoxycarbonylpropoxyimino)-2-(5-amino-1,2,4-thiadiazol-3-yl)acetamido]cephalosphoranic acid (syn isomer), mp 95° to 105° C. (dec.).

IR (Nujol): 3400, 3300, 3200, 1780, 1720, 1620, 1530, 1230, 1150, 1010, 890, 840, 740 cm$^{-1}$ NMR (DMSO-d$_6$, δ): 0.95 (3H, t, J=7 Hz), 1.39 (9H, s), 1.8 (2H, m), 2.02 (3H, s), 3.5 (2H, m), 4.47 (1H, m), 4.67 and 5.03 (2H, ABq, J=13 Hz), 5.14 (1H, d, J=5 Hz), 5.83 (1H, dd, J=5 and 8 Hz), 8.07 (2H, broad s), 9.37 and 9.43 (1H, d, J=8 Hz)

(22) 7-[2-(1-t-Butoxycarbonylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 120° to 128° C. (dec.).

IR (Nujol): 3280, 3180, 1770, 1720, 1680, 1620, 1520, 1240, 1150, 1000, 740, 720 cm$^{-1}$ NMR (DMSO-d$_6$, δ): 1.4 (12H, m), 3.76 (2H, m), 4.30 and 4.67 (2H, ABq, J=13 Hz), 4.70 (1H, q, J=7 Hz), 5.22 (1H, d, J=5 Hz), 5.88 (1H, dd, J=5 and 8 Hz), 8.20 (2H, broad s), 9.47 (1H, m), 9.60 (1H, s)

(23) 7-[2-(1-t-Butoxycarbonylethoxyimino)-2-(5-amino-1,2,4-thiadiazol-3-yl)acetamido]cephalosporanic acid (syn isomer), mp 138° to 145° C. (dec.).

IR (Nujol): 3280, 3180, 1780, 1720, 1680, 1620, 1520, 1230, 1150, 840 cm$^{-1}$

NMR (DMSO-d$_6$, δ): 1.47 (12H, m), 2.07 (3H, s), 3.58 (2H, m), 4.5–5.1 (3H, m), 5.19 (1H, d, J=5 Hz), 5.87 (1H, dd, J=5 and 8 Hz), 8.10 (2H, broad s), 9.40 and 9.50 (1H, d, J=8 Hz)

(24) 7-[2-(1-Methyl-1-t-butoxycarbonylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 115° to 120° C. (dec.).

IR (Nujol): 3280, 3170, 1780, 1720, 1680, 1520, 1140, 990, 750 cm$^{-1}$

NMR (DMSO-d$_6$, δ): 1.40 (9H, s), 1.46 (6H, s), 3.7 (2H, m), 4.26 and 4.63 (2H, ABq, J=13 Hz), 5.18 (1H, d, J=5 Hz), 5.83 (1H, dd, J=5 and 8 Hz), 8.13 (2H, broad s), 9.40 (1H, d, J=8 Hz), 9.53 (1H, s)

(25) 7-[2-(1-t-Butoxycarbonyl-1-cyclopentyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 143° C. (dec.).

IR (Nujol): 3300, 3180, 1770, 1720–1670, 1620, 1520, 1245, 1150, 1060, 995, 840 cm$^{-1}$ NMR (DMSO-d$_6$, δ): 1.40 (9H, s), 1.8 (4H, m), 2.1 (4H, m), 3.7 (2H, m), 4.27 and 4.68 (2H, ABq, J=13 Hz), 5.18 (1H, d, J=5 Hz), 5.85 (1H, dd, J=5 and 8 Hz), 8.1 (2H, broad s), 9.39 (1H, d, J=8 Hz), 9.53 (1H, s)

(26) 7-[2-(1-Methyl-1-t-butoxycarbonylethoxyimino)-2-(5-amino-1,2,4-thiadiazol-3-yl)acetamino]cephalosphoranic acid (syn isomer), mp 135° to 140° C. (dec.).

IR (Nujol): 3400, 3300, 3180, 1780, 1720, 1690, 1620, 1540, 1300, 1220, 1140, 1030, 990, 840, 740 cm$^{-1}$ NMR (DMSO-d$_6$, δ): 1.57 (9H, s), 1.62 (6H, s), 2.03 (3H, s), 3.57 (2H, m), 4.69 and 5.06 (2H, ABq, J=13 Hz), 5.19 (1H, d, J=5 Hz), 5.89 (1H, dd, J=5 and 8 Hz), 8.21 (2H, broad s), 9.32 (1H, d, J=8 Hz)

(27) 7-[2-(1-t-Butoxycarbonyl-1-cyclopentyloxyimino)-2-(5-amino-1,2,4-thiadiazol-3-yl)acetamido]- cephalosporanic acid (syn isomer), mp 98° to 102° C. (dec.).

IR (Nujol): 3350, 3230, 1790, 1730, 1630, 1530, 1340, 1160, 1070, 1040, 1000 cm$^{-1}$ NMR (DMSO-d$_6$, δ): 1.47 (9H, s), 1.80 (4H, m), 2.10 (4H, m), 2.13 (3H, s), 3.60 (2H, m), 4.73 and 5.1 (2H, ABq, J=14 Hz), 5.22 (1H, d, J=5 Hz), 5.88 (1H, dd, J=5 and 8 Hz), 8.15 (2H, m), 9.43 (1H, d, J=8 Hz)

(28) 7-[2-(1-Methyl-1-t-butoxycarbonylethoxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 96° to 100° C. (dec.).

IR (Nujol): 3300, 3150, 1780, 1680, 1570, 1240, 1160, 990 cm$^{-1}$

NMR (DMSO-d$_6$, δ): 1.45 (18H, s), 1.52 (6H, s), 3.33 (2H, m), 3.67 (2H, m), 4.30 (4H, m), 5.10 (1H, d, J=5 Hz), 5.85 (1H, dd, J=5 and 8 Hz), 6.92 (1H, m), 8.13 (2H, m), 9.40 (1H, d, J=8 Hz)

(29) 7-[2-(1-Methyl-1-t-butoxycarbonylethoxyimino)-2-(5-amino-1,2,4-thiadiazol-3-yl)acetamido]-3-cephem-4-carboxylic acid (syn isomer), which is decomposed by 215° C.

IR (Nujol): 3400, 3300, 3150, 1780, 1710, 1690, 1620, 1520, 1240, 1140, 980 cm$^{-1}$ NMR (DMSO-d$_6$, δ): 1.40 (9H, s), 1.47 (6H, s), 3.60 (2H, m), 5.17 (1H, d, J=5 Hz), 5.92 (1H, dd, J=5 and 8 Hz), 6.50 (1H, m), 8.22 (2H, m), 9.50 (1H, d, J=8 Hz)

(30) 7-[2-(1-t-Butoxycarbonylethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 96° to 100° C. (dec.).

IR (Nujol): 3300, 3150, 1780, 1720, 1680, 1620, 1520, 1240, 1150, 1090, 1000 cm$^{-1}$ NMR (DMSO-d$_6$, δ): 1.40 (12H, broad s), 3.67 (2H, m), 4.2 and 4.50 (2H, ABq, J=13 Hz), 4.67 (1H, q, J=6 Hz), 4.93 (2H, m), 5.07 (1H, d, J=5 Hz), 5.13-5.37 (2H, m), 5.83 (1H, dd, J=5 and 8 Hz), 5.83-6.22 (1H, m), 8.10 (2H, broad s), 9.40 and 9.52 (1H, d, J=8 Hz)

(31) 7-[2-(1-Phenylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), which is decomposed by 175° C.

IR (Nujol): 3400, 3250, 3150, 1750, 1650, 1610, 1520, 1400, 1240, 1160, 1060, 1000, 700 cm$^{-1}$ NMR (DMSO-d$_6$, δ): 1.57 (3H, d, J=8 Hz), 3.73 (2H, m), 4.32 and 4.72 (2H, ABq, J=13 Hz), 5.22 (1H, d, J=5 Hz), 5.3-5.5 (1H, m), 5.93 (2H, dd, J=5 and 8 Hz), 7.36 (5H, m), 8.13 (2H, m), 9.57 (1H, s), 9.72 (1H, d, J=8 Hz)

(32) 7-[2-(3,4-Dichlorophenoxyimino)-2-(5-amino-1,2,4-thiadiazol-3-yl)acetamido]-3-cephem-4-carboxylic acid (syn isomer), which is decomposed by 210° C.

IR (Nujol): 3450, 3300, 3200, 1760, 1660, 1560, 1290, 1210, 1000, 970, 940, 730 cm$^{-1}$ NMR (DMSO-d$_6$, δ): 3.63 (2H, m), 5.17 (1H, d, J=5 Hz), 5.91 (1H, dd, J=5 and 8 Hz), 6.41 (1H, m), 7.13-7.73 (3H, m), 8.28 (2H, broad s), 9.87 (1H, d, J=8 Hz)

(33) 7-[2-(p-Tolyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), which is decomposed by 150° C., which is a mixture with o-tolyl isomer.

IR (Nujol): 3350, 3250, 1780, 1680, 1630, 1530, 1510, 1230, 1050, 910, 820 cm$^{-1}$ NMR (DMSO-d$_6$, δ): 2.23 (1/5H, s), 2.27 (9/5H, s), 3.71 (2H, m), 4.21 and 4.61 (2H, ABq, J=13 Hz), 5.23 (1H, d, J=5 Hz), 5.90 (1H, m), 7.16 (4H, m), 8.23 (2H, m), 9.56 (1H, s), 9.86 (1H, d, J=8 Hz)

(34) 7-[2-(3-Trifluoromethylphenoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), which is decomposed by 155° C.

IR (Nujol): 3300, 3200, 1770, 1680, 1620, 1520, 1320, 1160, 1120, 1060, 980, 930, 700 cm$^{-1}$ NMR (DMSO-d$_6$, δ): 3.56 and 3.82 (2H, ABq, J=18 Hz), 4.20 and 4.60 (2H, ABq, J=14 Hz), 4.95 (2H, m), 5.18 (1H, d, J=5 Hz), 5.12-5.24 (2H, m), 5.92 (1H, dd, J=5 and 8 Hz), 5.72-6.12 (1H, m), 7.50 (4H, m), 8.26 (2H, m), 9.84 (1H, d, J=8 Hz)

(35) 7-[2-(3-Trifluoromethylphenoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), which is decomposed by 170° C.

IR (Nujol): 3300, 3200, 1770, 1680, 1620, 1520, 1320, 1160, 1120, 1060, 930, 790, 700 cm$^{-1}$ NMR (DMSO-d$_6$, δ): 3.77 (2H, m), 3.97 (3H, s), 4.37 (2H, m), 5.27 (1H, d, J=5 Hz), 5.95 (1H, dd, J=5 and 8 Hz), 7.60 (4H, m), 8.33 (2H, m), 9.97 (1H, d, J=8 Hz)

(36) 7-[2-(4-Fluorophenoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), which is decomposed by 170° C.

IR (Nujol): 3450, 3350, 3200, 1780, 1710, 1680, 1610, 1510, 1590, 1240, 1200, 1170, 1090, 990, 910, 840 cm$^{-1}$ NMR (DMSO-d$_6$, δ): 3.73 (2H, m), 3.93 (3H, s), 4.33 (2H, m), 5.23 (1H, d, J=5 Hz), 5.90 (1H, dd, J=5 and 8 Hz), 7.17-7.28 (4H, m), 8.37 (2H, m), 9.87 (1H, d, J=8 Hz)

(37) 7-[2-(2,4-Dichlorophenoxyimino)-2-(5-amino-1,2,4-thiadiazol-3-yl)acetamido]-3-cephem-4-carboxylic acid (syn isomer), which is decomposed by 240° C.

IR (Nujol): 3250, 1770, 1660, 1620, 1540, 1520, 1280, 1230, 1100, 1050, 970, 920, 810, 750 cm$^{-1}$ NMR (DMSO-d$_6$, δ): 3.56 (2H, m), 5.11 (1H, d, J=5 Hz), 5.91 (1H, dd, J=5 and 8 Hz), 6.47 (1H, m), 7.47-7.63 (3H, m), 8.21 (2H, m), 9.81 (1H, d, J=8 Hz)

(38) 7-[2-(2,4-Dichlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), which is decomposed by 165° C.

IR (Nujol): 3300, 3200, 1770, 1680, 1620, 1520, 1250, 1230, 1100, 1060, 960, 910, 810 cm$^{-1}$ NMR (DMSO-d$_6$, δ): 3.71 (2H, m), 4.23 and 4.67 (2H, ABq, J=14 Hz), 5.25 (1H, d, J=5 Hz), 5.93 (1H, dd, J=5 and 8 Hz), 7.50-7.67 (3H, m), 8.25 (2H, m), 9.57 (1H, s), 9.88 (1H, d, J=8 Hz)

(39) 7-[2-(2-Cyclopenten-1-yloxyimino)-2-(5-amino-1,2,4-thiadiazol-3-yl)acetamido]-3-methyl-3-cephem-4-carboxylic acid (syn isomer), mp 165° to 218° C. (dec.).

IR (Nujol): 3350, 3250, 3140, 3050, 1750, 1705, 1665, 1625, 1550, 1535 cm$^{-1}$ NMR (DMSO-d$_6$+D$_2$O, δ): 1.6-2.6 (4H, m), 2.00 (3H, s), 3.0-3.9 (2H, m), 5.05 (1H, d, J=4.5 Hz), 5.2-5.5 (1H, m), 5.70 (1H, d, J=4.5 Hz), 5.7-6.3 (2H, m)

(40) 7-[2-Cyclopentyloxyimino-2-(5-amino-1,2,4-thiadiazol-3-yl)acetamido]-3-methyl-3-cephem-4-carboxylic acid (syn isomer), mp 170° to 212° C. (dec.).

IR (Nujol): 3350, 3120, 3050, 1750, 1705, 1668, 1625, 1556, 1534 cm$^{-1}$

NMR (DMSO-d$_6$+D$_2$O, δ): 1.3-2.2 (8H, m), 2.03 (3H, s), 3.0-3.9 (2H, m), 4.77 (1H, broad s), 5.10 (1H, d, J=4.5 Hz), 5.73 (1H, d, J=4.5 Hz)

(41) 7-[2-(2-Cyclohexen-1-yloxyimino)-2-(5-amino-1,2,4-thiadiazol-3-yl)acetamido]-3-methyl-3-cephem-4-carboxylic acid (syn isomer), mp 180° to 205° C. (dec.).

IR (Nujol): 3340, 3250, 3120, 3050, 1750, 1705, 1665, 1625, 1535 cm$^{-1}$

NMR (DMSO-d$_6$+D$_2$O, δ): 1.3–2.4 (6H, m), 2.03 (3H, s), 3.1–3.7 (2H, m), 4.70 (1H, broad s), 5.10 (1H, d, J=4.5 Hz), 5.73 (1H, d, J=4.5 Hz), 5.7–6.0 (2H, m)

(42) 7-[2-(2-Cyclopenten-1-yloxyimino)-2-(5-amino-1,2,4-thiadiazol-3-yl)acetamido]-2-methyl-3-cephem-4-carboxylic acid (syn isomer), mp 142° to 148° C. (dec.).

IR (Nujol): 3300, 3200, 1775, 1650, 1630, 1525 cm$^{-1}$

NMR (DMSO-d$_6$+D$_2$O, δ): 1.41 (3H, d, J=7.5 Hz), 1.9–2.6 (4H, m), 3.5–4.1 (1H, m), 5.16 (1H, d, J=4.5 Hz), 5.2–5.5 (1H, m), 5.6–6.4 (3H, m), 6.62 (1H, d, J=6 Hz)

(43) 7-[2-{3-(N-t-Butoxycarbonylamino)propoxyimino}-2-(5-amino-1,2,4-thiadiazol-3-yl)acetamido]-3-(1,3,4-thiadiazol-2-yl)thiomethyl-3-cephem-4-carboxylic acid (syn isomer).

IR (Nujol): 3200, 3160, 1773, 1685, 1620 cm$^{-1}$

NMR (DMSO-d$_6$+D$_2$O, δ): 1.41 (9H, s), 1.6–2.1 (2H, m), 2.8–3.3 (2H, m), 3.75 (2H, broad s), 4.0–4.5 (2H, m), 4.35 and 4.65 (2H, ABq, J=14 Hz), 5.20 (1H, d, J=5 Hz), 5.83 (1H, d, J=5 Hz), 9.58 (1H, s)

(44) 7-[2-{3-(N-t-Butoxycarbonylamino)propoxyimino}-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer).

IR (Nujol): 3200, 3160, 1775, 1720, 1700, 1675, 1620 cm$^{-1}$

NMR (DMSO-d$_6$+D$_2$O, δ): 1.37 (9H, s), 1.5–1.9 (2H, m), 2.6–3.2 (2H, m), 3.4–3.9 (4H, m), 3.9–4.4 (6H, m), 5.10 (1H, d, J=5 Hz), 5.80 (1H, d, J=5 Hz)

(45) 7-[2-{3-(N-t-Butoxycarbonylamino)propoxyimino}-2-(5-amino-1,2,4-thiadiazol-3-yl)acetamido]-3-(5-methyl-1,3,4-thiadiazol-2-yl)thiomethyl-3-cephem-4-carboxylic acid (syn isomer).

IR (Nujol): 3300, 3150, 1775, 1710, 1700, 1670, 1650, 1620 cm$^{-1}$

NMR (DMSO-d$_6$+D$_2$O, δ): 1.40 (9H, s), 1.6–2.1 (2H, m), 2.71 (3H, s), 2.9–3.3 (2H, m), 3.71 (2H, broad s), 4.0–4.8 (4H, m), 5.18 (1H, d, J=4.5 Hz), 5.88 (1H, d, J=4.5 Hz)

(46) 7-[2-{3-(N-t-Butoxycarbonylamino)propoxyimino}-2-(5-amino-1,2,4-thiadiazol-3-yl)acetamido}-3-(1-methyl-1H-tetrazol-5-yl)thiomethyl-3-cephem-4-carboxylic acid (syn isomer), mp 81° to 119° C. (dec.).

IR (Nujol): 3300, 3180, 1773, 1715, 1700, 1670, 1620 cm$^{-1}$

NMR (DMSO-d$_6$+D$_2$O, δ): 1.35 (9H, s), 1.5–2.0 (2H, m), 2.7–3.2 (2H, m), 3.68 (2H, broad s), 3.9–4.5 (4H, m), 3.92 (3H, s), 5.12 (1H, d, J=4.5 Hz), 5.83 (1H, d, J=4.5 Hz)

(47) 7-[2-{4-(N-t-Butoxycarbonylaminomethyl)benzyloxyimino}-2-(5-amino-1,2,4-thiadiazol-3-yl)acetamido]-3-methyl-3-cephem-4-carboxylic acid (syn isomer).

IR (Nujol): 3300, 3170, 1760, 1680 cm$^{-1}$

NMR (DMSO-d$_6$, δ): 1.65 (9 H, s), 2.0 (3H, s), 3.4 (2H, m), 4.14 (2H, d, J=6 Hz), 5.1 (1H, d, J=4.5 Hz), 5.2 (2H, s), 5.73 (1H, dd, J=4.5 and 8 Hz)

(48) 7-[2-Cyclopentyloxyimino-2-(5-amino-1,2,4-thiadiazol-3-yl)acetamido]-3-hydroxycepham-4-carboxylic acid (syn isomer), mp 169° to 173° C. (dec.).

IR (Nujol): 3440, 3250, 1750, 1660, 1520, 1400, 1240, 1060, 990, 720 cm$^{-1}$

NMR (DMSO-d$_6$, δ): 1.7 (8H, m), 2.77 (1H, m), 3.0–3.5 (1H, m), 3.7–4.1 (1H, s), 4.43 (1H, d, J=6 Hz), 4.73 (1H, m), 5.16 (1H, d, J=5 Hz), 5.47 (1H, dd, J=5 and 8 Hz), 8.02 (2H, broad s), 9.33 (1H, d, J=8 Hz)

(49) 7-[2-{1-(Cyclohexyloxycarbonyl)ethoxyimino}-2-(5-amino-1,2,4-thiadiazol-3-yl)acetamido]-3-cephem-4-carboxylic acid (syn isomer), mp 160° to 163° C. (dec.).

IR (Nujol): 3420, 3300, 3180, 1775, 1720, 1685, 1610, 1520, 1290, 1230, 1040, 980, 740 cm$^{-1}$ NMR (DMSO-d$_6$, δ): 1.50 (3H, d, J=6 Hz), 1.0–2.1 (10H, m), 3.62 (2H, m), 4.80 (1H, q, J=6 Hz), 4.6–5.0 (1H, m), 5.15 (1H, d, J=5 Hz), 5.90 (1H, dd, J=5 and 8 Hz), 6.50 (1H, m), 8.13 (2H, broad s), 9.39 (½H, d, J=8 Hz), 9.53 (½H, d, J=8 Hz)

(50) 7-[2-(1-t-Butoxycarbonyl-1-cyclopentyloxyimino)-2-(5-amino-1,2,4-thiadiazol-3-yl)acetamido]-3-cephem-4-carboxylic acid (syn isomer), mp 165° to 169° C. (dec.).

IR (Nujol): 3400, 3300, 3200, 1770, 1710, 1680, 1610, 1520, 1290, 1240, 1150, 1000, 970, 740 cm$^{-1}$ NMR (DMSO-d$_6$, δ): 1.42 (9H, s), 1.77 (4H, m), 2.05 (4H, m), 3.60 (2H, m), 5.13 (1H, d, J=5 Hz), 5.87 (1H, dd, J=5 and 8 Hz), 6.47 (1H, m), 8.13 (2H, m), 9.33 (1H, d, J=8 Hz)

(51) 7-[2-Carboxymethoxyimino-2-(5-amino-1,2,4-thiadiazol-3-yl)acetaido]-3-[1-{2-(N,N-dimethylamino)ethyl}-1H-tetrazol-5-yl]thiomethyl-3-cephem-4-carboxylic acid (syn isomer), mp 170° to 173° C. (dec.).

IR (Nujol): 3400, 3280, 3150, 1760, 1665, 1610, 1520 cm$^{-1}$

(52) 7-[2-Carboxymethoxyimino-2-(5-amino-1,2,4-thiadiazol-3-yl)acetamido]-3-[1-{3-(N,N-dimethylamino)propyl}-1H-tetrazol-5-yl]thiomethyl-3-cephem-4-carboxylic acid (syn isomer), mp 170° to 175° C. (dec.).

IR (Nujol): 3400, 3280, 3160, 1760, 1665, 1610, 1520 cm$^{-1}$

(53) 7-[2-(2-Propynyloxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 85° to 90° C. (dec.).

IR (Nujol): 3400, 3290, 3200, 1770, 1680, 1620, 1520 cm$^{-1}$

(54) 7-[2-Carboxymethoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 185° to 190° C. (dec.).

IR (Nujol): 3300, 3200, 1770, 1680, 1620, 1520 cm$^{-1}$

(55) 7-[2-(2,2,2-Trifluoroethoxyimino)-2-(5-amino-1,2,4-thiadiazol-3-yl)acetamido]-3-(1-(carboxymethyl-1H-tetrazol-5-yl)thiomethyl-3-cephem-4-carboxylic acid (syn isomer), mp 130° to 132° C. (dec.).

IR (Nujol): 3300, 3200, 1770, 1720, 1670, 1620, 1520 cm$^{-1}$

(56) 7-[2-(1-Carboxy-2-methylpropoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 192° to 195° C. (dec.).

IR (Nujol): 3400–3200, 1780, 1680, 1520, 1450, 1360, 1240, 1160, 1620, 1020, 730 cm$^{-1}$

(57) 7-[2-(1-Carboxypropoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 185° to 192° C. (dec.).

IR (Nujol): 3300, 3200, 1770, 1680, 1620, 1520, 1450, 1360, 1250, 1160, 1000, 730–710 cm$^{-1}$

(58) 7-[2-{3-(N-t-Butoxycarbonylamino)propoxyimino}-2-(5-amino-1,2,4-thiadiazol-3-yl)acetamido]-3-[1-{3-(N-t-butoxycarbonylamino)propyl}-1H-tetrazol- 5-yl]thiomethyl-3-cephem-4-carboxylic acid (syn isomer).

IR (Nujol): 3300, 3150, 1775, 1715, 1675, 1650, 1615 cm$^{-1}$

(59) 7-[2-(1-Carboxyethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 110° to 115° C. (dec.).

IR (Nujol): 3300, 3200, 1770, 1680, 1600, 1520, 1250, 1000, 720 cm$^{-1}$

(60) 7-[2-(1-Carboxy-1-cyclopentyloxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 200° to 205° C. (dec.).

IR (Nujol): 3300, 3200, 1770, 1680, 1520, 1250, 1160, 1000 cm$^{-1}$

(61) 7-[2-Carboxymethoxyimino-2-(5-amino-1,2,4-thiadiazol-3-yl)acetamido]-3-[1-(3-morpholinopropyl)-1H-tetrazol-5-yl]thiomethyl-3-cephem-4-carboxylic acid (syn isomer), mp 190° to 194° C. (dec.).

IR (Nujol): 3300, 3200, 1770, 1680, 1610, 1530, 1240, 1180, 1090, 1060, 880, 760 cm$^{-1}$

(62) 7-[2-(1-Carboxy-1-methylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer).

IR (Nujol): 3300, 3150, 1770, 1680, 1520, 1240, 1160, 990 cm$^{-1}$

(63) 7-[2-Carboxymethoxyimino-2-(5-amino-1,2,4-thiadiazol-3-yl)acetamido]-3-(4-methyl-5-oxo-6-hydroxy-4,5-dihydro-1,2,4-triazin-3-yl)thiomethyl-3-cephem-4-carboxylic acid (syn isomer), mp 210° to 214° C. (dec.).

IR (Nujol): 3250, 3180, 1760, 1720–1660, 1590, 1520, 1240, 1090, 1050, 720 cm$^{-1}$

(64) 7-[2-Carboxymethoxyimino-2-(5-amino-1,2,4-thiadiazol-3-yl)acetamido]-3-[1-{4-(N-t-butoxycarbonylamino)butyl}-1H-tetrazol-5-yl]thiomethyl-3-cephem-4-carboxylic acid (syn isomer).

IR (Nujol): 3300, 3200, 1770, 1680, 1620, 1520, 1240, 1160, 1090, 1060, 890 cm$^{-1}$

(65) 7-[2-Carboxymethoxyimino-2-(5-amino-1,2,4-thiadiazol-3-yl)acetamido]-3-[1-(3-piperidinopropyl)-1H-tetrazol-5-yl]thiomethyl-3-cephem-4-carboxylic acid (syn isomer), mp 223° to 228° C. (dec.).

IR (Nujol): 3300, 3200, 1770, 1670, 1610, 1520 cm$^{-1}$

(66) 7-[2-Carboxymethoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 170° to 175° C. (dec.).

IR (Nujol): 3300, 3200, 1765, 1720, 1660, 1620, 1520 cm$^{-1}$

(67) 7-[2-Carboxymethoxyimino-2-(5-amino-1,2,4-thiadiazol-3-yl)acetamido]-3-[1-{6-(N-t-butoxycarbonylamino)hexyl}-1H-tetrazol-5-yl]thiomethyl-3-cephem-4-carboxylic acid (syn isomer), pale yellow powder.

(68) 7-[2-(1-Carboxyethoxyimino)-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp 210° to 215° C. (dec.).

IR (Nujol): 3300, 1770, 1680, 1620, 1520, 1240, 1140 cm$^{-1}$

(69) 7-[2-(2-Propynyloxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 165° to 170° C. (dec.).

IR (Nujol): 3450, 3300, 3210, 1770, 1670, 1620, 1525 cm$^{-1}$

(70) 7-[2-Carboxymethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 195° to 200° C. (dec.).

IR (Nujol): 3150, 1760, 1660, 1640, 1520 cm$^{-1}$

(71) 7-[2-(1-Carboxy-2-methylpropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 183° to 189° C. (dec.).

IR (Nujol): 3400–3100, 3150, 1770, 1670, 1620, 1520, 1380, 1280, 1230, 1180, 1100, 1020, 900, 730 cm$^{-1}$

(72) 7-[2-(1-Carboxypropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 183° to 188° C. (dec.).

IR (Nujol): 3400–3150, 1770, 1670, 1620, 1530, 1380, 1280, 1230, 1180, 1100, 1050, 1010, 730 cm$^{-1}$

(73) 7-[2-(1-Carboxyethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 185° to 188° C. (dec.).

IR (Nujol): 3300, 3150, 1760, 1660, 1620, 1520, 1230, 1000, 720 cm$^{-1}$

(74) 7-[2-Carboxymethoxyimino-2-(5-amino-1,2,4-thiadiazol-3-yl)acetamido]-3-[1-(4-aminobutyl)-1H-tetrazol-5-yl]thiomethyl-3-cephem-4-carboxylic acid (syn isomer), mp 191° to 194° C. (dec.).

IR (Nujol): 3300, 3150, 1760, 1670, 1620, 1520, 1230, 1170, 1050, 890, 740, 720 cm$^{-1}$

(75) 7-[2-(1-Carboxy-1-methylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 200° to 203° C. (dec.).

IR (Nujol): 3300, 3150, 1760, 1660, 1620, 1520, 1160, 990 cm$^{-1}$

(76) 7-[2-(1-Carboxy-1-cyclopentyloxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 202° to 205° C. (dec.).

IR (Nujol): 3300, 3200, 1760, 1660, 1620, 1520, 1180, 1060, 1000, 730 cm$^{-1}$

(77) 7-[2-(1-Carboxyethoxyimino)-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp 207° to 210° C. (dec.).

IR (Nujol): 3300, 3150, 1760, 1660, 1620, 1520, 1230, 1170, 1090, 1060, 1040, 990 cm$^{-1}$

(78) 7-[2-Carboxymethoxyimino-2-(5-amino-1,2,4-thiadiazol-3-yl)acetamido]-3-[1-(6-aminohexyl)-1H-tetrazol-5-yl]thiomethyl-3-cephem-4-carboxylic acid (syn isomer), mp 185° to 188° C. (dec.).

IR (Nujol): 3300, 3200, 1760, 1670, 1620, 1520, 1240, 1180, 1060 cm$^{-1}$

(79) 7-[2-(3-Aminopropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 183° C. (dec.).

IR (Nujol): 3150, 1765, 1660, 1630, 1570, 1520 cm$^{-1}$

(80) 7-[2-(3-Aminopropoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 170° to 185° C. (dec.).

IR (Nujol): 3140, 1760, 1660, 1610, 1580, 1520 cm$^{-1}$

(81) 7-[2-(3-Aminopropoxyimino)-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 192° to 195° C. (dec.).

(82) 7-[2-(3-Aminopropoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 180° to 184° C. (dec.).

IR (Nujol): 3160, 1760, 1660, 1590 cm$^{-1}$

(83) 7-[2-(4-Aminomethylbenzyloxyimino)-2-(5-amino-1,2,4-thiadiazol-3-yl)acetamido]-3-methyl-3-cephem-4-carboxylic acid formate (syn isomer), mp 230° to 240° C. (dec.).

IR (Nujol): 1750 cm$^{-1}$

(84) 7-[2-(3-Aminopropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer).

IR (Nujol): 3300, 3150, 1760, 1660, 1607, 1595, 1520 cm$^{-1}$

(85) 7-[2-(α-Carboxybenzyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

IR (Nujol): 3400, 3290, 3160, 2500, 1770, 1720, 1615, 1520 cm$^{-1}$

(86) 7-[2-(α-Carboxybenzyloxyimino)-2-(5-amino-1,2,4-thiadiazol-3-yl)acetamido]-3-cephem-4-carboxylic acid (syn isomer), mp 170° to 175° C. (dec.).

IR (Nujol): 3400, 3280, 3160, 2600, 1770, 1720, 1670, 1625, 1520 cm$^{-1}$

(87) 7-[2-(α-Carboxybenzyloxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 190° to 195° C. (dec.).

IR (Nujol): 3400, 3300, 3150, 1765, 1670, 1610, 1520 cm$^{-1}$

(88) 7-[2-Carboxymethoxyimino-2-(5-amino-1,2,4-thiadiazol-3-yl)acetamido]-3-cephem-4-carboxylic acid (syn isomer), mp 180° to 185° C. (dec.).

IR (Nujol): 3350, 3250, 1770, 1720, 1680, 1630, 1530 cm$^{-1}$

(89) 7-[2-Carboxymethoxyimino-2-(5-amino-1,2,4-thiadiazol-3-yl)acetamido]-3-[1-{3-(4-methyl-1-piperazinyl)propyl}-1H-tetrazol-5-yl]thiomethyl-3-cephem-4-carboxylic acid (syn isomer), mp 185° to 190° C. (dec.).

IR (Nujol): 3300, 1760, 1670, 1600, 1520 cm$^{-1}$

(90) 7-[2-(1-Carboxy-2-methylpropoxyimino)-2-(5-amino-1,2,4-thiadiazol-3-yl)acetamido]-cephalosporanic acid (syn isomer).

IR (Nujol): 3400–3150, 1770, 1730–1670, 1720, 1620, 1460, 1370, 1230, 1030, 730 cm$^{-1}$

(91) 7-[2-(1-Carboxypropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 153° to 158° C. (dec.).

IR (Nujol): 3300, 3180, 1770, 1720–1670, 1620, 1520, 1220, 1060, 1000, 900, 730 cm$^{-1}$

(92) 7-[2-(1-Carboxypropoxyimino)-2-(5-amino-1,2,4-thiadiazol-3-yl)acetamido]cephalosporanic acid (syn isomer), mp 115° to 120° C. (dec.).

IR (Nujol): 3400, 3300, 3200, 1770, 1720–1670, 1620, 1520, 1230, 1030–1010, 890, 740–720 cm$^{-1}$

(93) 7-[2-(1-Carboxyethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 168° C. (dec.).

IR (Nujol): 3400–3200, 1770, 1710, 1670, 1620, 1520, 1230, 1170, 1000, 900, 720 cm$^{-1}$

(94) 7-[2-(1-Carboxy-1-methylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 164° to 167° C. (dec.).

IR (Nujol): 3300, 3200, 2800–2300, 1770, 1720–1660, 1620, 1520, 1160, 1060, 990, 800 cm$^{-1}$

(95) 7-[2-(1-Carboxy-1-cyclopentyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 169° C. (dec.).

IR (Nujol): 3300, 3180, 1770, 1720–1660, 1620, 1520, 1240, 1180, 1060, 1000, 720 cm$^{-1}$

(96) 7-[2-(1-Carboxy-1-methylethoxyimino)-2-(5-amino-1,2,4-thiadiazol-3-yl)acetamido]-3-cephem-4-carboxylic acid (syn isomer), mp 215° to 220° C. (dec.).

IR (Nujol): 3400, 3250, 3200, 1770, 1670, 1520, 1290, 1240, 1160, 1000, 980, 740 cm$^{-1}$

(97) 7-[2-(1-Carboxyethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), which is decomposed by 180° C.

IR (Nujol): 3300, 3150, 1770, 1680, 1610, 1520, 1260, 1100, 1040, 1000 cm$^{-1}$

(98) 7-[2-(1-Carboxyethoxyimino)-2-(5-amino-1,2,4-thiadiazol-3-yl)acetamido]-3-cephem-4-carboxylic acid (syn isomer), mp 230° to 235° C. (dec.).

IR (Nujol): 3400, 3250, 3150, 1760, 1720, 1660, 1610, 1550, 1290, 1240, 1170, 970, 740 cm$^{-1}$

(99) 7-[2-(1-Carboxy-1-cyclopentyloxyimino)-2-(5-amino-1,2,4-thiadiazol-3-yl)acetamido]-3-cephem-4-carboxylic acid (syn isomer), mp 212° to 217° C. (dec.).

IR (Nujol): 3300, 3200, 1770, 1670, 1620, 1520, 1280, 1240, 1180, 1000, 970, 730 cm$^{-1}$ (100) 7-[2-(1-Carboxyethoxyimino)-2-(5-amino-1,2,4-thiadiazol-3-yl)acetamido]cephalosporanic acid (syn isomer).

IR (Nujol): 3300, 3200, 1770, 1710, 1670, 1520, 1230, 1040 cm$^{-1}$ (101) 7-[2-(1-Carboxy-1-methylethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 195° to 200° C. (dec.).

IR (Nujol): 3150, 1760, 1670, 1620, 1520, 1170, 990 cm$^{-1}$ (102) 7-[2-Cyclopentyloxyimino-2-(5-amino-1,2,4-thiadiazol-3-yl)acetamido]-3-[1-{3-(4-methyl-1-piperazinyl)propyl}-1H-tetrazol-5-yl]thiomethyl-3-cephem-4-carboxylic acid (syn isomer), mp 175° to 180° C. (dec.).

IR (Nujol): 3300, 1770, 1650, 1610, 1520 cm$^{-1}$

NMR (DMSO-d$_6$, δ): 1.50–1.80 (8H, m), 1.80–2.10 (2H, m), 2.30–2.50 (4H, m), 2.60 (3H, s), 2.8–3.3 (6H, m), 3.60 (2H, broad s), 4.30–4.50 (4H, m), 4.67–4.83 (1H, m), 5.10 (1H, d, J=4 Hz), 5.77 (1H, dd, J=4 and 8 Hz), 8.17 (2H, s), 9.50 (1H, d, J=8 Hz)

(103) 7-[2-Cyclopentyloxyimino-2-(5-amino-1,2,4-thiadiazol-3-yl)acetamido]-3-carbamoyloxymethyl-3-cephem-4-carboxylic acid (syn isomer), mp 175° to 180° C. (dec.).

IR (Nujol): 3400, 3300, 3180, 1770, 1710, 1670, 1620, 1520 cm$^{-1}$

NMR (DMSO-d$_6$, δ): 1.40–2.0 (8H, m), 3.53 (2H, broad s), 4.67 and 4.85 (2H, ABq, J=13 Hz), 4.67–5.07 (1H, m), 5.15 (1H, d, J=5 Hz), 5.78 (1H, dd, J=5 and 8 Hz), 6.55 (2H, broad s), 8.08 (2H, broad s), 9.45 (1H, d, J=8 Hz)

(104) 7-[2-(2-Cyclopenten-1-yloxyimino)-2-(5-amino-1,2,4-thiadiazol-3-yl)acetamido]-3-carbamoyloxymethyl-3-cephem-4-carboxylic acid (syn isomer), mp 165° to 170° C. (dec.).

IR (Nujol): 3400, 3300, 3180, 1770, 1710, 1670, 1615, 1520 cm$^{-1}$

NMR (DMSO-d$_6$, δ): 1.97-2.47 (4H, m), 3.50 (2H, broad s), 4.65 and 4.85 (2H, ABq, J=13 Hz), 5.12 (1H, d, J=5 Hz), 5.17-5.50 (1H, m), 5.67-6.27 (3H, m), 6.55 (2H, broad s), 8.10 (2H, broad s), 9.47 (1H, d, J=8 Hz)

(105) 7-[2-Cyclopentyloxyimino-2-(5-amino-1,2,4-thiadiazol-3-yl)acetamido]-2-methyl-3-cephem-4-carboxylic acid (syn isomer), IR (Nujol): 3420, 3400, 3270, 3180, 2430, 1790, 1775, 1690, 1675, 1640, 1615, 1600, 1495 cm$^{-1}$ NMR (DMSO-d$_6$, δ): 1.43 (3H, d, J=7 Hz), 1.5-2.1 (8H, m), 3.73 (1H, q, J=7 Hz), 4.5-4.9 (1H, m), 5.07 (1H, d, J=5 Hz), 5.84 (1H, dd, J=5 and 9 Hz), 6.50 (1H, d, J=6 Hz), 8.02 (2H, broad s), 9.38 (1H, d, J=9 Hz)

(106) 7-[2-(2-Oxo-3-tetrahydrofuryloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 170° C. (dec.).

IR (Nujol): 3300, 3200, 1770, 1680, 1620, 1525 cm$^{-1}$

NMR (DMSO-d$_6$, δ): 2.27-2.70 (2H, m), 3.70 (2H, broad s), 4.17-4.73 (4H, m), 5.15 (1H, d, J=4 Hz), 5.18 (1H, t, J=7 Hz), 5.83 (1H, dd, J=4 and 8 Hz), 8.13 (2H, broad s), 9.50 (1H, s), 9.60 (1H, d, J=8 Hz)

(107) 7-[2-(2-Oxo-3-tetrahydrofuryloxyimino)-2-(5-amino-1,2,4-thiadiazol-3-yl)acetamido]-3-cephem-4-carboxylic acid (syn isomer), mp 175° to 180° C. (dec.).

IR (Nujol): 3300, 3200, 1775, 1670, 1620, 1530 cm$^{-1}$

NMR (DMSO-d$_6$, δ): 2.35-2.67 (2H, m), 3.57 (2H, broad s), 4.17-4.50 (2H, m), 5.07 (1H, d, J=4 Hz), 5.15 (1H, t, J=8 Hz), 5.82 (1H, dd, J=4 and 8 Hz), 6.43 (1H, t, J=5 Hz), 8.17 (2H, broad s), 9.60 (1H, d, J=8 Hz)

(108) 7-[2-(1-Cyclohexyloxycarbonylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 145° to 150° C. (dec.).

IR (Nujol): 3400-3250, 1780, 1680, 1620, 1520, 1240, 1220, 1160, 1100, 1000, 740, 720 cm$^{-1}$ NMR (DMSO-d$_6$, δ): 1.0-2.3 (15H, m), 1.40 (9H, s), 3.0 (2H, m), 3.7 (2H, m), 4.3 (4H, m), 4.5-5.0 (1H, m), 4.77 (1H, q, J=7 Hz), 5.13 (1H, d, J=5 Hz), 5.86 (1H, m), 6.83 (1H, m), 8.12 (2H, broad s), 9.37 (½H, d, J=8 Hz), 9.51 (½H, d, J=8 Hz)

(109) 7-[2-(1-Benzyloxycarbonylethoxyimino)-2-(5-amino-1,2,4-thiadiazol-3-yl)acetamido]-3-cephem-4-carboxylic acid (syn isomer), mp 177° to 180° C. (dec.).

IR (Nujol): 3400, 3300, 3200, 1770, 1730, 1680, 1610, 1520, 1240, 1160, 1040, 980, 740 cm$^{-1}$ NMR (DMSO-d$_6$, δ): 1.47 (3H, d, J=7 Hz), 3.57 (2H, m), 4.88 (1H, q, J=7 Hz), 5.10 (1H, d, J=5 Hz), 5.18 (2H, s), 5.87 (1H, dd, J=5 and 8 Hz), 6.45 (1H, m), 7.31 (5H, broad s), 8.10 (2H, broad s), 9.40 and 9.55 (1H, d, J=8 Hz)

(110) 7-[2-(1-Benzyloxycarbonylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 113° to 117° C. (dec.).

IR (Nujol): 3300, 3200, 1780, 1680, 1620, 1520, 1250, 1160, 1100, 1040, 1000, 740, 700 cm$^{-1}$ NMR (DMSO-d$_6$, δ): 1.43 (9H, s), 1.53 (3H, d, J=6 Hz), 2.0 (2H, m), 3.03 (2H, m), 3.70 (2H, m), 4.10-4.67 (4H, m), 4.88 (1H, q, J=6 Hz), 5.10 (1H, d, J=5 Hz), 5.17 (2H, s), 5.80 (1H, dd, J=5 and 8 Hz), 6.53 (1H, m), 7.30 (5H, s), 8.10 (2H, broad s), 9.40 and 9.55 (1H, d, J=8 Hz)

(111) 7-[2-(1-Butoxycarbonylethoxyimino)-2-(5-amino-1,2,4-thiadiazol-3-yl)acetamido]-3-cephem-4-carboxylic acid (syn isomer), mp 147° to 151° C. (dec.).

IR (Nujol): 3400, 3300, 3200, 1770, 1720, 1680, 1610, 1520, 1280, 1235, 1155, 1045, 980, 740 cm$^{-1}$ NMR (DMSO-d$_6$, δ): 0.87 (3H, t, J=6 Hz), 1.46 (3H, d, J=7 Hz), 0.8-1.8 (4H, m), 3.6 (2H, m), 4.08 (2H, t, J=6 Hz), 4.74 (1H, q, J=7 Hz), 5.08 (1H, d, J=5 Hz), 5.83 (1H, dd, J=5 and 8 Hz), 6.4 (1H, m), 8.07 (2H, broad s), 9.39 and 9.44 (1H, d, J=6 Hz)

(112) 7-[2-(1-Butoxycarbonylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 149° to 155° C. (dec.).

IR (Nujol): 3300, 3200, 1780, 1700, 1620, 1520, 1250, 1160, 1100, 1040, 1000, 740, 720 cm$^{-1}$ NMR (DMSO-d$_6$, δ): 0.26 (3H, t, J=7 Hz),1.40(9H,s), 1.0-1.7 (4H, m), 1.43 (3H, d, J=7 Hz), 1.7-2.3 (2H, m), 3.0 (2H, m), 3.7 (2H, m), 4.0-4.5 (6H, m), 4.77 (1H, q, J=7 Hz), 5.15 (1H, d, J=6 Hz), 5.8 (1H, m), 6.9 (1H, m), 8.13 (2H, broad s), 9.5 (1H, m)

(113) 7-[2-(2-D-Phenylglycylaminoethoxyimino)-2-(5-amino-1,2,4-thiadiazol-3-yl)acetamido]-2-methyl-3-cephem-4-carboxylic acid (syn isomer), mp 204° to 222° C. (dec.).

IR (Nujol): 3260, 3150, 1760, 1665, 1616, 1512, 1400, 1045 cm$^{-1}$ (114) 7-[2-(3-D-Phenylglycylaminopropoxyimino)-2-(5-amino-1,2,4-thiadiazol-3-yl)acetamido]-2-methyl-3-cephem-4-carboxylic acid (syn isomer), mp 203° to 231° C. (dec.).

IR (Nujol): 3280, 1170, 1760, 1660, 1600, 1520, 1400 cm$^{-1}$

NMR (D$_2$O+DCl, δ): 1.47 (3H, d, J=7.5 Hz), 1.7-2.3 (2H, m), 3.40 (2H, t, J=7 Hz), 3.88 (1H, q, J=7.5 Hz), 4.33 (2H, t, J=6 Hz), 5.18 (1H, d, J=4.5 Hz), 5.20 (1H, s), 5.95 (1H, d, J=4.5 Hz), 6.90 (1H, d, J=6.0 Hz), 7.57 (5H, s)

(115) 7-[2-(1-Cyclohexyloxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 175° to 178° C. (dec.).

IR (Nujol): 3400-3200, 1765, 1680, 1610, 1520, 1220, 1100, 1000, 890, 790 cm$^{-1}$ NMR (DMSO-d$_6$, δ): 0.9-2.0 (13H, m), 2.2 (2H, m), 2.9 (2H, m), 3.6 (2H, m), 4.0-5.1 (5H, m), 4.76 (1H, q, J=7 Hz), 5.03 (1H, d, J=5 Hz), 5.77 (1H, m), 8.17 (2H, broad s), 9.45 (1H, m)

(116) 7-[2-(1-Benzyloxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 162° to 166° C. (dec.).

IR (Nujol): 3300, 3200, 1760, 1680, 1620, 1520, 1100, 1040, 1000, 740 cm$^{-1}$

NMR (DMSO-d$_6$, δ): 1.47 (3H, d, J=6 Hz), 2.23 (2H, m), 2.90 (2H, m), 3.60 (2H, m), 4.43 (4H, m), 4.90 (1H, q, J=6 Hz), 5.07 (1H, d, J=5 Hz), 5.20 (2H, s), 5.77 (1H, m), 7.43 (5H, s), 8.23 (2H, m), 9.57 (1H, m)

(117) 7-[2-(1-Butoxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 158° to 163° C. (dec.).

IR (Nujol): 3400-3200, 1770, 1680, 1610, 1530, 1300, 1290, 1050, 1040, 1000, 960, 900, 790, 740, 720 cm$^{-1}$ (118) Pivaloyloxymethyl 7-[2-(3-aminopropoxyimino)-2-(5-amino-1,2,4-thiadiazol-3-yl)acetamido]-2-methyl-3-cephem-4-carboxylate hydrochloride (syn isomer), mp 91° to 156° C. (dec.).

IR (Nujol): 3150, 1780, 1745, 1670, 1625, 1525 cm$^{-1}$ (119) Pivaloyloxymethyl 7-[2-(3-aminopropoxyimino)-2-(5-amino-1,2,4-thiadiazol-3-yl)acetamido]-3-

(1-methyl-1H-tetrazol-5-yl)thiomethyl-3-cephem-4-carboxylate hydrochloride (syn isomer), mp 110° to 125° C. (dec.).

IR (Nujol): 1780, 1745, 1670, 1625, 1525 cm$^{-1}$ (120) pivaloyloxymethyl 7-[2-(3-aminopropoxyimino)-2-(5-amino-1,2,4-thiadiazol-3-yl)acetamido]-3-(5-methyl-1,3,4-thiadiazol-2-yl)thiomethyl-3-cephem-4-carboxylate hydrochloride (syn isomer), mp 88° to 153° C. (dec.).

IR (Nujol): 2150, 1780, 1745, 1650, 1625, 1525 cm$^{-1}$
NMR (DMSO-d$_6$+D$_2$O, δ): 1.16 (9H, s), 1.6–2.2 (2H, m), 2.6–3.1 (2H, m), 2.68 (3H, s), 3.76 (2H, broad s), 4.20 and 4.53 (2H, ABq, J=18 Hz), 4.24 (2H, broad s), 5.18 (1H, d, J=4.5 Hz), 5.6–6.0 (3H, m)

(121) Pivaloyloxymethyl 7-[2-(3-aminopropoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylate hydrochloride (syn isomer), mp 150° to 175° C. (dec.).

IR (Nujol): 3150, 1780, 1740, 1670, 1630, 1520 cm$^{-1}$ (122) Pivaloyloxymethyl 7-[2-(3-aminopropoxyimino)-2-(5-amino-1,2,4-thiadiazol-3-yl)acetamido]-3-(1,3,4-thiadiazol-2-yl)thiomethyl-3-cephem-4-carboxylate hydrochloride (syn isomer), mp 96° to 155° C. (dec.).

IR (Nujol): 3300, 3150, 1775, 1730, 1670, 1625, 1530 cm$^{-1}$ (123) Pivaloyloxymethyl 7-[2-(4-aminomethylbenzyloxyimino)-2-(5-amino-1,2,4-thiadiazol-3-yl)acetamido]-3-methyl-3-cephem-4-carboxylate hydrochloride (syn isomer), mp 160° to 168° C. (dec.).

IR (Nujol): 1780, 1745, 1670, 1628 cm$^{-1}$ (124) Pivaloyloxymethyl 7-[2-(allyloxyimino)-2-(5-amino-1,2,4-thiadiazol-3-yl)acetamido]-3-[1-(2-aminoethyl)-1H-tetrazol-5-yl]thiomethyl-3-cephem-4-carboxylate formate (syn isomer), mp 95° to 105° C. (dec.).

IR (Nujol): 1790, 1735, 1452, 1370, 1118, 990 cm$^{-1}$
NMR (DMSO-d$_6$+D$_2$O, δ): 1.2 (9H, s), 3.2–3.35 (2H, m), 3.7 (2H, broad s), 4.2–4.6 (2H, m), 4.1–4.6 (2H, m), 4.7 (2H, broad s), 4.8–5.2 (1H, m), 5.25 (1H, d, J=4.5 Hz), 5.45 (2H, m), 5.7–6.25 (2H, m), 5.8 (1H, d, J=4.5 Hz)

(125) 1-Acetoxyethyl 7-[2-cyclopentyloxyimino-2-(5-amino-1,2,4-thiadiazol-3-yl)acetamido]-2-methyl-3-cephem-4-carboxylate (syn isomer).

IR (Nujol): 3400, 3310, 3150, 1780, 1770, 1750, 1675 cm$^{-1}$ (126) 1-Isobutyryloxyethyl 7-[2-cyclopentyloxyimino-2-(5-amino-1,2,4-thiadiazol-3-yl)acetamido]-2-methyl-3-cephem-4-carboxylate (syn isomer), amorphous powder.

IR (Nujol): 3400, 3300, 3170, 1780, 1745, 1675, 1620, 1525 cm$^{-1}$
NMR (DMSO-d$_6$, δ): 1.08 (6H, d, J=7 Hz), 1.2–2.2 (14H, m), 2.2–2.9 (1H, m), 3.88 (1H, q, J=7 Hz), 4.6–5.0 (1H, m), 5.12 (1H, d, J=4.5 Hz), 5.90 (1H, dd, J=4.5 and 8 Hz), 6.63 (1H, d, J=7 Hz), 8.06 (2H, broad s), 9.43 (1H, d, J=8 Hz)

(127) 1-Acetoxypropyl 7-[2-(2-cyclopenten-1-yloxyimino)-2-(5-amino-1,2,4-thiadiazol-3-yl)acetamido]-2-methyl-3-cephem-4-carboxylate (syn isomer), mp 110° to 128° C. (dec.).

IR (Nujol): 3400, 3280, 3150, 1780, 1750, 1730, 1620 cm$^{-1}$ (128) 1-(2-Azidoethoxycarbonyloxy)ethyl 7-[2-(2-cyclopenten-1-yloxyimino)-2-(5-amino-1,2,4-thiadiazol-3-yl)acetamido]-2-methyl-3-cephem-4-carboxylate (syn isomer), mp 85° to 100° C. (dec.).

IR (Nujol): 3310, 2200, 1760–1785, 1680 cm$^{-1}$
NMR (DMSO-d$_6$+D$_2$O, δ): 1.48 (3H, d, J=6 Hz), 1.5 (3H, d, J=4.5 Hz), 2.0–2.5 (4H, m), 3.5–4.1 (1H, m), 3.63 (2H, t, J=4 Hz), 4.30 (2H, t, J=4 Hz), 5.16 (1H, d, J=4.5 Hz), 5.2–5.45 (1H, m), 5.7–6.2 (2H, m), 6–6.2 (1H, m), 6.6–6.8 (1H, m), 6.7 (1H, d, J=6 Hz)

(129) 1-Ethoxycarbonyloxyethyl 7-[2-(2-cyclopenten-1-yloxyimino)-2-(5-amino-1,2,4-thiadiazol-3-yl)acetamido]-2-methyl-3-cephem-4-carboxylate (syn isomer).

IR (Nujol): 3420–3300, 3150, 1780, 1760, 1675, 1620 cm$^{-1}$ (130) Pivaloyloxymethyl 7-[2-{3-(N-t-butoxycarbonylamino)propoxyimino}-2-(5-amino-1,2,4-thiadiazol-3-yl)acetamido]-2-methyl-3-cephem-4-carboxylate (syn isomer), powder, mp 66° to 75° C. (dec.).

IR (Nujol): 3300, 1780, 1745, 1680, 1620 cm$^{-1}$ (131) Pivaloyloxymethyl 7-[2-{3-(N-t-butoxycarbonylamino)propoxyimino}-2-(5-amino-1,2,4-thiadiazol-3-yl)acetamido]-3-(1-methyl-1H-tetrazol-5-yl)-thiomethyl-3-cephem-4-carboxylate (syn isomer), powder.

IR (Nujol): 3300, 1780, 1745, 1680, 1620 cm$^{-1}$ (132) Pivaloyloxymethyl 7-[2-{3-(N-t-butoxycarbonylamino)propoxyimino}-2-(5-amino-1,2,4-thiadiazol-3-yl)acetamido]-3-(5-methyl-1,3,4-thiadiazol-2-yl)thiomethyl-3-cephem-4-carboxylate (syn isomer).

IR (Nujol): 3300, 3150, 1783, 1745, 1675, 1615 cm$^{-1}$
NMR (DMSO-d$_6$+D$_2$O, δ): 1.15 (9H, s), 1.37 (9H, s), 1.5–2.0 (2H, m), 2.65 (3H, s), 2.8–3.2 (2H, m), 3.5–3.8 (2H, m), 3.9–4.3 (2H, m), 4.16 and 4.53 (2H, ABq, J=13 Hz), 5.17 (1H, d, J=4.5 Hz), 5.6–6.0 (3H, m)

(133) Pivaloyloxymethyl 7-[2-{3-(N-t-butoxycarbonylamino)propoxyimino}-2-(5-amino-1,2,4-thiadiazol-3-yl)acetamido]-3-[1-(2-hydroxyethyl)-1H-tetrazol-5-yl]thiomethyl-3-cephem-4-carboxylate (syn isomer), powder, mp 88° to 101° C. (dec.).

IR (Nujol): 3300, 1780, 1750, 1675, 1620 cm$^{-1}$ (134) Pivaloyloxymethyl 7-[2-{3-(N-t-butoxycarbonylamino)propoxyimino}-2-(5-amino-1,2,4-thiadiazol-3-yl)acetamido]-3-(1,3,4-thiadiazol-2-yl)-thiomethyl-3-cephem-4-carboxylate (syn isomer), powder, mp 71° to 84° C. (dec.).

IR (Nujol): 3300, 1780, 1745, 1680, 1615 cm$^{-1}$ (135) Pivaloyloxymethyl 7-[2-(2-cyclohexen-1-yloxyimino)-2-(5-amino-1,2,4-thiadiazol-3-yl)acetamido]-cephalosporanate (syn isomer), mp 93° to 101° C. (dec.).

IR (Nujol): 3400, 3300, 3180, 1780, 1740, 1675, 1615, 1525 cm$^{-1}$ (136) Phthalid-3-yl ester of 7-[2-(2-cyclopenten-1-yloxyimino)-2-(5-amino-1,2,4-thiadiazol-3-yl)acetamido]-2-methyl-3-cephem-4-carboxylic acid (syn isomer), mp 131° to 144° C. (dec.).

IR (Nujol): 3420, 3210, 3150, 1780, 1740, 1675, 1620, 1525 cm$^{-1}$ (137) Pivaloyloxymethyl 7-[2-(2-cyclopenten-1-yloxyimino)-2-(5-amino-1,2,4-thiadiazol-3-yl)acetamido]-2-methyl-3-cephem-4-carboxylate (syn isomer), mp 111° to 124° C. (dec.).

IR (Nujol): 3400, 3300, 3270, 1775, 1740, 1670, 1620, 1520 cm$^{-1}$ (138) 1-Benzoyloxyethyl 7-[2-(2-cyclopenten-1-yloxyimino)-2-(5-amino-1,2,4-thiadiazol-3-yl)acetamido]-2-methyl-3-cephem-4-carboxylate (syn isomer), mp 132° to 137° C. (dec.).

IR (Nujol): 3400, 3300, 3160, 1780, 1738, 1680, 1620 cm$^{-1}$
NMR (DMSO-d$_6$+D$_2$O, δ): 1.43 (3H, d, J=7 Hz), 1.62 (3H, d, J=5 Hz), 1.7–2.4 (4H, m), 3.84 (1H, q, J=7 Hz), 5.0–5.4 (1H, m), 5.13 (1H, d, J=4.5 Hz), 5.6–6.3 (3H, m), 6.70 (1H, d, J=6 Hz), 7.16 (1H, q, J=5 Hz), 7.3–8.2 (5H, m)

(139) Pivaloyloxymethyl 7-[2-{4-(N-t-butoxycarbonylamino)methylbenzyloxyimino}-2-(5-amino-1,2,4-thiadiazol-3-yl)acetamido]-3-methyl-3-cephem-4-carboxylate (syn isomer), powder.

IR (Nujol): 3300, 1780, 1750, 1680 cm$^{-1}$ (140) Pivaloyloxymethyl 7-[2-allyloxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylate (syn isomer), powder.

IR (Nujol): 3300, 1780, 1750, 1680 cm$^{-1}$ (141) 7-[2-{2-(N-(N-t-Butoxycarbonyl)-D-phenylglycylamino)ethoxyimino}-2-(5-amino-1,2,4-thiadiazol-3-yl)acetamido]-2-methyl-3-cephem-4-carboxylic acid (syn isomer), mp 77° to 91° C. (dec.).

IR (Nujol): 3300, 3160, 1775, 1680, 1660, 1630, 1525 cm$^{-1}$

NMR (DMSO-d$_6$, δ): 1.37 (9H, s), 1.40 (3H, d, J=8 Hz), 3.1–4.2 (5H, m), 5.08 (1H, d, J=4.5 Hz), 5.10 (1H, d, J=8 Hz), 5.90 (1H, dd, J=4.5 and 9 Hz), 6.53 (1H, d, J=7.5 Hz), 7.32 (5H, s), 8.13 (2H, broad s), 9.48 (1H, d, J=9 Hz)

(142) 7-[2-{3-(N-(2-(1-amino-1-cyclohexyl)acetyl)amino)propoxyimino}-2-(5-amino-1,2,4-thiadiazol-3-yl)acetamido]-2-methyl-3-cephem-4-carboxylic acid (syn isomer), mp 198° to 224° C. (dec.).

IR (Nujol): 3250, 3150, 1760, 1640,1580, 1520 cm$^{-1}$ (143) 7-[2-{3-(N-(N-t-Butoxycarbonyl-D-phenylglycylamino)propoxyimino}-2-(5-amino-1,2,4-thiadiazol-3-yl)acetamido]-2-methyl-3-cephem-4-carboxylic acid (syn isomer).

IR (Nujol): 3300, 3200, 1775, 1700, 1650, 1525 cm$^{-1}$

NMR (DMSO-d$_6$+D$_2$O, δ): 1.3–1.6 (12H, m), 1.6–2.0 (2H, m), 2.8–3.4 (2H, m), 3.82 (1H, q, J=7.5 Hz), 3.9–4.3 (2H, m), 5.05 (1H, d, J=4.5 Hz), 5.83 (1H, d, J=4.5 Hz), 6.48 (1H, d, J=6 Hz).

EXAMPLE 42

A mixture of 7-[2-(1-t-butoxycarbonylethoxyimino)-2-(5-amino-1,2,4-thiadiazol-3-yl)acetamido]-cephalosporanic acid (syn isomer) (5.7 g), 1-[3-(N-t-butoxycarbonylamino)propyl]-1H-tetrazole-5-thiol (3.9 g) and sodium bicarbonate (2.5 g) in pH 6.8 phosphate buffer solution (150 ml) was stirred for 4.6 hours at 70° C. The reaction mixture was ice-cooled and washed few times with ethyl acetate. Ethyl acetate was added to an aqueous layer, and the mixture was acidified with hydrochloric acid and extracted with ethyl acetate. The extract was successively washed with water and an aqueous solution of sodium chloride, dried over magnesium sulfate and then evaporated. The residue was triturated with diethyl ether and precipitates were collected by filtration to give brown powder of 7-[2-(1-carboxyethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer)(3.5 g), mp 110° to 115° C. (dec.).

I.R. (Nujol): 3300, 3200, 1770, 1680, 1600, 1520, 1250, 1000, 720 cm$^{-1}$

N.M.R. (DMSO-d$_6$+D$_2$O, δ): 1.4 (12H, m), 2.02 (2H, m), 2.98 (2H, t, J=6 Hz), 3.70 (2H, m), 4.1–4.5 (4H, m), 4.70 (1H, q, J=7 Hz), 5.13 (1H, d, J=5 Hz), 5.85 (1H, d, J=5 Hz)

EXAMPLE 43

The following compounds were obtained according to similar manners to those of Examples 14 to 17 and 42.

(1)-7-[2-(4-Chlorophenoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 120° to 125° C. (dec.).

IR (Nujol): 3290, 3180, 1770, 1680, 1615, 1580, 1520, 1480 cm$^{-1}$ (2) 7-[2-(4-Chlorophenoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 130° to 135° C. (dec.).

IR (Nujol): 3400, 3300, 3280, 1770, 1670, 1615, 1580, 1520, 1480 cm$^{-1}$ (3) 7-[2-(4-Chlorophenoxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 135° to 140° C. (dec.).

IR (Nujol): 3400, 3270, 3190, 1770, 1680, 1620, 1585, 1520, 1480 cm$^{-1}$ (4) 7-[2-(4-Chlorophenoxyimino)-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp 140° to 145° C. (dec.).

IR (Nujol): 3400, 3300, 3190, 1765, 1700, 1620, 1580, 1540, 1520, 1480 cm$^{-1}$ (5) 7-[2-(4-Chlorophenoxyimino)-2-(5-amino-1,2,4-thiadiazol-3-yl)acetamido]-3-(tetrazolo[1,5-b]-pyridazin-6-yl)thiomethyl-3-cephem-4-carboxylic acid (syn isomer), mp 140° to 145° C. (dec.).

IR (Nujol): 3350, 3240, 1780, 1685, 1625, 1530, 1490 cm$^{-1}$ (6) 7-[2-(α-t-Butoxycarbonylbenzyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 105° to 110° C. (dec.).

IR (Nujol): 3400, 3300, 3180, 1780, 1720, 1680, 1620, 1520 cm$^{-1}$ (7) 7-[2-(α-t-Butoxycarbonylbenzyloxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 105° to 110° C. (dec.).

IR (Nujol): 3360, 3220, 1785, 1690, 1625, 1525 cm$^{-1}$ (8) 7-[2-(2-Propynyloxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 125° to 130° C. (dec.).

IR (Nujol): 3400, 3260, 3190, 2580, 1765, 1710, 1670, 1620, 1520 cm$^{-1}$ (9) 7-[2-(Thiolan-1,1-dioxide-3-yl)oxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 170° to 175° C. (dec.).

IR (Nujol): 3300, 3200, 1770, 1670, 1620, 1520 cm$^{-1}$

(10) 7-[2-Allyloxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 140° to 145° C. (dec.).

IR (Nujol): 3300, 3200, 1770, 1720, 1670, 1620, 1520 cm$^{-1}$

(11) 7-[2-(2-Propynyloxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 135° to 140° C. (dec.).

IR (Nujol): 3250, 3150, 1770, 1720, 1670, 1620, 1520 cm$^{-1}$

(12) 7-[2-Allyloxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 140° to 145° C. (dec.).

IR (Nujol): 3300, 3200, 1770, 1720, 1670, 1620, 1520 cm$^{-1}$

(13) 7-[2-(t-Butoxycarbonylmethoxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 150° to 155° C. (dec.).

IR (Nujol): 3300, 3200, 1770, 1720, 1700, 1620, 1520 cm⁻¹

(14) 7-[2-(t-Butoxycarbonylmethoxyimino)-2-(5-amino-1,2,4-thiadiazol-3-yl)acetamido]-3-[1-{3-(4-methyl-1-piperazinyl)propyl}-1H-tetrazol-5-yl]-thiomethyl-3-cephem-4-carboxylic acid (syn isomer), mp 220° to 225° C. (dec.).

IR (Nujol): 3300, 1700, 1680, 1605, 1520 cm⁻¹

(15) 7-[2-(1-t-Butoxycarbonylpropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 101° to 105° C. (dec.).

IR (Nujol): 3300, 3150, 1770, 1720, 1620, 1520, 1450, 1370, 1250, 1150, 1010, 900, 840, 720 cm⁻¹

(16) 7-[2-(1-t-Butoxycarbonylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 120° to 128° C. (dec.).

IR (Nujol): 3280, 3180, 1770, 1720, 1680, 1620, 1520, 1240, 1150, 1000, 740, 720 cm⁻¹

(17) 7-[2-(1-Methyl-1-t-butoxycarbonylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 115° to 120° C. (dec.).

IR (Nujol): 3280, 3170, 1780, 1720, 1680, 1520, 1140, 990, 750 cm⁻¹

(18) 7-[2-(1-t-Butoxycarbonyl-1-cyclopentyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 143° C. (dec.).

IR (Nujol): 3300, 3180, 1770, 1720–1670, 1620, 1520, 1245, 1150, 1060, 995, 840 cm⁻¹

(19) 7-[2-(1-Methyl-1-t-Butoxycarbonylethoxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 96° to 100° C. (dec.).

IR (Nujol): 3300, 3150, 1780, 1680, 1570, 1240, 1160, 990 cm⁻¹

(20) 7-[2-(1-t-Butoxycarbonylethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 96° to 100° C. (dec.).

IR (Nujol): 3300, 3150, 1780, 1720, 1680, 1620, 1520, 1240, 1150, 1090, 1000 cm⁻¹

(21) 7-[2-(1-Phenylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), which is decomposed by 175° C.

IR (Nujol): 3400, 3250, 3150, 1750, 1650, 1610, 1520, 1400, 1240, 1160, 1060, 1000, 700 cm⁻¹

(22) 7-[2-(p-Tolyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), which is decomposed by 150° C., which is a mixture with o-tolyl isomer.

IR (Nujol): 3350, 3250, 1780, 1680, 1630, 1530, 1510, 1230, 1050, 910, 820 cm⁻¹

(23) 7-[2-(3-Trifluoromethylphenoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), which is decomposed by 155° C.

IR (Nujol): 3300, 3200, 1770, 1680, 1620, 1520, 1320, 1160, 1120, 1060, 980, 930, 700 cm⁻¹

(24) 7-[2-(3-Trifluoromethylphenoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), which is decomposed by 170° C.

IR (Nujol): 3300, 3200, 1770, 1680, 1620, 1520, 1320, 1160, 1120, 1060, 930, 790, 700 cm⁻¹

(25) 7-[2-(4-Fluorophenoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), which is decomposed by 170° C.

IR (Nujol): 3450, 3350, 3200, 1780, 1710, 1680, 1610, 1510, 1590, 1240, 1200, 1170, 1090, 990, 910, 840 cm⁻¹

(26) 7-[2-(2,4-Dichlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), which is decomposed by 165° C.

IR (Nujol): 3300, 3200, 1770, 1680, 1620, 1520, 1250, 1230, 1100, 1060, 960, 910, 810 cm⁻¹

(27) 7-[2-{3-(N-t-Butoxycarbonylamino)propoxyimino}-2-(5-amino-1,2,4-thiadiazol-3-yl)acetamido]-3-(1,3,4-thiadiazol-2-yl)thiomethyl-3-cephem-4-carboxylic acid (syn isomer).

IR (Nujol): 3200, 3160, 1773, 1685, 1620 cm⁻¹

(28) 7-[2-{3-(N-t-Butoxycarbonylamino)propoxyimino}-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer).

IR (Nujol): 3200, 3160, 1775, 1720, 1700, 1675, 1620 cm⁻¹

(29) 7-[2-{3-(N-t-Butoxycarbonylamino)propoxyimino}-2-(5-amino-1,2,4-thiadiazol-3-yl)acetamido]-3-(5-methyl-1,3,4-thiadiazol-2-yl)thiomethyl-3-cephem-4-carboxylic acid (syn isomer).

IR (Nujol): 3300, 3150, 1775, 1710, 1700, 1670, 1650, 1620 cm⁻¹

(30) 7-[2-{3-(N-t-Butoxycarbonylamino)propoxyimino}-2-(5-amino-1,2,4-thiadiazol-3-yl)acetamido]-3-(1-methyl-1H-tetrazol-5-yl)thiomethyl-3-cephem-4-carboxylic acid (syn isomer), mp 81° to 119° C. (dec.).

IR (Nujol): 3300, 3180, 1773, 1715, 1700, 1670, 1620 cm⁻¹

(31) 7-[2-Carboxymethoxyimino-2-(5-amino-1,2,4-thiadiazol-3-yl)acetamido]-3-[1-{2-(N,N-dimethylamino)ethyl}-1H-tetrazol-5-yl]thiomethyl-3-cephem-4-carboxylic acid (syn isomer), mp 170° to 173° C. (dec.).

IR (Nujol): 3400, 3280, 3150, 1760, 1665, 1610, 1520 cm⁻¹

NMR (DMSO-d₆+D₂O, δ): 2.53 (6H, s), 3.07–3.37 (2H, m), 3.50–3.77 (2H, m), 4.10–4.37 (2H, m), 4.43–4.83 (4H, m), 5.10 (1H, d, J=5 Hz), 5.80 (1H, d, J=5 Hz)

(32) 7-[2-Carboxymethoxyimino-2-(5-amino-1,2,4-thiadiazol-3-yl)acetamido]-3-[1-{3-(N,N-dimethylamino)propyl}-1H-tetrazol-5-yl]thiomethyl-3-cephem-4-carboxylic acid (syn isomer), mp 170° to 175° C. (dec.).

IR (Nujol): 3400, 3280, 3160, 1760, 1665, 1610, 1520 cm⁻¹

NMR (DMSO-d₆, δ): 2.10–2.43 (2H, m), 2.70 (6H, s), 2.92–3.28 (2H, m), 3.45–3.80 (2H, m), 4.17–4.80 (6H, m), 5.10 (1H, d, J=5 Hz), 5.84 (1H, dd, J=5 and 8 Hz), 8.15 (2H, broad s), 10.1 (1H, d, J=8 Hz)

(33) 7-[2-(2-Propynyloxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 85° to 90° C. (dec.).

IR (Nujol): 3400, 3290, 3200, 1770, 1680, 1620, 1520 cm⁻¹

NMR (DMSO-d₆, δ): 1.40 (9H, s), 1.77–2.17 (2H, m), 2.78–3.23 (2H, m), 3.50 (1H, t, J=2 Hz), 3.73 (2H, broad s), 4.07–4.53 (4H, m), 4.82 (2H, d, J=2 Hz), 5.15 (1H, d, J=5 Hz), 5.85 (1H, dd, J=5 and 8 Hz), 8.17 (2H, broad s), 9.65 (1H, d, J=8 Hz)

(34) 7-[2-Carboxymethoxyimino-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 185° to 190° C. (dec.).

IR (Nujol): 3300, 3200, 1770, 1680, 1620, 1520 cm$^{-1}$

NMR (DMSO-d$_6$, δ): 1.33 (9H, s), 1.67-2.12 (2H, m), 2.77-3.07 (2H, m), 3.63 (2H, broad s), 4.07-4.43 (4H, m), 4.60 (2H, s), 5.05 (1H, d, J=4 Hz), 5.77 (1H, dd, J=4 and 8 Hz), 8.08 (2H, s), 9.47 (1H, d, J=8 Hz)

(35) 7-[2-(2,2,2-Trifluoroethoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 130° to 132° C. (dec.).

IR (Nujol): 3300, 3200, 1770, 1720, 1670, 1620, 1520 cm$^{-1}$

NMR (DMSO-d$_6$ δ): 3.73 (2H, broad s), 4.30 and 4.53 (2H, ABq, J=14 Hz), 4.73 and 4.97 (2H, ABq, J=8 Hz), 5.10 (1H, d, J=4 Hz), 5.35 (2H, s), 5.87 (1H, dd, J=4 and 8 Hz), 8.23 (2H, s), 9.80 (1H, d, J=8 Hz)

(36) 7-[2-(1-Carboxy-2-methylpropoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 192° to 195° C. (dec.).

IR (Nujol): 3400-3200, 1780, 1680, 1520, 1450, 1360, 1240, 1160, 1020, 730 cm$^{-1}$ NMR (DMSO-d$_6$, δ): 0.98 (6H, d, J=7 Hz), 1.38 (9H, s), 1.8-2.2 (3H, m), 2.8-3.2 (2H, m), 3.7 (2H, m), 4.1-4.7 (5H, m), 5.12 (1H, d, J=5 Hz), 5.7-6.9 (1H, m), 6.7-6.9 (1H, m), 8.03 (2H, broad s), 9.42 (1H, d, J=8 Hz)

(37) 7-[2-(1-Carboxypropoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 185° to 192° C. (dec.).

IR (Nujol): 3300, 3200, 1770, 1680, 1620, 1520, 1450, 1360, 1250, 1160, 1000, 730-710 cm$^{-1}$ NMR (DMSO-d$_6$, δ): 1.08 (3H, t, J=7 Hz), 1.35 (9H, s), 1.6-2.1 (4H, m), 2.6-3.1 (2H, m), 3.7 (2H, m), 4.1-4.6 (5H, m), 5.10 (1H, d, J=6 Hz), 5.81 (1H, dd, J=5 and 8 Hz), 6.8 (1H, m), 8.10 (2H, broad s), 9.45 and 9.47 (1H, d, J=8 Hz)

(38) 7-[2-{3-(N-t-Butoxycarbonylamino)propoxyimino}-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer).

IR (Nujol): 3300, 3150, 1775, 1715, 1675, 1650, 1615 cm$^{-1}$

NMR (DMSO-d$_6$+D$_2$O, δ): 1.37 (18H, s), 1.5-2.1 (4H, m), 2.7-3.3 (4H, m), 3.5-3.9 (2H, m), 3.9-4.5 (6H, m), 5.13 (1H, d, J=4.5 Hz), 5.83 (1H, d, J=4.5 Hz)

(39) 7-[2-(1-Carboxyethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 110° to 115° C. (dec.).

IR (Nujol): 3300, 3200, 1770, 1680, 1600, 1520, 1250, 1000, 720 cm$^{-1}$

NMR (DMSO-d$_6$+D$_2$O, δ): 1.4 (12H, m), 2.02 (2H, m), 2.98 (2H, t, J=6 Hz), 3.70 (2H, m), 4.1-4.5 (4H, m), 4.70 (1H, q, J=7 Hz), 5.13 (1H, d, J=5 Hz), 5.85 (1H, d, J=5 Hz)

(40) 7-[2-(1-Carboxy-1-cyclopentyloxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 200° to 205° C. (dec.).

IR (Nujol): 3300, 3200, 1770, 1680, 1520, 1250, 1160, 1000 cm$^{-1}$

NMR (DMSO-d$_6$, δ): 1.38 (9H, s), 1.68 (4H, m), 2.0 (6H, m), 2.96 (2H, m), 3.70 (2H, m), 4.26 (4H, m), 5.12 (1H, d, J=5 Hz), 5.82 (1H, dd, J=5 and 8 Hz), 6.86 (1H, m), 8.14 (2H, m), 9.40 (1H, d, J=8 Hz)

(41) 7-[2-Carboxymethoxyimino-2-(5-amino-1,2,4-thiadiazol-3-yl)acetamido]-3-[1-(3-morpholinopropyl)-1H-tetrazol-5-yl]thiomethyl-3-cephem-4-carboxylic acid (syn isomer), mp 190° to 194° C. (dec.).

IR (Nujol): 3300, 3200, 1770, 1680, 1610, 1530, 1240, 1180, 1090, 1060, 880, 760 cm$^{-1}$ NMR (DMSO-d$_6$, δ): 2.17 (2H, m), 2.63 (6H, m), 3.67 (6H, m), 4.37 (4H, m), 4.67 (2H, broad s), 5.15 (1H, d, J=5 Hz), 5.83 (1H, dd, J=5 and 8 Hz), 8.17 (2H, m), 9.73 (1H, d, J=8 Hz)

(42) 7-[2-(1-Carboxy-1-methylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer).

IR (Nujol): 3300, 3150, 1770, 1680, 1520, 1240, 1160, 990 cm$^{-1}$

NMR (DMSO-d$_6$, δ): 1.45 (15H, broad s), 2.0 (2H, m), 3.0 (2H, m), 3.77 (2H, m), 4.10-4.40 (4H, m), 5.20 (1H, d, J=5 Hz), 5.87 (1H, dd, J=5 and 8 Hz), 6.87 (1H, m), 8.20 (2H, broad s), 9.47 (1H, d, J=8 Hz)

(43) 7-[2-Carboxymethoxyimino-2-(5-amino-1,2,4-thiadiazol-3-yl)acetamido]-3-(4-methyl-5-oxo-6-hydroxy-4,5-dihydro-1,2,4-triazin-3-yl)thiomethyl-3-cephem-4-carboxylic acid (syn isomer), mp 210° to 214° C. (dec.).

IR (Nujol): 3250, 3180, 1760, 1720-1660, 1590, 1520, 1240, 1090, 1050, 720 cm$^{-1}$ NMR (DMSO-d$_6$+D$_2$O, δ): 3.30 (3H, s), 3.65 (2H, m), 4.10 (2H, m), 4.65 (2H, broad s), 5.11 (1H, d, J=5 Hz), 5.82 (1H, dd, J=5 and 8 Hz)

(44) 7-[2-Carboxymethoxyimino-2-(5-amino-1,2,4-thiadiazol-3-yl)acetamido]-3-[1-{4-(N-t-butoxycarbonylamino)butyl}-1H-tetrazol-5-yl]thiomethyl-3-cephem-4-carboxylic acid (syn isomer).

IR (Nujol): 3300, 3200, 1770, 1680, 1620, 1520, 1240, 1160, 1090, 1060, 890 cm$^{-1}$ NMR (DMSO-d$_6$, δ): 1.0-2.0 (4H, m), 1.33 (9H, s), 2.90 (2H, m), 3.66 (2H, m), 4.0-4.5 (4H, m), 4.62 (2H, broad s), 5.10 (1H, d, J=5 Hz), 5.80 (1H, dd, J=5 and 8 Hz), 6.75 (1H, m), 8.13 (2H, broad s), 9.55 (1H, d, J=8 Hz)

(45) 7-[2-Carboxymethoxyimino-2-(5-amino-1,2,4-thiadiazol-3-yl)acetamido]-3-[1-(3-piperidinopropyl)-1H-tetrazol-5-yl]thiomethyl-3-cephem-4-carboxylic a acid (syn isomer), mp 223° to 228° C. (dec.).

IR (Nujol): 3300, 3200, 1770, 1670, 1610, 1520 cm$^{-1}$

NMR (DMSO-d$_6$, δ): 1.30-1.83 (6H, m), 2.1-2.3 (2H, m), 2.8-3.3 (6H, m), 3.60 (2H, broad s), 4.0-4.50 (4H, m), 4.60 (2H, s), 5.06 (1H, d, J=4 Hz), 5.80 (1H, dd, J=4 and 8 Hz), 8.15 (2H, s), 10.1 (1H, d, J=8 Hz)

(46) 7-[2-Carboxymethoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 170° to 175° C. (dec.).

IR (Nujol): 3300, 3200, 1765, 1720, 1660, 1620, 1520 cm$^{-1}$

NMR (DMSO-d$_6$, δ): 3.67 (2H, broad s), 4.27 and 4.47 (2H, ABq, J=13 Hz), 4.67 (2H, s), 5.13 (1H, d, J=4 Hz), 5.33 (2H, s), 5.87 (1H, dd, J=4 and 8 Hz), 8.20 (2H, s), 9.60 (1H, d, J=8 Hz)

(47) 7-[2-Carboxymethoxyimino-2-(5-amino-1,2,4-thiadiazol-3-yl)acetamido]-3-[1-{6-(N-t-butoxycarbonylamino)hexyl}-1H-tetrazol-5-yl]thiomethyl-3-cephem-4-carboxylic acid (syn isomer), pale yellow powder.

(48) 7-[2-(1-Carboxyethoxyimino)-2-(5-amino-1,2,4-thiadiazol-3-yl)acetamido]-3-[5-(N-t-butoxycarbonylamino)methyl-1,3,4-thiadiazol-2-yl]thiomethyl-3-cephem-4-carboxylic acid (syn isomer), mp 210° to 215° C. (dec.).

IR (Nujol): 3300, 1770, 1680, 1620, 1520, 1240, 1140 cm$^{-1}$

NMR (DMSO-$d_6$, δ): 1.43 (12H, broad s), 3.70 (2H, m), 4.27–4.87 (5H, m), 5.20 (1H, d, J=5 Hz), 5.87 (1H, dd, J=5 and 8 Hz), 7.70 (1H, m), 8.17 (2H, broad s), 9.50 (1H, d, J=8 Hz)

(49) 7-[2-(2-Propynyloxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 165° to 170° C. (dec.).

IR (Nujol): 3450, 3300, 3210, 1770, 1670, 1620, 1525 cm$^{-1}$

(50) 7-[2-Carboxymethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 195° to 200° C. (dec.).

IR (Nujol): 3150, 1760, 1660, 1640, 1520 cm$^{-1}$

(51) 7-[2-(1-Carboxy-2-methylpropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 183° to 189° C. (dec.).

IR (Nujol): 3400–3100, 3150, 1770, 1670, 1620, 1520, 1380, 1280, 1230, 1180, 1100, 1020, 900, 730 cm$^{-1}$

(52) 7-[2-(1-Carboxypropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 183° to 188° C. (dec.).

IR (Nujol): 3400–1350, 1770, 1670, 1620, 1530, 1380, 1280, 1230, 1180, 1100, 1050, 1010, 730 cm$^{-1}$

(53) 7-[2-(1-Carboxyethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 185° to 188° C. (dec.).

IR (Nujol): 3300, 3150, 1760, 1660, 1620, 1520, 1230, 1000, 720 cm$^{-1}$

(54) 7-[2-Carboxymethoxyimino-2-(5-amino-1,2,4-thiadiazol-3-yl)acetamido]-3-[1-(4-aminobutyl)-1H-tetrazol-5-yl]thiomethyl-3-cephem-4-carboxylic acid (syn isomer), mp 191° to 194° C. (dec.).

IR (Nujol): 3300, 3150, 1760, 1670, 1620, 1520, 1230, 1170, 1050, 890, 740, 720 cm$^{-1}$

(55) 7-[2-(1-Carboxy-1-methylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 200° to 203° C. (dec.).

IR (Nujol): 3300, 3150, 1760, 1660, 1620, 1520, 1160, 990 cm$^{-1}$

(56) 7-[2-(1-Carboxy-1-cyclopentyloxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 202° to 205° C. (dec.).

IR (Nujol): 3300, 3200, 1760, 1660, 1620, 1520, 1180, 1060, 1000, 730 cm$^{-1}$

(57) 7-[2-(1-Carboxyethoxyimino)-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp 207° to 210° C. (dec.).

Ir (Nujol): 3300, 3150, 1760, 1660, 1620, 1520, 1230, 1170, 1090, 1060, 1040, 990 cm$^{-1}$

(58) 7-[2-Carboxymethoxyimino-2-(5-amino-1,2,4-thiadiazol-3-yl)acetamido]-3-[1-(6-aminohexyl)-1H-tetrazol-5-yl]thiomethyl-3-cephem-4-carboxylic acid (syn isomer), mp 185° to 188° C. (dec.).

IR (Nujol): 3300, 3200, 1760, 1670, 1620, 1520, 1240, 1180, 1060 cm$^{-1}$

(59) 7-[2-(3-Aminopropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 183° C. (dec.).

IR (Nujol): 3150, 1765, 1660, 1630, 1570, 1520 cm$^{-1}$

(60) 7-[2-(3-Aminopropoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 170° to 185° C. (dec.).

IR (Nujol): 3140, 1760, 1660, 1610, 1580, 1520 cm$^{-1}$

(61) 7-[2-(3-Aminopropoxyimino)-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 192° to 195° C. (dec.).

IR (Nujol): 3250, 3140, 1760, 1640, 1620, 1585, 1525 cm$^{-1}$

(62) 7-[2-(3-Aminopropoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 180° to 184° C. (dec.).

IR (Nujol): 3160, 1760, 1660, 1590 cm$^{-1}$

(63) 7-[2-(3-Aminopropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer).

Ir (Nujol): 3300, 3150, 1760, 1660, 1607, 1595, 1520 cm$^{-1}$

(64) 7-[2-(α-Carboxybenzyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

IR (Nujol): 3400, 3290, 3160, 2500, 1770, 1720, 1615, 1520 cm$^{-1}$

(65) 7-[2-(α-Carboxybenzyloxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 190° to 195° C. (dec.).

IR (Nujol): 3400, 3300, 3150, 1765, 1670, 1610, 1520 cm$^{-1}$

(66) 7-[2-Carboxymethoxyimino-2-(5-amino-1,2,4-thiadiazol-3-yl)acetamido]-3-[1-{3-(4-methyl-1-piperazinyl)propyl}-1H-tetrazol-5-yl]thiomethyl-3-cephem-4-carboxylic acid (syn isomer), mp 185° to 190° C. (dec.).

IR (Nujol): 3300, 1760, 1670, 1600, 1520 cm$^{-1}$

(67) 7-[2-(1-Carboxypropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 153° to 158° C. (dec.).

IR (Nujol): 3300, 3180, 1770, 1720–1670, 1620, 1520, 1220, 1060, 1000, 900, 730 cm$^{-1}$

(68) 7-[2-(1-Carboxyethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 168° C. (dec.).

IR (Nujol): 3400–3200, 1770, 1710, 1670, 1620, 1520, 1230, 1170, 1000, 900, 720 cm$^{-1}$

(69) 7-[2-(1-Carboxy-1-methylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 164° to 167° C. (dec.).

IR (Nujol): 3300, 3200, 2800–2300, 1770, 1720–1660, 1620, 1520, 1160, 1060, 990, 800 cm$^{-1}$

(70) 7-[2-(1-Carboxy-1-cyclopentyloxyimino)-2-(5-amino-1,2,4-thiadiazol-3-yl)acetamido]-3-(1,3,4- thiadiazol-2-yl)thiomethyl-3-cephem-4-carboxylic acid (syn isomer), mp 165° to 169° C. (dec.).

IR (Nujol): 3300, 3180, 1770, 1720–1660, 1620, 1520, 1240, 1180, 1060, 1000, 720 cm⁻¹

(71) 7-[2-(1-Carboxyethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), which is decomposed by 180° C.

IR (Nujol): 3300, 3150, 1770, 1680, 1610, 1520, 1260, 1100, 1040, 1000 cm⁻¹

(72) 7-[2-(1-Carboxy-1-methylethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 195° to 200° C. (dec.).

IR (Nujol): 3150, 1760, 1670, 1620, 1520, 1170, 990 cm⁻¹

(73) 7-[2-Cyclopentyloxyimino-2-(5-amino-1,2,4-thiadiazol-3-yl)acetamido]-3-[1-{3-(4-methyl-1-piperazinyl)propyl}-1H-tetrazol-5-yl]-thiomethyl-3-cephem-4-carboxylic acid (syn isomer), mp 175° to 180° C. (dec.).

IR (Nujol): 3300, 1770, 1650, 1610, 1520 cm⁻¹

(74) 7-[2-(2-Oxo-3-tetrahydrofuryloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 170° C. (dec.).

IR (Nujol): 3300, 3200, 1770, 1680, 1620, 1525 cm⁻¹

(75) 7-[2-(1-Cyclohexyloxycarbonylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 145° to 150° C. (dec.).

IR (Nujol): 3400–3250, 1780, 1680, 1620, 1520, 1240, 1220, 1160, 1100, 1000, 740, 720 cm⁻¹

(76) 7-[2-(1-Benzyloxycarbonylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 113° to 117° C. (dec.).

IR (Nujol): 3300, 3200, 1780, 1680, 1620, 1520, 1250, 1160, 1100, 1040, 1000, 740, 700 cm⁻¹

(77) 7-[2-(1-Butoxycarbonylethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer), mp 149° to 155° C. (dec.).

IR (Nujol): 3300, 3200, 1780, 1700, 1620, 1520, 1250, 1160, 1100, 1040, 1000, 740, 720 cm⁻¹

(78) 7-[2-(1-Cyclohexyloxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 175° to 178° C. (dec.).

IR (Nujol): 3400–3200, 1765, 1680, 1610, 1520, 1220, 1100, 1000, 890, 790 cm⁻¹

(79) 7-[2-(1-Benzyloxycarbonylethoxyimino)-2-(5-amino-1,2,4-thiadiazol-3-yl)acetamido]-3-[1-(3-aminopropyl)-1H-tetrazol-5-yl]-thiomethyl-3-cephem-4-carboxylic acid (syn isomer), mp 162° to 166° C. (dec.).

IR (Nujol): 3300, 3200, 1760, 1680, 1620, 1520, 1100, 1040, 1000, 740 cm⁻¹

(80) 7-[2-(1-Butoxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 158° to 163° C. (dec.).

IR (Nujol): 3400–3200, 1770, 1680, 1610, 1530, 1300, 1290, 1050, 1040, 1000, 960, 900, 790, 740, 720 cm⁻¹

(81) Pivaloyloxymethyl 7-[2-(3-aminopropoxyimino)-2-(5-amino-1,2,4-thiadiazol-3-yl)acetamido]-3-(1-methyl-1H-tetrazol-5-yl)thiomethyl-3-cephem-4-carboxylate hydrochloride (syn isomer), mp 110° to 125° C. (dec.).

IR (Nujol): 1780, 1745, 1670, 1625, 1525 cm⁻¹

(82) Pivaloyloxymethyl 7-[2-(3-amiopropoxyimino)-2-(5-amino-1,2,4-thiadiazol-3-yl)acetamido]-3-(5-methyl-1,3,4-thiadiazol-2-yl)thiomethyl-3-cephem-4-carboxylate hydrochloride (syn isomer), mp 88° to 153° C. (dec.).

IR (Nujol): 2150, 1780, 1745, 1650, 1625, 1525 cm⁻¹

(83) Pivaloyloxymethyl 7-[2-(3-aminopropoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylate hydrochloride (syn isomer), mp 150° to 175° C. (dec.).

IR (Nujol): 3150, 1780, 1740, 1670, 1630, 1520 cm⁻¹

(84) Pivaloyloxymethyl 7-[2-(3-aminopropoxyimino)-2-(5-amino-1,2,4-thiadiazol-3-yl)acetamido]-3-(1,3,4-thiadiazol-2-yl)thiomethyl-3-cephem-4-carboxylate hydrochloride (syn isomer), mp 96° to 155° C. (dec.).

IR (Nujol): 3300, 3150, 1775, 1730, 1670, 1625, 1530 cm⁻¹

(85) Pivaloyloxymethyl 7-[2-allyloxyimino-2-(5-amino-1,2,4-thiadiazol-3-yl)acetamido]-3-[1-(2-aminoethyl)-1H-tetrazol-5-yl]thiomethyl-3-cephem-4-carboxylate formate (syn isomer), mp 95° to 105° C. (dec.).

IR (Nujol): 1790, 1735, 1452, 1370, 1118, 990 cm⁻¹

(86) Pivaloyloxymethyl 7-[2-{3-(N-t-butoxycarbonylamino)propoxyimino}-2-(5-amino-1,2,4-thiadiazol-3-yl)acetamido]-3-(1-methyl-1H-tetrazol-5-yl)thiomethyl-3-cephem-4-carboxylate (syn isomer), powder.

IR (Nujol): 3300, 1780, 1745, 1680, 1620 cm⁻¹

(87) Pivaloyloxymethyl 7-[2-{3-(N-t-butoxycarbonylamino)propoxyimino}-2-(5-amino-1,2,4-thiadiazol-3-yl)acetamido]-3-(5-methyl-1,3,4-thiadiazol-2-yl)thiomethyl-3-cephem-4-carboxylate (syn isomer).

IR (Nujol): 3300, 3150, 1783, 1745, 1675, 1615 cm⁻¹

(88) Pivaloyloxymethyl 7-[2-{3-(N-t-butoxycarbonylamino)propoxyimino}-2-(5-amino-1,2,4-thiadiazol-3-yl)acetamido]-3-[1-(2-hydroxyethyl)-1H-tetrazol-5-yl]thiomethyl-3-cephem-4-carboxylate (syn isomer), powder, mp 88° to 101° C. (dec.).

IR (Nujol): 3300, 1780, 1750, 1675, 1620 cm⁻¹

(89) Pivaloyloxymethyl 7-[2-{3-(N-t-butoxycarbonylamino)propoxyimino}-2-(5-amino-1,2,4-thiadiazol-3-yl)acetamido]-3-(1,3,4-thiadiazol-2-yl)thiomethyl-3-cephem-4-carboxylate (syn isomer), powder, mp 71° to 84° C. (dec.).

IR (Nujol): 3300, 1780, 1745, 1680, 1615 cm⁻¹

(90) Pivaloyloxymethyl 7-[2-allyloxyimino-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylate (syn isomer), powder.

IR (Nujol): 3300, 1780, 1750, 1680 cm⁻¹

(91) 7-[2-(4-Chlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

I.R. (Nujol): 3300, 3200, 1770, 1670, 1620, 1520 cm⁻¹

(92) 7-[2-(4-Fluorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 145° C. (dec.).

I.R. (Nujol): 3300, 3200, 1770, 1680, 1620, 1520 cm⁻¹

(93) 7-[2-Phenoxyimino-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 175° to 180° C. (dec.).

I.R. (Nujol): 3400, 3200, 1770, 1700, 1660, 1620, 1580, 1510 cm⁻¹

(94) 7-[2-Phenoxyimino-2-(5-amino-1,2,4-thiadiazol-3-yl)acetamido]-3-(1-allyl-1H-tetrazol-5-yl)thiomethyl- 3-cephem-4-carboxylic acid (syn isomer), mp 145° to 150° C. (dec.)

I.R. (Nujol): 3450, 3350, 3180, 1780, 1710, 1680, 1610, 1590, 1510 cm$^{-1}$

(95) 7-[2-Phenoxyimino-2-(5-amino-1,2,4-thiadiazol-3-yl)acetamido]-3-(1-methyl-1H-tetrazol-5-yl)thiomethyl-3-cephem-4-carboxylic acid (syn isomer), mp 155° to 158° C. (dec.)

I.R. (Nujol): 3400, 3300, 3200, 1770, 1720, 1680, 1620, 1590, 1520 cm$^{-1}$

(96) 7-[2-(2-Methoxy-5-nitrophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 160° to 169° C. (dec.)

I.R. (Nujol): 3380, 3220, 3100, 1780, 1690, 1620, 1600, 1520, 1340, 1280, 1085, 1065, 820, 750 cm$^{-1}$

(97) 7-[2-(4-Fluorophenoxyimino)-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 125° to 130° C. (dec.).

I.R. (Nujol): 3300, 3190, 1770, 1670, 1615, 1520, 1495 cm$^{-1}$

(98) 7-[2-(4-Chlorophenoxyimino)-2-(5-amino-1,2,4-thiadiazol-3-yl)acetamido]-3-(5-hydroxymethyl-1,3,4-thiadiazol-2-yl)thiomethyl-3-cephem-4-carboxylic acid (syn isomer), mp 135° to 140° C. (dec.).

I.R. (Nujol): 3450, 3280, 3180, 1760, 1720, 1660, 1620, 1580, 1520, 1480 cm$^{-1}$

(99) 7-[2-(4-Chlorophenoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 135° to 140° C. (dec.).

I.R. (Nujol): 3400, 3250, 3170, 1765, 1700, 1680, 1650, 1615, 1580, 1510, 1480 cm$^{-1}$ (100) 7-[2-(4-Chlorophenoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 120° to 125° C. (dec.).

I.R. (Nujol): 3400, 3300, 3180, 1765, 1670, 1615, 1580, 1520, 1480 cm$^{-1}$ (101) 7-[2-(3,4-Dichlorophenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), decomposed by 160° C.

I.R. (Nujol): 3300, 3200, 1770, 1680, 1620, 1520, 1250, 1205, 1060 cm$^{-1}$ (102) 7-[2-(3-Trifluoromethylphenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), decomposed by 164° C.

I.R. (Nujol): 3300, 3180, 1765, 1670, 1610, 1520, 1320, 1165, 1120, 1060, 930, 790, 700 cm$^{-1}$ (103) 7-[2-(3-Ethoxycarbonylphenoxyimino)-2-(5-amino-1,2,4-thiadiazol-3-yl)acetamido]-3-(1,3,4-thiadiazol-2-yl)thiomethyl-3-cephem-4-carboxylic acid (syn isomer), decomposed by 162° C.

I.R. (Nujol): 3350–3150, 1770, 1720–1660, 1620, 1520, 1290, 1270, 1100, 1060, 900, 760 cm$^{-1}$ (104) 7-[2-(4-Fluorophenoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 145° to 150° C. (dec.).

I.R. (Nujol): 3300, 3200, 1770, 1670, 1610, 1520 cm$^{-1}$ (105) 7-[2-(4-Fluorophenoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 150° to 155° C. (dec.).

I.R. (Nujol): 3300, 3200, 1770, 1720, 1670, 1620, 1520, 1500 cm$^{-1}$ (106) 7-[2-(4-Fluorophenoxyimino)-2-(5-amino-1,2,4-thiadiazol-3-yl)acetamido]-3-[2-carboxymethyl-3-oxo-2,3-dihydro-1,2,4-triazolo[4,3-b]pyridazin-6-yl]thiomethyl-3-cephem-4-carboxylic acid (syn isomer), mp 165° to 170° C. (dec.).

I.R. (Nujol): 3300, 3200, 1770, 1710, 1620, 1540, 1520, 1500 cm$^{-1}$ (107) 7-[2-(4-Fluorophenoxyimino)-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 140° to 145° C. (dec.).

I.R. (Nujol): 3300, 3200, 1770, 1700, 1620, 1520, 1500 cm$^{-1}$ (108) 7-[2-(4-Fluorophenoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 145° to 150° C. (dec.).

I.R. (Nujol): 3450, 3350, 3150, 1780, 1705, 1670, 1610, 1510 cm$^{-1}$ (109) 7-[2-Phenoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 180° to 185° C. (dec.).

I.R. (Nujol): 3300, 3250, 1760, 1670, 1620, 1590, 1520 cm$^{-1}$ (110) 7-[2-(t-Butoxycarbonylmethoxyimino)-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 125° to 130° C. (dec.).

I.R. (Nujol): 3400, 3300, 3180, 1770, 1720, 1680, 1620, 1525 cm$^{-1}$ (111) 7-[2-{3-(N-t-Butoxycarbonylamino)propoxyimino}-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 107° to 112° C. (dec.).

(112) 7-[2-(2,2,2-Trifluoroethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 125° to 130° C. (dec.).

I.R. (Nujol): 3300, 3200, 1770, 1680, 1620, 1520 cm$^{-1}$ (113) 7-[2(2,2,2-Trifluoroethoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 145° to 150° C. (dec.).

I.R. (Nujol): 3300, 3200, 1770, 1680, 1620, 1525 cm$^{-1}$ (114) 7-[2-{2-(N-t-Butoxycarbonylamino)ethoxyimino}-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 181° to 186° C. (dec.).

I.R. (Nujol): 3320, 1780, 1680, 1620, 1520, 1165 cm$^{-1}$ (115) 7-[2-Trityloxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 147° to 161° C. (dec.).

I.R. (Nujol): 3420, 1780, 1680, 1615, 1525 cm$^{-1}$ (116) 7-[2-{2-(N-t-Butoxycarbonylamino)ethoxyimino}-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 105° C. (dec.).

I.R. (Nujol): 3305, 3160, 1770, 1670, 1520, 1245 cm$^{-1}$ (117) 7-[2-(t-Butoxycarbonylmethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 140° to 145° C. (dec.).

I.R. (Nujol): 3300, 3175, 1770, 1720, 1680, 1620, 1520 cm$^{-1}$ (118) 7-[2-(t-Butoxycarbonylmethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), mp 130° to 135° C. (dec.).

I.R. (Nujol): 3400, 3280, 3180, 1770, 1720, 1680, 1620, 1520 cm$^{-1}$ (119) 7-[2-(t-Butoxycarbonylmethoxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer), mp 110° to 115° C. (dec.).

I.R. (Nujol): 3300, 3200, 1775, 1680, 1620, 1520 cm$^{-1}$ (120) 7-[2-(t-Butoxycarbonylmethoxyimino)-2-(5-amino-1,2,4-thiadiazol-3-yl)acetamido]-3-(1-phenyl-1H-tetrazol-5-yl)thiomethyl-3-cephem-4-carboxylic acid (syn isomer), mp 135° to 140° C. (dec.).

I.R. (Nujol): 3400, 3300, 3200, 1775, 1720, 1685, 1620, 1525, 1500 cm$^{-1}$ (121) 7-[2-(3-Aminopropoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 184° to 196° C. (dec.).

I.R. (Nujol): 3400–3100, 1760, 1660, 1610, 1520, 1170, 1060, 1010 cm$^{-1}$ (122) 7-[2-(2-Aminoethoxyimino)-2-(5-amino-1,2,4-thiadiazol-3-yl)acetamido]-3-(1-carboxymethyl-1H-tetrazol-5-yl)thiomethyl-3-cephem-4-carboxylic acid (syn isomer), mp 190° to 198° C. (dec.).

I.R. (Nujol): 3250, 3160, 1760, 1650, 1615, 1522, 1020 cm$^{-1}$ (123) 7-[2-Carboxymethoxyimino-2-(5-amino-1,2,4-thiadiazol-3-yl)acetamido]-3-(1,3,4-thiadiazol-2-yl)thiomethyl-3-cephem-4-carboxylic acid (syn isomer), mp 170° to 175° C. (dec.).

I.R. (Nujol): 3250, 3150, 1770, 1710, 1680, 1610, 1520 cm$^{-1}$ (124) 7-[2-Carboxymethoxyimino-2-(5-amino-1,2,4-thiadiazol-3-yl)acetamido]-3-(1-allyl-1H-tetrazol-5-yl)thiomethyl-3-cephem-4-carboxylic acid (syn isomer), mp 145° to 150° C. (dec.).

I.R. (Nujol): 3400, 3300, 3200, 1765, 1720, 1680, 1620, 1520 cm$^{-1}$ (125) 7-[2-Carboxymethoxyimino-2-(5-amino-1,2,4-thiadiazol-3-yl)acetamido]-3-(tetrazolo[1,5-b]pyridazin-6-yl)thiomethyl-3-cephem-4-carboxylic acid (syn isomer), mp 170° to 175° C. (dec.).

I.R. (Nujol): 3400, 3300, 3180, 1765, 1720, 1680, 1615, 1520 cm$^{-1}$ (126) 7-[2-(2-Aminoethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 182° to 187° C. (dec.).

I.R. (Nujol): 3350, 3150, 1760, 1660, 1625, 1565, 1520 cm$^{-1}$ (127) 7-[2-Carboxymethoxyimino-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 185° to 190° C. (dec.).

I.R. (Nujol): 3250, 1755, 1660, 1590, 1520 cm$^{-1}$ (128) 7-[2-(2,2,2-Trifluoroethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 185° to 190° C. (dec.).

I.R. (Nujol): 3300, 3170, 1760, 1670, 1615, 1500 cm$^{-1}$ (129) 7-[2-Carboxymethoxyimino-2-(5-amino-1,2,4-thiadiazol-3-yl)acetamido]-3-(1-phenyl-1H-tetrazol-5-yl)thiomethyl-3-cephem-4-carboxylic acid (syn isomer), mp 155° to 160° C. (dec.).

I.R. (Nujol): 3400, 3300, 3180, 1765, 1720, 1680, 1615, 1520, 1495 cm$^{-1}$ (130) 7-[2-Hydroxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 153° to 162° C. (dec.).

I.R. (Nujol): 3260, 3160, 1763, 1665, 1608, 1520 cm$^{-1}$ (131) Pivaloyloxymethyl 7-[2-hydroxyimino-2-(5-amino-1,2,4-thiadiazol-3-yl)acetamido]-3-(5-methyl-1,3,4-thiadiazol-2-yl)thiomethyl-3-cephem-4-carboxylate (syn isomer), mp 132° to 135° C. (dec.).

I.R. (Nujol): 3270, 3160, 1775, 1745, 1675, 1610, 1520, 1115 cm$^{-1}$

EXAMPLE 44

A solution of 7-[2-(1-carboxyethoxyimino)-2-(5-amino-1,2,4-thiadiazol-3-yl)acetamido]-3-[1-{3-(N-t-butoxycarbonylamino)propyl}-1H-tetrazol-5-yl]thiomethyl-3-cephem-4-carboxylic acid (syn isomer) (3.4 g) in formic acid (34 ml) was stirred for 2 hours at ambient temperature. The reaction mixture was post-treated in a conventional manner to give 7-[2-(1-carboxyethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer) (1.1 g), mp 185° to 188° C. (dec.).

IR (Nujol): 3300, 3150, 1760, 1660, 1620, 1520, 1230, 1000, 720 cm$^{-1}$

NMR (DMSO-d$_6$+D$_2$O, δ): 1.48 (3H, d, J=7 Hz), 2.3 (2H, m), 2.9 (2H, m), 3.6 (2H, m), 4.1–5.0 (4H, m), 4.70 (1H, q, J=7 Hz), 5.10 (1H, d, J=5 Hz), 5.85 (1H, m)

EXAMPLE 45

A solution of pivaloyloxymethyl 7-[2-{3-(N-t-butoxycarbonylamino)propoxyimino}-2-(5-amino-1,2,4-thiadiazol-3-yl)acetamido]-3-(1,3,4-thiadiazol-2-yl)thiomethyl-3-cephem-4-carboxylate (syn isomer) (2.7 g), anisole (24 drops) and 0.6 N hydrochloric acid (26.6 ml) in dioxane (18 ml) was stirred for 30 minutes at ambient temperature. An insoluble material was collected by decantation, and dissolved in water. The aqueous solution was washed twice with ethyl acetate and then lyophilized to give pivaloyloxymethyl 7-[2-(3-aminopropoxyimino)-2-(5-amino-1,2,4-thiadiazol-3-yl)acetamido]-3-(1,3,4-thiadiazol-2-yl)thiomethyl-3-cephem-4-carboxylate hydrochloride (syn isomer) (1.8 g), mp 90° to 155° C. (dec.).

IR (Nujol): 3300, 3150, 1775, 1730, 1670, 1625, 1530 cm$^{-1}$

NMR (DMSO-d$_6$+D$_2$O, δ): 1.20 (9H, s), 1.9–2.5 (2H, m), 2.9–3.5 (2H, m), 3.78 (2H, broad s), 4.27 and 4.63 (2H, ABq, J=14 Hz), 4.2–4.8 (2H, m), 5.25 (1H, d, J=2.5 Hz), 5.6–6.1 (3H, m), 9.42 (1H, s)

EXAMPLE 46

The following compounds were obtained according to similar manners to those of Examples 22 to 25, 44 and 45.

(1) 7-[2-(2-Propynyloxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 165° to 170° C. (dec.).

IR (Nujol): 3450, 3300, 3210, 1770, 1670, 1620, 1525 cm$^{-1}$

NMR (DMSO-d$_6$, δ): 1.90–2.37 (2H, m), 2.67–3.03 (2H, m), 3.47 (1H, t, J=2 Hz), 3.37–3.53 (2H, m), 3.93–4.60 (4H, m), 4.75 (2H, d, J=2 Hz), 5.0 (1H, d, J=5 Hz), 5.68 (1H, dd, J=5 and 8 Hz), 8.12 (2H, broad s), 9.50 (1H, d, J=8 Hz)

(2) 7-[2-Carboxymethoxyimino-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 195° to 200° C. (dec.).

IR (Nujol): 3150, 1760, 1660, 1640, 1520 cm$^{-1}$

NMR (DMSO-d₆, δ): 2.0-2.30 (2H, m), 2.73-3.0 (2H, m), 3.60 (2H, broad s), 4.20-4.50 (4H, m), 4.60 (2H, s), 5.08 (1H, d, J=4 Hz), 5.83 (1H, dd, J=4 and 8 Hz), 8.23 (2H, s), 10.20 (1H, d, J=8 Hz)

(3) 7-[2-(1-Carboxy-2-methylpropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 183° to 189° C. (dec.).

IR (Nujol): 3400-3100, 3150, 1770, 1670, 1620, 1520, 1380, 1280, 1230, 1180, 1100, 1020, 900, 730 cm⁻¹

NMR (DMSO-d₆+D₂O, δ): 0.98 (6H, d, J=7 Hz), 2.2 (3H, m), 3.6 (2H, m), 3.9 (2H, m), 4.3 (5H, m), 5.06 (1H, d, J=5 Hz), 5.70 (½H, d, J=5 Hz), 5.82 (½H, d, J=5 Hz)

(4) 7-[2-(1-Carboxypropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 183° to 188° C. (dec.).

IR (Nujol): 3400-3150, 1770, 1670, 1620, 1530, 1380, 1280, 1230, 1180, 1100, 1050, 1010, 730 cm⁻¹

NMR (DMSO-d₆, δ): 0.98 (3H, t, J=7 Hz), 1.7-2.3 (4H, m), 2.7-3.1 (2H, m), 3.4-3.7 (2H, m), 4.2-4.8 (5H, m), 5.07 (1H, d, J=5 Hz), 5.6-5.9 (1H, m), 8.13 (2H, broad s), 10.08 (1H, m)

(5) 7-[2-Carboxymethoxyimino-2-(5-amino-1,2,4-thiadiazol-3-yl)acetamido]-3-[1-(4-aminobutyl)-1H-tetrazol-5-yl]thiomethyl-3-cephem-4-carboxylic acid (syn isomer), mp 191° to 194° C. (dec.).

IR (Nujol): 3300, 3150, 1760, 1670, 1620, 1520, 1230, 1170, 1050, 890, 740, 720 cm⁻¹

NMR (DMSO-d₆+D₂O, δ): 1.2-2.1 (4H, m), 2.80 (2H, t, J=6 Hz), 3.6 (2H, m), 4.3 (4H, m), 4.60 (2H, broad s), 5.10 (1H, d, J=5 Hz), 5.82 (1H, d, J=5 Hz)

(6) 7-[2-(1-Carboxy-1-methylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 200° to 203° C. (dec.).

IR (Nujol): 3300, 3150, 1760, 1660, 1620, 1520, 1160, 990 cm⁻¹

NMR (DMSO-d₆, δ): 1.50 (6H, s), 2.20 (2H, m), 2.90 (2H, m), 3.60 (2H, m), 4.30 (4H, m), 5.10 (1H, d, J=5 Hz), 5.83 (1H, m), 8.20 (2H, broad s), 9.87 (1H, d, J=8 Hz)

(7) 7-[2-(1-Carboxy-1-cyclopentyloxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 202° to 205° C. (dec.).

IR (Nujol): 3300, 3200, 1760, 1660, 1620, 1520, 1180, 1060, 1000, 730 cm⁻¹

NMR (DMSO-d₆, δ): 1.70 (4H, m), 2.10 (6H, m), 2.90 (2H, m), 3.11 and 3.60 (2H, ABq, J=18 Hz), 4.40 (4H, m), 5.08 (1H, d, J=5 Hz), 5.80 (1H, dd, J=5 and 8 Hz), 8.23 (2H, m), 9.78 (1H, m)

(8) 7-[2-(1-Carboxyethoxyimino)-2-(5-amino-1,2,4-thiadiazol-3-yl)acetamido]-3-(5-aminomethyl-1,3,4-thiadiazol-2-yl)thiomethyl-3-cephem-4-carboxylic acid (syn isomer), mp 207° to 210° C. (dec.).

IR (Nujol): 3300, 3150, 1760, 1660, 1620, 1520, 1230, 1170, 1090, 1060, 1040, 990 cm⁻¹

NMR (DMSO-d₆+D₂O, δ): 1.43 (3H, d, J=5 Hz), 3.60 (2H, m), 4.0-4.93 (5H, m), 5.05 and 5.15 (1H, d, J=5 Hz), 5.70 (1H, m), 8.1 (2H, broad s), 9.5 (1H, d, J=8 Hz)

(9) 7-[2-Carboxymethoxyimino-2-(5-amino-1,2,4-thiadiazol-3-yl)acetamido-3-[1-(6-aminohexyl)-1H-tetrazol-5-yl]thiomethyl-3-cephem-4-carboxylic acid (syn isomer), mp 185° to 188° C. (dec.).

IR (Nujol): 3300, 3200, 1760, 1670, 1620, 1520, 1240, 1180, 1060 cm⁻¹

NMR (DMSO-d₆, δ): 1.10-1.57 (6H, m), 1.57-1.97 (2H, m), 2.70 (2H, m), 3.83 (2H, m), 4.27 (4H, m), 4.57 (2H, broad s), 5.03 (1H, d, J=5 Hz), 5.72 (1H, dd, J=5 and 8 Hz), 8.13 (2H, m), 9.80 (1H, d, J=8 Hz)

(10) 7-[2-(3-Aminopropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 183° C. (dec.).

IR (Nujol): 3150, 1765, 1660, 1630, 1570, 1520 cm⁻¹

NMR (DMSO-d₆+D₂O, δ): 1.6-2.3 (2H, m), 2.6-3.2 (2H, m), 3.2-3.7 (2H, m), 3.9-4.7 (4H, m), 4.97 (1H, d, J=4.5 Hz), 5.68 (1H, d, J=4.5 Hz), 9.50 (1H, s)

(11) 7-[2-(3-Aminopropoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 170° to 185° C. (dec.).

IR (Nujol): 3140, 1760, 1660, 1610, 1580, 1520 cm⁻¹

NMR (DMSO-d₆+D₂O, δ): 1.6-2.4 (2H, m), 2.7-3.4 (2H, m), 3.3-3.9 (4H, m), 3.9-4.7 (6H, m), 4.97 (1H, d, J=4.5 Hz), 5.67 (1H, d, J=5 Hz)

(12) 7-[2-(3-Aminopropoxyimino)-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 192° to 195° C. (dec.).

IR (Nujol): 3250, 3140, 1760, 1640, 1620, 1585, 1525 cm⁻¹

NMR (D₂O+DCl, δ): 2.0-3.4 (2H, m), 3.00 (3H, s), 3.22 (2H, t, J=7 Hz), 3.74 and 3.92 (2H, ABq, J=18 Hz), 4.36 and b 4.53 (2H, ABq, J=14 Hz), 4.54 (2H, t, J=7 Hz), 5.28 (1H, d, J=4.5 Hz), 5.82 (1H, d, J=4.5 Hz)

(13) 7-[2-(3-Aminopropoxyimino)-2-(5-amino-1,2,4-thiadiazol-3-yl)acetamido]-3-(1-methyl-1H-tetrazol-5-yl)thiomethyl-3-cephem-4-carboxylic acid (syn isomer), mp 180° to 184° C. (dec.).

IR (Nujol): 3160, 1760, 1660, 1590 cm⁻¹

NMR (D₂O+DCl, δ): 1.9-2.4 (2H, m), 3.20 (3H, t, J=8 Hz), 3.80 (2H, broad s), 4.02 (3H, s), 4.22 (2H broad s), 4.52 (2H, t, J=6 Hz), 5.25 (1H, d, J=5 Hz), 5.85 (1H, d, J=5 Hz)

(14) 7-[2-(4-Aminomethylbenzyloxyimino)-2-(5-amino-1,2,4-thiadiazol-3-yl)acetamido]-3-methyl-3-cephem-4-carboxylic acid formate (syn isomer), mp 230° to 240° C. (dec.).

IR (Nujol): 1750 cm⁻¹

NMR (DMSO-d₆+D₂O, δ): 1.86 (3H, s), 3.25 (2H, m), 3.97 (2H, s), 4.94 (1H, d, J=4.5 Hz), 5.16 (2H, s), 5.6 (1H, d, J=4.5 Hz), 7.35 (4H, s), 8.20 (1H, s)

(15) 7-[2-(3-Aminopropoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer).

IR (Nujol): 3300, 3150, 1760, 1660, 1607, 1595, 1520 cm⁻¹

NMR (DMSO-d₆+D₂O, δ): 2.0-2.7 (4H, m), 3.0-3.5 (4H, m), 3.4-4.0 (2H, m), 4.0-4.9 (6H, m), 5.20 (1H, d, J=4.5 Hz), 5.81 (1H, d, J=4.5 Hz)

(16) 7-[2-(2-D-Phenylglycylaminoethoxyimino)-2-(5-amino-1,2,4-thiadiazol-3-yl)acetamido]-2-methyl-3-cephem-4-carboxylic acid (syn isomer), mp 204° to 222° C. (dec.).

IR (Nujol): 3260, 3150, 1760, 1665, 1615, 1512, 1400, 1045 cm⁻¹

NMR (DMSO-d₆+D₂O, δ): 1.43 (3H, d, J=7 Hz), 3.13-4.45 (5H, m), 4.98 (1H, s), 5.02 (1H, d, J=4.5 Hz), 5.85 (1H, d, J=4.5 Hz), 6.27 (1H, d, J=6 Hz), 7.43 (5H, s)

(17) 7-[2-(3-D-Phenylglycylaminopropoxyimino)-2-(5-amino-1,2,4-thiadiazol-3-yl)acetamido]-2-methyl-3- cephem-4-carboxylic acid (syn isomer), mp 203° to 231° C. (dec.).

IR (Nujol): 3280, 1170, 1760, 1660, 1600, 1520, 1400 cm$^{-1}$

NMR (D$_2$O+DCl, δ): 1.47 (3H, d, J=7.5 Hz), 1.7–2.3 (2H, m), 3.40 (2H, t, J=7 Hz), 3.88 (1H, q, J=7.5 Hz), 4.33 (2H, t, J=6 Hz), 5.18 (1H, d, J=4.5 Hz), 5.20 (1H, s), 5.95 (1H, d, J=4.5 Hz), 6.90 (1H, d, J=6.0 Hz), 7.57 (5H, s)

(18) 7-[2-(1-Cyclohexyloxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 175° to 178° C. (dec.).

IR (Nujol): 3400–3200, 1765, 1680, 1610, 1520, 1220, 1100, 1000, 890, 790 cm$^{-1}$ NMR (DMSO-d$_6$, δ): 0.9–2.0 (13H, m), 2.2 (2H, m), 2.9 (2H, m), 3.6 (2H, m), 4.0–5.1 (5H, m), 4.76 (1H, q, J=7 Hz), 5.03 (1H, d, J=5 Hz), 5.77 (1H, m), 8.17 (2H, broad s), 9.45 (1H, m)

(19) 7-[2-(1-Benzyloxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 162° to 166° C. (dec.).

IR (Nujol): 3300, 3200, 1760, 1680, 1620, 1520, 1100, 1040, 1000, 740 cm$^{-1}$

NMR (DMSO-d$_6$, δ): 1.47 (3H, d, J=6 Hz), 2.23 (2H, m), 2.90 (2H, m), 3.60 (2H, m), 4.43 (4H, m), 4.90 (1H, q, J=6 Hz), 5.07 (1H, d, J=5 Hz), 5.20 (2H, s), 5.77 (1H, m), 7.43 (5H, s), 8.23 (2H, m), 9.57 (1H, m)

(20) 7-[2-(1-Butoxycarbonylethoxyimino)-2-(5-amino-1,2,4-thiadiazol-3-yl)acetamido]-3-[1-(3-aminopropyl)-1H-tetrazol-5-yl]thiomethyl-3-cephem-4-carboxylic acid (syn isomer), mp 158° to 163° C. (dec.).

IR (Nujol): 3400–3200, 1770, 1680, 1610, 1530, 1300, 1290, 1050, 1040, 1000, 960, 900, 790, 740, 720 cm$^{-1}$ NMR (DMSO-d$_6$, δ): 0.85 (3H, t, J=6 Hz), 1.1–1.8 (4H, m), 1.43 (3H, d, J=6 Hz), 1.9–2.4 (2H, m), 2.7–3.1 (2H, m), 3.5 (2H, m), 3.9–4.4 (2H, m), 4.10 (2H, t, J=6 Hz), 4.3–4.6 (2H, m), 4.78 (1H, q, J=7 Hz), 5.02 (1H, d, J=5 Hz), 5.7 (1H, m), 8.2 (2H, broad s), 10.1 (1H, m)

(21) Pivaloyloxymethyl 7-[2-(3-aminopropoxyimino)-2-(5-amino-1,2,4-thiadiazol-3-yl)acetamido]-2-methyl-3-cephem-4-carboxylate hydrochloride (syn isomer), mp 91° to 156° C. (dec.)

IR (Nujol): 3150, 1780, 1745, 1670, 1625, 1525 cm$^{-1}$

NMR (DMSO-d$_6$+D$_2$O, δ): 1.13 (9H, s), 1.43 (3H, d, J=7 Hz), 1.7–2.3 (2H, m), 2.5–3.2 (2H, m), 3.5–4.5 (3H, m), 5.10 (1H, d, J=5 Hz), 5.6–6.1 (3H, m), 6.63 (1H, d, J=7 Hz)

(22) Pivaloyloxymethyl 7-[2-(3-aminopropoxyimino)-2-(5-amino-1,2,4-thiadiazol-3-yl)acetamido]-3-(1-methyl-1H-tetrazol-5-yl)thiomethyl-3-cephem-4-carboxylate hydrochloride (syn isomer), mp 110° to 125° C. (dec.).

IR (Nujol): 1780, 1745, 1670, 1625, 1525 cm$^{-1}$

NMR (DMSO-d$_6$+D$_2$O, δ): 1.13 (9H, s), 1.7–2.3 (2H, m), 2.6–3.2 (2H, m), 3.75 (2H, broad s), 3.90 (3H, s), 4.0–4.7 (4H, m), 5.12 (1H, d, J=4.5 Hz), 5.6–6.1 (3H, m)

(23) Pivaloyloxymethyl 7-[2-(3-aminopropoxyimino)-2-(5-amino-1,2,4-thiadiazol-3-yl)acetamido]-3-(5-methyl-1,3,4-thiadiazol-2-yl)thiomethyl-3-cephem-4-carboxylate hydrochloride (syn isomer), mp 88° to 153° C. (dec.)

IR (Nujol): 2150, 1780, 1745, 1650, 1625, 1525 cm$^{-1}$

NMR (DMSO-d$_6$+D$_2$O, δ): 1.16 (9H, s), 1.6–2.2 (2H, m), 2.6–3.1 (2H, m), 2.68 (3H, s), 3.76 (2H, broad s), 4.20 and 4.53 (2H, ABq, J=18 Hz), 4.24 (2H, broad s), 5.18 (1H, d, J=4.5 Hz), 5.6–6.0 (3H, m)

(24) Pivaloyloxymethyl 7-[2-(3-aminopropoxyimino)-2-(5-amino-1,2,4-thiadiazol-3-yl)acetamido]-3-[1-(2-hydroxyethyl)-1H-tetrazol-5-yl]thiomethyl-3-cephem-4-carboxylate hydrochloride (syn isomer), mp 150° to 175° C. (dec.).

IR (Nujol): 3150, 1780, 1740, 1670, 1630, 1520 cm$^{-1}$

NMR (DMSO-d$_6$+D$_2$O, δ): 1.20 (9H, s), 1.7–2.3 (2H, m), 2.6–3.2 (2H, m), 3.5–4.0 (4H, m), 4.0–4.6 (6H, m), 5.17 (1H, d, J=5Hz), 5.6–6.1 (3H, m)

(25) Pivaloyloxymethyl 7-[2-(4-aminomethylbenzyloxyimino)-2-(5-amino-1,2,4-thiadiazol-3-yl)acetamido]-3-methyl-3-cephem-4-carboxylate hydrochloride (syn isomer), mp 160° to 168° C. (dec.).

IR (Nujol): 1780, 1745, 1670, 1628 cm$^{-1}$

(26) Pivaloyloxymethyl 7-[2-allyloxyimino-2-(5-amino-1,2,4-thiadiazol-3-yl)acetamido]-3-[1-(2-aminoethyl)-1H-tetrazol-5-yl]thiomethyl-3-cephem-4-carboxylate formate (syn isomer), mp 95° to 105° C. (dec.).

IR (Nujol): 1790, 1735, 1452, 1370, 1118, 990 cm$^{-1}$

NMR (DMSO-d$_6$+D$_2$O, δ): 1.2 (9H, s), 3.2–3.35 (2H, m), 3.7 (2H, broad s), 4.2–4.6 (2H, m), 4.1–4.6 (2H, m), 4.7 (2H, broad s), 4.8–5.2 (1H, m), 5.25 (1H, d, J=4.5 Hz), 5.45 (2H, m), 5.7–6.25 (2H, m), 5.8 (1H, d, J=4.5 Hz)

EXAMPLE 47

A mixture of 7-[2-(1-t-butoxycarbonylethoxyimino)-2-(5-amino-1,2,4-thiadiazol-3-yl)acetamido]-3-cephem-4-carboxylic acid (syn isomer) (2.35 g), trifluoroacetic acid (16 ml) and anisole (3 ml) was stirred for 40 minutes at ambient temperature. The reaction mixture was evaporated and the residue was triturated with diisopropyl ether and washed with diisopropyl ether to give white powder of 7-[2-(1-carboxyethoxyimino)-2-(5-amino-1,2,4-thiadiazol-3-yl)acetamido]-3-cephem-4-carboxylic acid (syn isomer) (2.3 g). The powder (2.3 g) was reprecipitated from a mixture of sodium bicarbonate (0.44 g) in water (50 ml) and precipitates were collected by filtration and washed with water to give pale brown powder of the same compound (1.1 g), mp 230° to 235° C. (dec.).

IR (Nujol): 3400, 3250, 3150, 1760, 1720, 1660, 1610, 1550, 1290, 1240, 1170, 970, 740 cm$^{-1}$ NMR (DMSO-d$_6$, δ): 1.46 (3H, d, J=8 Hz), 3.46 (2H, m), 4.72 (1H, q, J=7 Hz), 5.15 (1H, d, J=5 Hz), 5.58 (1H, dd, J=5 and 8 Hz), 6.50 (1H, m), 8.20 (2H, m), 9.40 and 9.57 (1H, d, J=8 Hz)

EXAMPLE 48

A mixture of 7-[2-(α-t-butoxycarbonylbenzyloxyimino)-2-(5-amino-1,2,4-thiadiazol-3-yl)acetamido]-3-[1-{2-(N-t-butoxycarbonylamino)ethyl}-1H-tetrazol-5-yl]thiomethyl-3-cephem-4-carboxylic acid (syn isomer) (3.0 g), trifluoroacetic acid (30 ml) and anisole (6 ml) was stirred for 1 hour at ambient temperature. The reaction mixture was post-treated in a conventional manner to give 7-[2-(α-carboxybenzyloxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer) (1.16 g), mp 190° to 195° C. (dec.).

IR (Nujol): 3400, 3300, 3150, 1765, 1670, 1610, 1520 cm$^{-1}$

NMR (DMSO-d$_6$, δ): 3.10–3.77 (4H, m), 4.13–4.37 (2H, m), 4.40–4.77 (2H, m), 5.0–5.23 (1H, m), 5.57 (½H, s), 5.65 (½H, s), 5.53–5.93 (1H, m), 7.27–7.80 (5H, m), 8.28 (2H, broad s)

EXAMPLE 49

The following compounds were obtained according to similar manners to those of Examples 27, 47 and 48.

(1) 7-[2-(α-Carboxybenzyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 150° to 155° C. (dec.).

IR (Nujol): 3400, 3290, 3160, 2500, 1770, 1720, 1615, 1520 cm$^{-1}$

NMR (DMSO-d$_6$, δ): 3.12–3.88 (2H, m), 4.08–4.68 (2H, m), 5.04 (½H, d, J=5 Hz), 5.10 (½H, d, J=5 Hz), 5.62 (1H, s), 5.64–5.88 (1H, m), 7.12–7.68 (5H, m), 8.14 (2H, broad s), 9.52 (½H, s), 9.54 (½H, s), 9.36–9.72 (1H, m)

(2) 7-[2-(α-Carboxybenzyloxyimino)-2-(5-amino-1,2,4-thiadiazol-3-yl)acetamido]-3-cephem-4-carboxylic acid (syn isomer), mp 170° to 175° C. (dec.).

IR (Nujol): 3400, 3280, 3160, 2600, 1770, 1720, 1670, 1625, 1520 cm$^{-1}$

NMR (DMSO-d$_6$, δ): 3.24–3.68 (2H, m), 5.02 (½H, d, J=5 Hz), 5.08 (½H, d, J=5 Hz), 5.64 (1H, s), 5.68–5.96 (1H, m), 6.28–6.60 (1H, m), 7.16–7.64 (5H, m), 8.16 (2H, broad s), 9.54 (½H, d, J=8 Hz), 9.62 (½H, d, J=8 Hz)

(3) 7-[2-Carboxymethoxyimino-2-(5-amino-1,2,4-thiadiazol-3-yl)acetamido]-3-cephem-4-carboxylic acid (syn isomer), mp 180° to 185° C. (dec.).

IR (Nujol): 3350, 3250, 1770, 1720, 1680, 1630, 1530 cm$^{-1}$

NMR (DMSO-d$_6$, δ): 3.53 (2H, d, J=3 Hz), 4.63 (2H, s), 5.07 (1H, d, J=4 Hz), 5.85 (1H, dd, J=4 and 8 Hz), 6.45 (1H, t, J=3 Hz), 8.13 (2H, s), 9.50 (1H, d, J=8 Hz)

(4) 7-[2-Carboxymethoxyimino-2-(5-amino-1,2,4-thiadiazol-3-yl)acetamido]-3-[1-{3-(4-methyl-1-piperazinyl)propyl}-1H-tetrazol-5-yl]thiomethyl-3-cephem-4-carboxylic acid (syn isomer), mp 185° to 190° C. (dec.).

IR (Nujol): 3300, 1760, 1670, 1600, 1520 cm$^{-1}$

NMR (DMSO-d$_6$, δ): 1.80–2.10 (2H, m), 2.30–2.50 (4H, m), 2.60 (3H, s), 2.8–3.3 (6H, m), 3.60 (2H, broad s), 4.20–4.50 (4H, m), 4.60 (2H, s), 5.10 (1H, d, J=4 Hz), 5.83 (1H, dd, J=4 and 8 Hz), 8.15 (2H, s), 10.17 (1H, d, J=8 Hz)

(5) 7-[2-(1-Carboxy-2-methylpropoxyimino)-2-(5-amino-1,2,4-thiadiazol-3-yl)acetamido]-cephalosporanic acid (syn isomer).

IR (Nujol): 3400–3150, 1770, 1730–1670, 1720, 1620, 1460, 1370, 1230, 1030, 730 cm$^{-1}$ NMR (DMSO-d$_6$, δ): 0.97 (6H, d, J=7 Hz), 2.03 (3H, s), 1.9–2.3 (1H, m), 3.6 (2H, m), 4.27 and 4.35 (1H, d, J=6 Hz), 4.65 and 5.02 (2H, ABq, J=13 Hz), 5.15 (1H, d, J=5 Hz), 5.7–6.0 (1H, m), 8.03 (2H, broad s), 9.42 (1H, d, J=8 Hz)

(6) 7-[2-(1-Carboxypropoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 153° to 158° C. (dec.).

IR (Nujol): 3300, 3180, 1770, 1720–1670, 1620, 1520, 1220, 1060, 1000, 900, 730 cm$^{-1}$ NMR (DMSO-d$_6$, δ): 0.97 (3H, t, J=7 Hz), 1.83 (2H, m), 3.56 and 3.80 (2H, ABq, J=18 Hz), 4.25 and 4.55 (2H, ABq, J=14 Hz), 4.52 (1H, t, J=7 Hz), 5.14 (1H, d, J=5 Hz), 5.82 (1H, dd, J=5 and 8 Hz), 8.1 (2H, broad s), 9.46 (1H, d, J=8 Hz), 9.52 (1H, s)

(7) 7-[2-(1-Carboxypropoxyimino)-2-(5-amino-1,2,4-thiadiazol-3-yl)acetamido]cephalosporanic acid (syn isomer), mp 115° to 120° C. (dec.).

IR (Nujol): 3400, 3300, 3200, 1770, 1720–1670, 1620, 1520, 1230, 1030–1010, 890, 740–720 cm$^{-1}$ NMR (DMSO-d$_6$, δ): 1.07 (3H, t, J=6 Hz), 1.8 (2H, m), 2.00 (3H, s), 3.5 (2H, m), 4.63 and 5.02 (2H, ABq, J=14 Hz), 4.5 (1H, m), 5.14 (2H, d, J=5 Hz), 5.84 (1H, dd, J=5 and 9 Hz), 8.11 (2H, broad s), 9.5 (1H, m)

(8) 7-[2-(1-Carboxyethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 168° C. (dec.).

IR (Nujol): 3400–3200, 1770, 1710, 1670, 1620, 1520, 1230, 1170, 1000, 900, 720 cm$^{-1}$ NMR (DMSO-d$_6$, δ): 1.43 (3H, d, J=7 Hz), 3.7 (2H, m), 4.23 and 4.60 (2H, ABq, J=14 Hz), 4.68 (1H, q, J=7 Hz), 5.15 (1H, d, J=5 Hz), 5.83 (1H, dd, J=5 and 8 Hz), 8.1 (2H, broad s), 9.3–9.6 (1H, m), 9.50 (1H, s)

(9) 7-[2-(1-Carboxy-1-methylethoxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 164° to 167° C. (dec.).

IR (Nujol): 3300, 3200, 2800–2300, 1770, 1720–1660, 1620, 1520, 1160, 1060, 990, 800 cm$^{-1}$ NMR (DMSO-d$_6$, δ): 1.47 (6H, s), 3.53 and 3.87 (2H, ABq, J=20 Hz), 4.24 and 4.63 (2H, ABq, J=14 Hz), 5.17 (1H, d, J=5 Hz), 5.83 (1H, dd, J=5 and 8 Hz), 8.2 (2H, broad s), 9.44 (1H, d, J=8 Hz), 9.50 (1H, s)

(10) 7-[2-(1-Carboxy-1-cyclopentyloxyimino)-2-(5-amino-1,2,4-thiadiazol-3-yl)acetamido]-3-(1,3,4-thiadiazol-2-yl)thiomethyl-3-cephem-4-carboxylic acid (syn isomer), mp 165° to 169° C. (dec.).

IR (Nujol): 3300, 3180, 1770, 1720–1660, 1620, 1520, 1240, 1180, 1060, 1000, 720 cm$^{-1}$ NMR (DMSO-d$_6$, δ): 1.8 (4H, m), 2.1 (4H, m), 3.7 (2H, m), 4.30 and 4.68 (2H, ABq, J=13 Hz), 5.20 (1H, d, J=5 Hz), 5.87 (1H, dd, J=5 and 8 Hz), 8.3 (2H, broad s), 9.48 (1H, d, J=8 Hz),

(11) 7-[2-(1-Carboxy-1-methylethoxyimino)-2-(5-amino-1,2,4-thiadiazol-3-yl)acetamido]-3-cephem-4-carboxylic acid (syn isomer), mp 215° to 220° C. (dec.).

IR (Nujol): 3400, 3250, 3200, 1770, 1670, 1520, 1290, 1240, 1160, 1000, 980, 740 cm$^{-1}$ NMR (DMSO-d$_6$, δ): 1.57 (6H, s), 3.70 (2H, m), 5.22 (1H, d, J=5 Hz), 5.97 (1H, dd, J=5 and 8 Hz), 6.58 (1H, m), 8.25 (2H, broad s), 9.52 (1H, d, J=8 Hz)

(12) 7-[2-(1-Carboxyethoxyimino)-2-(5-amino-1,2,4-thiadiazol-3-yl)acetamido]-3-(1-allyl-1H-tetrazol-5-yl)thiomethyl-3-cephem-4-carboxylic acid (syn isomer), which is decomposed by 180° C.

IR (Nujol): 3300, 3150, 1770, 1680, 1610, 1520, 1260, 1100, 1040, 1000 cm$^{-1}$ NMR (DMSO-d$_6$, δ): 1.46 (3H, d, J=8 Hz), 3.50 and 3.74 (2H, ABq, J=18 Hz), 4.2 and 4.46 (2H, ABq, J=14 Hz), 4.72 (1H, q, J=8 Hz), 4.98 (2H, m), 5.12 (1H, d, J=5 Hz), 5.2–5.36 (2H, m), 5.76–6.1 (3H, m), 8.12 (2H, m), 9.48 and 9.56 (1H, d, J=8 Hz)

(13) 7-[2-(1-Carboxy-1-cyclopentyloxyimino)-2-(5-amino-1,2,4-thiadiazol-3-yl)acetamido]-3-cephem-4-carboxylic acid (syn isomer), mp 212° to 217° C. (dec.).

IR (Nujol): 3300, 3200, 1770, 1670, 1620, 1520, 1280, 1240, 1180, 1000, 970, 730 cm$^{-1}$ NMR (DMSO-d$_6$, δ): 1.70 (4H, m), 2.30 (4H, m), 3.60 (2H, m), 5.10 (1H, d, J=5 Hz), 5.87 (1H, dd, J=5 and 8 Hz), 6.47 (1H, m), 8.20 (2H, m), 9.50 (1H, d, J=8 Hz)

(14) 7-[2-(1-Carboxyethoxyimino)-2-(5-amino-1,2,4-thiadiazol-3-yl)acetamido]cephalosporanic acid (syn isomer).

IR (Nujol): 3300, 3200, 1770, 1710, 1670, 1520, 1230, 1040 cm$^{-1}$

NMR (DMSO-d$_6$, δ): 1.47 (3H, d, J=8 Hz), 2.03 (3H, s), 3.58 (2H, m), 4.13–5.00 (1H, m), 4.68 and 5.03 (2H, ABq, J=8 Hz), 5.26 (1H, d, J=5 Hz), 5.87 (1H, dd, J=5 and 8 Hz), 8.15 (2H, broad s), 9.42 and 9.55 (1H, d, J=8 Hz)

(15) 7-[2-(1-Carboxy-1-methylethoxyimino)-2-(5-amino-1,2,4-thiadiazol-3-yl)acetamido]-3-[1-(2-aminoethyl)-1H-tetrazol-5-yl]thiomethyl-3-cephem-4-carboxylic acid (syn isomer), mp 195° to 200° C. (dec.).

IR (Nujol): 3150, 1760, 1670, 1620, 1520, 1170, 990 cm$^{-1}$

NMR (DMSO-d$_6$+D$_2$O, δ): 1.50 (6H, s), 3.27 (2H, m), 3.60 (2H, m), 4.17 (2H, m), 4.57 (2H, m), 5.10 (1H, d, J=5 Hz), 5.80 (1H, d, J=5 Hz)

EXAMPLE 50

Pivaloyl chloride (66 mg) was added to ambient temperature to a stirred solution of 7-[2-cyclopentyloxyimino-2-(5-amino-1,2,4-thiadiazol-3-yl)acetamido]-3-hydroxy-cephem-4-carboxylic acid (syn isomer) (115 mg) in tetrahydrofuran (1.5 ml). Sodium acetate (82 mg) was added thereto after 5 minutes and it was stirred for 10 hours at ambient temperature. The reaction mixture was evaporated and to the residue were added ethyl acetate and diluted aqueous solution of sodium bicarbonate. To the aqueous layer was added ethyl acetate and the mixture was adjusted to pH 1 to 2 with hydrochloric acid and extracted. The extract was washed with water and an aqueous solution of sodium chloride, dried over magnesium sulfate and evaporated. The residue was triturated with diethyl ether to give white powder of 7-[2-cyclopentyloxyimino-2-(5-amino-1,2,4-thiadiazol-3-yl)acetamido]-3-cephem-4-carboxylic acid (syn isomer) (70 mg), mp 170° to 175° C. (dec.).

IR (Nujol): 3520, 3420, 3320, 3220, 3160, 1770, 1685, 1655, 1635, 1625, 1570, 1505 cm$^{-1}$ NMR (DMSO-d$_6$, δ): 1.33-2.07 (8H, m), 3.43-3.77 (2H, m), 4.60-4.93 (1H, m), 5.15 (1H, d, J=5 Hz), 5.90 (1H, dd, J=5 and 8 Hz), 6.43-6.67 (1H, m), 8.23 (2H, broad s), 9.63 (1H, d, J=8 Hz)

EXAMPLE 51

The following compounds were obtained according to a similar manner to that of Example 50.

(1) 7-[2-(α-t-Butoxycarbonylbenzyloxyimino)-2-(5-amino-1,2,4-thiadiazol-3-yl)acetamido]-3-cephem-4-carboxylic acid (syn isomer), mp 90° to 95° C. (dec.).

IR (Nujol): 3400, 3380, 3230, 1780, 1730, 1685, 1635, 1530 cm$^{-1}$ (2) 7-[2-t-Butoxycarbonylmethoxyimino-2-(5-amino-1,2,4-thiadiazol-3-yl)acetamido]-3-cephem-4-carboxylic acid (syn isomer), mp 165° to 170° C. (dec.).

IR (Nujol): 3350, 3250, 3180, 1790, 1720, 1660, 1630, 1620, 1520 cm$^{-1}$ (3) 7-[2-(1-Methyl-1-t-butoxycarbonylethoxyimino)-2-(5-amino-1,2,4-thiadiazol-3-yl)acetamido]-3-cephem-4-carboxylic acid (syn isomer), which is decomposed by 215° C.

IR (Nujol): 3400, 3300, 3150, 1780, 1710, 1690, 1620, 1520, 1240, 1140, 980 cm$^{-1}$ (4) 7-[2-(1-t-Butoxycarbonylethoxyimino)-2-(5-amino-1,2,4-thiadiazol-3-yl)acetamido]-3-cephem-4-carboxylic acid (syn isomer), which is decomposed by 250° C.

IR (Nujol): 3400, 3250, 3150, 1770, 1720, 1680, 1610, 1520, 1290, 1240, 1150, 980, 740 cm$^{-1}$ (5) 7-[2-(3,4-Dichlorophenoxyimino)-2-(5-amino-1,2,4-thiadiazol-3-yl)acetamido]-3-cephem-4-carboxylic acid (syn isomer), which is decomposed by 210° C.

IR (Nujol): 3450, 3300, 3200, 1760, 1660, 1560, 1290, 1210, 1000, 970, 940, 730 cm$^{-1}$ (6) 7-[2-(2,4-Dichlorophenoxyimino)-2-(5-amino-1,2,4-thiadiazol-3-yl)acetamido]-3-cephem-4-carboxylic acid (syn isomer), which is decomposed by 240° C.

IR (Nujol): 3250, 1770, 1660, 1620, 1540, 1520, 1280, 1230, 1100, 1050, 970, 920, 810, 750 cm$^{-1}$ (7) 7-[2-{1-Cyclohexyloxycarbonyl)ethoxyimino}-2-(5-amino-1,2,4-thiadiazol-3-yl)acetamido]-3-cephem-4-carboxylic acid (syn isomer), mp 160° to 163° C. (dec.).

IR (Nujol): 3420, 3300, 3180, 1775, 1720, 1685, 1610, 1520, 1290, 1230, 1040, 980, 740 cm$^{-1}$ (8) 7-[2-(1-t-Butoxycarbonyl-1-cyclopentyloxyimino)-2-(5-amino-1,2,4-thiadiazol-3-yl)acetamido]-3-cephem-4-carboxylic acid (syn isomer), mp 165° to 169° C. (dec.).

IR (Nujol): 3400, 3300, 3200, 1770, 1710, 1680, 1610, 1520, 1290, 1240, 1150, 1000, 970, 740 cm$^{-1}$ (9) 7-[2-(α-Carboxybenzyloxyimino)-2-(5-amino-1,2,4-thiadiazol-3-yl)acetamido]-3-cephem-4-carboxylic acid (syn isomer), mp 170° to 175° C. (dec.).

IR (Nujol): 3400, 3280, 3160, 2600, 1770, 1720, 1670, 1625, 1520 cm$^{-1}$

(10) 7-[2-Carboxymethoxyimino-2-(5-amino-1,2,4-thiadiazol-3-yl)acetamido]-3-cephem-4-carboxylic acid (syn isomer), mp 180° to 185° C. (dec.).

IR (Nujol): 3350, 3250, 1770, 1720, 1680, 1630, 1530 cm$^{-1}$

(11) 7-[2-(1-Carboxy-1-methylethoxyimino)-2-(5-amino-1,2,4-thiadiazol-3-yl)acetamido]-3-cephem-4-carboxylic acid (syn isomer), mp 215° to 220° C. (dec.).

IR (Nujol): 3400, 3250, 3200, 1770, 1670, 1520, 1290, 1240, 1160, 1000, 980, 740 cm$^{-1}$

(12) 7-[2-(1-Carboxyethoxyimino)-2-(5-amino-1,2,4-thiadiazol-3-yl)acetamido]-3-cephem-4-carboxylic acid (syn isomer), mp 230° to 235° C. (dec.).

IR (Nujol): 3400, 3250, 3150, 1760, 1720, 1660, 1610, 1550, 1290, 1240, 1170, 970, 740 cm$^{-1}$

(13) 7-[2-(1-Carboxy-1-cyclopentyloxyimino)-2-(5-amino-1,2,4-thiadiazol-3-yl)acetamido]-3-cephem-4-carboxylic acid (syn isomer), mp 212° to 217° C. (dec.).

IR (Nujol): 3300, 3200, 1770, 1670, 1620, 1520, 1280, 1240, 1180, 1000, 970, 730 cm$^{-1}$

(14) 7-[2-(2-Oxo-3-tetrahydrofuryloxyimino)-2-(5-amino-1,2,4-thiadiazol-3-yl)acetamido]-3-cephem-4-carboxylic acid (syn isomer), mp 175° to 180° C. (dec.).

IR (Nujol): 3300, 3200, 1775, 1670, 1620, 1530 cm$^{-1}$

(15) 7-[2-(1-Benzyloxycarbonylethoxyimino)-2-(5-amino-1,2,4-thiadiazol-3-yl)acetamido]-3-cephem-4-carboxylic acid (syn isomer), mp 177° to 180° C. (dec.).

IR (Nujol): 3400, 3300, 3200, 1770, 1730, 1680, 1610, 1520, 1240, 1160, 1040, 980, 740 cm$^{-1}$

(16) 7-[2-(1-Butoxycarbonylethoxyimino)-2-(5-amino-1,2,4-thiadiazol-3-yl)acetamido]-3-cephem-4-carboxylic acid (syn isomer), mp 147° to 151° C. (dec.).

IR (Nujol): 3400, 3300, 3200, 1770, 1720, 1680, 1610, 1520, 1280, 1235, 1155, 1045, 980, 740 cm$^{-1}$

(17) 4-Nitrobenzyl 7-[2-phenoxyimino-2-(5-amino-1,2,4-thiadiazol-3-yl)acetamido]-3-cephem-4-carboxylate (syn isomer), mp 140° to 145° C. (dec.).

I.R. (Nujol): 3300, 1775, 1720, 1680, 1625, 1600, 1590, 1520 cm$^{-1}$

(18) 4-Nitrobenzyl 7-[2-(4-fluorophenoxyimino)-2-(5-amino-1,2,4-thiadiazol-3-yl)acetamido]-3-cephem-4-carboxylic (syn isomer), mp 135° to 140° C. (dec.).

I.R. (Nujol): 3300, 3200, 1770, 1720, 1680, 1625, 1605, 1500, 1495 cm$^{-1}$

(19) 4-Nitrobenzyl 7-[2-(4-Chlorophenoxyimino)-2-(5-amino-1,2,4-thiadiazol-3-yl)acetamido]-3-cephem-4-carboxylate (syn isomer), mp 155° to 160° C. (dec.).

I.R. (Nujol): 3300, 3180, 1770, 1720, 1680, 1625, 1600, 1580, 1520, 1480 cm$^{-1}$

(20) 4-Nitrobenzyl 7-[2-(3-trifluoromethylphenoxyimino)-2-(5-amino-1,2,4-thiadiazol-3-yl)acetamido]-3-cephem-4-carboxylate (syn isomer), mp 136° to 140° C. (dec.).

I.R. (Nujol): 3370, 3200, 1780, 1730, 1690, 1680, 1630, 1610, 1520, 1450, 1325, 1280, 1160, 1125, 975, 850, 740 cm$^{-1}$

(21) 7-[2-(3-Trifluoromethylphenoxyimino)-2-(5-amino-1,2,4-thiadiazol-3-yl)acetamido]-3-cephem-4-carboxylic acid (syn isomer), which is decomposed by 193° C.

I.R. (Nujol): 3450, 3320, 3200, 1770, 1710, 1665, 1630, 1560, 1515, 1325, 1170, 1110, 940 cm$^{-1}$

(22) 7-[2-Phenoxyimino-2-(5-amino-1,2,4-thiadiazol-3-yl)acetamido]-3-cephem-4-carboxylic acid (syn isomer), mp 168° to 170° C. (dec.).

I.R. (Nujol): 3400, 3200, 1780, 1660, 1620, 1600, 1590, 1540 cm$^{-1}$

(23) 7-[2-(4-Chlorophenoxyimino)-2-(5-amino-1,2,4-thiadiazol-3-yl)acetamido]-3-cephem-4-carboxylic acid (syn isomer), mp 145° to 150° C. (dec.).

I.R. (Nujol): 3400, 3260, 3180, 1775, 1675, 1625, 1600, 1520, 1480 cm$^{-1}$

(24) 7-[2-(4-Fluorophenoxyimino)-2-(5-amino-1,2,4-thiadiazol-3-yl)acetamido]-3-cephem-4-carboxylic acid (syn isomer), mp 130° to 135° C. (dec.).

I.R. (Nujol): 3400, 3270, 3180, 1765, 1675, 1605, 1500 cm$^{-1}$

(25) 4-Nitrobenzyl 7-[2-allyloxyimino-2-(5-amino-1,2,4-thiadiazol-3-yl)acetamido]-3-cephem-4-carboxylate (syn isomer), mp 125° to 130° C. (dec.).

I.R. (Nujol): 3300, 1770, 1720, 1680, 1630, 1610, 1520 cm$^{-1}$

(26) 7-[2-Allyloxyimino-2-(5-amino-1,2,4-thiadiazol-3-yl)acetamido]-3-cephem-4-carboxylic acid (syn isomer), mp 160° to 165° C. (dec.).

(27) 7-[2-(2-Cyclopenten-1-yl)oxyimino-2-(5-amino-1,2,4-thiadiazol-3-yl)acetamido]-3-cephem-4-carboxylic acid (syn isomer). mp 180° to 185° C. (dec.).

I.R. (Nujol): 3500, 3430, 3300, 3200, 1770, 1690, 1660, 1640, 1620, 1580, 1510 cm$^{-1}$

(28) 7-[2-Cyclopentyloxyimino-2-(5-amino-1,2,4-thiadiazol-3-yl)acetamido]-3-cephem-4-carboxylic acid (syn isomer). mp 170° to 175° C.

I.R. (Nujol): 3520, 3420, 3320, 3220, 3160, 1770, 1685, 1655, 1635, 1625, 1570, 1505 cm$^{-1}$

(29) 7-[2-(2-Cyclohexen-1-yl)oxyimino-2-(5-amino-1,2,4-thiadiazol-3-yl)acetamido]-3-cephem-4-carboxylic acid (syn isomer). mp 175° to 180° C. (dec.).

I.R. (Nujol): 3300, 3200, 1770, 1670, 1630, 1520 cm$^{-1}$

(30) 7-[2-Cycloheptyloxyimino-2-(5-amino-1,2,4-thiadiazol-3-yl)acetamido]-3-cephem-4-carboxylic acid (syn isomer). white powder. mp 170° to 175° C. (dec.).

I.R. (Nujol): 3400, 3300, 3200, 1770, 1670, 1620, 1520, 1280, 1240, 1160, 1000, 980, 730 cm$^{-1}$

EXAMPLE 52

The following compounds were obtained according to a similar manner to that of Example 30.

(1) 1-Acetoxyethyl 7-[2-cyclopentyloxyimino-2-(5-amino-1,2,4-thiadiazol-3-yl)acetamido]-2-methyl-3-cephem-4-carboxylate (syn isomer).

IR (Nujol): 3400, 3310, 3150, 1780, 1750, 1675 cm$^{-1}$

NMR (DMSO-d$_6$, δ): 1.2–1.6 (6H, m), 1.5–2.1 (8H, m), 2.07 (3H, s), 3.6–4.1 (1H, m), 4.6–5.0 (1H, m), 5.17 (1H, d, J=4.5 Hz), 5.95 (1H, dd, J=4.5 and 8 Hz), 6.67 (1H, d, J=6 Hz), 6.90 (1H, q, J=5 Hz), 8.12 (2H, broad s), 9.45 (1H, d, J=8 Hz)

(2) 1-Isobutyryloxyethyl 7-[2-cyclopentyloxyimino-2-(5-amino-1,2,4-thiadiazol-3-yl)acetamido]-2-methyl-3-cephem-4-carboxylate (syn isomer), amorphous powder.

IR (Nujol): 3400, 3300, 3170, 1780, 1745, 1675, 1620, 1525 cm$^{-1}$

NMR (DMSO-d$_6$, δ): 1.08 (6H, d, J=7 Hz), 1.2–2.2 (14H, m), 2.2–2.9 (1H, m), 3.88 (1H, q, J=7 Hz), 4.6–5.0 (1H, m), 5.12 (1H, d, J=4.5 Hz), 5.90 (1H, dd, J=4.5 and 8 Hz), 6.63 (1H, d, J=7 Hz), 8.06 (2H, broad s), 9.43 (1H, d, J=8 Hz)

(3) 1-Acetoxypropyl 7-[2-(2-cyclopenten-1-yloxyimino)-2-(5-amino-1,2,4-thiadiazol-3-yl)acetamido]-2-methyl-3-cephem-4-carboxylate (syn isomer), mp 110° to 128° C. (dec.).

IR (Nujol): 3400, 3280, 3150, 1780, 1750, 1730, 1620 cm$^{-1}$

NMR (DMSO-d$_6$+D$_2$O, δ): 0.92 (3H, t, J=7.5 Hz), 1.42 (3H, d, J=7 Hz), 1.8–2.5 (4H, m), 1.5–2.3 (2H, m), 2.05 (3H, s), 3.6–4.1 (1H, m), 5.10 (1H, d, J=4.5 Hz), 5.1–5.5 (1H, m), 5.7–6.3 (3H, m), 6.4–6.9 (2H, m)

(4) 1-(2-Azidoethoxycarbonyloxy)ethyl 7-[2-(2-cyclopenten-1-yloxyimino)-2-(5-amino-1,2,4-thiadiazol-3-yl)acetamido]-2-methyl-3-cephem-4-carboxylate (syn isomer), mp 85° to 100° C. (dec.).

IR (Nujol): 3310, 2200,1760–1785, 1680 cm$^{-1}$

NMR (DMSO-d$_6$+D$_2$O, δ): 1.48 (3H, d, J=6 Hz), 1.5 (3H, d, J=4.5 Hz), 2.0–2.5 (4H, m), 3.5–4.1 (1H, m), 3.63 (2H, t, J=4 Hz), 4.30 (2H, t, J=4 Hz), 5.16 (1H, d, J=4.5 Hz), 5.2–5.45 (1H, m), 5.7–6.2 (2H, m), 6–6.2 (1H, m), 6.6–6.8 (1H, m), 6.7 (1H, d, J=6 Hz)

(5) 1-Ethoxycarbonyloxyethyl 7-[2-(2-cyclopenten-1-yloxyimino)-2-(5-amino-1,2,4-thiadiazol-3-yl)acetamido]-2-methyl-3-cephem-4-carboxylate (syn isomer).

IR (Nujol): 3420, 3300, 3150, 1780, 1760 1675, 1620 cm$^{-1}$

NMR (DMSO-d$_6$+D$_2$O, δ): 1 23 (3H, t, J=8 Hz), 1.42 (3H, d, J=7 Hz), 1.88 (3H, d, J=5 Hz), 1.8–2.5 (4H, m), 3.6–4.1 (1H, m), 4.19 (2H, q, J=8 Hz), 5.18 (1H, d, J=5 Hz), 5.2–5.6 (1H, m), 5.9–6.3 (2H, m), 5.95 (1H, d, J=5 Hz), 6.8 (1H, d, J=7 Hz), 6.83 (1H, q, J=5 Hz)

(6) Pivaloyloxymethyl 7-[2-{3-(N-t-butoxycarbonylamino)propoxyimino}-2-(5-amino-1,2,4-thiadiazol-3-yl)acetamido]-2-methyl-3-cephem-4-carboxylate (syn isomer), powder, mp 66° to 75° C. (dec.).

IR (Nujol): 3300, 1780, 1745, 1680, 1620 cm$^1$ (7) Pivaloyloxymethyl 7-[2-{3-(N-t-butoxycarbonylamino)propoxyimino}-2-(5-amino-1,2,4-thiadiazol-3-yl)acetamido]-3-(1-methyl-1H-tetrazol-5-yl)thiomethyl-3-cephem-4-carboxylate (syn isomer), powder.

IR (Nujol): 3300, 1780, 1745, 1680, 1620 cm$^{-1}$ (8) Pivaloyloxymethyl 7-[2-{3-(N-t-butoxycarbonylamino)propoxyimino}-2-(5-amino-1,2,4-thiadiazol-3-yl)acetamido]-3-(5-methyl-1,3,4-thiadiazol-2-yl)thiomethyl-3-cephem-4-carboxylate (syn isomer).

IR (Nujol): 3300, 3150, 1783, 1745, 1675, 1615 cm$^{-1}$

NMR (DMSO-d$_6$+D$_2$O, δ): 1.15 (9H, s), 1.37 (9H, s), 1.5–2.0 (2H, m), 2.65 (3H, s), 2.8–3.2 (2H, m), 3.5–3.8 (2H, m), 3.9–4.3 (2H, m), 4.16 and 4.53 (2H, ABq, J=13 Hz), 5.17 (1H, d, J=4.5 Hz), 5.6–6.0 (3H, m)

(9) Pivaloyloxymethyl 7-[2-{3-(N-t-butoxycarbonylamino)propoxyimino}-2-(5-amino-1,2,4-thiadiazol-3-yl)acetamido]-3-[1-(2-hydroxyethyl)-1H-tetrazol-5-yl)thiomethyl-3-cephem-4-carboxylate (syn isomer), powder, mp 88° to 101° C. (dec.).

IR (Nujol): 3300, 1780, 1750, 1675, 1620 cm$^{-1}$

(10) Pivaloyloxymethyl 7-[2-{3-(N-t-butoxycarbonylamino)propoxyimino}-2-(5-amino-1,2,4-thiadiazol-3-yl)acetamido]-3-(1,3,4-thiadiazol-2-yl)thiomethyl-3-cephem-4-carboxylate (syn isomer), powder, mp 71° to 84° C. (dec.).

IR (Nujol): 3300, 1780, 1745, 1680, 1615 cm$^{-1}$

(11) Pivaloyloxymethyl 7-[2-(2-cyclohexen-1-yloxyimino)-2-(5-amino-1,2,4-thiadiazol-3-yl)acetamido]-cephalosporanate (syn isomer), mp 93° to 101° C. (dec.).

IR (Nujol): 3400, 3300, 3180, 1780, 1740, 1675, 1615, 1525 cm$^{-1}$

NMR (DMSO-d$_6$+D$_2$O, δ): 1.13 (9H, s), 1.4–2.2 (6H, m), 2.02 (3H, s), 3.58 (2H, s), 4.50–4.93 (1H, m), 4.68 and 4.90 (2H, ABq, J=13.5 Hz), 5.18 (1H, d, J=4.5 Hz), 5.6–6.2 (5H, m)

(12) Phthalid-3-yl ester of 7-[2-(2-cyclopenten-1-yloxyimino)-2-(5-amino-1,2,4-thiadiazol-3-yl)acetamido]-2-methyl-3-cephem-4-carboxylic acid (syn isomer), mp 131° to 144° C. (dec.).

IR (Nujol): 3420, 3210, 3150, 1780, 1740, 1675, 1620, 1525 cm$^{-1}$

NMR (DMSO-d$_6$+D$_2$O, δ): 1.45 (3H, d, J=7 Hz), 1.9–2.5 (4H, m), 5.13 (1H, d, J=4.5 Hz), 5.2–5.5 (1H, m), 5.7–6.3 (3H, m), 6.75 (½H, d, J=6 Hz), 6.77 (½H, d, J=6 Hz), 7.62 (½H, s), 7.65 (½H, s), 7.83 (4H, broad s)

(13) Pivaloyloxymethyl 7-[2-(2-cyclopenten-1-yloxyimino)-2-(5-amino-1,2,4-thiadiazol-3-yl)acetamido]-2-methyl-3-cephem-4-carboxylate (syn isomer), mp 111° to 124° C. (dec.).

IR (Nujol): 3400, 3300, 3270, 1775, 1740, 1670, 1620, 1520 cm$^{-1}$

NMR (DMSO-d$_6$+D$_2$O, δ): 1.17 (9H, s), 1.45 (3H, d, J=7 Hz), 1.9–2.4 (4H, m), 3.7–4.0 (1H, m), 5.1–5.6 (1H, m), 5.13 (1H, d, J=4.5 Hz), 5.7–6.3 (5H, m), 6.65 (1H, d, J=7 Hz)

(14) 1-Benzoyloxyethyl 7-[2-(2-cyclopenten-1-yloxyimino)-2-(5-amino-1,2,4-thiadiazol-3-yl)acetamido]-2-methyl-3-cephem-4-carboxylate (syn isomer), mp 132° to 137° C. (dec.).

IR (Nujol): 3400, 3300, 3160, 1780, 1738, 1680, 1620 cm$^{-1}$

NMR (DMSO-d$_6$+D$_2$O, δ): 1.43 (3H, d, J=7 Hz), 1.62 (3H, d, J=5 Hz), 1.7–2.4 (4H, m), 3.84 (1H, q, J=7 Hz), 5.0–5.4 (1H, m), 5.13 (1H, d, J=4.5 Hz), 5.6–6.3 (3H, m), 6.70 (1H, d, J=6 Hz), 7.16 (1H, q, J=5 Hz), 7.3–8.2 (5H, m)

(15) Pivaloyloxymethyl 7-[2-{4-(N-t-butoxycarbonylamino)methylbenzyloxyimino}-2-(5-amino-1,2,4-thiadiazol-3-yl)acetamido]-3-methyl-3-cephem-4-carboxylate (syn isomer), powder.

IR (Nujol): 3300, 1780, 1750, 1680 cm$^{-1}$

(16) Pivaloyloxymethyl 7-[2-allyloxyimino-2-(5-amino-1,2,4-thiadiazol-3-yl)acetamido]-3-[1-{2-(N-t-butoxycarbonylamino)ethyl)}-1H-tetrazol-5-yl]thiomethyl-3-cephem-4-carboxylate (syn isomer), powder.

IR (Nujol): 3300, 1780, 1750, 1680 cm$^{-1}$

EXAMPLE 53

A solution of 2-(1-amino-1-cyclohexyl)acetyl chloride hydrochloride (127.2 mg) in methylene chloride (2 ml) was dropwise added over 5 minutes to a stirred solution of 7-[2-(3-amino-propoxyimino)-2-(5-amino-1,2,4-thiadiazol-3-yl)acetamido]-2-methyl-3-cephem-4-carboxylic acid (syn isomer) (132 mg) and bis(trimethylsilyl)acetamide (0.6 ml) in methylene chloride (6 ml) at −30° C. and then the mixture was stirred for 30 minutes at −30° to −35° C. The stirring was continued after addition of a saturated aqueous solution of sodium bicarbonate and the reaction mixture was post-treated in a conventional manner to give 7-[2-{3-(N-(2-(1-amino-1-cyclohexyl)acetyl)amino)propoxyimino}-2-(5-amino-1,2,4-thiadiazol-3-yl)acetamido]-2-methyl-3-cephem-4-carboxylic acid (syn isomer) (85 mg), mp 198°–224° C. (dec.).

IR (Nujol): 3250, 3150, 1760, 1640, 1580, 1520 cm$^{-1}$

NMR (D$_2$O+DCl, δ): 1.0–2.2 (15H, m), 2.65 (2H, s), 3.1–3.6 (2H, m), 3.6–4.1 (1H, m), 4.1–4.6 (2H, m), 5.0–5.3 (1H, m), 5.95 (1H, d, J=4.5 Hz), 6.82 (1H, d, J=6 Hz)

EXAMPLE 54

The following compounds were obtained according to a similar manner to that of Example 53.

(1) 7-[2-{2-(N-(N-t-Butoxycarbonyl)-D-phenylglycylamino)ethoxyimino}-2-(5-amino-1,2,4-thiadiazol-3-yl)acetamido]-2-methyl-3-cephem-4-carboxylic acid (syn isomer), mp 77° to 91° C. (dec.).

IR (Nujol): 3300, 3160, 1775, 1680, 1660, 1630, 1525 cm$^{-1}$

NMR (DMSO-d$_6$, δ): 1.37 (9H, s), 1.40 (3H, d, J=8 Hz), 3.1–4.2 (5H, m), 5.08 (1H, d, J=4.5 Hz), 5.10 (1H, d, J=8 Hz), 5.90 (1H, dd, J=4.5 and 9 Hz), 6.53 (1H, d, J=7.5 Hz), 7.32 (5H, s), 8.13 (2H, broad s), 9.48 (1H, d, J=9 Hz)

(2) 7-[2-{3-(N-(N-t-Butoxycarbonyl)-D-phenylglycylamino)propoxyimino}-2-(5-amino-1,2,4-thiadiazol-3-yl)acetamido]-2-methyl-3-cephem-4-carboxylic acid (syn isomer).

IR (Nujol): 3300, 3200, 1775, 1700, 1650, 1525 cm$^{-1}$

NMR (DMSO-d$_6$+D$_2$O, δ): 1.3–1.6 (12H, m), 1.6–2.0 (2H, m), 2.8–3.4 (2H, m), 3.82 (1H, q, J=7.5 Hz), 3.9–4.3 (2H, m), 5.05 (1H, d, J=4.5 Hz), 5.83 (1H, d, J=4.5 Hz), 6.48 (1H, d, J=6 Hz)

PREPARATION 23

Potassium iodate (20.0 g) was added at ambient temperature to a stirred solution of iodine (7.7 g) in conc. sulfuric acid (70 ml), and the mixture was stirred for 1.5 hours at 35° to 40° C. Acetic anhydride (30 ml) was added thereto under 10° C. over 0.5 hour and then 1,2-dichlorobenzene (44.69 g) was added thereto under 10° C. over 0.5 hour. The mixture was stirred for 1 hour at the same temperature and then stirred for 19 hours at ambient temperature. The reaction mixture was poured into ice-water (500 ml) and washed with diethyl ether. To the aqueous layer was added an aqueous solution (50 ml) of sodium chloride (8.9 g) and precipitates were collected by filtration and washed with ice-water to give 3,4,3',4'-tetrachlorodiphenyliodonium chloride (58 g), mp 183° to 186° C. (dec.).

IR (Nujol): 1555, 1450, 1250, 1210, 1170, 1125, 1030 cm$^{-1}$

PREPARATION 24

The following compounds were obtained according to a similar manner to that of Preparation 23.

(1) 3,3'-Di(trifluoromethyl)diphenyliodonium chloride.

IR (Nujol): 3600–3200, 1600, 1420, 1320, 1310, 1190, 1170, 1120, 1095, 1085, 1055, 800, 700, 685 cm$^{-1}$ (2) 3,3'-Dicarboxydiphenyliodonium bromide IR (Nujol): 3400, 1700, 1290, 1250, 1210, 1170, 1050, 750 cm$^{-1}$ (3) 3,3'-Di(ethoxycarbonyl)diphenyliodonium bromide, mp 154° to 157° C.

IR (Nujol): 1730, 1295, 1280, 1255, 1110, 1020, 750 cm$^{-1}$

PREPARATION 25

The following compounds were obtained according to similar manners to those of Preparations 1-(1) and 1-(2).

(1) N-(3-Phthalimidopropoxy)phthalimide, mp 168° to 170° C.

IR (Nujol): 1790, 1770, 1730, 1710, 1390, 1060, 725, 705 cm$^{-1}$ (2) N-(1-Cyclohexyloxycarbonylethoxy)phthalimide, mp 50° to 54° C.

NMR (d$_6$-DMSO, δ): 1.51 (3H, d, J=7 Hz), 0.9–2.1 (10H, m), 4.7 (1H, m), 4.82 (1H, 9, J=7 Hz), 7.87 (4H, s)

(3) N-(α-t-Butoxycarbonylbenzyloxy)phthalimide.

(4) N-(1-t-Butoxycarbonyl-2-methylpropoxy)phthalimide, mp 84° to 87° C.

IR (Nujol): 1790, 1730, 1360, 1160, 1140, 1000, 880, 780, 700 cm$^{-1}$ (5) N-(1-t-Butoxycarbonylpropoxy)phthalimide, mp 49° to 52° C.

NMR (d$_6$-DMSO, δ): 1.02 (3H, t, J=7 Hz), 1.40 (9H, s), 1.9 (2H, m), 4.55 (1H, t, J=6 Hz), 7.82 (4H, s)

(6) N-(1-t-Butoxycarbonylethoxy)phthalimide, mp 80° to 82° C.

NMR (d$_6$-DMSO, δ): 1.42 (9H, s), 1.48 (3H, d, J=7 Hz), 4.72 (1H, q, J=7 Hz), 7.86 (4H, s)

(7) N-(1-t-Butoxycarbonyl-1-methylethoxy)phthalimide, mp 96° to 100° C.

NMR (d$_6$-DMSO, δ): 1.42 (9H, s), 1.48 (6H, s), 7.87 (4H, s)

(8) N-(1-Butoxycarbonylethoxy)phthalimide, mp 48° to 53° C.

IR (Nujol): 1755, 1720, 1210, 1140, 1110, 1080, 875, 695 cm$^{-1}$ (9) N-(1-Benzyloxycarbonylethoxy)phthalimide, mp 65° to 68° C.

IR (Nujol): 1790, 1740, 1450, 1210, 1190, 1110, 1080, 980, 880, 735, 700 cm$^{-1}$

(10) N-(2-Oxo-3-tetrahydrofuryloxy)phthalimide, mp 140° to 142° C.

IR (Nujol): 1785, 1760, 1720, 1605, 1215, 1185, 870, 695 cm$^{-1}$

PREPARATION 26

The following compounds were obtained according to a similar manner to that of Preparation 2.

(1) 3-Aminopropoxyamine dihydrochloride

NMR (D$_2$O, δ): 2.20 (2H, m), 3.27 (2H, t, J=7 Hz), 4.33 (2H, t, J=6 Hz)

(2) 1-Phenylethoxyamine (3) 1-t-Butoxycarbonyl-2-methylpropoxyamine (4) α-t-Butoxycarbonylbenzyloxyamine (5) 1-Butoxycarbonylethoxyamine

PREPARATION 27

The following compounds were obtained according to a similar manner to that of Preparation 17.

(1) 2-(t-Butoxycarbonylmethoxyimino)-2-(5-amino-1,2,4-thiadiazol-3-yl)acetic acid (syn isomer), mp 150° to 155° C. (dec.).

IR (Nujol): 3420, 3230, 3100, 1725, 1610, 1530 cm$^{-1}$

NMR (DMSO-d$_6$, δ): 1.45 (9H, s), 4.70 (2H, s), 8.12 (2H, broad s)

(2) 2-(1-Cyclohexyloxycarbonylethoxyimino)-2-(5-amino-1,2,4-thiadiazol-3-yl)acetic acid (syn isomer), mp 175° to 180° C. (dec.).

IR (Nujol): 3380, 3260, 3170, 1720, 1610, 1520, 1220, 990, 710 cm$^{-1}$

NMR (d$_6$-DMSO, δ): 0.9–2.1 (13H, m), 4.7 (1H, m), 4.85 (1H, q, J=6 Hz), 8.13 (2H, broad s)

(3) 2-(Thiolan-1,1-dioxide-3-yloxyimino)-2-(5-amino-1,2,4-thiadiazol-3-yl)acetic acid (syn isomer), mp 200° to 205° C. (dec.).

IR (Nujol): 3300, 1720, 1620, 1530 cm$^{-1}$

NMR (d$_6$-DMSO, δ): 2.20–2.50 (2H, m), 3.00–3.50 (4H, m), 5.00–5.27 (1H, m), 8.20 (2H, s)

(4) 2-(α-t-Butoxycarbonylbenzyloxyimino)-2-(5-amino-1,2,4-thiadiazol-3-yl)acetic acid (syn isomer), mp 155° to 160° C. (dec.).

IR (Nujol): 3440, 3350, 3250, 1750, 1730, 1640, 1535 cm$^{-1}$

NMR (d$_6$-DMSO, δ): 1.37 (9H, s), 5.67 (1H, s), 7.45 (5H, s), 8.25 (2H, broad s)

(5) 2-(1-t-Butoxycarbonyl-2-methylpropoxyimino)-2-(5-amino-1,2,4-thiadiazol-3-yl)acetic acid (syn isomer), mp 158° to 162° C. (dec.).

IR (Nujol): 3600, 3400, 1740, 1720, 1630 cm$^{-1}$

NMR (d$_6$-DMSO, δ): 0.95 (6H, d, J=7 Hz), 1.8–2.4 (1H, m), 4.33 (1H, d, J=6 Hz), 8.13 (2H, broad s)

(6) 2-(1-t-Butoxycarbonylpropoxyimino)-2-(5-amino-1,2,4-thiadiazol-3-yl)acetic acid (syn isomer), mp 152° to 155° C. (dec.).

NMR (d$_6$-DMSO, δ): 0.94 (3H, t, J=7 Hz), 1.42 (9H, s), 1.80 (2H, m), 4.51 (1H, t, J=6 Hz), 8.16 (2H, broad s)

(7) 2-(1-t-Butoxycarbonylethoxyimino)-2-(5-amino-1,2,4-thiadiazol-3-yl)acetic acid (syn isomer), mp 155° to 156° C. (dec.).

IR (Nujol): 3400, 3300, 3200, 1720, 1710, 1620, 1520 cm$^{-1}$

NMR (d$_6$-DMSO, δ): 1.2–1.7 (12H, m), 4.72 (1H, q, J=7 Hz), 8.2 (2H, broad s)

(8) 2-(1-t-Butoxycarbonyl-1-methylethoxyimino)-2-(5-amino-1,2,4-thiadiazol-3-yl)acetic acid (syn isomer), mp 180° to 181° C. (dec.).

IR (Nujol): 3400, 3300, 3200, 1745, 1715, 1630, 1530 cm$^{-1}$

NMR (d$_6$-DMSO, δ): 1.38 (9H, s), 1.43 (6H, s), 815 (2H, broad s)

(9) 2-(1-Butoxycarbonylethoxyimino)-2-(5-amino-1,2,4-thiadiazol-3-yl)acetic acid (syn isomer), mp 120° to 123° C. (dec.).

IR (Nujol): 3400, 3300, 3200, 1725, 1615, 1510, 1410, 1210, 1170, 1135, 1100, 1040, 990, 870, 720 cm$^{-1}$ NMR (DMSO-d$_6$, δ): 0.85 (3H, t, J=6 Hz), 1.43 (3H, d, J=7 Hz), 1.0–1.7 (4H, m), 4.12 (2H, t, J=6 Hz), 4.85 (1H, q, J=7 Hz), 8.04 (2H, broad s)

(10) 2-(1-Benzyloxycarbonylethoxyimino)-2-(5-amino-1,2,4-thiadiazol-3-yl)acetic acid (syn isomer), mp 129° to 133° C. (dec.).

IR (Nujol): 3300, 3200, 1720, 1620, 1530 cm$^{-1}$

NMR (DMSO-d$_6$, δ): 1.45 (3H, d, J=6 Hz), 4.97 (1H, q, J=6 Hz), 5.18 (2H, s), 7.31 (5H, s), 8.17 (2H, broad s)

PREPARATION 28

The following compounds were obtained according to a similar manner to that of Preparation 15.

(1) 2-(Thiolan-1,1-dioxide-3-yloxyimino)-2-(5-formamido-1,2,4-thiadiazol-3-yl)acetic acid (syn isomer), mp 214° C. (dec.).

IR (Nujol): 3200, 1720, 1680, 1600, 1530 cm$^{-1}$

NMR (DMSO-d$_6$, δ): 2.30–2.50 (2H, m), 2.90–3.83 (4H, m), 5.10–5.50 (1H, m), 8.92 (1H, s)

(2) 2-(1-Phenylethoxyimino)-2-(5-formamido-1,2,4-thiadiazol-3-yl)acetic acid (syn isomer), mp 174° to 175° C. (dec.).

IR (Nujol): 3100, 1720, 1690, 1550 cm$^{-1}$

NMR (d$_6$-DMSO, δ): 1.58 (3H, d, J=6 Hz), 5.44 (1H, q, J=6 Hz), 7.32 (5H, m), 8.78 (1H, m), 13.34 (1H, broad s)

PREPARATION 29

To the aqueous solution containing sodium 2-(3-aminopropoxyimino)-2-(5-formamido-1,2,4-thiadiazol-3-yl)acetate (syn isomer), which was prepared by a similar manner to that of Preparation 15, were added triethylamine (20 g) and a solution of 2-t-butoxycarbonyloxyimino-2-phenylacetonitrile (27 g) in dioxane (270 ml) and the mixture was stirred at ambient temperature for 2 hours. After evaporation of dioxane, the aqueous solution was adjusted to pH 6 with 10% hydrochloric acid and washed with ethyl acetate. To the aqueous layer was added ethyl acetate and the mixture was adjusted to pH 3 with 10% hydrochloric acid. The organic layer was washed with brine, dried over magnesium sulfate and evaporated to dryness. The residue was triturated with diisopropyl ether to give 2-[3-(N-t-butoxycarbonylamino)propoxyimino]-2-(5-formamido-1,2,4-thiadiazol-3-yl)acetic acid (syn isomer) (14.2 g), mp 115°-117° C. (dec.).

IR (Nujol): 3320, 3150, 1740, 1680, 1560–1530, 1400, 1230, 1140, 1040, 1030, 890 cm$^{-1}$ NMR (DMSO-d$_6$, δ): 1.47 (9H, s), 1.97 (2H, m), 3.10 (2H, t, J=7 Hz), 4.30 (2H, t, J=7 Hz), 8.80 (1H, s)

PREPARATION 30

The following compounds were obtained according to similar manners to those of Preparations 13 and 29.

(1) 2-[2-(N-t-Butoxycarbonylamino)ethoxyimino]-2-(5-formamido-1,2,4-thiadiazol-3-yl)acetic acid (syn isomer), mp 139° to 154° C. (dec.).

IR (Nujol): 3400, 3150, 1748, 1700, 1690, 1540 cm$^{-1}$

NMR (DMSO-d$_6$+D$_2$O, δ): 1.45 (9H, s), 3.40 (2H, t, J=6 Hz), 4.32 (2H, t, J=6 Hz), 8.07 (1H, s)

(2) 2-[4-(N-t-Butoxycarbonylaminomethyl)benzyloxyimino]-2-(5-amino-1,2,4-thiadiazol-3-yl)acetic acid (syn isomer).

IR (Nujol): 3300, 3150, 1700 cm$^{-1}$

NMR (DMSO-d$_6$, δ): 1.65 (9H, s), 4.12 (2H, d, J=5.5 Hz), 5.19 (2H, s), 7.21 (4H, s)

PREPARATION 31

The following compounds were obtained according to a similar manner to that of Preparation 4.

(1) 2-[2-(N-t-Butoxycarbonylamino)ethoxyimino]-2-(5-amino-1,2,4-thiadiazol-3-yl)acetic acid (syn isomer), mp 172°-177° C. (dec.).

IR (Nujol): 3300, 3140, 1738, 1680, 1628, 1595, 1550, 1527, 1285, 1245, 1165, 1120 cm$^{-1}$ NMR (DMSO-d$_6$+D$_2$O, δ): 1.42 (9H, s), 3.35 (2H, t, J=6 Hz), 4.22 (2H, t, J=6 Hz)

(2) 2-[3-(N-t-Butoxycarbonylamino)propoxyimino]-2-(5-amino-1,2,4-thiadiazol-3-yl)acetic acid (syn isomer).

IR (Nujol): 3300, 3150, 2600–2400, 1720–1660, 1620, 1530, 1250, 1160, 1030, 720 cm$^{-1}$ NMR (DMSO-d$_6$, δ): 1.33 (9H, s), 1.82 (2H, m), 3.03 (2H, m), 4.17 (2H, t, J=6 Hz), 6.73 (1H, broad s), 8.13 (2H, broad s)

(3) 2-(4-Chlorophenoxyimino)-2-(5-amino-1,2,4-thiadiazol-3-yl)acetic acid (syn isomer), mp 150°-155° C. (dec.).

IR (Nujol): 3300, 3200, 1710, 1640, 1580, 1530 cm$^{-1}$

NMR (DMSO-d$_6$, δ): 7.37 (2H, d, J=9 Hz), 7.67 (2H, d, J=9 Hz), 8.50 (2H, broad s)

(4) 2-(4-Fluorophenoxyimino)-2-(5-amino-1,2,4-thiadiazol-3-yl)acetic acid (syn isomer), mp 140°-145° C. (dec.).

IR (Nujol): 3450, 3300, 3200, 1730, 1630, 1530, 1500 cm$^{-1}$

NMR (DMSO-d$_6$, δ): 7.17 (2H, s), 7.27 (2H, s), 8.27 (2H, s)

(5) 2-[1-t-Butoxycarbonyl-1-cyclopentyloxyimino]-2-(5-amino-1,2,4-thiadiazol-3-yl)acetic acid (syn isomer), mp 174°-175° C. (dec.).

IR (Nujol): 3400, 3300, 3200, 1745, 1715, 1630, 1530 cm$^{-1}$

NMR (d$_6$-DMSO, δ): 1.37 (9H, s), 1.65 (4H, m), 1.97 (4H, m), 8.17 (2H, broad s)

(6) 2-(1-Phenylethoxyimino)-2-(5-amino-1,2,4-thiadiazol-3-yl)acetic acid (syn isomer), mp 103°-107° C. (dec.).

IR (Nujol): 3250, 3150, 1710, 1610, 1520 cm$^{-1}$

NMR (d$_6$-DMSO, δ): 1.57 (3H, d, J=6 Hz), 5.42 (1H, q, J=6 Hz), 7.40 (5H, m), 8.20 (2H, m)

PREPARATION 32

To a solution of 2-hydroxyimino-2-(5-formamido-1,2,4-thiadiazol-3-yl)acetic acid (syn isomer) (7.2 g) in an aqueous methanolic sodium hydroxide prepared from methanol (83.7 ml) and 1 N aqueous solution of sodium hydroxide (83.7 ml) was added 4,4'-difluorodiphenyliodonium chloride (11.8 g) and the mixture was stirred at ambient temperature for an hour. The resulting oily substance was removed by decantation and the solution was concentrated under reduced pressure to remove methanol. The aqueous solution was acidified with 10% hydrochloric acid and extracted with ethyl acetate. The extract was washed with water, dried over magnesium sulfate and evaporated to dryness. The residue was triturated with diisopropyl ether to give 2-(4-fluorophenoxyimino)-2-(5-formamido-1,2,4-thiadiazol-3-yl)acetic acid (syn isomer) (6.0 g), mp 130°-135° C. (dec.).

IR (Nujol): 3100, 3050, 1730, 1690, 1530, 1500 cm$^{-1}$

NMR (DMSO-d$_6$, δ): 7.17 (2H, s), 7.27 (2H, s), 8.83 (1H, s), 13.43 (1H, s)

PREPARATION 33

The following compounds were obtained by a similar manner to that of Preparation 32.

(1) 2-(4-Chlorophenoxyimino)-2-(5-formamido-1,2,4-thiadiazol-3-yl)acetic acid (syn iosmer), mp 155° to 160° C. (dec.).

IR (Nujol): 3180, 1725, 1690, 1580, 1530 cm$^{-1}$

NMR (DMSO-d$_6$, δ): 7.30 (2H, d, J=9 Hz), 7.57 (2H, d, J=9 Hz), 9.0 (1H, s)

(2) 2-(2-Methoxy-5-nitrophenoxyimino)-2-(5-amino-1,2,4-thiadiazol-3-yl)acetic acid (syn isomer), mp 125° to 128° C. (dec.).

IR (Nujol): 3400, 3280, 1740, 1720, 1690, 1630, 1590, 1510, 1340, 1275, 970, 720 cm$^{-1}$ NMR (DMSO-d$_6$, δ): 3.93 (3H, s), 7.27 (1H, d, J=8 Hz), 8.01 (1H, d, J=8 Hz), 8.07 (1H, s), 8.30 (2H, broad s)

PREPARATION 34

The following compound was obtained by a similar manner to that of Preparation 21.

2-(1-t-Butoxycarbonyl-1-cyclopentyloxyimino)-2-(5-formamido-1,2,4-thiadiazol-3-yl)acetic acid (syn isomer), mp 140° to 141° C. (dec.).

IR (Nujol): 3550, 1730, 1670, 1550, 1540, 1280, 1255, 1150, 980, 720 cm$^{-1}$

NMR (DMSO-d$_6$, δ): 1.48 (9H, s), 1.83 (4H, m), 2.03 (4H, m), 8.87 (1H, s), 13.6 (1H, broad s)

PREPARATION 35

The following compounds were obtained according to a similar manner to that of Preparation 32 by using 2-hydroxyimino-2-(5-amino-1,2,4-thiadiazol-3-yl)acetic acid (syn isomer) as a starting compound, which was prepared by a similar manner to that of Preparation 4.

(1) 2-(O-and P-Tolyloxyimino)-2-(5-amino-1,2,4-thiadiazol-3-yl)acetic acid (syn isomer).

NMR (d$_6$-DMSO, δ): 2.20 (1H, s), 2.27 (2H, s), 6.97-7.43 (4H, m), 8.33 (2H, bs)

(2) 2-(3,4-Dichlorophenoxyimino)-2-(5-amino-1,2,4-thiadiazol-3-yl)acetic acid (syn isomer), mp 177° to 178° C.

IR (Nujol): 3300, 1710, 1625, 1585, 1530, 1300, 1210, 1120, 980 cm$^{-1}$

NMR (DMSO-d$_6$, δ): 6.83-7.73 (3H, m), 8.38 (2H, broad s)

(3) 2-(3-Trifluoromethylphenoxyimino)-2-(5-amino-1,2,4-thiadiazol-3-yl)acetic acid (syn isomer), mp 167° to 168° C. (dec.).

IR (Nujol): 3250, 1645, 1620, 1590, 1450, 1320, 1170, 1140, 1010, 995, 845, 730 cm$^{-1}$ NMR (DMSO-d$_6$, δ): 7.63 (4H, m), 8.44 (2H, broad s)

(4) 2-(3-Ethoxycarbonylphenoxyimino)-2-(5-amino-1,2,4-thiadiazol-3-yl)acetic acid (syn isomer), mp 161° to 164° C. (dec.).

IR (Nujol): 3400, 3300, 3180, 1755, 1720, 1690, 1630, 1590, 1545, 1410, 1290, 1275, 970, 900, 755 cm$^{-1}$ NMR (DMSO-d$_6$, δ): 1.36 (3H, t, J=7 Hz), 4.40 (12H, q, J=7 Hz), 7.4-8.0 (3H, m), 8.5 (2H, broad s)

(5) 2-(3-Carboxyphenoxyimino)-2-(5-amino-1,2,4-thiadiazol-3-yl)acetic acid (syn isomer), mp 186° to 188° C. (dec.).

IR (Nujol): 3420, 3150, 1735, 1690, 1620, 1580, 1265, 1200, 1000, 980, 760 cm$^{-1}$ NMR (DMSO-d$_6$, δ): 7.3-8.0 (4H, m), 8.30 (2H, broad s)

(6) 2-Phenoxyimino-2-(5-amino-1,2,4-thiadiazol-3-yl)acetic acid (syn isomer), mp 145° to 147° C. (dec.).

IR (Nujol): 3350, 3170, 2500, 1730, 1710, 1645, 1630, 1595, 1535 cm$^{-1}$

NMR (DMSO-d$_6$, δ): 7.0-7.5 (5H, m), 8.30 (2H, broad s)

PREPARATION 36

S-Methyl (5-formamido-1,2,4-thiadiazol-3-yl)thioglyoxylate (64.8 g) and 1-carboxy-3-hydroxypropoxyamine, which was prepared by refluxing a mixture of N-(2-oxo-3-tetrahydrofuryloxy)phthalimide (65.0 g), conc. hydrochloric acid (50 ml) and water (200 ml) for 1 hour, were treated according to a similar manner to that of Preparation 17 to give 2-(1-carboxy-3-hydroxypropoxyimino)-2-(5-amino-1,2,4-thiadiazol-3-yl)acetic acid (syn isomer) (33.2 g), mp 186° to 188° C. (dec.).

IR (Nujol): 3400, 3250, 3100, 1710, 1620, 1540 cm$^{-1}$

NMR (DMSO-d$_6$, δ): 1.73-2.10 (2H, m), 3.50 (2H, t, J=6 Hz), 4.73 (1H, t, J=6 Hz), 8.13 (2H, s)

PREPARATION 37

To a solution of 2 -(1-carboxy-3-hydroxypropoxyimino)-2-(5-amino-1,2,4-thiadiazol-3-yl)acetic acid (syn isomer) (33.0 g) in methanol (2.8 l) were added anhydrous magnesium sulfate (120 g) and acetic anhydride (60 g). The mixture was stirred at ambient temperature for 30 minutes, filtered and the filtrate was evaporated to dryness. The residue was triturated in acetone (200 ml) and ethyl acetate (1 l) was added thereto. The mixture was stirred at ambient temperature for 1 hour and the precipitates were collected by filtration and washed with ethyl acetate.

The precipitates were dissolved in water (200 ml) and then ethyl acetate (500 ml), acetone (200 ml) and 6 N hydrochloric acid (40 ml) were added thereto.

An organic layer was separated out and the aqueous layer was extracted with ethyl acetate. The organic layers were combined, dried over anhydrous magnesium sulfate and evaporated to dryness. The residue was triturated in diethyl ether, filtered and washed with diisopropyl ether to give 2-(2-oxo-3-tetrahydrofuryloxyimino)-2-(5-amino-1,2,4-thiadiazol-3-yl)acetic acid (syn isomer) (26.5 g), mp 185°-187° C. (dec.).

IR (Nujol): 3400, 3300, 3200, 1775, 1730, 1640, 1605, 1535 cm$^{-1}$

NMR (d$_6$-DMSO, δ): 2.27-2.70 (2H, m), 4.17-4.50 (2H, m), 5.27 (1H, t, J=8 Hz), 8.22 (2H, s)

PREPARATION 38

(1) The following compound was obtained by a similar manner to that of Preparation 22-(1).

Methyl N-(6-acetamidohexyl)dithiocarbamate

NMR (DMSO-d$_6$, δ): 1.33 (8H, broad s), 1.80 (3H, s), 2.50 (3H, s), 3.07 (2H, m), 3.53 (2H, m), 7.77 (1H, m), 9.80 (1H, m)

(2) The following compounds were obtained by a similar manner to that of Preparation 22-(2).

(a) 1-(4-Acetamidobutyl)-1H-tetrazole-5-thiol

IR (Nujol): 3300, 1620, 1560, 1520 cm$^{-1}$

NMR (d$_6$-DMSO, δ): 1.23-1.93 (4H, m), 1.77 (3H, s), 3.10 (2H, m), 4.23 (2H, m), 7.80 (1H, broad s)

(b) 1-(6-Acetamidohexyl)-1H-tetrazole-5-thiol, oil.

(3) The following compounds were obtained by a similar manner to that of Preparation 22-(3).

(a) 1-(4-Aminobutyl)-1H-tetrazole-5-thiol hydrochloride, white powder.

(b) 1-(6-Aminohexyl)-1H-tetrazole-5-thiol hydrochloride, red oil.

(4) The following compounds were obtained by a similar manner to that of Preparation 22-(4).

(a) 1-[4-(N-t-Butoxycarbonylamino)butyl]-1H-tetrazole-5-thiol, mp 107°-108.5° C.

IR (Nujol): 3200, 1640, 1520 cm$^{-1}$

NMR (d$_6$-DMSO, δ): 1.37 (9H, s), 1.38-2.1 (4H, m), 2.97 (2H, m), 4.23 (2H, m), 6.73 (1H, broad s)

(b) 1-[6-(N-t-Butoxycarbonylamino)hexyl]-1H-tetrazole-5-thiol, oil

NMR (d$_6$-DMSO, δ): 1.40 (15H, m), 1.77 (2H, m), 2.93 (2H, m), 4.20 (2H, m), 6.70 (1H, broad s)

PREPARATION 39

(1) To the solution of N-(3-bromoporpyl)phthalimide (402 g) in acetone (2.5 l) were added 1-methylpiperazine (225 g) and potassium carbonate (4.15 g). The resulting mixture was refluxed with stirring for 3.5 hours. The reaction mixture was cooled and then filtered. The filter cake was washed with acetone (500 ml). The filtrate and washing were combined and evaporated under reduced pressure. The remaining starting materials in the residual oil were azeotropically removed with benzene to give an oil of N-[3-(4-methyl-1-piperazinyl)propyl]phthalimide (502 g). I.R. (Film): 1770, 1700 cm$^{-1}$ (2) To a solution of N-[3-(4-methyl-1-piperazinyl)propyl]phthalimide (502 g) in ethanol (3.0 l) was added 100% hydrazine hydrate (187.6 g). The resulting mixture was refluxed with stiving for 1.5 hours. The reaction mixture was cooled and then filtered. The filter cake was washed with ethanol (1 l). The filtrate and washing were combined and evaporated, under reduced pressure. The residual oil was distilled under reduced pressure to give 3-(4-methyl-1-piperazinyl)propylamine (146.6 g), bp 34 mmHg/127° to 128° C.

(3) To a solution of potassium hydroxide (57.3 g) in methanol (250 ml) was added 3-(4-methyl-1-piperazinyl)propylamine (146 g) and thereto was added carbon disulfide (70.6 g) with stirring under ice cooling over a period of 40 minutes. The resulting mixture was stirred for 3.5 hours under ice cooling. The reaction mixture was evaporated under reduced pressure. The residual oil was dissolved in water (400 ml) and washed with diethyl ether twice. The washed aqueous layer was ice-cooled and thereto was added methyl iodide (132.1 g) with stirring. The resulting mixture was stirred for 2 hours under ice-cooling, and extracted with ethyl acetate (400 ml×3) and chloroform (400 ml×2). The extracts were combined, dried over magnesium sulfate and then evaporated under reduced pressure to give methyl N-[3-(4-methyl-1-peperazinyl)propyl]dithiocarbamate (139.3 g).

Thus obtained product was used directly in the next step reaction without further purification.

(4) To a solution of methyl N-[3-(4-methyl-1-piperazinyl)propyl]dithiocarbamate obtained in Preparation 39 (3) (139.3 g) in a mixture of water (420 ml) and ethanol (280 ml) was added sodium azide (47.6 g). The resulting mixture was refluxed with stirring for 3 hours. The reaction mixture was concentrated under reduced pressure. The concentrate was washed successively with ethyl acetate and diethyl ether and then evaporated. To the residue was added ethanol and the mixture was filtered. The filtrate was evaporated under reduced pressure, and to the residual oil was added 6 N hydrochloric acid. The mixture was evaporated under reduced pressure. The residue was recrystallized from isopropyl alcohol containing water to give 1-[3-(4-methyl-1-piperazinyl)propyl]-1H-tetrazole-5-thiol dihydrochloride (48.1 g), mp 239° to 243° C.

N.M.R. (D$_2$O, δ): 2.3–2.8 (2H, m), 3.07 (3H, s) 3.3–3.7 (2H, m), 3.75 (8H, s), 4.42 (2H, t, J=6 Hz).

EXAMPLE 55

The following compound was obtained according to a similar manner to that of Example 40, 42 or 47. 7-[2-Carboxymethoxyimino-2-(5-amino-1,2,4-thiadiazol-3-yl)acetamido]-3-[1-(2-carboxyethyl)-1H-tetrazol-5-yl]thiomethyl-3-cephem-4-carboxylic acid (syn isomer), mp 215° to 220° C. (dec.).

IR (Nujol): 3300, 3200, 1770, 1720, 1680, 1620, 1520 cm$^{-1}$

NMR (DMSO-d$_6$, δ): 2.93 (2H, t, J=6 Hz), 3.67 (2H, broad s), 4.33 (2H, broad s), 4.43 (2H, t, J=6 Hz), 4.67 (2H, s), 5.10 (1H, d, J=4 Hz), 5.83 (1H, dd, J=4 and 8 Hz), 8.13 (2H, s), 9.50 (1H, d, J=8 Hz)

EXAMPLE 56

The following compounds were obtained according to a similar manner to that of Example 30, 40, 42, 44, 45, 47 or 48.

(1) 7-(2-(2-Oxo-3-tetrahydrofuryloxyimino)-2-(5-amino-1,2,4-thiadiazol-3-yl)acetamido)-3-(1-(3-(N-t-butoxycarbonylamino)propyl)-1H-tetrazol-5-yl)-thiomethyl-3-cephem-4-carboxylic acid (syn isomer), mp 130° to 135° C. (dec).

IR (Nujol): 3300, 3200, 1780, 1680, 1620, 1525 cm$^{-1}$ (2) 7-(2-(2-Oxo-3-tetrahydrofuryloxyimino)-2-(5-amino-1,2,4-thiadiazol-3-yl)acetamido)-3-(1-(3-amino-propyl)-1H-tetrazol-5yl)-thiomethyl-3-cephem-4-carboxylic acid (syn isomer), mp 210° to 215° C. (dec).

IR (Nujol): 3300, 3200, 1770, 1670, 1620, 1525 cm$^{-1}$ (3) 7-(2-(1-Methyl-1-carboxyethoxyimino)-2-(5-amino-1,2,4-thiadiazol-3-yl)acetamido)cephalosporanic acid (syn isomer) mp 210° to 220° C. (dec).

IR (Nujol): 3400, 3300, 3200, 1770, 1720, 1700–1670, 1620, 1520, 1230, 1150, 1060, 1020, 995, 975, 920, 740, 720 cm$^{-1}$ (4) Pivaloyloxymethyl 7-(2-cyclopentyloxyimino-2-(5-amino-1,2,4-thiadiazol-3-yl)acetamido)-2-methyl-3-cephem-4-carboxylate (syn isomer), amorphous powder.

IR (Nujol): 3450, 3360, 3200, 1790, 1750, 1680, 1625, 1530 cm$^{-1}$ (5) 7-(2-(1-Methyl-1-t-butoxycarbonylethoxyimino)-2-(5-amino-1,2,4-thiadiazol-3-yl)acetamido-3-(1-(3-aminopropyl)-1H-tetra-zol-5-yl)thiomethyl-3-cephem-4-carboxylic acid (syn isomer), mp 198° to 203° C. (dec).

IR (Nujol): 3450–3300, 3200, 1770, 1680, 1600–1615, 1525, 1140, 990, 970, 750, 720 cm$^{-1}$ (6) 7-(2-(1-Carboxyethoxyimino)-2-(5-amino-1,2,4-thiadiazol-3-yl)acetamido)-3-(5-(2-(N-t-butoxycarbonyamino)ethyl)-1,3,4-thiadiazol-2-yl)thiomethyl-3-cephem-4-carboxylic acid (syn isomer), mp 202° to 204° C. (dec).

IR (Nujol): 3350, 3200, 1780, 1680, 1620, 1520, 1250, 1170, 1100, 1050, 1000 cm$^{-1}$ (7) 7-(2-(1-Carboxyethoxyimino)-2-(5-amino-1,2,4-thiadiazol-3-yl)acetamido)-3-(5-(2-aminoethyl)-1,3,4-thiadiazol-2-yl)-thiomethyl-3-cephem-4-carboxylic acid (syn isomer), mp 200° to 204° C. (dec).

IR (Nujol): 3350, 3200, 1770, 1680, 1620, 1520, 1240, 1180, 1100, 1060, 1040, 1000 cm$^{-1}$ (8) N-(7-(2-(2-Cyclopenten-1-yl-oxyimino)-2-(5-amino-1,2,4-thiadiazol-3-yl)acetamido)-3-cephem-3-ylmethyl)-4'-carbamoyl-pyridinium-4-carboxylate (syn isomer), mp 155° to 160° C. (dec.)

IR (Nujol): 3300, 3150, 1770, 1675, 1610, 1560, 1520 cm$^{-1}$ (9) N-(7-(2-(1-Methyl-1-carboxyethoxyimino)-2-(5-amino-1,2,4-thiadiazol-3-yl)acetamido)-3-cephem-3-ylmethyl)-4'-carbamoyl-pyridinium-4-carboxylate (syn isomer), mp 180° to 185° C. (dec.)

IR (Nujol): 3300, 1770, 1680, 1620, 1560, 1520 cm$^{-1}$

EXAMPLE 57

To a cold solution of phosphorus pentachloride (1.25 g) in methylene chloride (30 ml) was added 2-(2-cyclopenten-1-yloxyimino)-2-(5-amino-1,2,4-thiadiazol-3-yl) acetic acid (syn isomer) (1.5 g) at −15° C. and the mixture was stirred for 30 minutes at −13° to −10° C. On the other hand, a mixture of N-[7-amino-3-cephem-5-ylmethyl]pyridinium-4-carboxylate dihydrochloride (1.82 g) and trimethylsilylacetamide (10 g) in methylene chloride (50 ml) was stirred for 10 minutes at room temperature and cooled to −10° C. The cooled solution was added to the above activated mixture and the mixture was stirred for 15 minutes at −10° C. The reaction mixture was poured into an aqueous solution (100 ml) of sodium bicarbonate (3.6 g) and stirred for 15 minutes at room temperature. The aqueous layer was separated out, adjusted to pH 2 with 10% hydrochloric acid and washed with ethyl acetate. The aqueous solution was subjected to column chromatography on a non ionic adsorption resin, Diaion HP-20 (Trademark, prepared by Mitsubishi Chemical Industries) (100 ml). After the column was washed with water, the elution was carried out with 40% aqueous methanol. The eluates containing an object compound were collected, evaporated to remove methanol under reduced pressure and lyophilized to give white powder of N-[7-{2-(2-cyclopenten-1-yloxyimino)-2-(5-amino-1,2,4-thiadiazol-3-yl)acetamido}-3-cephem-3-ylmethyl]pyridinium-4-carboxylate (syn isomer) (1.5 g), mp 190° to 195° C. (dec.).

I.R. (Nujol): 3350, 3200, 1780, 1660, 1620, 1530 cm$^{-1}$

N.M.R. (D$_2$O+NaHCO$_3$, δ): 1.9-2.5 (4H, m), 3.23, 3.60 (2H, ABq, J=16 Hz), 5.2-6.1 (7H, m), 7.9-9.1 (5H, m)

EXAMPLE 58

The following compounds were obtained according to similar manners to those of Examples 1 to 3, 5, 7 to 12, 32 to 34, 40 and 57.

(1) N-[7-{2-(t-Butoxycarbonylmethoxyimino)-2-(5-amino-1,2,4-thiadiazol-3-yl)acetamido}-3-cephem-3-ylmethyl]pyridinium-4-carboxylate (syn isomer), mp. 150° to 155° C. (dec.).

I.R. (Nujol): 3300, 3200, 1770, 1680, 1620, 1530 cm$^{-1}$ (2) N-[7-{2-Carboxymethoxyimino-2-(5-amino-1,2,4-thiadiazol-3-yl)acetamido}-3-cephem-3-ylmethyl]pyridinium-4-carboxylate (syn isomer), mp. 150° to 155° C. (dec.).

I.R. (Nujol): 3350, 3200, 1780, 1680, 1530 cm$^{-1}$ (3) N-[7-{2-Cyclopentyloxyimino-2-(5-amino-1,2,4-thiadiazol-3-yl)acetamido}-3-cephem-3-ylmethyl]pyridinium-4-carboxylate (syn isomer), mp. 180° to 185° C. (dec.).

I.R. (Nujol): 3300, 3200, 1780, 1670, 1620, 1530 cm$^{-1}$ (4) N-[7-{2-(1-Carboxyethoxyimino)-2-(5-amino-1,2,4-thiadiazol-3-yl)acetamido}-3-cephem-3-ylmethyl]-4'-carbamoylpyridinium-4-carboxylate (syn isomer), mp. 170° to 175° C. (dec.).

I.R. (Nujol): 3300, 3160, 1770, 1680, 1610, 1560, 1520 cm$^{-1}$ (5) N-[7-{2-(1-t-Butoxycarbonylethoxyimino)-2-(5-amino-1,2,4-thiadiazol-3-yl)acetamido}-3-cephem-3-ylmethyl]pyridinium-4-carboxylate (syn isomer), mp. 160° to 165° C. (dec.).

I.R. (Nujol): 3290, 3160, 1770, 1725, 1670, 1620, 1525 cm$^{-1}$

N.M.R. (CD$_3$OD+D$_2$O, δ): 1.2-1.6 (12H, m), 3.20 and 3.67 (2H, ABq, J=18 Hz), 4.40-4.90 (1H, m), 5.20 (1H, d, J=5 Hz), 5.33-5.80 (2H, m), 5.92 (1H, d, J=5 Hz), 7.9-9.4 (5H, m).

(6) N-[7-{2-(1-Carboxyethoxyimino)-2-(5-amino-1,2,4-thiadiazol-3-yl)acetamido}-3-cephem-3-ylmethyl]pyridinium-4-carboxylate (syn isomer), mp. 175° to 180° C. (dec.).

I.R. (Nujol): 3300, 3200, 1775, 1670, 1620,1520 cm$^{-1}$ (7) N-[7-{2-(1-Benzyloxycarbonylethoxyimino)-2-(5-amino-1,2,4-thiadiazol-3-yl)acetamido}-3-cephem-3-ylmethyl]pyridinium-4-carboxylate (syn isomer), mp. 178° to 182° C. (dec.).

I.R. (Nujol): 3250, 3150, 1770, 1670, 1620,1520 cm$^{-1}$

N.M.R. (DMSO-d$_6$+D$_2$O, δ): 1.45 (3H, d, J=7 Hz), 3.10 and 3.60 (2H, ABq, J=16 Hz), 4.87 (1H, q, J=7 Hz), 5.20 (2H, s), 4.97-5.10 (2H, m), 5.25 (1H, d, J=5 Hz), 5.83 (1H, d, J=5 Hz), 7.43 (5H, s), 8.27 (2H, m), 8.63 (1H, m), 9.38 (2H, m)

(8) 7-[2-Cyclopentyloxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp. 150° to 155° C. (dec.).

I.R. (Nujol): 3300, 3190, 1770, 1670, 1620,1520 cm$^{-1}$ (9) 7-[2-(2-Cyclopenten-1-yloxyimino)-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp. 150° to 155° C. (dec.).

I.R. (Nujol): 3350, 3220, 1775, 1680, 1620, 1525 cm$^{-1}$

N.M.R. (DMSO-d$_6$, δ): 1.90-2.50 (4H, m), 2.70 (3H, s), 3.68 (2H, broad s), 4.25 and 4.53 (2H, ABq, J=13 Hz), 5.15 (1H, d, J=5 Hz), 5.23-5.53 (1H, m), 5.70-6.30 (3H, m), 8.15 (2H, broad s), 9.52 (1H, d, J=8 Hz)

(10) 7-[2-(Cyclopentyloxyimino-2-(5-amino-1,2,4-thiadiazol-3-yl)acetamido]-3-(1H-tetrazol-5-yl)thiomethyl-3-cephem-4-carboxylic acid (syn isomer), mp. 150° to 155° C. (dec.).

I.R. (Nujol): 3300, 3200, 1770, 1670, 1620,1530 cm$^{-1}$

(11) N-[7-{2-Ethoxycarbonylmethoxyimino-2-(5-amino-1,2,4-thiadiazol-3-yl)acetamido}-3-cephem-3-ylmethyl]pyridinium-4-carboxylate (syn isomer), mp. 184° to 188° C. (dec.).

I.R. (Nujol): 3400-3100, 1770, 1670, 1610, 1520 cm$^{-1}$

N.M.R. (DMSO-d$_6$, δ): 1.17 (3H, t, J=7 Hz), 3.05 and 3.53 (2H, ABq, J=18 Hz), 4.13 (2H, q, J=7 Hz), 4.70 (2H, s), 5.08 (1H, d, J=5 Hz), 5.17 and 5.70 (2H, ABq, J=13 Hz), 5.72 (1H, dd, J=5 and 8 Hz), 8.16 (4H, m), 8.62 (1H, m), 9.50 (3H, m)

(12) 7-[2-Cyclopentyloxyimino-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp 145° to 150° C. (dec.).

I.R. (Nujol): 3350, 3220, 1775, 1670, 1620, 1525 cm$^{-1}$

(13) 7-[2-(2-Cyclopenten-1-yloxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp. 135° to 140° C. (dec.).

I.R. (Nujol): 3350, 3250, 1775, 1675, 1620,1525 cm$^{-1}$

(14) 7-[2-(2-Cyclopenten-1-yloxyimino)-2-(5-amino-1,2,4-thiadiazol-3-yl)acetamido]-3-(1H-tetrazol-5-yl)thiomethyl-3-cephem-4-carboxylic acid (syn isomer), mp. 150° to 155° C. (dec.).

I.R. (Nujol): 3350, 3200, 1780, 1680, 1620,1520 cm$^{-1}$

EXAMPLE 59

The following compounds were obtained according to similar manners to those of Examples 14 to 17 and 42.

(1) N-[7-{2-(2-Cyclopenten-1-yloxyimino)-2-(5-amino-1,2,4-thiadiazol-3-yl)acetamido}-3-cephem-3-ylmethyl]pyridinium-4-carboxylate (syn isomer), mp. 190° to 195° C. (dec.).

I.R. (Nujol): 3350,3200,1780,1660,1620,1530 cm$^{-1}$ (2) N-[7-{2-(t-Butoxycarbonylmethoxyimino)-2-(5-amino-1,2,4-thiadiazol-3-yl)acetamido}-3-cephem-3-ylmethyl]pyridinium-4-carboxylate (syn isomer), mp. 150° to 155° C. (dec.).

I.R. (Nujol): 3300, 3200, 1770, 1680, 1620, 1530 cm$^{-1}$ (3) N-[7-{2-Carboxymethoxyimino-2-(5-amino-1,2,4-thiadiazol-3-yl)acetamido}-3-cephem-3-ylmethyl]pyridinium-4-carboxylate (syn isomer), mp. 150° to 155° C. (dec.).

I.R. (Nujol): 3350, 3200, 1780, 1680, 1530 cm$^{-1}$ (4) N-[7-{2-Cyclopentyloxyimino-2-(5-amino-1,2,4-thiadiazol-3-yl)acetamido}-3-cephem-3-ylmethyl]pyridinium-4-carboxylate (syn isomer), mp. 180° to 185° C. (dec.).

I.R. (Nujol): 3300, 3200, 1780, 1670, 1620, 1530 cm$^{-1}$

N.M.R. (DMSO-d$_6$, δ): 1.4-2.0 (8H, m), 3.17, 3.53 (2H, ABq, J=18 Hz), 4.60-4.83 (1H, m), 5.10 (1H, d, J=4 Hz), 5.30 and 5.83 (2H, ABq, J=14 Hz), 5.87 (1H, dd, J=4 and 8 Hz), 8.17 (2H, s), 9.50 (1H, d, J=8 Hz), 8.0-9.7 (5H, m)

(5) N-[7-{2-(1-Carboxyethoxyimino)-2-(5-amino-1,2,4-thiadiazol-3-yl)acetamido}-3-cephem-3-ylmethyl]-4'-carbamoylpyridinium-4-carboxylate (syn isomer), mp. 170° to 175° C. (dec.).

I.R. (Nujol): 3300, 3160, 1770, 1680, 1610, 1560, 1520 cm$^{-1}$

N.M.R. (DMSO-d$_6$, δ): 1.38 (3H, d, J=7 Hz), 3.10–3.60 (2H, m), 4.40–4.83 (1H, m), 5.10 (1H, d, J=5 Hz), 5.28–6.00 (3H, m), 8.22 (2H, broad s), 8.48 (2H, d, J=6 Hz), 9.48 (2H, d, J=6 Hz), 9.32–9.65 (1H, m)

(6) N-[7-{2-(1-t-Butoxycarbonylethoxyimino)-2-(5-amino-1,2,4-thiadiazol-3-yl)acetamido}-3-cephem-3-ylmethyl]pyridinium-4-carboxylate (syn isomer), mp. 160° to 165° C. (dec.).

I.R. (Nujol): 3290, 3160, 1770, 1725, 1670, 1620, 1525 cm$^{-1}$ (7) N-[7-{2-(1-Carboxyethoxyimino)-2-(5-amino-1,2,4-thiadiazol-3-yl)acetamido}-3-cephem-3-ylmethyl]pyridinium-4-carboxylate (syn isomer), mp. 175° to 180° C. (dec.).

I.R. (Nujol): 3300, 3200, 1775, 1670, 1620, 1520 cm$^{-1}$ (8) N-[7-{2-(1-Benzyloxycarbonylethoxyimino)-2-(5-amino-1,2,4-thiadiazol-3-yl)acetamido}-3-cephem-3-ylmethyl]pyridinium-4-carboxylate (syn isomer), mp. 178° to 182° C. (dec.).

I.R. (Nujol): 3250, 3150, 1770, 1670, 1620, 1520 cm$^{-1}$ (9) 7-[2-Cyclopentyloxyimino-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp. 150° to 155° C. (dec.).

I.R. (Nujol): 3300, 3190, 1770, 1670, 1620, 1520 cm$^{-1}$

N.M.R. (DMSO-d$_6$, δ): 1.27–2.07 (8H, m), 2.67 (3H, s), 3.68 (2H, broad s), 4.23 and 4.53 (2H, ABq, J=13 Hz), 4.60–4.93 (1H, m), 5.13 (1H, d, J=5 Hz), 5.80 (1H, dd, J=5 and 8 Hz), 8.10 (2H, broad s), 9.47 (1H, d, J=8 Hz)

(10) 7-[2-(2-Cyclopenten-1-yloxyimino)-2-(5-amino-1,2,4-thiadiazol-3-yl)acetamido]-3-(5-methyl-1,3,4-thiadiazol-2-yl)thiomethyl-3-cephem-4-carboxylic acid (syn isomer), mp 150° to 155° C. (dec.).

I.R. (Nujol): 3350, 3220, 1775, 1680, 1620, 1525 cm$^{-1}$

(11) 7-[2-Cyclopentyloxyimino-2-(5-amino-1,2,4-thiadiazol-3-yl)acetamido]-3-(1H-tetrazol-5-yl)thiomethyl-3-cephem-4-carboxylic acid (syn isomer), mp. 150° to 155° C. (dec.).

I.R. (Nujol): 3300, 3200, 1770, 1670, 1620, 1530 cm$^{-1}$

N.M.R. (DMSO-d$_6$, δ): 1.5–2.0 (8H, m), 3.62 and 3.72 (2H, ABq, J=17 Hz), 4.20 and 4.42 (2H, ABq, J=14 Hz), 4.65–4.84 (1H, m), 5.15 (1H, d, J=4 Hz), 5.80 (1H, dd, J=4 and 8 Hz), 8.10 (2H, s), 9.50 (1H, d, J=8 Hz)

(12) N-[7-{2-Ethoxycarbonylmethoxyimino-2-(5-amino-1,2,4-thiadiazol-3-yl)acetamido}-3-cephem-3-ylmethyl]pyridinium-4-carboxylate (syn isomer), mp. 184° to 188° C. (dec.).

I.R. (Nujol): 3400–3100, 1770, 1670, 1610, 1520 cm$^{-1}$

(13) 7-[2-Cyclopentyloxyimino-2-(5-amino-1,2,4-thiadiazol-3-yl)acetamido]-3[1-(2-hydroxyethyl)-1H-tetrazol-5-yl]thiomethyl-3-cephem-4-carboxylic acid (syn isomer), mp. 145° to 150° C. (dec.).

I.R. (Nujol): 3350, 3220, 1775, 1670, 1620, 1525 cm$^{-1}$

N.M.R. (DMSO-d$_6$, δ): 1.22–2.15 (8H, m), 3.47–4.00 (4H, m), 4.10–4.57 (4H, m), 4.57–4.90 (1H, m), 5.12 (1H, d, J=5 Hz), 5.80 (1H, dd, J=5 and 8 Hz), 8.10 (2H, broad s), 9.47 (1H, d, J=8 Hz)

(14) 7-[2-(2-Cyclopenten-1-yloxyimino)-2-(5-amino-1,2,4-thiadiazol-3-yl)acetamido]-3-[1-(2-hydroxyethyl)-1H-tetrazol-5-yl]thiomethyl-3-cephem-4-carboxylic acid (syn isomer), mp. 135° to 140° C. (dec.).

I.R. (Nujol): 3350, 3250, 1775, 1675, 1620, 1525 cm$^{-1}$

N.M.R. (DMSO-d$_6$, δ): 1.90–2.47 (4H, m), 3.53–3.90 (4H, m), 4.13–4.53 (4H, m), 5.10 (1H, d, J=5 Hz), 5.20–5.50 (1H, m), 5.63–6.23 (3H, m), 8.12 (2H, broad s), 9.43 (1H, d, J=8 Hz)

(15) 7-[2-(2-Cyclopenten-1-yloxyimino)-2-(5-amino-1,2,4-thiadiazol-3-yl)acetamido]-3-(1H-tetrazol-5-yl)thiomethyl-3-cephem-4-carboxylic acid (syn isomer), mp. 150° to 155° C. (dec.).

I.R. (Nujol): 3350, 3200, 1780, 1680, 1620, 1520 cm$^{-1}$

N.M.R. (DMSO-d$_6$, δ): 1.8–2.5 (4H, m), 3.67 (2H, broad s), 4.20 and 4.43 (2H, ABq, J=15 Hz), 5.13 (1H, d, J=4 Hz), 5.3–5.5 (1H, m), 5.80 (1H, dd, J=4 and 8 Hz), 5.8–6.4 (2H, m), 8.13 (2H, s), 9.53 (1H, d, J=8 Hz)

EXAMPLE 60

To a solution of N-[7-{2-t-butoxycarbonylmethoxyimino-2-(5-amino-1,2,4-thiadiazol-3-yl)acetamido}-3-cephem-3-ylmethyl]pyridinium-4-carboxylate (syn isomer) (1.8 g) in formic acid (18 ml) was added conc. hydrochloric acid (0.5 ml) and the mixture was stirred for one hour at room temperature. The solvent was distilled off under reduced pressure and the residue was pulverized with acetone, collected by filtration, washed with acetone and diisopropyl ether to give a powder. The powder was dissolved in water (5 ml) and subjected to column chromatography on a non ionic adsorption resin Diaion HP 20 (Trademark, prepared by Mitsubishi Chemical Industries) (50 ml). After the column was washed with water (500 ml), the elution was carried out with 40% aqueous methanol. The eluates containing an object compound were collected, evaporated to remove methanol under reduced pressure and lyophilized to give white powder of N-[7-{2-carboxymethoxyimino-2-(5-amino-1,2,4-thiadiazol-3-yl)acetamido}-3-cephem-3-ylmethyl]pyridinium-4-carboxylate (syn isomer) (800 mg), mp. 150° to 155° C. (dec.).

I.R. (Nujol): 3350, 3200, 1780, 1680, 1530 cm$^{-1}$

N.M.R. (D$_2$O+NaHCO$_3$, δ): 3.27 and 3.63 (2H, ABq, J=18 Hz), 4.70 (2H, s), 5.30 (1H, d, J=4 Hz), 5.40 and 5.60 (2H, ABq, J=14 Hz), 5.93 (1H, d, J=4 Hz), 8.0–9.1 (5H, m)

EXAMPLE 61

The following compounds were obtained according to similar manners to those of Examples 27, 47, 48 and 60.

(1) N-[7-{2-(1-Carboxyethoxyimino)-2-(5-amino-1,2,4-thiadiazol-3-yl)acetamido}-3-cephem-3-ylmethyl]-4'-carbamoylpyridinium-4-carboxylate (syn isomer), mp. 170° to 175° C. (dec.).

I.R. (Nujol): 3300, 3160, 1770, 1680, 1610, 1560, 1520 cm$^{-1}$ (2) N-[7-{2-(1-Carboxyethoxyimino)-2-(5-amino-1,2,4-thiadiazol-3-yl)acetamido}-3-cephem-3-ylmethyl]pyridinium-4-carboxylate (syn isomer), mp. 175° to 180° C. (dec.).

I.R. (Nujol): 3300, 3200, 1775, 1670, 1620, 1520 cm$^{-1}$

N.M.R. (D$_2$O+NaHCO$_3$, δ): 1.50 (3H, d, J=7 Hz), 3.25 and 3.67 (2H, ABq, J=18 Hz), 4.40–4.90 (1H, m), 5.32 (1H, d, J=5 Hz), 5.42 and 5.60 (2H, ABq, J=15 Hz), 5.83–6.00 (1H, m), 7.9–9.1 (5H, m)

PREPARATION 40

The following compound was prepared according to a similar manner to that of Preparation 17. 2-Methoxycarbonylmethoxyimino-2-(5-amino-1,2,4-thiadiazol-3-yl)acetic acid (syn isomer), mp. 190°–193° C. (dec.).

IR (Nujol): 3380, 3280, 3180, 1750, 1710, 1610, 1510, 1260, 1230 cm$^{-1}$

NMR (DMSO-d$_6$, δ): 3.73 (3H, s), 4.87 (2H, s), 8.2 (2H, bs)

PREPARATION 41

To a suspension of N-[7-(2-thienylacetamido)-3-cephem-3-ylmethyl]-3'-hydroxymethylpyridinium-4-carboxylate (27.0 g) and N,N-dimethylaniline (50.8 g) in methylene chloride (240 ml) was dropped trimethylsilyl chloride (26.0 g) under stirring and the mixture was stirred for 1.5 hours at room temperature. To the resulting solution was added phosphorous pentachloride (31.2 g) at −30° C. and the mixture was stirred for one hour at −30° C. to −25° C. The mixture was added to a solution of n-butanol (120 g) in methylene chloride (240 ml) at −25° C. under stirring, and the stirring was continued for 1.5 hours at room temperature. A resulting precipitate was collected by filtration, washed with methylene chloride and dried on phosphorous pentoxide to give N-[7-amino-3-cephem-3-ylmethyl]-3'-hydroxymethylpyridinium-4-carboxylate dihydrochloride (25.5 g), mp. 120° to 125° C. (dec.).

IR (Nujol): 1780, 1700, 1630 cm$^{-1}$

NMR (DCl-D$_2$O, δ): 3.60,3.83 (2H, ABq, J=18 Hz), 4.97 (2H, s), 5.33 (1H, d, J=5 Hz), 5.47 (1H, d, J=5 Hz), 5.60,5.93 (2H, ABq, J=14 Hz), 8.0-8.33 (1H, m), 8.50-8.76 (1H, m), 8.83-9.16 (2H, m)

EXAMPLE 62

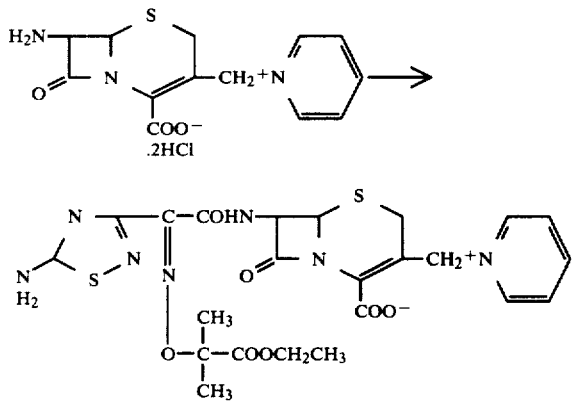

To a cold solution of phosphorous pentachloride (1.46 g) in methylene chloride (30 ml) was added 2-(1-methyl-1-ethoxycarbonylethoxyimino)-2-(5-amino-1,2,4-thiadiazol-3-yl)acetic acid (syn isomer) (2.11 g) at −18° C. and the mixture was stirred for 30 minutes at −14° to −11° C. To the reaction mixture was added dry n-hexane (90 ml) below −10° C. and the mixture was stirred for several minutes and the solvent was removed by decantation. The residue was triturated with n-hexane and collected by filtration to obtain a powder of the activated acid. On the other hand, a mixture of N-[7-amino-3-cephem-3-ylmethyl]pyridinium-4-carboxylate dihydrochloride (2 g) and trimethylsilylacetamide (10 g) in methylene chloride was stirred for 10 minutes at room temperature and cooled to −18° C. To the cold solution was added the powder obtained above and the mixture was stirred for 30 minutes at −13° to −10° C. and for 30 minutes at −5° to 0° C. The reaction mixture was poured into an aqueous solution (100 ml) of sodium bicarbonate (3.6 g) and stirred for 15 minutes at room temperature and then adjusted to pH 1 with 6 N hydrochloric acid. The aqueous layer was separated out, washed with ethyl acetate and subjected to column chromatography on a non ionic adsorption resin, Diaion HP-20 (100 ml). After the column was washed with water, 5% aqueous ethanol and 10% aqueous ethanol successively, the elution was carried out with 20% aqueous ethanol. The eluates containing an object compound were collected, evaporated to remove ethanol under reduced pressure and lyophilized to give N-[7-{2-(1-methyl-1-ethoxycarbonylethoxyimino)-2-(5-amino-1,2,4-thiadiazol-3-yl)acetamido}-3-cephem-3-ylmethyl]pyridinium-4-carboxylate (syn isomer) (1.30 g), white powder, mp. 164° to 168° C. (dec.).

IR (Nujol): 3350-3150, 1770, 1720, 1670, 1620, 1520 cm$^{-1}$

NMR (DMSO-d$_6$, δ): 1.15 (3H, t, J=7 Hz), 1.45 (6H, s), 3.03 and 3.55 (2H, ABq, J=18 Hz), 4.10 (2H, q, J=7 Hz), 5.11 (1H, d, J=5 Hz), 5.20 and 5.67 (2H, ABq, J=13 Hz), 5.75 (1H, 2d, J=5 and 8 Hz), 8.20 (4H, m), 8.57 (1H, m), 9.47 (3H, m)

EXAMPLE 63

The following compounds were prepared according to the similar manners to those of Examples 1 to 3, 5, 7 to 12, 32 to 34, 40, 57 and 62.

(1) 7-[2-Cyclopentyloxyimino-2-(5-amino-1,2,4-thiadiazol-3-yl)acetamido]-3-acetoacetoxymethyl-3-cephem-4-carboxylic acid (syn isomer), powder, mp. 130° to 135° C. (dec.).

IR (Nujol): 3300, 1780, 1720, 1680, 1620, 1525 cm$^{-1}$

NMR (DMSO-d$_6$, δ): 1.3-2.0 (8H, m), 2.15 (3H, s), 3.52 (2H, bs), 3.60 (2H, s), 4.5-4.7 (1H, m), 4.77,5.00 (2H, ABq, J=14 Hz), 5.13 (1H, d, J=4 Hz), 5.80 (1H, 2d, J=4 and 8 Hz), 8.10 (2H, s), 9.50 (1H, d, J=8 Hz)

(2) N-[7-{2-Cyclopentyloxyimino-2-(5-amino-1,2,4-thiadiazol-3-yl)acetamido}-3-cephem-3-ylmethyl]-4'-hydroxymethylpyridinium-4-carboxylate (syn isomer), mp. 155° to 160° C. (dec.).

IR (Nujol): 3350, 3200, 1775, 1670, 1615, 1525 cm$^{-1}$ (3) N-[7-{2-Cyclopentyloxyimino-2-(5-amino-1,2,4-thiadiazol-3-yl)acetamido}-3-cephem-3-ylmethyl]-3'-hydroxymethylpyridinium-4-carboxylate (syn isomer), white powder, mp. 160° to 165° C. (dec.).

IR (Nujol): 3260, 3170, 1770, 1655, 1610, 1520 cm$^{-1}$ (4) N-[7-{2-Cyclopentyloxyimino-2-(5-amino-1,2,4-thiadiazol-3-yl)acetamido}-3-cephem-3-ylmethyl]-4'-acetylpyridinium-4-carboxylate (syn isomer), mp. 145° to 150° C. (dec.).

IR (Nujol): 3270, 1770, 1700, 1670, 1610, 1520 cm$^{-1}$ (5) N-[7-{2-Cyclopentyloxyimino-2-(5-amino-1,2,4-thiadiazol-3-yl)acetamido}-3-cephem-3-ylmethyl]-3'-carboxymethylpyridinium-4-carboxylate (syn isomer), mp. 165° to 170° C. (dec.).

IR (Nujol): 3350, 3200, 1775, 1720, 1670, 1620, 1525 cm$^{-1}$ (6) N-[7-{2-Cyclopentyloxyimino-2-(5-amino-1,2,4-thiadiazol-3-yl)acetamido}-3-cephem-3-ylmethyl]-4'-hydroxyiminomethylpyridinium-4-carboxylate (syn isomer), mp. 140° to 145° C. (dec.).

IR (Nujol): 3280, 3160, 1770, 1680, 1630, 1610, 1520 cm$^{-1}$ (7) N-[7-{2-Cyclopentyloxyimino-2-(5-amino-1,2,4-thiadiazol-3-yl)acetamido}-3-cephem-3-ylmethyl]-4'-methyl-5'-(2-hydroxyethyl)thiazolium-4-carboxylate (syn isomer), mp. 150° to 155° C. (dec.).

IR (Nujol): 3330, 1780, 1670, 1610, 1530 cm$^{-1}$ (8) Acetoxymethyl 7-[2-cyclopentyloxyimino-2-(5-amino-1,2,4-thiadiazol-3-yl)acetamido]-2-methyl-3-cephem-4-carboxylate (syn isomer), mp. 183°-185° C. (dec.).

IR (Nujol): 3350, 3250, 1790, 1760, 1740, 1715, 1675, 1610, 1535 cm$^{-1}$

NMR (DMSO-d$_6$, δ): 1.43 (3H, d, J=7 Hz), 1.4–2.0 (8H, m), 2.08 (3H, s), 3.6–4.1 (1H, m), 4.6–4.9 (1H, m), 5.17 (1H, d, J=5 Hz), 5.8–6.0 (3H, m), 6.73 (1H, d, J=6 Hz), 8.16 (2H, s)

(9) 7-[2-(2-Cyclopenten-1-yloxyimino)-2-(5-amino-1,2,4-thiadiazol-3-yl)acetamido]-3-acetoacetoxymethyl-3-cephem-4-carboxylic acid (syn isomer), mp. 135° to 140° C. (dec.).

IR (Nujol): 3400, 3300, 3200, 1775, 1735, 1710, 1675, 1620, 1525 cm$^{-1}$

NMR (DMSO-d$_6$, δ): 1.93–2.47 (4H, m), 2.18 (3H, s), 3.55 (2H, bs), 3.65 (2H, s), 4.80,5.07 (2H, ABq, J=13 Hz), 5.13 (1H, d, J=5 Hz), 5.23–5.53 (1H, m), 5.70–6.23 (3H, m), 8.12 (2H, bs), 9.50 (1H, d, J=8 Hz)

(10) N-[7-{2-(2-Cyclopenten-1-yloxyimino)-2-(5-amino-1,2,4-thiadiazol-3-yl)acetamido}-3-cephem-3-ylmethyl]-4'-hydroxymethylpyridinium-4-carboxylate(-syn isomer), mp. 140° to 145° C. (dec.).

IR (Nujol): 3300, 3200, 1770, 1660, 1620, 1520 cm$^{-1}$

(11) N-[7-{2-(2-Cyclopenten-1-yloxyimino)-2-(5-amino-1,2,4-thiadiazol-3-yl)acetamido}-3-cephem-3-ylmethyl]-3'-hydroxymethylpyridinium-4-carboxylate (syn isomer), mp. 143° to 148° C. (dec.).

IR (Nujol): 3300, 3200, 1770, 1660, 1610, 1520 cm$^{-1}$

(12) N-[7-{2-(2-Cyclohexen-1-yloxyimino)-2-(5-amino-1,2,4-thiadiazol-3-yl)acetamido}-3-cephem-3-ylmethyl]pyridinium-4-carboxylate (syn isomer), mp. 150° to 155° C. (dec.).

IR (Nujol): 3300, 3200, 1775, 1660, 1610, 1520 cm$^{-1}$

NMR (DMSO-d$_6$, δ): 1.5–2.0 (6H, m), 3.13,3.57 (2H, ABq, J=17 Hz), 4.6–4.7 (1H, m), 5.07 (1H, d, J=4 Hz), 5.27,5.60 (2H, ABq, J=14 Hz), 5.80 (1H, 2d, J=4 and 8 Hz), 5.77–6.0 (2H, m), 8.17 (2H, s), 8.0–8.4 (2H, m), 8.43–8.80 (1H, m), 9.4–9.5 (2H, m), 9.55 (1H, d, J=8 Hz)

(13) 7-{2-Carboxymethoxyimino-2-(5-amino-1,2,4-thiadiazol-3-yl)acetamido}-3-acetoacetoxymethyl-3-cephem-4-carboxylic acid (syn isomer), mp. 95° to 100° C. (dec.).

IR (Nujol): 3400, 3290, 3190, 1770, 1720, 1615, 1520 cm$^{-1}$

(14) N-[7-{2-Carboxymethoxyimino-2-(5-amino-1,2,4-thiadiazol-3-yl)acetamido}-3-cephem-3-ylmethyl]-3'-hydroxymethylpyridinium-4-carboxylate (syn isomer), mp. 170° to 175° C. (dec.).

IR (Nujol): 3300, 1770, 1670, 1620, 1525 cm$^{-1}$

(15) N-[7-{2-Carboxymethoxyimino-2-(5-amino-1,2,4-thiadiazol-3-yl)acetamido}-3-cephem-3-ylmethyl]-4'-carbamoylpyridinium-4-carboxylate (syn isomer), mp. 175° to 180° C. (dec.).

IR (Nujol): 3350, 3200, 1775, 1680, 1615, 1565, 1525 cm$^{-1}$

(16) N-[7-{2-Methoxycarbonylmethoxyimino-2-(5-amino-1,2,4-thiadiazol-3-yl)acetamido}-3-cephem-3-ylmethyl]pyridinium-4-carboxylate (syn isomer), mp. 165° to 170° C. (dec.).

IR (Nujol): 3300–3150,1760, 1670, 1620, 1520 cm$^{-1}$

NMR (D$_2$O, δ): 3.17,3.70 (2H, ABq, J=18 Hz), 3.80 (3H, s), 4.93 (2H, s), 5.30 (1H, d, J=5 Hz), 5.44,5.73 (2H, ABq, J=14 Hz), 5.93 (1H, d, J=5 Hz), 8.10 (2H, m), 8.60 (1H, m), 8.98 (2H, m)

(17) N-[7-{2-Ethoxycarbonylmethoxyimino-2-(5-amino-1,2,4-thiadiazol-3-yl)acetamido}-3-cephem-3-ylmethyl]-3'-hydroxymethylpyridinium-4-carboxylate (syn isomer), mp. 155° to 160° C. (dec.).

IR (Nujol): 3400–3150, 1770, 1670, 1610 cm$^{-1}$

NMR (DMSO-d$_6$-D$_2$O, δ): 1.23 (3H, t, J=7 Hz), 3.11,3.67 (2H, ABq, J=18 Hz), 4.23 (2H, q, J=7 Hz), 4.82 (4H, bs), 5.17 (1H, d, J=5 Hz), 5.30,5.73 (2H, ABq, J=13 Hz), 5.83 (1H, d, J=5 Hz), 8.17 (1H, m), 8.60 (1H, m), 9.23 (2H, m)

(18) 7-[2-t-Butoxycarbonylmethoxyimino-2-(5-amino-1,2,4-thiadiazol-3-yl)acetamido]-3-acetoacetoxymethyl-3-cephem-4-carboxylic acid (syn isomer), mp. 105° to 110° C. (dec.).

IR (Nujol): 3350, 3250, 1780, 1720, 1620, 1525 cm$^{-1}$

NMR (DMSO-d$_6$, δ): 1.43 (9H, s), 2.17 (3H, s), 3.53 (2H, bs), 3.63 (2H, s), 4.63 (2H, s), 4.82,5.05 (2H, ABq, J=13 Hz), 5.15 (1H, d, J=5 Hz), 5.85 (1H, 2d, J=5 and 8 Hz), 8.15 (2H, bs), 9.53 (1H, d, J=8 Hz)

(19) N-[7-{2-t-Butoxycarbonylmethoxyimino-2-(5-amino-1,2,4-thiadiazol-3-yl)acetamido}-3-cephem-3-ylmethyl]-3'-hydroxymethylpyridinium-4-carboxylate (syn isomer), mp. 145° to 150° C. (dec.).

IR (Nujol): 3300, 1775, 1740, 1670, 1610, 1525 cm$^{-1}$

NMR (DMSO-d$_6$-D$_2$O, δ): 1.50 (9H, s), 3.23, 3.60 (2H, ABq, J=17 Hz), 4.65 (2H, s), 4.80 (2H, s), 5.13 (1H, d, J=4 Hz), 5.37, 5.67 (2H, ABq, J=14 Hz), 5.80 (1H, d, J=4 Hz), 8.23 (2H, s), 8.0–8.27 (1H, m), 8.43–8.67 (1H, m), 9.30–9.50 (2H, m)

(20) 7-[2-(1-Carboxy)ethoxyimino-2-(5-amino-1,2,4-thiadiazol-3-yl)acetamido]-3-acetoxyacetoxymethyl-3-cephem-4-carboxylic acid (syn isomer), brownish powder, mp. 95° to 100° C. (dec.).

IR (Nujol): 3450, 3350, 3230, 1780, 1720, 1630, 1525 cm$^{-1}$

(21) 7-[2-(1-t-Butoxycarbonyl)ethoxyimino-2-(5-amino-1,2,4-thiadiazol-3-yl)acetamido]-3-acetoacetoxymethyl-3-cephem-4-carboxylic acid (syn isomer), brownish powder, mp. 110° to 115° C. (dec.).

IR (Nujol): 3400, 3300, 3200, 1780, 1720, 1620, 1525 cm$^{-1}$

NMR (DMSO-d$_6$, δ): 1.40 (3H, d, J=7 Hz), 1.42 (9H, s), 2.17 (3H, s), 3.57 (2H, bs), 3.63 (2H, s), 4.58–5.22 (3H, m), 5.17 (1H, d, J=5 Hz), 5.73–5.97 (1H, m), 8.10 (2H, bs), 9.33–9.57 (1H, m)

(22) 7-[2-(1-Methyl-1-carboxyethoxyimino)-2-(5-amino-1,2,4-thiadiazol-3-yl)acetamido]-3-acetoacetoxymethyl-3-cephem-4-carboxylic acid (syn isomer), mp. 180° to 185° C. (dec.).

IR (Nujol): 3350, 3250, 1780, 1720, 1625, 1525 cm$^{-1}$

(23) N-[7-{2-(1-Methyl-1-carboxyethoxyimino)-2-(5-amino-1,2,4-thiadiazol-3-yl)acetamido}-3-cephem-3-ylmethyl]pyridinium-4-carboxylate (syn isomer), white powder, mp. 176° to 180° C. (dec.).

IR (Nujol): 3400–3150, 1770, 1670, 1620, 1520 cm$^{-1}$

(24) N-[7-{2-(1-Methyl-1-ethoxycarbonylethoxyimino)-2-(5-amino-1,2,4-thiadiazol-3-yl)acetamido}-3-cephem-3-ylmethyl]-3'-hydroxymethylpyridinium-4-carboxylate (syn isomer), mp. 155° to 160° C. (dec.).

IR (Nujol): 3400–3200, 1780, 1740, 1680 cm$^{-1}$

NMR (DMSO-d$_6$-D$_2$O, δ): 1.16 (3H, t, J=7 Hz), 1.48 (6H, s), 3.16,3.62 (2H, ABq, J=18 Hz), 4.16 (2H, q, J=7 Hz), 4.80 (2H, s), 5.14 (1H, d, J=5 Hz), 5.2–5.8 (2H, m), 5.80 (1H, d, J=5 Hz), 8.20 (1H, m), 8.56 (1H, m), 9.32 (2H, m)

(25) 7-[2-(1-Methyl-1-t-butoxycarbonylethoxyimino)-2-(5-amino-1,2,4-thiadiazol-3-yl)acetamido]-3-acetoacetoxymethyl-3-cephem-4-carboxylic acid (syn isomer), mp. 140° to 145° C. (dec.).

IR (Nujol): 3350, 3250, 1785, 1720, 1620, 1530 cm$^{-1}$

NMR (DMSO-d$_6$, δ): 1.47 (6H, s), 1.50 (9H, s), 2.17 (3H, s), 3.57 (2H, bs), 3.63 (2H, s), 4.80,5.07 (2H, ABq, J=14 Hz), 5.17 (1H, d, J=4 Hz), 5.86 (1H, 2d, J=4 and 8 Hz), 8.13 (2H, s), 9.43 (1H, d, J=8 Hz)

(26) N-[7-{2-(1-Methyl-1-t-butoxycarbonylethoxyimino)-2-(5-amino-1,2,4-thiadiazol-3-yl)acetamido}-3- cephem-3-ylmethyl]pyridinium-4-carboxylate (syn isomer), mp. 176° to 180° C. (dec.).

IR (Nujol): 3300, 3200, 1780, 1730, 1680, 1620, 1520 cm$^{-1}$

NMR (DMSO-d$_6$-D$_2$O, δ): 1.40 (15H, bs), 3.08, 3.42 (2H, ABq, J=18 Hz), 5.13 (1H, d, J=5 Hz), 5.40 (2H, m), 5.80 (1H, d, J=5 Hz), 8.17 (2H, m), 8.65 (1H, m), 9.37 (2H, m)

EXAMPLE 64

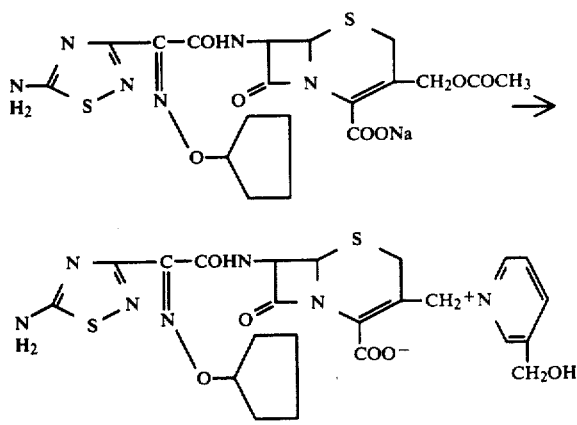

A mixture of 3-hydroxymethylpyridine (1.3 g) and potassium iodide (7.95 g) in water (5.3 ml) was warmed to 60° C. under stirring and sodium 7-[2-cyclopentyloxyimino-2-(5-amino-1,2,4-thiadiazol-3-yl)acetamido]-cephalosporanate (syn isomer) (5.32 g) was added thereto. The mixture was stirred for 5 hours at 60° C. and diluted with a mixture of water (100 ml), ethyl acetate (50 ml) and acetone (10 ml). The mixture was adjusted to pH 1 with 6 N hydrochloric acid and the aqueous layer was separated out. The aqueous solution was evaporated to remove acetone and ethyl acetate and subjected to column chromatography on a non ionic adsorption resin, Diaion HP20 (160 ml). After the column was washed with water (500 ml), the elution was carried out with 40% aqueous methanol. The eluates containing a object compound were collected, evaporated to remove methanol under reduced pressure and lyophilized to give N-[7-{2-cyclopentyloxyimino-2-(5-amino-1,2,4-thiadiazol-3-yl)acetamido}-3-cephem-3-ylmethyl]-3'-hydroxymethylpyridinium-4-carboxylate (syn isomer) (1.2 g), white powder, mp. 160° to 165° C. (dec.).

IR (Nujol): 3260, 3170, 1770, 1655, 1610, 1520 cm$^{-1}$

NMR (DMSO-d$_6$, δ): 1.33-2.00 (8H, m), 3.17, 3.50 (2H, ABq, J=18 Hz), 4.57-4.90 (3H, m), 5.08 (1H, d, J=5 Hz), 5.30, 5.65 (2H, ABq, J=14 Hz), 5.70 (1H, 2d, J=5 and 8 Hz), 8.00-8.33 (3H, m), 8.33-8.67 (1H, m), 9.17-9.43 (2H, m), 9.42 (1H, d, J=8 Hz)

EXAMPLE 65

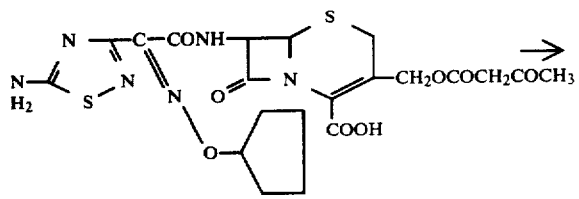

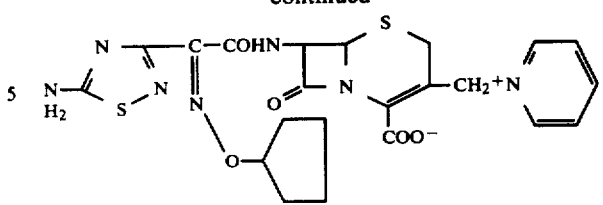

A mixture of 7-[2-cyclopentyloxyimino-2-(5-amino-1,2,4-thiadiazol-3-yl)acetamido]-3-acetoacetoxymethyl-3-cephem-4-carboxylic acid (syn isomer) (2.8 g), sodium bicarbonate (420 mg), potassium iodide (28 g) and pyridine (590 mg) in water (28 ml) was stirred for one hour at 55° C. After cooling, ethyl acetate (20 ml), 1 N hydrochloric acid (5.5 ml) and acetone (10 ml) were added thereto under stirring. The aqueous layer was separated out, washed with ethyl acetate and concentrated to 30 ml under reduced pressure. An insoluble substance was filtered off and the filtrate was subjected to column chromatography on a non ionic adsorption resin, Diaion HP20 (100 ml). After the column was washed with water (500 ml), the elution was carried out with 30% aqueous methanol. The eluates containing a object compound were collected, evaporated to remove methanol under reduced pressure and lyophilized to give N-[7-{2-cyclopentyloxyimino-2-(5-amino-1,2,4-thiadiazol-3-yl)acetamido}-3-cephem-3-ylmethyl]pyridinium-4-carboxylate (syn isomer) (620 mg), white powder, mp. 180° to 185° C. (dec.).

IR (Nujol): 3300, 3200, 1780, 1670, 1620, 1530 cm$^{-1}$

NMR (DMSO-d$_6$, δ): 1.4-2.0 (8H, m), 3.17 3.53 (2H, ABq, J=18 Hz), 4.60-4.83 (1H, m), 5.10 (1H, d, J=4 Hz), 5.30, 5.83 (2H, ABq, J=14 Hz), 5.87 (1H, 2d, J=4 and 8 Hz), 8.17 (2H, s), 9.50 (1H, d, J=8 Hz), 8.0-9.7 (5H, m)

EXAMPLE 66

The following compounds were prepared according to the similar manners to those of Examples 14 to 17, 42, 64 and 65.

(1) N-[7-{2-Cyclopentyloxyimino-2-(5-amino-1,2,4thiadiazol-3-yl)acetamido}-3-cephem-3-ylmethyl]-4'-hydroxymethylpyridinium-4-carboxylate (syn isomer), mp. 155° to 160° C. (dec.).

IR (Nujol): 3350, 3200, 1775, 1670, 1615, 1525 cm$^{-1}$

NMR (DMSO-d$_6$, δ): 1.20-2.00 (8H, m), 3.13, 3.50 (2H, ABq, J=18 Hz), 4.57-4.98 (3H, m), 5.08 (1H, d, J=5 Hz) 5.25, 5.60 (2H, ABq, J=14 Hz), 5.67 (1H, 2d, J=5 and 8 Hz), 8.05 (2H, d, J=6 Hz), 8.10 (2H, bs), 9.27 (2H, d, J=6 Hz), 9.40 (1H, d, J=8 Hz)

(2) N-[7-{2-Cyclopentyloxyimino-2-(5-amino-1,2,4-thiadiazol-3-yl)acetamido}-3-cephem-3-ylmethyl]-4'-acetylpyridinium-4-carboxylate (syn isomer), mp. 145° to 150° C. (dec.).

IR (Nujol): 3270, 1770, 1700, 1670, 1610, 1520 cm$^{-1}$

NMR (DMSO-d$_6$-D$_2$O, δ): 1.33-2.00 (8H, m), 2.67 (3H, s), 3.07, 3.45 (2H, ABq, J=18 Hz), 4.50-4.77 (1H, m), 5.02 (1H, d, J=5 Hz), 5.25, 5.58 (2H, ABq, J=14 Hz), 5.63 (1H, d, J=5 Hz), 8.40 (2H, d, J=6 Hz), 9.52 (2H, d, J=6 Hz)

(3) N-[7-{2-Cyclopentyloxyimino-2-(5-amino-1,2,4-thiadiazol-3-yl)acetamido}-3-cephem-3-ylmethyl]-3'-carboxymethylpyridinium-4-carboxylate (syn isomer), mp. 165° to 170° C. (dec.).

IR (Nujol): 3350, 3200, 1775, 1720, 1670, 1620, 1525 cm$^{-1}$

NMR (DMSO-d₆-D₂O, δ): 1.30–2.00 (8H, m), 3.17, 3.52 (2H, ABq, J=18 Hz), 3.93 (2H, s), 4.57–4.87 (1H, m), 5.07 (1H, d, J=5 Hz), 5.27, 5.63 (2H, ABq, J=14 Hz), 5.70 (1H, d, J=5 Hz), 7.93–8.23 (1H, m), 8.37–8.63 (1H, m), 9.10–9.37 (2H, m)

(4) N-[7-{2-Cyclopentyloxyimino-2-(5-amino-1,2,4-thiadiazol-3-yl)acetamido}-3-cephem-3-ylmethyl]-4′-hydroxyiminomethylpyridinium-4-carboxylate (syn isomer), mp. 140° to 145° C. (dec.).

IR (Nujol): 3280, 3160, 1770, 1680, 1630, 1610, 1520 cm⁻¹

NMR (DMSO-d₆, δ): 1.33–2.00 (8H, m), 3.23, 3.57 (2H, ABq, J=18 Hz), 4.57–4.90 (1H, m), 5.12 (1H, d, J=5 Hz), 5.28, 5.65 (2H, ABq, J=14 Hz), 5.73 (1H, 2d, J=5 and 8 Hz), 8.18 (2H, bs), 8.25 (2H, d, J=6 Hz), 8.42 (1H, s), 9.35 (2H, d, J=6 Hz), 9.43 (1H, d, J=8 Hz)

(5) N-[7-{2-Cyclopentyloxyimino-2-(5-amino-1,2,4-thiadiazol-3-yl)acetamido}-3-cephem-3-ylmethyl]-4′-methyl-5′-(2-hydroxyethyl)thiazolium-4-carboxylate (syn isomer), mp. 150° to 155° C. (dec.).

IR (Nujol): 3330, 1780, 1670, 1610, 1530 cm⁻¹

NMR (DMSO-d₆, δ): 1.33–2.00 (8H, m), 2.57 (3H, s), 2.90–3.17 (2H, m), 3.17–3.43 (2H, m), 3.57–3.80 (2H, m), 4.60–4.90 (1H, m), 5.07 (1H, d, J=5 Hz), 5.37 (2H, bs), 5.70 (1H, 2d, J=5 and 8 Hz), 8.17 (2H, bs), 9.43 (1H, d, J=8 Hz), 10.23 (1H, s)

(6) N-[7-{2-(2-Cyclopenten-1-yloxyimino)-2-(5-amino-1,2,4-thiadiazol-3-yl)acetamido}-3-cephem-3-ylmethyl]-4′-hydroxymethylpyridinium-4-carboxylate (syn isomer), mp. 140° to 145° C. (dec.).

IR (Nujol): 3300, 3200, 1770, 1660, 1620, 1520 cm⁻¹

NMR (DMSO-d₆, δ): 1.8–2.5 (4H, m), 3.13, 3.50 (2H, ABq, J=18 Hz), 4.83 (2H, s), 5.07 (1H, d, J=4 Hz), 5.20–5.40 (1H, m), 5.27, 5.67 (2H, ABq, J=14 Hz), 5.80 (1H, 2d, J=4 and 8 Hz), 5.87–6.20 (2H, m), 8.07 (2H, d, J=7 Hz), 8.17 (2H, s), 9.33 (2H, d, J=7 Hz), 9.47 (1H, d, J=8 Hz)

(7) N-[7-{2-(2-Cyclopenten-1-yloxyimino)-2-(5-amino-1,2,4-thiadiazol-3-yl)acetamido}-3-cephem-3-ylmethyl]-3′-hydroxymethylpyridinium-4-carboxylate (syn isomer), mp. 143° to 148° C. (dec.).

IR (Nujol): 3300, 3200, 1770, 1660, 1610, 1520 cm⁻¹

NMR (DMSO-d₆, δ): 1.8–2.5 (4H, m), 3.13, 3.47 (2H, ABq, J=17 Hz), 4.73 (2H, s), 5.35 (1H, d, J=4 Hz), 5.17–5.40 (1H, m), 5.40–6.20 (5H, m), 8.13 (2H, s), 8.0–8.30 (1H, m), 8.37–8.60 (1H, m), 9.27–9.43 (2H, m), 9.47 (1H, d, J=8 Hz)

(8) N-[7-{2-(2-Cyclohexen-1-yloxyimino)-2-(5-amino-1,2,4-thiadiazol-3-yl)acetamido}-3-cephem-3-ylmethyl]pyridinium-4-carboxylate (syn isomer), mp. 150° to 155° C. (dec.).

IR (nujol): 3300, 3200, 1775, 1660, 1610, 1520 cm⁻¹

(9) N-[7-{2-Carboxymethoxyimino-2-(5-amino-1,2,4-thiadiazol-3-yl)acetamido}-3-cephem-3-ylmethyl]-3′-hydroxymethylpyridinium-4-carboxylate (syn isomer), mp. 170° to 175° C. (dec.).

IR (Nujol): 3300, 1770, 1670, 1620, 1525 cm⁻¹

(10) N-[7-{2-Carboxymethoxyimino-2-(5-amino-1,2,4-thiadiazol-3-yl)acetamido}-3-cephem-3-ylmethyl]-4′-carbamoylpyridinium-4-carboxylate (syn isomer), mp. 175° to 180° C. (dec.).

IR (Nujol): 3350, 3200, 1775, 1680, 1615, 1565, 1525 cm⁻¹

NMR (DMSO-d₆-D₂O, δ): 3.23, 3.55 (2H, ABq, J=18 Hz), 4.67 (2H, s), 5.10 (1H, d, J=5 Hz), 5.35, 5.72 (2H, ABq, J=15 Hz), 5.80 (1H, d, J=5Hz), 8.43 (2H, d, J=6 Hz), 9.38 (2H, d, J=6 Hz)

(11) N-[7-{2-Methoxycarbonylmethoxyimino-2-(5-amino-1,2,4-thiadiazol-3-yl)acetamido}-3-cephem-3-ylmethyl]pyridinium-4-carboxylate (syn isomer), mp. 165°–170° C. (dec.).

IR (Nujol): 3300–3150, 1760, 1670, 1620, 1520 cm⁻¹

(12) N-[7-{2-Ethoxycarbonylmethoxyimino-2-(5-amino-1,2,4-thiadiazol-3-yl)acetamido}-3-cephem-3-ylmethyl]-3′-hydroxymethylpyridinium-4-carboxylate (syn isomer), mp. 155° to 160° C. (dec.).

IR (Nujol): 3400–3150, 1770, 1670, 1610 cm⁻¹

(13) N-[7-{2-t-Butoxycarbonylmethoxyimino-2-(5-amino-1,2,4-thiadiazol-3-yl)acetamido}-3-cephem-3-ylmethyl]-3′-hydroxymethylpyridinium-4-carboxylate (syn isomer), mp. 145° to 150° C. (dec.).

IR (Nujol): 3300, 1775, 1740, 1670, 1610, 1525 cm⁻¹

(14) N-[7-{2-(1-Methyl-1-carboxyethoxyimino)-2-(5-amino-1,2,4-thiadiazol-3-yl)acetamido}-3-cephem-3-ylmethyl]pyridinium-4-carboxylate (syn isomer), white powder, mp. 176° to 180° C. (dec.).

IR (Nujol): 3400–3150, 1770, 1670, 1620, 1520 cm⁻¹

(15) N-[7-{2-(1-Methyl-1-ethoxycarbonylethoxyimino)-2-(5-amino-1,2,4-thiadiazol-3-yl)acetamido}-3-cephem-3-ylmethyl]pyridinium-4-carboxylate (syn isomer), white powder, mp. 164° to 168° C. (dec.).

IR (Nujol): 3350–3150, 1700, 1720, 1670, 1620, 1520 cm⁻¹

(16) N-[7-{2-(1-Methyl-1-ethoxycarbonylethoxyimino)-2-(5-amino-1,2,4-thiadiazol-3-yl)acetamido}-3-cephem-3-ylmethyl]-3′-hydroxymethylpyridinium-4-carboxylate (syn isomer), mp. 155° to 160° C. (dec.).

IR (Nujol): 3400–3200, 1780, 1740, 1680 cm⁻¹

(17) N-[7-{2-(1-Methyl-1-t-butoxycarbonylethoxyimino)-2-(5-amino-1,2,4-thiadiazol-3-yl)acetamido}-3-cephem-3-ylmethyl]pyridinium-4-carboxylate (syn isomer), mp. 176° to 180° C. (dec.).

IR (Nujol): 3300, 3200, 1780, 1730, 1680, 1620, 1520 cm⁻¹

EXAMPLE 67

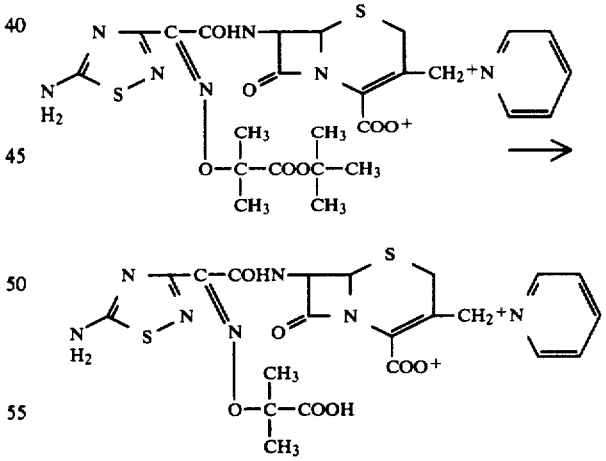

To a cold mixture of trifluoroacetic acid (22 ml) and anisole (4.4 ml) was added N-[7-{2-(1-methyl-1-t-butoxycarbonylethoxyimino)-2-(5-amino-1,2,4-thiadiazol-3-yl)acetamido}-3-cephem-3-ylmethyl]-pyridinium-4-carboxylate (3.18 g) and the mixture was stirred for 40 minutes at room temperature. The mixture was evaporated to remove trifluoroacetic acid and the residue was triturated with isopropyl ether to give a yellowish powder. The powder was dissolved in an aqueous sodium bicarbonate, adjusted to pH 1 with 6 N hydrochloric acid and washed with ethyl acetate. The aqueous solution was subjected to a column chromatography on a non ionic adsorption resin, Diaion HP-20 (140 ml). After the column was washed with water, the elution was carried out with 5% and 10% aqueous isopropyl alcohol. The eluates containing an object compound were collected, evaporated to remove isopropyl alcohol under reduced pressure and lyophilized to give N-[7-{2-(1-methyl-1-carboxyethoxyimino)-2-(5-amino-1,2,4-thiadiazol-3-yl)acetamido]-3-cephem-3-ylmethyl]-pyridinium-4-carboxylate (syn isomer) (2.20 g), white powder, mp. 176° to 180° C. (dec.).

IR (Nujol): 3400-3150, 1770, 1670, 1620, 1520 cm$^{-1}$

NMR (DMSO-d$_6$+D$_2$O, δ): 1.48 (6H, s), 3.10, 3.62 (2H, ABq, J=18 Hz), 5.12 (1H, d, J=5 Hz), 5.45 (2H, m), 5.78 (1H, d, J=5 Hz), 8.13 (2H, m), 8.58 (1H, m), 9.38 (2H, m)

EXAMPLE 68

The following compounds were prepared according to the similar manners to those of Examples 27, 47, 48, 60 and 67.

(1) 7-[2-Carboxymethoxyimino-2-(5-amino-1,2,4-thiadiazol-3-yl)acetamido]-3-acetoacetoxymethyl-3-cephem-4-carboxylic acid (syn isomer), mp. 95° to 100° C. (dec.).

IR (Nujol): 3400, 3290, 3190, 1770, 1720, 1615, 1520 cm$^{-1}$

NMR (DMSO-d$_6$, δ): 2.17 (3H, s), 3.53 (2H, bs), 3.63 (2H, s), 4.67 (2H, s), 4.80, 5.07 (2H, ABq, J=13 Hz), 5.15 (1H, d, J=5 Hz), 5.87 (1H, 2d, J=5 and 8 Hz), 8.15 (2H, bs), 9.53 (1H, d, J=8 Hz)

(2) N-[7-{2-Carboxymethoxyimino-2-(5-amino-1,2,4-thiadiazol-3-yl)acetamido}-3-cephem-3-ylmethyl]-3'-hydroxymethylpyridinium-4-carboxylate (syn isomer), mp. 170° to 175° C. (dec.).

IR (Nujol): 3300, 1770, 1670, 1620, 1525 cm$^{-1}$

NMR (DMSO-d$_6$+D$_2$O, δ): 3.20, 3.50 (2H, ABq, J=18 Hz), 4.63 (2H, s), 4.73 (2H, s), 5.07 (1H, d, J=4 Hz), 5.27, 5.60 (2H, ABq, J=14 Hz), 5.87 (1H, d, J=4 Hz), 7.90-8.17 (1H, m), 8.37-8.60 (1H, m), 9.0-9.3 (2H, m)

(3) N-[7-{2-Carboxymethoxyimino-2-(5-amino-1,2,4-thiadiazol-3-yl)acetamido}-3-cephem-3-ylmethyl]-4'-carbamoylpyridinium-4-carboxylate (syn isomer), mp. 175° to 180° C. (dec.).

IR (Nujol): 3350, 3200, 1775, 1680, 1615, 1565, 1525 cm$^{-1}$ (4) 7-[2-(1-Carboxy)ethoxyimino-2-(5-amino-1,2,4-thiadiazol-3-yl)acetamido]-3-acetoacetoxymethyl-3-cephem-4-carboxylic acid (syn isomer), brownish powder, mp. 95° to 100° C. (dec.).

IR (Nujol): 3450, 3350, 3230, 1780, 1720, 1630, 1525 cm$^{-1}$

NMR (DMSO-d$_6$, δ): 1.45 (3H, d, J=7 Hz), 2.20 (3H, s), 3.58 (2H, bs), 3.67 (2H, s), 4.65-5.30 (3H, m), 5.22 (1H, d, J=5 Hz), 5.77-6.10 (1H, m), 8.23 (2H, bs), 9.40-9.68 (1H, m)

(5) 7-[2-(1-Methyl-1-carboxyethoxyimino)-2-(5-amino-1,2,4-thiadiazol-3-yl)acetamido]-3-acetoacetoxymethyl-3-cephem-4-carboxylic acid (syn isomer), mp. 180° to 185° C. (dec.).

IR (Nujol): 3350, 3250, 1780, 1720, 1625, 1525 cm$^{-1}$

NMR (DMSO-d$_6$, δ): 1.47 (6H, s), 2.17 (3H, s), 3.55 (2H, bs), 3.62 (2H, s), 4.80, 5.03 (2H, ABq, J=14 Hz), 5.17 (1H, d, J=4 Hz), 5.87 (1H, 2d, J=4 and 8 Hz), 8.13 (2H, s), 9.47 (1H, d, J=8 Hz)

EXAMPLE 69

The following compounds were obtained according to similar manners to those of Examples 1-3, 5, 7-12, 14-17, 32-34, 40, 42, 57, 62, 64 and 65.

(1) 7-[2-Allyloxyimino-2-(5-amino-1,2,4-thiadiazol-3-yl)acetamido]-3-(1-pyridiniomethyl)-3-cephem-4-carboxylate (syn isomer), mp 160° to 165° C. (dec.).

IR (Nujol): 3290, 3180, 1770, 1660, 1610, 1525 cm$^{-1}$

NMR (DMSO-d$_6$+D$_2$O, δ): 3.12, 3.50 (2H, ABq, J=18 Hz), 4.44-4.76 (2H, m), 5.10 (1H, d, J=5 Hz), 5.0-6.1 (6H, m), 8.0-8.4 (2H, m), 8.44-8.76 (1H, m), 9.32-9.68 (2H, m)

(2) 7-[2-(2-Propynyloxyimino)-2-(5-amino-1,2,4-thiadiazol-3-yl)acetamido]-3-(1-pyridiniomethyl)-3-cephem-4-carboxylate (syn isomer), mp 145° to 150° C. (dec.).

IR (Nujol): 3250, 2100, 1770, 1660, 1630, 1610, 1525 cm$^{-1}$

NMR (DMSO-d$_6$, δ): 3.10, 3.55 (2H, ABq, J=18 Hz), 3.47 (1H, t, J=2 Hz), 4.73 (2H, d, J=2 Hz), 5.08 (1H, d, J=5 Hz), 5.25, 5.65 (2H, ABq, J=14 Hz), 5.60-5.93 (1H, m), 8.0-8.4 (4H, m), 8.4-8.8 (1H, m), 9.3-9.7 (3H, m)

(3) 7-[2-Hydroxyimino-2-(5-amino-1,2,4-thiadiazol-3-yl)acetamido]-3-(1-pyridiniomethyl)-3-cephem-4-carboxylate (syn isomer), mp 170° to 175° C. (dec.).

IR (Nujol): 3350, 3200, 1780, 1620, 1530, 1490 cm$^{-1}$ (4) 7-[2-Methylthiomethoxyimino-2-(5-amino-1,2,4-thiadiazol-3-yl)acetamido]-3-(1-pyridiniomethyl)-3-cephem-4-carboxylate (syn isomer), mp 195° to 205° C. (dec.).

IR (Nujol): 3350-3150, 1770, 1670, 1620, 1520, 1150 cm$^{-1}$

NMR (DMSO-d$_6$+D$_2$O, δ): 2.17 (3H, s), 3.00, 3.62 (2H, ABq, J=18 Hz), 5.10 (1H, d, J=5 Hz), 5.22 (2H, s), 5.73 (1H, d, J=5 Hz), 5.00-5.83 (2H, m), 8.13 (2H, m), 8.53 (1H, m), 9.33 (2H, m)

(5) 7-[2-Trityloxyimino-2-(5-amino-1,2,4-thiadiazol-3-yl)acetamido]-3-(1-pyridiniomethyl)-3-cephem-4-carboxylate (syn isomer), mp 165° to 170° C. (dec.).

IR (Nujol): 3450, 1780, 1670, 1620, 1530, 1490 cm$^{-1}$

NMR (DMSO-d$_6$, δ): 3.18, 3.64 (2H, ABq, J=18 Hz), 5.18 (1H, d, J=5 Hz), 5.34, 5.74 (2H, ABq, J=12 Hz), 5.92 (1H, dd, J=5 and 8 Hz), 7.28 (15H, s), 7.94-8.30 (4H, m), 8.42-8.66 (1H, m), 9.22-9.54 (2H, m), 9.78 (1H, d, J=8 Hz)

(6) 7-[2-(2,2,2-Trifluoroethoxyimino)-2-(5-amino-1,2,4-thiadiazol-3-yl)acetamido]-3-)1-pyridiniomethyl)-3-cephem-4-carboxylate (syn isomer), mp 150° to 155° C. (dec.).

IR (Nujol): 3300, 1780, 1675, 1630, 1530 cm$^{-1}$

NMR (DMSO-d$_6$+D$_2$O, δ): 3.23, 3.50 (2H, ABq, J=18 Hz), 4.63, 4.93 (2H, ABq, J=9 Hz), 5.17 (1H, d, J=5 Hz), 5.37, 5.73 (2H, ABq, J=14 Hz), 5.83 (1H, d, J=5 Hz), 8.1-8.4 (2H, m), 8.5-8.8 (1H, m), 9.3-9.6 (2H, m)

(7) 7-[2-(2-Oxotetrahydrofuran-3-yloxyimino)-2-(5-amino-1,2,4-thiadiazol-3-yl)acetamio]-3-(1-pyridiniomethyl)-3-cephem-4-carboxylate (syn isomer), mp 140° to 145° C. (dec.).

IR (Nujol): 3350, 1780, 1670, 1620, 1530, 1490 cm$^{-1}$

NMR (DMSO-d$_6$+D$_2$O, δ): 2.43-2.83 (2H, m), 3.27, 3.63 (2H, ABq, J=18 Hz), 4.23-4.67 (2H, m), 5.17-5.37 (1H, m), 5.20 (1H, d, J=5 Hz), 5.38, 5.73 (2H, ABq, J=13 Hz), 5.87 (1H, d, J=5 Hz), 8.07-8.43 (2H, m), 8.53-8.80 (1H, m), 9.23-9.50 (2H, m)

(8) 7-[2-Allyloxyimino-2-(5-amino-1,2,4-thiadiazol-3-yl)acetamido]-3-(4-carbamoyl-1-pyridiniomethyl)-3- cephem-4-carboxylate (syn isomer), mp 161° to 165° C. (dec.).

IR (Nujol): 3400–3150, 1770, 1670, 1610, 1560, 1520 cm$^{-1}$ (9) 7-[2-(2,2,2-Trifluoroethoxyimino)-2-(5-amino-1,2,4-thiadiazol-3-yl)acetamido]-3-(4-carbamoyl-1-pyridiniomethyl)-3-cephem-4-carboxylate (syn isomer), mp 160° to 165° C. (dec.).

IR (Nujol): 3300, 3150, 1780, 1680, 1610, 1580, 1520 cm$^{-1}$

(10) 7-[2-Methylthiomethoxyimino-2-(5-amino-1,2,4-thiadiazol-3-yl)acetamido]-3-(4-carbamoyl-1-pyridiniomethyl)-3-cephem-4-carboxylate (syn isomer), mp 160° to 165° C. (dec.).

IR (Nujol): 3300, 3150, 1770, 1680, 1610, 1560, 1520 cm$^{-1}$

(11) 7-[2-(2-Propynyloxyimino)-2-(5-amino-1,2,4-thiadiazol-3-yl)acetamido]-3-(4-carbamoyl-1-pyridiniomethyl)-3-cephem-4-carboxylate (syn isomer), mp. 155° to 160° C. (dec.).

IR (Nujol): 3400, 3250, 3150, 2120, 1770, 1685, 1610, 1560, 1525 cm$^{-1}$

(12) Sodium 7-[2-cyclopentyloxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylate (syn isomer), mp 169° to 174° C. (dec.).

IR (Nujol): 3600–3100, 1760, 1690, 1665, 1640, 1610, 1520, 1005 cm$^{-1}$

(13) 7-[2-(2-Cyclopenten-1-yloxyimino)-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer), mp 158° to 164° C. (dec.).

IR (Nujol): 3450–3150, 1770, 1680, 1630, 1510, 1260, 1180, 1100, 1030, 1010 cm$^{-1}$ NMR (DMSO-d$_6$, δ): 2.0–2.6 (4H, m), 3.2–4.0 (2H, m), 3.62 (3H, s), 4.13, 4.45 (2H, ABq, J=13 Hz), 5.13 (1H, d, J=5 Hz), 5.2–5.5 (1H, m), 5.7–6.0 (2H, m), 6.0–6.2 (1H, m), 8.20 (2H, broad s), 9.50 (1H, d, J=8 Hz)

(14) 7-[2-(2-Propynyloxyimino)-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer), mp 161° to 166° C. (dec.).

IR (Nujol): 3260, 3180, 1770, 1670, 1620, 1520, 1335 cm$^{-1}$

NMR (DMSO-d$_6$+D$_2$O, δ): 3.48 (1H, s), 3.61 (3H, s), 3.3–3.9 (2H, m), 4.10, 4.38 (2H, ABq, J=14 Hz), 4.77 (2H, s), 5.12 (1H, d, J=5 Hz), 5.78 (1H, d, J=5 Hz)

(15) 7-[2-Allyloxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer), mp 169° to 173° C. (dec.).

IR (Nujol): 3360, 3210, 1775, 1670, 1625, 1560, 1520, 1250, 1175, 1100, 1020 cm$^{-1}$ NMR (DMSO-d$_6$, δ): 3.3–4.0 (2H, m), 3.58 (3H, s), 4.0–4.6 (2H, m), 4.5–4.8 (2H, m), 5.13 (1H, d, J=5 Hz), 5.0–5.6 (3H, m), 5.81 (1H, dd, J=5 and 9 Hz), 8.18 (2H, broad s), 9.53 (1H, d, J=9 Hz)

(16) Sodium 7-[2-allyloxyimino-2-(5-amino-1,2,4-thiadiazol-3-yl)acetamido]-3-acetoacetoxymethyl-3-cephem-4-carboxylate (syn isomer), mp 160° to 170° C. (dec.).

IR (Nujol): 3450, 3300, 3100, 1790, 1720, 1670, 1550 cm$^{-1}$

NMR (D$_2$O, δ): 2.31 (3H, s), 3.33, 3.64 (2H, ABq, J=18 Hz), 4.6–5.1 (4H, m), 5.1–5.5 (2H, m), 5.20 (1H, d, J=5 Hz), 5.8–6.3 (1H, m), 5.84 (1H, d, J=5 Hz)

(17) Sodium 7-[2-(2,2,2-trifluoroethoxyimino)-2-(5-amino-1,2,4-thiadiazol-3-yl)acetamido]-3-acetoacetoxymethyl-3-cephem-4-carboxylate (syn isomer), mp 128° to 132° C. (dec.).

IR (Nujol): 3300, 1780, 1710, 1670, 1600, 1530 cm$^{-1}$

NMR (D$_2$O, δ): 2.32 (3H, s), 3.50, 3.63 (2H, ABq, J=17 Hz), 4.60–5.07 (4H, m), 5.23 (1H, d, J=4 Hz), 5.87 (1H, d, J=4 Hz)

(18) Sodium 7-[2-methylthiomethoxyimino-2-(5-amino-1,2,4-thiadiazol-3-yl)acetamido]-3-acetoacetoxymethyl-3-cephem-4-carboxylate (syn isomer), mp 180° to 190° C. (dec.).

IR (Nujol): 3500–3200, 1770, 1670, 1620, 1530 cm$^{-1}$

NMR (DMSO-d$_6$, δ): 2.18 (3H, s), 2.20 (3H, s), 3.16, 3.48 (2H, ABq, J=18 Hz), 3.58 (2H, s), 4.84, 5.08 (2H, ABq, J=12 Hz), 4.98 (1H, d, J=5 Hz), 5.22 (2H, s), 5.62 (1H, dd, J=5 and 8 Hz), 8.14 (2H, broad s), 9.48 (1H, d, J=8 Hz)

(19) 7-[2-(2-Propynyloxyimino)-2-(5-amino-1,2,4-thiadiazol-3-yl)acetamido]-3-acetoacetoxymethyl-3-cephem-4-carboxylic acid (syn isomer), mp 90° to 95° C. (dec.).

IR (Nujol): 3400, 3280, 3200, 2100, 1770, 1740, 1710, 1670, 1620 cm$^{-1}$

NMR (DMSO-d$_6$, δ): 2.18 (3H, s), 3.46 (1H, t, J=2 Hz), 3.46, 3.58 (2H, ABq, J=18 Hz), 3.62 (2H, s), 4.76 (2H, d, J=2 Hz), 4.78, 5.02 (2H, ABq, J=14 Hz), 5.12 (1H, d, J=5 Hz), 5.80 (1H, dd, J=5 and 8 Hz), 8.10 (2H, broad s), 9.60 (1H, d, J=8 Hz)

EXAMPLE 70

A mixture of 7-[2-trityloxyimino-2-(5-amino-1,2,4-thiadiazol-3-yl)acetamido]-3-(1-pyridiniomethyl)-3-cephem-4-carboxylate (syn isomer) (5.55 g) and concentrated hydrochloric acid (2.3 ml) in formic acid (60 ml) was stirred for two hours at ambient temperature. After an insoluble material was filtered off, the filtrate was evaporated to dryness and the residue was pulverized with acetone and collected by filtration. The powder was dissolved in water (13 ml) and subjected to column chromatography on a non-ionic adsorption resin Diaion HP20 (Trademark, prepared by Mitsubishi Chemical Industries) (100 ml), using water as an eluent. The eluates containing an object compound were collected and lyophilized to give yellowish white powder of 7-[2-hydroxyimino-2-(5-amino-1,2,4-thiadiazol-3-yl)acetamido]-3-(1-pyridiniomethyl)-3-cephem-4-carboxylate (syn isomer) (675 mg), mp 170° to 175° C. (dec.).

IR (Nujol): 3350, 3200, 1780, 1620, 1530, 1490 cm$^{-1}$

NMR (DMSO-d$_6$+D$_2$O, δ): 3.14, 3.54 (2H, ABq, J=18 Hz), 5.08 (1H, d, J=5 Hz), 5.28, 5.62 (2H, ABq, J=12 Hz), 5.86 (1H, d, J=5 Hz), 7.96–8.24 (2H, m), 8.40–8.68 (1H, m), 9.16–9.42 (2H, m)

EXAMPLE 71

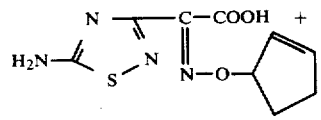

145
-continued

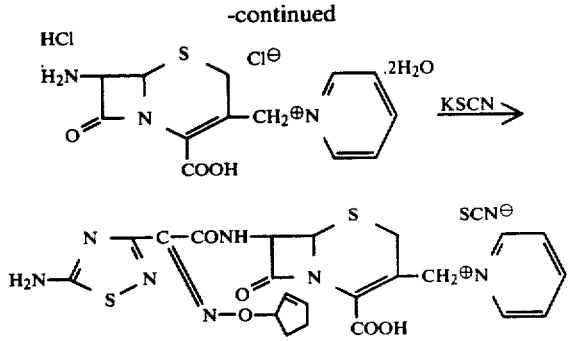

To a cold solution of phosphorus pentachloride (20.8 g) in methylene chloride (375 ml) was added 2-(2-cyclopenten-1-yloxyimino)-2-(5-amino-1,2,4-thiadiazol-3-yl)acetic acid (syn isomer) (25.4 g) at −18° C. and the mixture was stirred for 40 minutes at −12° to −10° C. To the reaction mixture was added diisopropyl ether (1.2 l) below −10° C. under stirring, which was continued until the mixture was warmed to ambient temperature. The resulting precipitates were collected by filtration, washed with diisopropyl ether and then kept in a desiccator for several minutes. On the other hand, a mixture of 1-[(7-amino-4-carboxy-3-cephem-3-yl)methyl]pyridinium chloride hydrochloride dihydrate (30.77 g) and trimethylsilylacetamide (154.5 g) in methylene chloride (800 ml) was warmed at 35° C. to make a solution, which was cooled to −18° C. To the cold solution were added the precipitates prepared above and the mixture was stirred for 30 minutes at −12° to −10° C. A solution of sodium bicarbonate (26 g) in water (400 ml) was added to the reaction mixture and the aqueous layer was separated out, adjusted to pH 1.5 with 6 N hydrochloric acid, and washed with ethyl acetate. The aqueous solution was adjusted to pH 4 with an aqueous solution of sodium bicarbonate and passed through a column packed with acidic alumina (117 g). To the eluate (1.2 l) were added potassium thiocyanate (56.2 g) and sodium chloride (171.5 g) and then the mixture was adjusted to pH 2.6 with 1 N hydrochloric acid under cooling in an ice-bath. After an insoluble material was filtered off, sodium chloride (171.5 g) was added to the filtrate and the solution was adjusted to pH 1.6 with 1 N hydrochloric acid under stirring and cooling in an ice-bath. The resulting precipitates were filtered, washed with cold water (2×150 ml) and dried to give 1-[[7-{2-(2-cyclopenten-1-yloxyimino)-2-(5-amino-1,2,4-thiadiazol-3-yl)acetamido}-4-carboxy-3-cephem-3-yl]methyl]pyridinium thiocyanate (syn isomer) (28.1 g), mp 151° to 156° C. (dec.).

IR (Nujol): 2050, 1780, 1670, 1630, 1610, 1530 cm⁻¹
NMR (DMSO-d₆+D₂O, δ): 1.6–2.7 (4H, m), 3.33, 3.66 (2H, ABq, J=18 Hz), 5.20 (1H, d, J=5 Hz), 4.9–6.3 (5H, m), 5.86 (1H, d, J=5 Hz), 8.2 (2H, m), 8.7 (1H, m), 9.15 (2H, m)

EXAMPLE 72

1-[[7-{2-(2-Cyclopenten-1-yloxyimino)-2-(5-amino-1,2,4-thiadiazol-3-yl)acetamido}-4-carboxy-3-cephem-3-yl]methyl]pyridinium iodide (syn isomer) was obtained according to a similar manner to that of Example 71 by using sodium iodide instead of potassium thiocyanate.

IR (Nujol): 3400–3100, 1775, 1670, 1620, 1520 cm⁻¹
NMR (DMSO-d₆+D₂O, δ): 1.6–2.8 (4H, m), 3.35, 3.80 (2H, ABq, J=19 Hz), 5.31 (1H, d, J=5 Hz), 5.93 (1H, d, J=5 Hz), 5.0–6.4 (5H, m), 8.28 (2H, m), 8.74 (1H, m), 9.15 (2H, m)

EXAMPLE 73

To a solution of 1-[[7-{2-(2-cyclopenten-1-yloxyimino)-2-(5-amino-1,2,4-thiadiazol-3-yl)acetamido}-4-carboxy-3-cephem-3-yl]methyl]pyridinium thiocyanate (syn isomer) (11.7 g) in dimethylformamide (30 ml) was added a solution of lithium chloride (1.7 g) in methanol (20 ml) under stirring, which was continued for 10 minutes at ambient temperature. An insoluble material was filtered, washed with dimethylformamide (6 ml) and then the filtrate and the washings were combined. The combined solution was added to acetone (300 ml) under stirring, which was continued for five minutes at ambient temperature. The resulting precipitates were filtered, washed with acetone (40 ml×3) and dried in vacuo to give 1-[[7-{2-(2-cyclopenten-1-yloxyimino)-2-(5-amino-1,2,4-thiadiazol-3-yl)acetamido}-4-carboxy-3-cephem-3-yl]methyl]pyridinium chloride (syn isomer) (11.0 g).

IR (Nujol): 3400–3100, 1780, 1660, 1630, 1530 cm⁻¹
NMR (DMSO-d₆, δ): 1.6–2.6 (4H, m), 3.39, 3.61 (2H, ABq, J=18 Hz), 5.19 (1H, d, J=5 Hz), 4.9–5.6 (2H, m), 5.64 (1H, broad s), 5.81 (1H, dd, J=5 and 8 Hz), 5.7–6.2 (2H, m), 8.20 (2H, m), 8.64 (1H, m), 9.22 (2H, m), 9.48 (1H, d, J=8 Hz)

What we claim is:

1. 7-substituted-3-cephem and cepham-4-carboxylic acid of the formula:

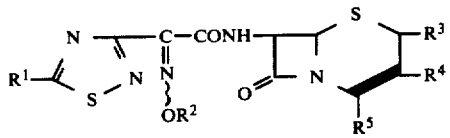

where
R¹ is amino or a protected amino;
R² is hydrogen, lower alkylthio(lower)alkyl, halo(lower)alkyl, ar(lower)alkyl, lower alkenyl, lower alkynyl, cyclo(lower)alkyl, cyclo(lower)alkenyl, or O containing 5-membered heterocyclic group substituted with an oxo group;
R³ is hydrogen;
R⁴ is pyridinium(lower)alkyl or pyridinium(lower)alkyl substituted with carbamoyl; and
R⁵ is COO⁻; or
R⁴ is lower alkanoyl(lower)alkanoyloxy(lower)alkyl or 2-lower alkyl-5-oxo-6-hydroxy-2,5-dihydro-1,2,4-triazinylthio(lower)alkyl; and R⁵ is carboxy or protected carboxy; and the heavy solid line means single or double bond; and pharmaceutically acceptable salt thereof.

2. Syn-isomer of a compound of claim 1.
3. A compound of claim 2, wherein the heavy solid line is double bond.
4. A compound of claim 3, wherein
R¹ is amino;
R² is hydrogen, lower alkylthio(lower)alkyl, halo(lower)alkyl, ar(lower)alkyl, lower alkenyl, lower alkynyl, cyclo(lower)alkyl, cyclo(lower)alkenyl, or O containing 5-membered heterocyclic group substituted with oxo group(s);
R³ is hydrogen;
R⁴ is pyridinium(lower)alkyl which may be substituted with carbamoyl; and $R^5$ is COO$^-$; or $R^4$ is lower alkanoyl(lower)alkanoyloxy(lower)alkyl or 2-lower alkyl-5-oxo-6-hydroxy-2,5-dihydro-1,2,4-triazinylthio(lower)alkyl; and $R^5$ is carboxy.

5. A compound of claim 4, wherein
$R^2$ is hydrogen, lower alkylthio(lower)alkyl, trihalo(lower)alkyl, triphenyl(lower)alkyl, lower alkenyl, lower alkynyl, or tetrahydrofuryl substituted with an oxo group,
$R^4$ is pyridinium (lower)alkyl which may be substituted with carbamoyl; and
$R^5$ is COO$^-$; or
$R^4$ is lower alkanoyl(lower)alkanoyloxy(lower)alkyl; and
$R^5$ is carboxy.

6. A compound of claim 5, wherein
$R^4$ is pyridinium(lower)alkyl which may be substituted with carbamoyl and $R^5$ is COO$^-$.

7. A compound of claim 6, wherein $R^2$ is hydrogen, methylthiomethyl, trifluoroethyl, trityl, allyl, 2-propynyl or 2-oxotetrahydrofuryl and $R^4$ is pyridiniummethyl which may be substituted with carbamoyl.

8. A compound of claim 7, which is 7-[2-hydroxyimino-2-(5-amino-1,2,4-thiadiazol-3-yl)acetamido]-3-(1-pyridiniomethyl)-3-cephem-4-carboxylate (syn isomer).

9. A compound of claim 7, which is 7-[2-(2,2,2-trifluoroethoxyimino)-2-(5-amino-1,2,4-thiadiazol-3-yl)acetamido]-3-(1-pyridiniomethyl)-3-cephem-4-carboxylate (syn isomer).

10. A compound of claim 7, which is 7-[2-(2,2,2-trifluoroethoxyimino)-2-(5-amino-1,2,4-thiadiazol-3-yl)acetamido]-3-(4-carbamoyl-1-pyridiniomethyl)-3-cephem-4-carboxylate (syn isomer).

11. A compound of claim 7, which is 7-[2-methylthiomethoxyimino-2-(5-amino-1,2,4-thiadiazol-3-yl)acetamido]-3-(1-pyridiniomethyl)-3-cephem-4-carboxylate (syn isomer).

12. A compound of claim 7, which is 7-[2-methylthiomethoxyimino-2-(5-amino-1,2,4-thiadiazol-3-yl)acetamido]-3-(4-carbamoyl-1-pyridiniomethyl)-3-cephem-4-carboxylate (syn isomer).

13. A compound of claim 7, which is 7-[2-allyloxyimino-2-(5-amino-1,2,4-thiadiazol-3-yl)acetamido]-3-(1-pyridiniomethyl)-3-cephem-4-carboxylate (syn isomer).

14. A compound of claim 7, which is 7-[2-(2-oxotetrahydrofuran-3-yloxyimino)-2-(5-amino-1,2,4-thiadiazol-3-yl)acetamido]-3-(1-pyridiniomethyl)-3-cephem-4-carboxylate (syn isomer).

15. A compound of claim 7, which is 7-[2-allyloxyimino-2-(5-amino-1,2,4-thiadiazol-3-yl)acetamido]-3-(4-carbamoyl-1-pyridiniomethyl)-3-cephem-4-carboxylate (syn isomer).

16. A compound of claim 7, which is 7-[2-(2-propynyloxyimino)-2-(5-amino-1,2,4-thiadiazol-3-yl)acetamido]-3-(1-pyridiniomethyl)-3-cephem-4-carboxylate (syn isomer).

17. A compound of claim 7, which is 7-[2-(2-propynyloxyimino)-2-(5-amino-1,2,4-thiadiazol-3-yl)acetamido]-3-(4-carbamoyl-1-pyridiniomethyl)-3-cephem-4-carboxylate (syn isomer).

18. A compound of claim 5, wherein
$R^2$ is lower alkylthio(lower)alkyl, trihalo(lower)alkyl, lower alkenyl or lower alkynyl,
$R^4$ is lower alkanoyl(lower)alkanoyloxy(lower)alkyl and $R^5$ is carboxy.

19. A compound of claim 18, wherein
$R^2$ is methylthiomethyl, trifluoroethyl, allyl or 2-propynyl and $R^4$ is acetoacetoxymethyl.

20. A compound of claim 4, wherein
$R^2$ is lower alkenyl, lower alkynyl, cyclo(lower)alkyl or cyclo(lower)alkenyl,
$R^4$ is 2-lower alkyl-5-oxo-6-hydroxy-2,5-dihydro-1,2,4-triazinylthio(lower)alkyl and $R^5$ is carboxy.

21. A compound of claim 20, wherein
$R^2$ is allyl, 2-propynyl, cyclopentyl, or 2-cyclopenten-1-yl and
$R^4$ is 2-methyl-5-oxo-6-hydroxy-2,5-dihydro-1,2,4-triazinylthiomethyl.

22. A compound of claim 21, which is 7-[2-allyloxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer).

23. A compound of claim 21, which is 7-[2-(2-propynyloxyimino)-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer).

24. A compound of claim 21, which is sodium 7-[2-cyclopentyloxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylate (syn isomer).

25. A compound of claim 21, which is 7-[2-(2-cyclopenten-1-yloxyimino)-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer).

26. A compound of claim 19, which is 7-[2-allyloxyimino-2-(5-amino-1,2,4-thiadiazol-3-yl)acetamido]-3-acetoacetoxymethyl-3-cephem-4-carboxylic acid (syn isomer) and its sodium salt.

27. A compound of claim 19, which is 7-[2-(2,2,2-trifluoroethoxyimino)-2-(5-amino-1,2,4-thiadiazol-3-yl)acetamido]-3-acetoacetoxymethyl-3-cephem-4-carboxylic acid (syn-isomer) and its sodium salt.

28. A compound of claim 19 which is 7-[2-methylthiomethoxyimino-2-(5-amino-1,2,4-thiadiazol-3-yl)acetamido]-3-acetoacetoxymethyl-3-cephem-4-carboxylic acid (syn isomer) and its sodium salt.

29. A compound of claim 19, which is 7-[2-(2-propynyloxyimino)-2-(5-amino-1,2,4-thiadiazol-3-yl)acetamido]-3-acetoacetoxymethyl-3-cephem-4-carboxylic acid (syn isomer).

30. An antibacterial composition comprising an effective amount of a compound of claim 1 or pharmaceutically acceptable salt thereof in association with a pharmaceutically acceptable, substantially non-toxic carrier or excipient.

* * * * *